US006429014B1

(12) United States Patent
Steele et al.

(10) Patent No.: US 6,429,014 B1
(45) Date of Patent: Aug. 6, 2002

(54) **MONOTERPENE SYNTHASES FROM GRAND FIR (*ABIES GRANDIS*)**

(75) Inventors: C. L. Steele, Ardmore, OK (US); Joerg Bohlmann, Jena (DE); Rodney B. Croteau, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/360,545

(22) Filed: Jul. 26, 1999

Related U.S. Application Data

(63) Continuation-in-part of application No. PCT/US98/14528, filed on Jul. 10, 1998.
(60) Provisional application No. 60/052,249, filed on Jul. 11, 1997.
(51) Int. Cl.[7] .................. A61K 38/43; C07H 21/04; C07K 14/415; C12N 5/10
(52) U.S. Cl. .................. 435/419; 435/6; 435/69.1; 435/183; 435/410; 435/252.3; 435/320.1; 530/370; 536/23.6; 536/23.2; 800/278; 424/94.1; 424/195.1
(58) Field of Search .................. 435/6, 69.1, 183, 435/410, 419, 252.3, 320.1; 530/370; 536/23.6, 23.2; 800/278; 424/94.1, 195.1

(56) References Cited

U.S. PATENT DOCUMENTS 4,948,811 A    8/1990    Spinner et al.

FOREIGN PATENT DOCUMENTS

WO    WO 95/11913 A1    5/1995

OTHER PUBLICATIONS

Wildung et al., "A cDNA Clone for Taxadiene Synthase, the Diterpene Cyclase That Catalyzes the Committed Step of Taxol Biosynthesis," *The Journal of Biological Chemistry*, 271(16):9201–9204 (1996).
Bohlmann et al., "Terpenoid–based defenses in conifers: cDNA cloning, characterization and functional expression of wound–inducible (E)–alpha–bisabolene synthases from grand fir (*Abies grandis*)," *PNAS USA* 95(12):6756–6761 (1998).
Bohlmann et al., "Monoterpene Synthases from Grand Fir (*Abies grandis*): cDNA Isolation, Characterization, and Functional Expression of Myrcene Synthase, (–)–(4S)–Limonene Synthase, and (–)–(1S,5S)–Pinene Synthase," *The Journal of Biological Chemistry*, 272(35):21784–21782 (1997).
Rajaonarivony, J.I.M., Gershenzon, J., and Croteau, R. (1992) *Arch. Biochem. Biophys*. 296:49–57.
Gijzen, M., Lewinsohn, E., and Croteau, R. (1991) *Arch. Biochem. Biophys*. 289:267–273.
Lewinsohn, E., Gijzen, M., and Croteau, R. (1992) *Arch. Biochem. Biophys*. 293:167–173.
Wagschal, K., Savage, T.J., and Croteau, R. (1991) *Tetrahedron* 47:5933–5944.
Funk, C., Lewinsohn, E., Stofer Vogel, B., Steele C., and Croteau, R. (1994) *Plant Physiol*. 106:999–1005.
LaFever, R.E., Stofer Vogel, B., and Croteau, R. (1994) *Arch. Biochem. Biophys*. 313:139–149.
Stofer Vogel, B., Wildung, M.R., Vogel, G., and Croteau, R. (1996) *J. Biol. Chem*. 271:23262–23268.
Steele, C., Lewinsohn, E., and Croteau, R. (1995) *Proc. Natl. Acad. Sci. USA* 92:4164–4168.
Colby, S.M., Alonso, W.R., Katahira, E.J., McGarvey, D.J., and Croteau, R. (1993) *J. Biol. Chem*. 268:23016–23024.
Facchini, P.J., and Chappell, J. (1992) *Proc. Natl. Acad. Sci. USA* 89:11088–11092.
Mau, C.J.D., and West, C.A. (1994) *Proc. Natl. Acad. Sci. USA* 91:8497–8501.
Yuba, A., Yazaki, K., Tabata, M., Honda, G., and Croteau, R. (1996) *Arch. Biochem. Biophys*. 332:280–287.

*Primary Examiner*—Phuong T. Bui
(74) *Attorney, Agent, or Firm*—Christensen O'Connor Johnson Kindness PLLC

(57) ABSTRACT cDNAs encoding gymnosperm monoterpene synthases have been isolated and sequenced, and the corresponding amino acid sequences have been determined. Modified host cells are provided that have been transformed, transfected, infected and/or injected with a recombinant cloning vehicle and/or DNA sequence encoding a monoterpene synthase of the invention. Thus, systems and methods are provided for the recombinant expression of recombinant monoterpene synthases that may be used to facilitate their production, isolation and purification in significant amounts.

12 Claims, 25 Drawing Sheets

SEQUENCE LISTING

<160> NUMBER OF SEQ ID NOS: 107

<210> SEQ ID NO 1
<211> LENGTH: 2196
<212> TYPE: DNA
<213> ORGANISM: Abies grandis
<220> FEATURE:
<221> NAME/KEY: CDS
<222> LOCATION: (69)..(1952)
<223> OTHER INFORMATION: Clone AG2.2 encoding myrcene synthase

<400> SEQUENCE: 1

```
tgccggcacg aggttatctt gagcttcctc catataggcc aacacatatc atatcaaagg      60 gagcaaga atg gct ctg gtt tct atc tca ccg ttg gct tcg aaa tct tgc     110
         Met Ala Leu Val Ser Ile Ser Pro Leu Ala Ser Lys Ser Cys
           1               5                  10 ctg cgc aag tcg ttg atc agt tca att cat gaa cat aag cct ccc tat     158
Leu Arg Lys Ser Leu Ile Ser Ser Ile His Glu His Lys Pro Pro Tyr
 15                  20                  25                  30 aga aca atc cca aat ctt gga atg cgt agg cga ggg aaa tct gtc acg     206
Arg Thr Ile Pro Asn Leu Gly Met Arg Arg Arg Gly Lys Ser Val Thr
                 35                  40                  45 cct tcc atg agc atc agt ttg gcc acc gct gca cct gat gat ggt gta     254
Pro Ser Met Ser Ile Ser Leu Ala Thr Ala Ala Pro Asp Asp Gly Val
             50                  55                  60 caa aga cgc ata ggt gac tac cat tcc aat atc tgg gac gat gat ttc     302
Gln Arg Arg Ile Gly Asp Tyr His Ser Asn Ile Trp Asp Asp Asp Phe
         65                  70                  75 ata cag tct cta tca acg cct tat ggg gaa ccc tct tac cag gaa cgt     350
Ile Gln Ser Leu Ser Thr Pro Tyr Gly Glu Pro Ser Tyr Gln Glu Arg
     80                  85                  90 gct gag aga tta att gtg gag gta aag aag ata ttc aat tca atg tac     398
Ala Glu Arg Leu Ile Val Glu Val Lys Lys Ile Phe Asn Ser Met Tyr
 95                 100                 105                 110 ctg gat gat gga aga tta atg agt tcc ttt aat gat ctc atg caa cgc     446
Leu Asp Asp Gly Arg Leu Met Ser Ser Phe Asn Asp Leu Met Gln Arg
                115                 120                 125 ctt tgg ata gtc gat agc gtt gaa cgt ttg ggg ata gct aga cat ttc     494
Leu Trp Ile Val Asp Ser Val Glu Arg Leu Gly Ile Ala Arg His Phe
            130                 135                 140 aag aac gag ata aca tca gct ctg gat tat gtt ttc cgt tac tgg gag     542
Lys Asn Glu Ile Thr Ser Ala Leu Asp Tyr Val Phe Arg Tyr Trp Glu
        145                 150                 155 gaa aac ggc att gga tgt ggg aga gac agt att gtt act gat ctc aac     590
Glu Asn Gly Ile Gly Cys Gly Arg Asp Ser Ile Val Thr Asp Leu Asn
    160                 165                 170 tca act gcg ttg ggg ttt cga act ctt cga tta cac ggg tac act gta     638
Ser Thr Ala Leu Gly Phe Arg Thr Leu Arg Leu His Gly Tyr Thr Val
175                 180                 185                 190 tct cca gag gtt tta aaa gct ttt caa gat caa aat gga cag ttt gta     686
Ser Pro Glu Val Leu Lys Ala Phe Gln Asp Gln Asn Gly Gln Phe Val
                195                 200                 205
```

```
tgc tcc ccc ggt cag aca gag ggt gag atc aga agc gtt ctt aac tta    734
Cys Ser Pro Gly Gln Thr Glu Gly Glu Ile Arg Ser Val Leu Asn Leu
            210                 215                 220 tat cgg gct tcc ctc att gcc ttc cct ggt gag aaa gtt atg gaa gaa    782
Tyr Arg Ala Ser Leu Ile Ala Phe Pro Gly Glu Lys Val Met Glu Glu
        225                 230                 235 gct gaa atc ttc tcc aca aga tat ttg aaa gaa gct cta caa aag att    830
Ala Glu Ile Phe Ser Thr Arg Tyr Leu Lys Glu Ala Leu Gln Lys Ile
    240                 245                 250 cca gtc tcc gct ctt tca caa gag ata aag ttt gtt atg gaa tat ggc    878
Pro Val Ser Ala Leu Ser Gln Glu Ile Lys Phe Val Met Glu Tyr Gly
255                 260                 265                 270 tgg cac aca aat ttg cca aga ttg gaa gca aga aat tac ata gac aca    926
Trp His Thr Asn Leu Pro Arg Leu Glu Ala Arg Asn Tyr Ile Asp Thr
                275                 280                 285 ctt gag aaa gac acc agt gca tgg ctc aat aaa aat gct ggg aag aag    974
Leu Glu Lys Asp Thr Ser Ala Trp Leu Asn Lys Asn Ala Gly Lys Lys
            290                 295                 300 ctt tta gaa ctt gca aaa ttg gag ttc aat ata ttt aac tcc tta caa   1022
Leu Leu Glu Leu Ala Lys Leu Glu Phe Asn Ile Phe Asn Ser Leu Gln
        305                 310                 315 caa aag gaa tta caa tat ctt ttg aga tgg tgg aaa gag tcg gat ttg   1070
Gln Lys Glu Leu Gln Tyr Leu Leu Arg Trp Trp Lys Glu Ser Asp Leu
    320                 325                 330 cct aaa ttg aca ttt gct cgg cat cgt cat gtg gaa ttc tac act ttg   1118
Pro Lys Leu Thr Phe Ala Arg His Arg His Val Glu Phe Tyr Thr Leu
335                 340                 345                 350 gcc tct tgt att gcc att gac cca aaa cat tct gca ttc aga cta ggc   1166
Ala Ser Cys Ile Ala Ile Asp Pro Lys His Ser Ala Phe Arg Leu Gly
                355                 360                 365 ttc gcc aaa atg tgt cat ctt gtc aca gtt ttg gac gat att tac gac   1214
Phe Ala Lys Met Cys His Leu Val Thr Val Leu Asp Asp Ile Tyr Asp
            370                 375                 380 act ttt gga acg att gac gag ctt gaa ctc ttc aca tct gca att aag   1262
Thr Phe Gly Thr Ile Asp Glu Leu Glu Leu Phe Thr Ser Ala Ile Lys
        385                 390                 395 aga tgg aat tca tca gag ata gaa cac ctt cca gaa tat atg aaa tgt   1310
Arg Trp Asn Ser Ser Glu Ile Glu His Leu Pro Glu Tyr Met Lys Cys
    400                 405                 410 gtg tac atg gtc gtg ttt gaa act gta aat gaa ctg aca cga gag gcg   1358
Val Tyr Met Val Val Phe Glu Thr Val Asn Glu Leu Thr Arg Glu Ala
415                 420                 425                 430 gag aag act caa ggg aga aac act ctc aac tat gtt cga aag gct tgg   1406
Glu Lys Thr Gln Gly Arg Asn Thr Leu Asn Tyr Val Arg Lys Ala Trp
                435                 440                 445 gag gct tat ttt gat tca tat atg gaa gaa gca aaa tgg atc tct aat   1454
Glu Ala Tyr Phe Asp Ser Tyr Met Glu Glu Ala Lys Trp Ile Ser Asn
            450                 455                 460 ggt tat ctg cca atg ttt gaa gag tac cat gag aat ggg aaa gtg agc   1502
Gly Tyr Leu Pro Met Phe Glu Glu Tyr His Glu Asn Gly Lys Val Ser
        465                 470                 475 tct gca tat cgc gta gca aca ttg caa ccc atc ctc act ttg aat gca   1550
Ser Ala Tyr Arg Val Ala Thr Leu Gln Pro Ile Leu Thr Leu Asn Ala
    480                 485                 490 tgg ctt cct gat tac atc ttg aag gga att gat ttt cca tcc agg ttc   1598
Trp Leu Pro Asp Tyr Ile Leu Lys Gly Ile Asp Phe Pro Ser Arg Phe
495                 500                 505                 510 aat gat ttg gca tcg tcc ttc ctt cgg cta cga ggt gac aca cgc tgc   1646
Asn Asp Leu Ala Ser Ser Phe Leu Arg Leu Arg Gly Asp Thr Arg Cys
```

-continued

```
                515                 520                 525
tac aag gcc gat agg gat cgt ggt gaa gaa gct tcg tgt ata tca tgt      1694
Tyr Lys Ala Asp Arg Asp Arg Gly Glu Glu Ala Ser Cys Ile Ser Cys
            530                 535                 540 tat atg aaa gac aat cct gga tca acc gaa gaa gat gcc ctc aat cat      1742
Tyr Met Lys Asp Asn Pro Gly Ser Thr Glu Glu Asp Ala Leu Asn His
        545                 550                 555 atc aat gcc atg gtc aat gac ata atc aaa gaa tta aat tgg gaa ctt      1790
Ile Asn Ala Met Val Asn Asp Ile Ile Lys Glu Leu Asn Trp Glu Leu
    560                 565                 570 cta aga tcc aac gac aat att cca atg ctg gcc aag aaa cat gct ttt      1838
Leu Arg Ser Asn Asp Asn Ile Pro Met Leu Ala Lys Lys His Ala Phe
575                 580                 585                 590 gac ata aca aga gct ctc cac cat ctc tac ata tat cga gat ggc ttt      1886
Asp Ile Thr Arg Ala Leu His His Leu Tyr Ile Tyr Arg Asp Gly Phe
                595                 600                 605 agt gtt gcc aac aag gaa aca aaa aaa ttg gtt atg gaa aca ctc ctt      1934
Ser Val Ala Asn Lys Glu Thr Lys Lys Leu Val Met Glu Thr Leu Leu
            610                 615                 620 gaa tct atg ctt ttt taa ctataaccat atccataata ataagctcat             1982
Glu Ser Met Leu Phe
        625 aatgctaaat tattggcctt atgacatagt ttatgtatgt acttgtgtga attcaatcat    2042 atcgtgtggg tatgattaaa aagctagagc ttactaggtt agtaacatgg tgataaaagt    2102 tataaaatgt gagttataga gatacccatg ttgaataatg aattacaaaa agagaaattt    2162 atgtagaata agattggaag cttttcaatt gttt                                2196

<210> SEQ ID NO 2
<211> LENGTH: 627
<212> TYPE: PRT
<213> ORGANISM: Abies grandis

<400> SEQUENCE: 2

Met Ala Leu Val Ser Ile Ser Pro Leu Ala Ser Lys Ser Cys Leu Arg
  1               5                  10                  15

Lys Ser Leu Ile Ser Ser Ile His Glu His Lys Pro Pro Tyr Arg Thr
             20                  25                  30

Ile Pro Asn Leu Gly Met Arg Arg Gly Lys Ser Val Thr Pro Ser
         35                  40                  45

Met Ser Ile Ser Leu Ala Thr Ala Ala Pro Asp Asp Gly Val Gln Arg
     50                  55                  60

Arg Ile Gly Asp Tyr His Ser Asn Ile Trp Asp Asp Phe Ile Gln
 65                  70                  75                  80

Ser Leu Ser Thr Pro Tyr Gly Glu Pro Ser Tyr Gln Glu Arg Ala Glu
                 85                  90                  95

Arg Leu Ile Val Glu Val Lys Lys Ile Phe Asn Ser Met Tyr Leu Asp
                100                 105                 110

Asp Gly Arg Leu Met Ser Ser Phe Asn Asp Leu Met Gln Arg Leu Trp
            115                 120                 125

Ile Val Asp Ser Val Glu Arg Leu Gly Ile Ala Arg His Phe Lys Asn
        130                 135                 140

Glu Ile Thr Ser Ala Leu Asp Tyr Val Phe Arg Tyr Trp Glu Glu Asn
145                 150                 155                 160

Gly Ile Gly Cys Gly Arg Asp Ser Ile Val Thr Asp Leu Asn Ser Thr
                165                 170                 175
```

```
Ala Leu Gly Phe Arg Thr Leu Arg Leu His Gly Tyr Thr Val Ser Pro
            180                 185                 190

Glu Val Leu Lys Ala Phe Gln Asp Gln Asn Gly Gln Phe Val Cys Ser
        195                 200                 205

Pro Gly Gln Thr Glu Gly Glu Ile Arg Ser Val Leu Asn Leu Tyr Arg
    210                 215                 220

Ala Ser Leu Ile Ala Phe Pro Gly Glu Lys Val Met Glu Glu Ala Glu
225                 230                 235                 240

Ile Phe Ser Thr Arg Tyr Leu Lys Glu Ala Leu Gln Lys Ile Pro Val
                245                 250                 255

Ser Ala Leu Ser Gln Glu Ile Lys Phe Val Met Glu Tyr Gly Trp His
            260                 265                 270

Thr Asn Leu Pro Arg Leu Glu Ala Arg Asn Tyr Ile Asp Thr Leu Glu
        275                 280                 285

Lys Asp Thr Ser Ala Trp Leu Asn Lys Asn Ala Gly Lys Lys Leu Leu
    290                 295                 300

Glu Leu Ala Lys Leu Glu Phe Asn Ile Phe Asn Ser Leu Gln Gln Lys
305                 310                 315                 320

Glu Leu Gln Tyr Leu Leu Arg Trp Trp Lys Glu Ser Asp Leu Pro Lys
                325                 330                 335

Leu Thr Phe Ala Arg His Arg His Val Glu Phe Tyr Thr Leu Ala Ser
            340                 345                 350

Cys Ile Ala Ile Asp Pro Lys His Ser Ala Phe Arg Leu Gly Phe Ala
        355                 360                 365

Lys Met Cys His Leu Val Thr Val Leu Asp Asp Ile Tyr Asp Thr Phe
    370                 375                 380

Gly Thr Ile Asp Glu Leu Glu Leu Phe Thr Ser Ala Ile Lys Arg Trp
385                 390                 395                 400

Asn Ser Ser Glu Ile Glu His Leu Pro Glu Tyr Met Lys Cys Val Tyr
                405                 410                 415

Met Val Val Phe Glu Thr Val Asn Glu Leu Thr Arg Glu Ala Glu Lys
            420                 425                 430

Thr Gln Gly Arg Asn Thr Leu Asn Tyr Val Arg Lys Ala Trp Glu Ala
        435                 440                 445

Tyr Phe Asp Ser Tyr Met Glu Glu Ala Lys Trp Ile Ser Asn Gly Tyr
    450                 455                 460

Leu Pro Met Phe Glu Glu Tyr His Glu Asn Gly Lys Val Ser Ser Ala
465                 470                 475                 480

Tyr Arg Val Ala Thr Leu Gln Pro Ile Leu Thr Leu Asn Ala Trp Leu
                485                 490                 495

Pro Asp Tyr Ile Leu Lys Gly Ile Asp Phe Pro Ser Arg Phe Asn Asp
            500                 505                 510

Leu Ala Ser Ser Phe Leu Arg Leu Arg Gly Asp Thr Arg Cys Tyr Lys
        515                 520                 525

Ala Asp Arg Asp Arg Gly Glu Glu Ala Ser Cys Ile Ser Cys Tyr Met
    530                 535                 540

Lys Asp Asn Pro Gly Ser Thr Glu Glu Asp Ala Leu Asn His Ile Asn
545                 550                 555                 560

Ala Met Val Asn Asp Ile Ile Lys Glu Leu Asn Trp Glu Leu Leu Arg
                565                 570                 575

Ser Asn Asp Asn Ile Pro Met Leu Ala Lys Lys His Ala Phe Asp Ile
            580                 585                 590

Thr Arg Ala Leu His His Leu Tyr Ile Tyr Arg Asp Gly Phe Ser Val
```

```
Ala Asn Lys Glu Thr Lys Lys Leu Val Met Glu Thr Leu Leu Glu Ser
        610             615                 620
Met Leu Phe
625

<210> SEQ ID NO 3
<211> LENGTH: 2018
<212> TYPE: DNA
<213> ORGANISM: Abies grandis
<220> FEATURE:
<221> NAME/KEY: CDS
<222> LOCATION: (6)..(1892)
<223> OTHER INFORMATION: Clone AG3.18 encoding pinene synthase

<400> SEQUENCE: 3 cagca atg gct cta gtt tct acc gca ccg ttg gct tcc aaa tca tgc ctg      50
      Met Ala Leu Val Ser Thr Ala Pro Leu Ala Ser Lys Ser Cys Leu
       1               5                  10                  15 cac aaa tcg ttg atc agt tct acc cat gag ctt aag gct ctc tct aga       98
His Lys Ser Leu Ile Ser Ser Thr His Glu Leu Lys Ala Leu Ser Arg
                 20                  25                  30 aca att cca gct cta gga atg agt agg cga ggg aaa tct atc act cct      146
Thr Ile Pro Ala Leu Gly Met Ser Arg Arg Gly Lys Ser Ile Thr Pro
             35                  40                  45 tcc atc agc atg agc tct acc acc gtt gta acc gat gat ggt gta cga      194
Ser Ile Ser Met Ser Ser Thr Thr Val Val Thr Asp Asp Gly Val Arg
         50                  55                  60 aga cgc atg ggc gat ttc cat tcc aac ctc tgg gac gat gat gtc ata      242
Arg Arg Met Gly Asp Phe His Ser Asn Leu Trp Asp Asp Asp Val Ile
     65                  70                  75 cag tct tta cca acg gct tat gag gaa aaa tcg tac ctg gag cgt gct      290
Gln Ser Leu Pro Thr Ala Tyr Glu Glu Lys Ser Tyr Leu Glu Arg Ala
 80                  85                  90                  95 gag aaa ctg atc ggg gaa gta aag aac atg ttc aat tcg atg tca tta      338
Glu Lys Leu Ile Gly Glu Val Lys Asn Met Phe Asn Ser Met Ser Leu
                100                 105                 110 gaa gat gga gag tta atg agt ccg ctc aat gat ctc att caa cgc ctt      386
Glu Asp Gly Glu Leu Met Ser Pro Leu Asn Asp Leu Ile Gln Arg Leu
            115                 120                 125 tgg att gtc gac agc ctt gaa cgt ttg ggg atc cat aga cat ttc aaa      434
Trp Ile Val Asp Ser Leu Glu Arg Leu Gly Ile His Arg His Phe Lys
        130                 135                 140 gat gag ata aaa tcg gcg ctt gat tat gtt tac agt tat tgg ggc gaa      482
Asp Glu Ile Lys Ser Ala Leu Asp Tyr Val Tyr Ser Tyr Trp Gly Glu
    145                 150                 155 aat ggc atc gga tgc ggg agg gag agt gtt gtt act gat ctg aac tca      530
Asn Gly Ile Gly Cys Gly Arg Glu Ser Val Val Thr Asp Leu Asn Ser
160                 165                 170                 175 act gcg ttg ggg ctt cga acc cta cga cta cac gga tac ccg gtg tct      578
Thr Ala Leu Gly Leu Arg Thr Leu Arg Leu His Gly Tyr Pro Val Ser
                180                 185                 190 tca gat gtt ttc aaa gct ttc aaa ggc caa aat ggg cag ttt tcc tgc      626
Ser Asp Val Phe Lys Ala Phe Lys Gly Gln Asn Gly Gln Phe Ser Cys
            195                 200                 205 tct gaa aat att cag aca gat gaa gag atc aga ggc gtt ctg aat tta      674
Ser Glu Asn Ile Gln Thr Asp Glu Glu Ile Arg Gly Val Leu Asn Leu
        210                 215                 220 ttc cgg gcc tcc ctc att gcc ttt cca ggg gag aaa att atg gat gag      722
Phe Arg Ala Ser Leu Ile Ala Phe Pro Gly Glu Lys Ile Met Asp Glu
    225                 230                 235
```

```
gct gaa atc ttc tct acc aaa tat tta aaa gaa gcc ctg caa aag att    770
Ala Glu Ile Phe Ser Thr Lys Tyr Leu Lys Glu Ala Leu Gln Lys Ile
240             245                 250                 255 ccg gtc tcc agt ctt tcg cga gag atc ggg gac gtt ttg gaa tat ggt    818
Pro Val Ser Ser Leu Ser Arg Glu Ile Gly Asp Val Leu Glu Tyr Gly
            260                 265                 270 tgg cac aca tat ttg ccg cga ttg gaa gca agg aat tac atc caa gtc    866
Trp His Thr Tyr Leu Pro Arg Leu Glu Ala Arg Asn Tyr Ile Gln Val
        275                 280                 285 ttt gga cag gac act gag aac acg aag tca tat gtg aag agc aaa aaa    914
Phe Gly Gln Asp Thr Glu Asn Thr Lys Ser Tyr Val Lys Ser Lys Lys
    290                 295                 300 ctt tta gaa ctc gca aaa ttg gag ttc aac atc ttt caa tcc tta caa    962
Leu Leu Glu Leu Ala Lys Leu Glu Phe Asn Ile Phe Gln Ser Leu Gln
305                 310                 315 aag agg gag tta gaa agt ctg gtc aga tgg tgg aaa gaa tcg ggt ttt   1010
Lys Arg Glu Leu Glu Ser Leu Val Arg Trp Trp Lys Glu Ser Gly Phe
320                 325                 330                 335 cct gag atg acc ttc tgc cga cat cgt cac gtg gaa tac tac act ttg   1058
Pro Glu Met Thr Phe Cys Arg His Arg His Val Glu Tyr Tyr Thr Leu
            340                 345                 350 gct tcc tgc att gcg ttc gag cct caa cat tct gga ttc aga ctc ggc   1106
Ala Ser Cys Ile Ala Phe Glu Pro Gln His Ser Gly Phe Arg Leu Gly
        355                 360                 365 ttt gcc aag acg tgt cat ctt atc acg gtt ctt gac gat atg tac gac   1154
Phe Ala Lys Thr Cys His Leu Ile Thr Val Leu Asp Asp Met Tyr Asp
    370                 375                 380 acc ttc ggc aca gta gac gag ctg gaa ctc ttc aca gcg aca atg aag   1202
Thr Phe Gly Thr Val Asp Glu Leu Glu Leu Phe Thr Ala Thr Met Lys
385                 390                 395 aga tgg gat ccg tcc tcg ata gat tgc ctt cca gaa tat atg aaa gga   1250
Arg Trp Asp Pro Ser Ser Ile Asp Cys Leu Pro Glu Tyr Met Lys Gly
400                 405                 410                 415 gtg tac ata gcg gtt tac gac acc gta aat gaa atg gct cga gag gca   1298
Val Tyr Ile Ala Val Tyr Asp Thr Val Asn Glu Met Ala Arg Glu Ala
            420                 425                 430 gag gag gct caa ggc cga gat acg ctc aca tat gct cgg gaa gct tgg   1346
Glu Glu Ala Gln Gly Arg Asp Thr Leu Thr Tyr Ala Arg Glu Ala Trp
        435                 440                 445 gag gct tat att gat tcg tat atg caa gaa gca agg tgg atc gcc act   1394
Glu Ala Tyr Ile Asp Ser Tyr Met Gln Glu Ala Arg Trp Ile Ala Thr
    450                 455                 460 ggt tac ctg ccc tcc ttt gat gag tac tac gag aat ggg aaa gtt agc   1442
Gly Tyr Leu Pro Ser Phe Asp Glu Tyr Tyr Glu Asn Gly Lys Val Ser
465                 470                 475 tgt ggt cat cgc ata tcc gca ttg caa ccc att ctg aca atg gac atc   1490
Cys Gly His Arg Ile Ser Ala Leu Gln Pro Ile Leu Thr Met Asp Ile
480                 485                 490                 495 ccc ttt cct gat cat atc ctc aag gaa gtt gac ttc cca tca aag ctt   1538
Pro Phe Pro Asp His Ile Leu Lys Glu Val Asp Phe Pro Ser Lys Leu
            500                 505                 510 aac gac ttg gca tgt gcc atc ctt cga tta cga ggt gat acg cgg tgc   1586
Asn Asp Leu Ala Cys Ala Ile Leu Arg Leu Arg Gly Asp Thr Arg Cys
        515                 520                 525 tac aag gcg gac agg gct cgt gga gaa gaa gct tcc tct ata tca tgt   1634
Tyr Lys Ala Asp Arg Ala Arg Gly Glu Glu Ala Ser Ser Ile Ser Cys
    530                 535                 540 tat atg aaa gac aat cct gga gta tca gag gaa gat gct ctc gat cat   1682
Tyr Met Lys Asp Asn Pro Gly Val Ser Glu Glu Asp Ala Leu Asp His
```

-continued

```
      545                 550                 555
atc aac gcc atg atc agt gac gta atc aaa gga tta aat tgg gaa ctt      1730
Ile Asn Ala Met Ile Ser Asp Val Ile Lys Gly Leu Asn Trp Glu Leu
560                 565                 570                 575 ctc aaa cca gac atc aat gtt ccc atc tcg gcg aag aaa cat gct ttt      1778
Leu Lys Pro Asp Ile Asn Val Pro Ile Ser Ala Lys Lys His Ala Phe
                580                 585                 590 gac atc gcc aga gct ttc cat tac ggc tac aaa tac cga gac ggc tac      1826
Asp Ile Ala Arg Ala Phe His Tyr Gly Tyr Lys Tyr Arg Asp Gly Tyr
                595                 600                 605 agc gtt gcc aac gtt gaa acg aag agt ttg gtc acg aga acc ctc ctt      1874
Ser Val Ala Asn Val Glu Thr Lys Ser Leu Val Thr Arg Thr Leu Leu
            610                 615                 620 gaa tct gtg cct ttg tag caacagctca aatctatgcc ctatgctatg             1922
Glu Ser Val Pro Leu
        625 tcgggttaaa atatatgtgg aaggtagccg ttggatgtag aggataagtt tgttataatt    1982 taataaagtt gtaatttaaa aaaaaaaaaa aaaaaa                              2018
```

<210> SEQ ID NO 4
<211> LENGTH: 628
<212> TYPE: PRT
<213> ORGANISM: Abies grandis

<400> SEQUENCE: 4

```
Met Ala Leu Val Ser Thr Ala Pro Leu Ala Ser Lys Ser Cys Leu His
 1               5                  10                  15

Lys Ser Leu Ile Ser Ser Thr His Glu Leu Lys Ala Leu Ser Arg Thr
                20                  25                  30

Ile Pro Ala Leu Gly Met Ser Arg Arg Gly Lys Ser Ile Thr Pro Ser
            35                  40                  45

Ile Ser Met Ser Ser Thr Thr Val Val Thr Asp Asp Gly Val Arg Arg
        50                  55                  60

Arg Met Gly Asp Phe His Ser Asn Leu Trp Asp Asp Val Ile Gln
 65                  70                  75                  80

Ser Leu Pro Thr Ala Tyr Glu Glu Lys Ser Tyr Leu Glu Arg Ala Glu
                85                  90                  95

Lys Leu Ile Gly Glu Val Lys Asn Met Phe Asn Ser Met Ser Leu Glu
            100                 105                 110

Asp Gly Glu Leu Met Ser Pro Leu Asn Asp Leu Ile Gln Arg Leu Trp
        115                 120                 125

Ile Val Asp Ser Leu Glu Arg Leu Gly Ile His Arg His Phe Lys Asp
    130                 135                 140

Glu Ile Lys Ser Ala Leu Asp Tyr Val Tyr Ser Tyr Trp Gly Glu Asn
145                 150                 155                 160

Gly Ile Gly Cys Gly Arg Glu Ser Val Val Thr Asp Leu Asn Ser Thr
                165                 170                 175

Ala Leu Gly Leu Arg Thr Leu Arg Leu His Gly Tyr Pro Val Ser Ser
            180                 185                 190

Asp Val Phe Lys Ala Phe Lys Gly Gln Asn Gly Gln Phe Ser Cys Ser
        195                 200                 205

Glu Asn Ile Gln Thr Asp Glu Glu Ile Arg Gly Val Leu Asn Leu Phe
    210                 215                 220

Arg Ala Ser Leu Ile Ala Phe Pro Gly Glu Lys Ile Met Asp Glu Ala
225                 230                 235                 240
```

```
Glu Ile Phe Ser Thr Lys Tyr Leu Lys Glu Ala Leu Gln Lys Ile Pro
                245                 250                 255

Val Ser Ser Leu Ser Arg Glu Ile Gly Asp Val Leu Glu Tyr Gly Trp
        260                 265                 270

His Thr Tyr Leu Pro Arg Leu Glu Ala Arg Asn Tyr Ile Gln Val Phe
            275                 280                 285

Gly Gln Asp Thr Glu Asn Thr Lys Ser Tyr Val Lys Ser Lys Lys Leu
290                 295                 300

Leu Glu Leu Ala Lys Leu Glu Phe Asn Ile Phe Gln Ser Leu Gln Lys
305                 310                 315                 320

Arg Glu Leu Glu Ser Leu Val Arg Trp Trp Lys Glu Ser Gly Phe Pro
                325                 330                 335

Glu Met Thr Phe Cys Arg His Arg His Val Glu Tyr Tyr Thr Leu Ala
                340                 345                 350

Ser Cys Ile Ala Phe Glu Pro Gln His Ser Gly Phe Arg Leu Gly Phe
            355                 360                 365

Ala Lys Thr Cys His Leu Ile Thr Val Leu Asp Asp Met Tyr Asp Thr
        370                 375                 380

Phe Gly Thr Val Asp Glu Leu Glu Leu Phe Thr Ala Thr Met Lys Arg
385                 390                 395                 400

Trp Asp Pro Ser Ser Ile Asp Cys Leu Pro Glu Tyr Met Lys Gly Val
                405                 410                 415

Tyr Ile Ala Val Tyr Asp Thr Val Asn Glu Met Ala Arg Glu Ala Glu
                420                 425                 430

Glu Ala Gln Gly Arg Asp Thr Leu Thr Tyr Ala Arg Glu Ala Trp Glu
            435                 440                 445

Ala Tyr Ile Asp Ser Tyr Met Gln Glu Ala Arg Trp Ile Ala Thr Gly
        450                 455                 460

Tyr Leu Pro Ser Phe Asp Glu Tyr Tyr Glu Asn Gly Lys Val Ser Cys
465                 470                 475                 480

Gly His Arg Ile Ser Ala Leu Gln Pro Ile Leu Thr Met Asp Ile Pro
                485                 490                 495

Phe Pro Asp His Ile Leu Lys Glu Val Asp Phe Pro Ser Lys Leu Asn
                500                 505                 510

Asp Leu Ala Cys Ala Ile Leu Arg Leu Arg Gly Asp Thr Arg Cys Tyr
            515                 520                 525

Lys Ala Asp Arg Ala Arg Gly Glu Glu Ala Ser Ser Ile Ser Cys Tyr
530                 535                 540

Met Lys Asp Asn Pro Gly Val Ser Glu Glu Asp Ala Leu Asp His Ile
545                 550                 555                 560

Asn Ala Met Ile Ser Asp Val Ile Lys Gly Leu Asn Trp Glu Leu Leu
                565                 570                 575

Lys Pro Asp Ile Asn Val Pro Ile Ser Ala Lys Lys His Ala Phe Asp
            580                 585                 590

Ile Ala Arg Ala Phe His Tyr Gly Tyr Lys Tyr Arg Asp Gly Tyr Ser
        595                 600                 605

Val Ala Asn Val Glu Thr Lys Ser Leu Val Thr Arg Thr Leu Leu Glu
    610                 615                 620

Ser Val Pro Leu
625

<210> SEQ ID NO 5
<211> LENGTH: 2089
<212> TYPE: DNA
```

-continued

```
<213> ORGANISM: Abies grandis
<220> FEATURE:
<221> NAME/KEY: CDS
<222> LOCATION: (73)..(1986)
<223> OTHER INFORMATION: Clone AG10 encoding limonene synthase

<400> SEQUENCE: 5
tgccgtttaa tcggtttaaa gaagctacca tagttcggtt taaagaagct accatagttt        60
aggcaggaat cc atg gct ctc ctt tct atc gta tct ttg cag gtt ccc aaa       111
              Met Ala Leu Leu Ser Ile Val Ser Leu Gln Val Pro Lys
                1               5                  10 tcc tgc ggg ctg aaa tcg ttg atc agt tcc agc aat gtg cag aag gct         159
Ser Cys Gly Leu Lys Ser Leu Ile Ser Ser Ser Asn Val Gln Lys Ala
         15                  20                  25 ctc tgt atc tct aca gca gtc cca aca ctc aga atg cgt agg cga cag         207
Leu Cys Ile Ser Thr Ala Val Pro Thr Leu Arg Met Arg Arg Arg Gln
 30                  35                  40                  45 aaa gct ctg gtc atc aac atg aaa ttg acc act gta tcc cat cgt gat         255
Lys Ala Leu Val Ile Asn Met Lys Leu Thr Thr Val Ser His Arg Asp
                 50                  55                  60 gat aat ggt ggt ggt gta ctg caa aga cgc ata gcc gat cat cat ccc         303
Asp Asn Gly Gly Gly Val Leu Gln Arg Arg Ile Ala Asp His His Pro
             65                  70                  75 aac ctg tgg gaa gat gat ttc ata caa tca ttg tcc tca cct tat ggg         351
Asn Leu Trp Glu Asp Asp Phe Ile Gln Ser Leu Ser Ser Pro Tyr Gly
         80                  85                  90 gga tct tcg tac agt gaa cgt gct gag aca gtc gtt gag gaa gta aaa         399
Gly Ser Ser Tyr Ser Glu Arg Ala Glu Thr Val Val Glu Glu Val Lys
     95                 100                 105 gag atg ttc aat tca ata cca aat aat aga gaa tta ttt ggt tcc caa         447
Glu Met Phe Asn Ser Ile Pro Asn Asn Arg Glu Leu Phe Gly Ser Gln
110                 115                 120                 125 aat gat ctc ctt aca cgc ctt tgg atg gtg gat agc att gaa cgt ctg         495
Asn Asp Leu Leu Thr Arg Leu Trp Met Val Asp Ser Ile Glu Arg Leu
                130                 135                 140 ggg ata gat aga cat ttc caa aat gag ata aga gta gcc ctc gat tat         543
Gly Ile Asp Arg His Phe Gln Asn Glu Ile Arg Val Ala Leu Asp Tyr
            145                 150                 155 gtt tac agt tat tgg aag gaa aag gaa ggc att ggg tgt ggc aga gat         591
Val Tyr Ser Tyr Trp Lys Glu Lys Glu Gly Ile Gly Cys Gly Arg Asp
        160                 165                 170 tct act ttt cct gat ctc aac tcg act gcc ttg gcg ctt cga act ctt         639
Ser Thr Phe Pro Asp Leu Asn Ser Thr Ala Leu Ala Leu Arg Thr Leu
    175                 180                 185 cga ctg cac gga tac aat gtg tct tca gat gtg ctg gaa tac ttc aaa         687
Arg Leu His Gly Tyr Asn Val Ser Ser Asp Val Leu Glu Tyr Phe Lys
190                 195                 200                 205 gat gaa aag ggg cat ttt gcc tgc cct gca atc cta acc gag gga cag         735
Asp Glu Lys Gly His Phe Ala Cys Pro Ala Ile Leu Thr Glu Gly Gln
                210                 215                 220 atc act aga agt gtt cta aat tta tat cgg gct tcc ctg gtc gcc ttt         783
Ile Thr Arg Ser Val Leu Asn Leu Tyr Arg Ala Ser Leu Val Ala Phe
            225                 230                 235 ccc ggg gag aaa gtt atg gaa gag gct gaa atc ttc tcg gca tct tat         831
Pro Gly Glu Lys Val Met Glu Glu Ala Glu Ile Phe Ser Ala Ser Tyr
        240                 245                 250 ttg aaa aaa gtc tta caa aag att ccg gtc tcc aat ctt tca gga gag         879
Leu Lys Lys Val Leu Gln Lys Ile Pro Val Ser Asn Leu Ser Gly Glu
    255                 260                 265 ata gaa tat gtt ttg gaa tat ggt tgg cac acg aat ttg ccg aga ttg         927
```

```
Ile Glu Tyr Val Leu Glu Tyr Gly Trp His Thr Asn Leu Pro Arg Leu
270                 275                 280                 285 gaa gca aga aat tat atc gag gtc tac gag cag agc ggc tat gaa agc      975
Glu Ala Arg Asn Tyr Ile Glu Val Tyr Glu Gln Ser Gly Tyr Glu Ser
                290                 295                 300 tta aac gag atg cca tat atg aac atg aag aag ctt tta caa ctt gca     1023
Leu Asn Glu Met Pro Tyr Met Asn Met Lys Lys Leu Leu Gln Leu Ala
            305                 310                 315 aaa ttg gag ttc aat atc ttt cac tct ttg caa cta aga gag tta caa     1071
Lys Leu Glu Phe Asn Ile Phe His Ser Leu Gln Leu Arg Glu Leu Gln
        320                 325                 330 tct atc tcc aga tgg tgg aaa gaa tca ggt tcg tct caa ctg act ttt     1119
Ser Ile Ser Arg Trp Trp Lys Glu Ser Gly Ser Ser Gln Leu Thr Phe
    335                 340                 345 aca cgg cat cgt cac gtg gaa tac tac act atg gca tct tgc att tct     1167
Thr Arg His Arg His Val Glu Tyr Tyr Thr Met Ala Ser Cys Ile Ser
350                 355                 360                 365 atg ttg cca aaa cat tca gct ttc aga atg gag ttt gtc aaa gtg tgt     1215
Met Leu Pro Lys His Ser Ala Phe Arg Met Glu Phe Val Lys Val Cys
                370                 375                 380 cat ctt gta aca gtt ctc gat gat ata tat gac act ttt gga aca atg     1263
His Leu Val Thr Val Leu Asp Asp Ile Tyr Asp Thr Phe Gly Thr Met
            385                 390                 395 aac gaa ctc caa ctt ttt acg gat gca att aag aga tgg gat ttg tca     1311
Asn Glu Leu Gln Leu Phe Thr Asp Ala Ile Lys Arg Trp Asp Leu Ser
        400                 405                 410 acg aca agg tgg ctt cca gaa tat atg aaa gga gtg tac atg gac ttg     1359
Thr Thr Arg Trp Leu Pro Glu Tyr Met Lys Gly Val Tyr Met Asp Leu
    415                 420                 425 tat caa tgc att aat gaa atg gtg gaa gag gct gag aag act caa ggc     1407
Tyr Gln Cys Ile Asn Glu Met Val Glu Glu Ala Glu Lys Thr Gln Gly
430                 435                 440                 445 cga gat atg ctc aac tat att caa aat gct tgg gaa gcc cta ttt gat     1455
Arg Asp Met Leu Asn Tyr Ile Gln Asn Ala Trp Glu Ala Leu Phe Asp
                450                 455                 460 acc ttt atg caa gaa gca aag tgg atc tcc agc agt tat ctc cca acg     1503
Thr Phe Met Gln Glu Ala Lys Trp Ile Ser Ser Ser Tyr Leu Pro Thr
            465                 470                 475 ttt gag gag tac ttg aag aat gca aaa gtt agt tct ggt tct cgc ata     1551
Phe Glu Glu Tyr Leu Lys Asn Ala Lys Val Ser Ser Gly Ser Arg Ile
        480                 485                 490 gcc aca tta caa ccc att ctc act ttg gat gta cca ctt cct gat tac     1599
Ala Thr Leu Gln Pro Ile Leu Thr Leu Asp Val Pro Leu Pro Asp Tyr
    495                 500                 505 ata ctg caa gaa att gat tat cca tcc aga ttc aat gag tta gct tcg     1647
Ile Leu Gln Glu Ile Asp Tyr Pro Ser Arg Phe Asn Glu Leu Ala Ser
510                 515                 520                 525 tcc atc ctt cga cta cga ggt gac acg cgc tgc tac aag gcg gat agg     1695
Ser Ile Leu Arg Leu Arg Gly Asp Thr Arg Cys Tyr Lys Ala Asp Arg
                530                 535                 540 gcc cgt gga gaa gaa gct tca gct ata tcg tgt tat atg aaa gac cat     1743
Ala Arg Gly Glu Glu Ala Ser Ala Ile Ser Cys Tyr Met Lys Asp His
            545                 550                 555 cct gga tca ata gag gaa gat gct ctc aat cat atc aac gcc atg atc     1791
Pro Gly Ser Ile Glu Glu Asp Ala Leu Asn His Ile Asn Ala Met Ile
        560                 565                 570 agt gat gca atc aga gaa tta aat tgg gag ctt ctc aga ccg gat agc     1839
Ser Asp Ala Ile Arg Glu Leu Asn Trp Glu Leu Leu Arg Pro Asp Ser
    575                 580                 585
```

```
aaa agt ccc atc tct tcc aag aaa cat gct ttt gac atc acc aga gct    1887
Lys Ser Pro Ile Ser Ser Lys Lys His Ala Phe Asp Ile Thr Arg Ala
590             595                 600                 605 ttc cat cat gtc tac aaa tat cga gat ggt tac act gtt tcc aac aac    1935
Phe His His Val Tyr Lys Tyr Arg Asp Gly Tyr Thr Val Ser Asn Asn
                610                 615                 620 gaa aca aag aat ttg gtg atg aaa acc gtt ctt gaa cct ctc gct ttg    1983
Glu Thr Lys Asn Leu Val Met Lys Thr Val Leu Glu Pro Leu Ala Leu
            625                 630                 635 taa aaacatatag aatgcattaa aatgtgggaa gtctataatc tagactattc         2036
tctatctttc ataatgtaga tctggatgtg tattgaactc taaaaaaaaa aaa         2089

<210> SEQ ID NO 6
<211> LENGTH: 637
<212> TYPE: PRT
<213> ORGANISM: Abies grandis

<400> SEQUENCE: 6

Met Ala Leu Leu Ser Ile Val Ser Leu Gln Val Pro Lys Ser Cys Gly
 1               5                  10                  15

Leu Lys Ser Leu Ile Ser Ser Asn Val Gln Lys Ala Leu Cys Ile
                20                  25                  30

Ser Thr Ala Val Pro Thr Leu Arg Met Arg Arg Gln Lys Ala Leu
            35                  40                  45

Val Ile Asn Met Lys Leu Thr Thr Val Ser His Arg Asp Asp Asn Gly
 50                  55                  60

Gly Gly Val Leu Gln Arg Arg Ile Ala Asp His His Pro Asn Leu Trp
 65                  70                  75                  80

Glu Asp Asp Phe Ile Gln Ser Leu Ser Ser Pro Tyr Gly Gly Ser Ser
                85                  90                  95

Tyr Ser Glu Arg Ala Glu Thr Val Val Glu Glu Val Lys Glu Met Phe
            100                 105                 110

Asn Ser Ile Pro Asn Asn Arg Glu Leu Phe Gly Ser Gln Asn Asp Leu
        115                 120                 125

Leu Thr Arg Leu Trp Met Val Asp Ser Ile Glu Arg Leu Gly Ile Asp
130                 135                 140

Arg His Phe Gln Asn Glu Ile Arg Val Ala Leu Asp Tyr Val Tyr Ser
145                 150                 155                 160

Tyr Trp Lys Glu Lys Glu Gly Ile Gly Cys Gly Arg Asp Ser Thr Phe
                165                 170                 175

Pro Asp Leu Asn Ser Thr Ala Leu Ala Leu Arg Thr Leu Arg Leu His
            180                 185                 190

Gly Tyr Asn Val Ser Ser Asp Val Leu Glu Tyr Phe Lys Asp Glu Lys
        195                 200                 205

Gly His Phe Ala Cys Pro Ala Ile Leu Thr Glu Gly Gln Ile Thr Arg
    210                 215                 220

Ser Val Leu Asn Leu Tyr Arg Ala Ser Leu Val Ala Phe Pro Gly Glu
225                 230                 235                 240

Lys Val Met Glu Glu Ala Glu Ile Phe Ser Ala Ser Tyr Leu Lys Lys
                245                 250                 255

Val Leu Gln Lys Ile Pro Val Ser Asn Leu Ser Gly Glu Ile Glu Tyr
            260                 265                 270

Val Leu Glu Tyr Gly Trp His Thr Asn Leu Pro Arg Leu Glu Ala Arg
        275                 280                 285

Asn Tyr Ile Glu Val Tyr Glu Gln Ser Gly Tyr Glu Ser Leu Asn Glu
```

-continued

```
                    290                 295                 300
Met Pro Tyr Met Asn Met Lys Lys Leu Leu Gln Leu Ala Lys Leu Glu
305                 310                 315                 320

Phe Asn Ile Phe His Ser Leu Gln Leu Arg Glu Leu Gln Ser Ile Ser
                325                 330                 335

Arg Trp Trp Lys Glu Ser Gly Ser Ser Gln Leu Thr Phe Thr Arg His
                340                 345                 350

Arg His Val Glu Tyr Tyr Thr Met Ala Ser Cys Ile Ser Met Leu Pro
                355                 360                 365

Lys His Ser Ala Phe Arg Met Glu Phe Val Lys Val Cys His Leu Val
                370                 375                 380

Thr Val Leu Asp Asp Ile Tyr Asp Thr Phe Gly Thr Met Asn Glu Leu
385                 390                 395                 400

Gln Leu Phe Thr Asp Ala Ile Lys Arg Trp Asp Leu Ser Thr Thr Arg
                405                 410                 415

Trp Leu Pro Glu Tyr Met Lys Gly Val Tyr Met Asp Leu Tyr Gln Cys
                420                 425                 430

Ile Asn Glu Met Val Glu Glu Ala Glu Lys Thr Gln Gly Arg Asp Met
                435                 440                 445

Leu Asn Tyr Ile Gln Asn Ala Trp Glu Ala Leu Phe Asp Thr Phe Met
450                 455                 460

Gln Glu Ala Lys Trp Ile Ser Ser Ser Tyr Leu Pro Thr Phe Glu Glu
465                 470                 475                 480

Tyr Leu Lys Asn Ala Lys Val Ser Ser Gly Ser Arg Ile Ala Thr Leu
                485                 490                 495

Gln Pro Ile Leu Thr Leu Asp Val Pro Leu Pro Asp Tyr Ile Leu Gln
                500                 505                 510

Glu Ile Asp Tyr Pro Ser Arg Phe Asn Glu Leu Ala Ser Ser Ile Leu
                515                 520                 525

Arg Leu Arg Gly Asp Thr Arg Cys Tyr Lys Ala Asp Arg Ala Arg Gly
530                 535                 540

Glu Glu Ala Ser Ala Ile Ser Cys Tyr Met Lys Asp His Pro Gly Ser
545                 550                 555                 560

Ile Glu Glu Asp Ala Leu Asn His Ile Asn Ala Met Ile Ser Asp Ala
                565                 570                 575

Ile Arg Glu Leu Asn Trp Glu Leu Leu Arg Pro Asp Ser Lys Ser Pro
                580                 585                 590

Ile Ser Ser Lys Lys His Ala Phe Asp Ile Thr Arg Ala Phe His His
                595                 600                 605

Val Tyr Lys Tyr Arg Asp Gly Tyr Thr Val Ser Asn Asn Glu Thr Lys
                610                 615                 620

Asn Leu Val Met Lys Thr Val Leu Glu Pro Leu Ala Leu
625                 630                 635

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Degenerate
      oligonucleotide PCR primer A wherein the letter
      "n" indicates an inosine residue
<220> FEATURE:
<221> NAME/KEY: misc_feature
<222> LOCATION: (1)..(25)
<223> OTHER INFORMATION: Degenerate oligonucleotide Primer A wherein n
      represents inosine
```

<400> SEQUENCE: 7
arraygarra nggnrartay aarga                                     25

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: degenerate
      oligonucleotide PCR primer B wherein the letter
      "n" represents an inosine residue
<220> FEATURE:
<221> NAME/KEY: misc_feature
<222> LOCATION: (1)..(20)
<223> OTHER INFORMATION: oligonucleotide PCR primer B wherein the
      letter n represents an inosine residue

<400> SEQUENCE: 8
atgytncary tntaygargc                                           20

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: degenerate
      oligonucleotide PCR primer C wherein the letter
      "n" represents an inosine residue
<220> FEATURE:
<221> NAME/KEY: misc_feature
<222> LOCATION: (1)..(24)
<223> OTHER INFORMATION: PCR primer C wherein the letter n represents
      inosine

<400> SEQUENCE: 9
ctnkynrang gnctratrta ckty                                      24

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: degenerate
      oligonucleotide PCR primer D wherein the letter
      "n" represents an inosine residue
<220> FEATURE:
<221> NAME/KEY: misc_feature
<222> LOCATION: (1)..(23)
<223> OTHER INFORMATION: PCR primer D wherein the letter n represents
      inosine

<400> SEQUENCE: 10
gaygaynnnt wygaygcnya ygg                                       23

<210> SEQ ID NO 11
<211> LENGTH: 108
<212> TYPE: DNA
<213> ORGANISM: Artificial Sequence

<400> SEQUENCE: 11
gatgatgggt tgatgcgca cggaaccta gatgaattga agctattcac tgaggctgtg     60
agaagatggg acctctcctt tacagacaac ttccccgatt acatgaaa              108

<210> SEQ ID NO 12
<211> LENGTH: 104
<212> TYPE: DNA
<213> ORGANISM: Abies grandis

<400> SEQUENCE: 12
gacgacgggt atgatgcgca tggaacgatt gacgagcttg aactcttcac atctgcaatt      60
aagagatgga attcatcaga gatagacagc ttccccgact atat                      104

<210> SEQ ID NO 13
<211> LENGTH: 105
<212> TYPE: DNA
<213> ORGANISM: Abies grandis
<220> FEATURE:
<221> NAME/KEY: misc_feature
<222> LOCATION: (89)
<223> OTHER INFORMATION: nucleotide may be a or c or g or t

<400> SEQUENCE: 13
gatgatgggt atgatgcgta cggaacgttg aagaaatca aaatcatgac agagggagtg       60
agacgatggg atctttcgtt gaccgcttnc cccgactata tgaaa                     105

<210> SEQ ID NO 14
<211> LENGTH: 117
<212> TYPE: DNA
<213> ORGANISM: Abies grandis
<220> FEATURE:
<221> NAME/KEY: misc_feature
<222> LOCATION: (93)
<223> OTHER INFORMATION: nucleotide may be a or c or g or t

<400> SEQUENCE: 14
gacgatgggt atgatgcgca tggaaccttg gaccaactca aaatctttac agagggagtg      60
agacgatggg atgtttcgtt ggtagaccac ttnccccgac tacatgcaat ctagacc       117

<210> SEQ ID NO 15
<211> LENGTH: 2424
<212> TYPE: DNA
<213> ORGANISM: Abies grandis
<220> FEATURE:
<221> NAME/KEY: CDS
<222> LOCATION: (2)..(2350)
<223> OTHER INFORMATION: Clone AG1.28

<400> SEQUENCE: 15

```
g ggt tat gat ctt gtg cat tct ctt aaa tca cct tat att gat tct agt     49
  Gly Tyr Asp Leu Val His Ser Leu Lys Ser Pro Tyr Ile Asp Ser Ser
   1               5                  10                  15 tac aga gaa cgc gcg gag gtc ctt gtt agc gag att aaa gtg atg ctt       97
Tyr Arg Glu Arg Ala Glu Val Leu Val Ser Glu Ile Lys Val Met Leu
             20                  25                  30 aat cca gct att aca gga gat gga gaa tca atg att act cca tct gct     145
Asn Pro Ala Ile Thr Gly Asp Gly Glu Ser Met Ile Thr Pro Ser Ala
         35                  40                  45 tat gac aca gca tgg gta gcg agg gtg ccc gcc att gat ggc tct gct     193
Tyr Asp Thr Ala Trp Val Ala Arg Val Pro Ala Ile Asp Gly Ser Ala
     50                  55                  60 cgc ccg caa ttt ccc caa aca gtt gac tgg att ttg aaa aac cag tta     241
Arg Pro Gln Phe Pro Gln Thr Val Asp Trp Ile Leu Lys Asn Gln Leu
 65                  70                  75                  80 aaa gat ggt tca tgg gga att cag tcc cac ttt ctg ctg tcc gac cgt     289
Lys Asp Gly Ser Trp Gly Ile Gln Ser His Phe Leu Leu Ser Asp Arg
                 85                  90                  95 ctt ctt gcc act ctt tct tgt gtt ctt gtg ctc ctt aaa tgg aac gtt     337
Leu Leu Ala Thr Leu Ser Cys Val Leu Val Leu Leu Lys Trp Asn Val
            100                 105                 110
```

```
ggg gat ctg caa gta gag cag gga att gaa ttc ata aag agc aat ctg      385
Gly Asp Leu Gln Val Glu Gln Gly Ile Glu Phe Ile Lys Ser Asn Leu
        115                 120                 125 gaa cta gta aag gat gaa acc gat caa gat agc ttg gta aca gac ttt      433
Glu Leu Val Lys Asp Glu Thr Asp Gln Asp Ser Leu Val Thr Asp Phe
    130                 135                 140 gag atc ata ttt cct tct ctg tta aga gaa gct caa tct ctg cgc ctc      481
Glu Ile Ile Phe Pro Ser Leu Leu Arg Glu Ala Gln Ser Leu Arg Leu
145                 150                 155                 160 gga ctt ccc tac gac ctg cct tat ata cat ctg ttg cag act aaa cgg      529
Gly Leu Pro Tyr Asp Leu Pro Tyr Ile His Leu Leu Gln Thr Lys Arg
                165                 170                 175 cag gaa aga tta gca aaa ctt tca agg gag gaa att tat gcg gtt ccg      577
Gln Glu Arg Leu Ala Lys Leu Ser Arg Glu Glu Ile Tyr Ala Val Pro
            180                 185                 190 tcg cca ttg ttg tat tct tta gag gga ata caa gat ata gtt gaa tgg      625
Ser Pro Leu Leu Tyr Ser Leu Glu Gly Ile Gln Asp Ile Val Glu Trp
        195                 200                 205 gaa cga ata atg gaa gtt caa agt cag gat ggg tct ttc tta agc tca      673
Glu Arg Ile Met Glu Val Gln Ser Gln Asp Gly Ser Phe Leu Ser Ser
    210                 215                 220 cct gct tct act gcc tgc gtt ttc atg cac aca gga gac gcg aaa tgc      721
Pro Ala Ser Thr Ala Cys Val Phe Met His Thr Gly Asp Ala Lys Cys
225                 230                 235                 240 ctt gaa ttc ttg aac agt gtg atg atc aag ttt gga aat ttt gtt ccc      769
Leu Glu Phe Leu Asn Ser Val Met Ile Lys Phe Gly Asn Phe Val Pro
                245                 250                 255 tgc ctg tat cct gtg gat ctg ctg gaa cgc ctg ttg atc gta gat aat      817
Cys Leu Tyr Pro Val Asp Leu Leu Glu Arg Leu Leu Ile Val Asp Asn
            260                 265                 270 att gta cgc ctt gga atc tat aga cac ttt gaa aag gaa atc aag gaa      865
Ile Val Arg Leu Gly Ile Tyr Arg His Phe Glu Lys Glu Ile Lys Glu
        275                 280                 285 gct ctt gat tat gtt tac agg cat tgg aac gaa aga gga att ggg tgg      913
Ala Leu Asp Tyr Val Tyr Arg His Trp Asn Glu Arg Gly Ile Gly Trp
    290                 295                 300 ggc aga cta aat ccc ata gca gat ctt gag acc act gct ttg gga ttt      961
Gly Arg Leu Asn Pro Ile Ala Asp Leu Glu Thr Thr Ala Leu Gly Phe
305                 310                 315                 320 cga ttg ctt cgg ctg cat agg tac aat gta tct cca gcc att ttt gac     1009
Arg Leu Leu Arg Leu His Arg Tyr Asn Val Ser Pro Ala Ile Phe Asp
                325                 330                 335 aac ttc aaa gat gcc aat ggg aaa ttc att tgc tcg acc ggt caa ttc     1057
Asn Phe Lys Asp Ala Asn Gly Lys Phe Ile Cys Ser Thr Gly Gln Phe
            340                 345                 350 aac aaa gat gta gca agc atg ctg aat ctt tat aga gct tcc cag ctc     1105
Asn Lys Asp Val Ala Ser Met Leu Asn Leu Tyr Arg Ala Ser Gln Leu
        355                 360                 365 gca ttt ccc gga gaa aac att ctt gat gaa gct aaa agc ttc gct act     1153
Ala Phe Pro Gly Glu Asn Ile Leu Asp Glu Ala Lys Ser Phe Ala Thr
    370                 375                 380 aaa tat ttg aga gaa gct ctt gag aaa agt gag act tcc agt gca tgg     1201
Lys Tyr Leu Arg Glu Ala Leu Glu Lys Ser Glu Thr Ser Ser Ala Trp
385                 390                 395                 400 aac aac aaa caa aac ctg agc caa gag atc aaa tac gcg ctg aag act     1249
Asn Asn Lys Gln Asn Leu Ser Gln Glu Ile Lys Tyr Ala Leu Lys Thr
                405                 410                 415 tct tgg cat gcc agt gtt ccg aga gtg gaa gca aag aga tac tgt caa     1297
Ser Trp His Ala Ser Val Pro Arg Val Glu Ala Lys Arg Tyr Cys Gln
            420                 425                 430
```

```
gtg tat cgc cca gat tat gca cgc ata gca aaa tgc gtt tac aag cta    1345
Val Tyr Arg Pro Asp Tyr Ala Arg Ile Ala Lys Cys Val Tyr Lys Leu
        435                 440                 445 ccc tac gtg aac aat gaa aag ttt tta gag ctg gga aaa tta gat ttc    1393
Pro Tyr Val Asn Asn Glu Lys Phe Leu Glu Leu Gly Lys Leu Asp Phe
450                 455                 460 aac att atc cag tcc atc cac caa gaa gaa atg aag aat gtt acc agc    1441
Asn Ile Ile Gln Ser Ile His Gln Glu Glu Met Lys Asn Val Thr Ser
465                 470                 475                 480 tgg ttt aga gat tcg ggg ttg cca cta ttc acc ttc gct cgg gag agg    1489
Trp Phe Arg Asp Ser Gly Leu Pro Leu Phe Thr Phe Ala Arg Glu Arg
            485                 490                 495 ccg ctg gaa ttc tac ttc tta gta gcg gcg ggg acc tat gaa ccc cag    1537
Pro Leu Glu Phe Tyr Phe Leu Val Ala Ala Gly Thr Tyr Glu Pro Gln
                500                 505                 510 tat gcc aaa tgc agg ttc ctc ttt aca aaa gtg gca tgc ttg cag act    1585
Tyr Ala Lys Cys Arg Phe Leu Phe Thr Lys Val Ala Cys Leu Gln Thr
                    515                 520                 525 gtt ctg gac gat atg tat gac act tat gga acc cta gat gaa ttg aag    1633
Val Leu Asp Asp Met Tyr Asp Thr Tyr Gly Thr Leu Asp Glu Leu Lys
        530                 535                 540 cta ttc act gag gct gtg aga aga tgg gac ctc tcc ttt aca gaa aac    1681
Leu Phe Thr Glu Ala Val Arg Arg Trp Asp Leu Ser Phe Thr Glu Asn
545                 550                 555                 560 ctt cca gac tat atg aaa cta tgt tac caa atc tat tat gac ata gtt    1729
Leu Pro Asp Tyr Met Lys Leu Cys Tyr Gln Ile Tyr Tyr Asp Ile Val
                565                 570                 575 cac gag gtg gct tgg gag gca gag aag gaa cag ggg cgt gaa ttg gtc    1777
His Glu Val Ala Trp Glu Ala Glu Lys Glu Gln Gly Arg Glu Leu Val
            580                 585                 590 agc ttt ttc aga aag gga tgg gag gat tat ctt ctg ggt tat tat gaa    1825
Ser Phe Phe Arg Lys Gly Trp Glu Asp Tyr Leu Leu Gly Tyr Tyr Glu
                595                 600                 605 gaa gct gaa tgg tta gct gct gag tat gtg cct acc ttg gac gag tac    1873
Glu Ala Glu Trp Leu Ala Ala Glu Tyr Val Pro Thr Leu Asp Glu Tyr
        610                 615                 620 ata aag aat gga atc aca tct atc ggc caa cgt ata ctt ctg ttg agt    1921
Ile Lys Asn Gly Ile Thr Ser Ile Gly Gln Arg Ile Leu Leu Leu Ser
625                 630                 635                 640 gga gtg ttg ata atg gat ggg caa ctc ctt tcg caa gag gca tta gag    1969
Gly Val Leu Ile Met Asp Gly Gln Leu Leu Ser Gln Glu Ala Leu Glu
                645                 650                 655 aaa gta gat tat cca gga aga cgt gtt ctc aca gag ctg aat agc ctc    2017
Lys Val Asp Tyr Pro Gly Arg Arg Val Leu Thr Glu Leu Asn Ser Leu
            660                 665                 670 att tcc cgc ctg gcg gat gac acg aag aca tat aaa gct gag aag gct    2065
Ile Ser Arg Leu Ala Asp Asp Thr Lys Thr Tyr Lys Ala Glu Lys Ala
                675                 680                 685 cgt gga gaa ttg gcg tcc agc att gaa tgt tac atg aaa gac cat cct    2113
Arg Gly Glu Leu Ala Ser Ser Ile Glu Cys Tyr Met Lys Asp His Pro
        690                 695                 700 gaa tgt aca gag gaa gag gct ctc gat cac atc tat agc att ctg gag    2161
Glu Cys Thr Glu Glu Glu Ala Leu Asp His Ile Tyr Ser Ile Leu Glu
705                 710                 715                 720 ccg gcg gtg aag gaa ctg aca aga gag ttt ctg aag ccc gac gac gtc    2209
Pro Ala Val Lys Glu Leu Thr Arg Glu Phe Leu Lys Pro Asp Asp Val
                725                 730                 735 cca ttc gcc tgc aag aag atg ctt ttc gag gag aca aga gtg acg atg    2257
Pro Phe Ala Cys Lys Lys Met Leu Phe Glu Glu Thr Arg Val Thr Met
```

-continued

```
                   740                 745                 750
gtg ata ttc aag gat gga gat gga ttc ggt gtt tcc aaa tta gaa gtc       2305
Val Ile Phe Lys Asp Gly Asp Gly Phe Gly Val Ser Lys Leu Glu Val
            755                 760                 765 aaa gat cat atc aaa gag tgt ctc att gaa ccg ctg cca ctg taa           2350
Lys Asp His Ile Lys Glu Cys Leu Ile Glu Pro Leu Pro Leu
770                 775                 780 tcaaaatagt tgcaataata attgaaataa tgtcaactat gtttcacaaa aaaaaaaaaa     2410
aaaaaaaaaa aaaa                                                       2424
```

<210> SEQ ID NO 16
<211> LENGTH: 782
<212> TYPE: PRT
<213> ORGANISM: Abies grandis

<400> SEQUENCE: 16

```
Gly Tyr Asp Leu Val His Ser Leu Lys Ser Pro Tyr Ile Asp Ser Ser
 1               5                  10                  15

Tyr Arg Glu Arg Ala Glu Val Leu Val Ser Glu Ile Lys Val Met Leu
            20                  25                  30

Asn Pro Ala Ile Thr Gly Asp Gly Glu Ser Met Ile Thr Pro Ser Ala
        35                  40                  45

Tyr Asp Thr Ala Trp Val Ala Arg Val Pro Ala Ile Asp Gly Ser Ala
    50                  55                  60

Arg Pro Gln Phe Pro Gln Thr Val Asp Trp Ile Leu Lys Asn Gln Leu
65                  70                  75                  80

Lys Asp Gly Ser Trp Gly Ile Gln Ser His Phe Leu Leu Ser Asp Arg
                85                  90                  95

Leu Leu Ala Thr Leu Ser Cys Val Leu Val Leu Leu Lys Trp Asn Val
            100                 105                 110

Gly Asp Leu Gln Val Glu Gln Gly Ile Glu Phe Ile Lys Ser Asn Leu
        115                 120                 125

Glu Leu Val Lys Asp Glu Thr Asp Gln Asp Ser Leu Val Thr Asp Phe
    130                 135                 140

Glu Ile Ile Phe Pro Ser Leu Leu Arg Glu Ala Gln Ser Leu Arg Leu
145                 150                 155                 160

Gly Leu Pro Tyr Asp Leu Pro Tyr Ile His Leu Leu Gln Thr Lys Arg
                165                 170                 175

Gln Glu Arg Leu Ala Lys Leu Ser Arg Glu Glu Ile Tyr Ala Val Pro
            180                 185                 190

Ser Pro Leu Leu Tyr Ser Leu Glu Gly Ile Gln Asp Ile Val Glu Trp
        195                 200                 205

Glu Arg Ile Met Glu Val Gln Ser Gln Asp Gly Ser Phe Leu Ser Ser
    210                 215                 220

Pro Ala Ser Thr Ala Cys Val Phe Met His Thr Gly Asp Ala Lys Cys
225                 230                 235                 240

Leu Glu Phe Leu Asn Ser Val Met Ile Lys Phe Gly Asn Phe Val Pro
                245                 250                 255

Cys Leu Tyr Pro Val Asp Leu Leu Glu Arg Leu Leu Ile Val Asp Asn
            260                 265                 270

Ile Val Arg Leu Gly Ile Tyr Arg His Phe Glu Lys Glu Ile Lys Glu
        275                 280                 285

Ala Leu Asp Tyr Val Tyr Arg His Trp Asn Glu Arg Gly Ile Gly Trp
    290                 295                 300
```

-continued

```
Gly Arg Leu Asn Pro Ile Ala Asp Leu Glu Thr Thr Ala Leu Gly Phe
305                 310                 315                 320

Arg Leu Leu Arg Leu His Arg Tyr Asn Val Ser Pro Ala Ile Phe Asp
            325                 330                 335

Asn Phe Lys Asp Ala Asn Gly Lys Phe Ile Cys Ser Thr Gly Gln Phe
            340                 345                 350

Asn Lys Asp Val Ala Ser Met Leu Asn Leu Tyr Arg Ala Ser Gln Leu
            355                 360                 365

Ala Phe Pro Gly Glu Asn Ile Leu Asp Glu Ala Lys Ser Phe Ala Thr
370                 375                 380

Lys Tyr Leu Arg Glu Ala Leu Glu Lys Ser Glu Thr Ser Ser Ala Trp
385                 390                 395                 400

Asn Asn Lys Gln Asn Leu Ser Gln Glu Ile Lys Tyr Ala Leu Lys Thr
            405                 410                 415

Ser Trp His Ala Ser Val Pro Arg Val Glu Ala Lys Arg Tyr Cys Gln
            420                 425                 430

Val Tyr Arg Pro Asp Tyr Ala Arg Ile Ala Lys Cys Val Tyr Lys Leu
            435                 440                 445

Pro Tyr Val Asn Asn Glu Lys Phe Leu Glu Leu Gly Lys Leu Asp Phe
            450                 455                 460

Asn Ile Ile Gln Ser Ile His Gln Glu Met Lys Asn Val Thr Ser
465                 470                 475                 480

Trp Phe Arg Asp Ser Gly Leu Pro Leu Phe Thr Phe Ala Arg Glu Arg
            485                 490                 495

Pro Leu Glu Phe Tyr Phe Leu Val Ala Ala Gly Thr Tyr Glu Pro Gln
            500                 505                 510

Tyr Ala Lys Cys Arg Phe Leu Phe Thr Lys Val Ala Cys Leu Gln Thr
            515                 520                 525

Val Leu Asp Asp Met Tyr Asp Thr Tyr Gly Thr Leu Asp Glu Leu Lys
530                 535                 540

Leu Phe Thr Glu Ala Val Arg Arg Trp Asp Leu Ser Phe Thr Glu Asn
545                 550                 555                 560

Leu Pro Asp Tyr Met Lys Leu Cys Tyr Gln Ile Tyr Tyr Asp Ile Val
            565                 570                 575

His Glu Val Ala Trp Glu Ala Glu Lys Glu Gln Gly Arg Glu Leu Val
            580                 585                 590

Ser Phe Phe Arg Lys Gly Trp Glu Asp Tyr Leu Leu Gly Tyr Tyr Glu
            595                 600                 605

Glu Ala Glu Trp Leu Ala Ala Glu Tyr Val Pro Thr Leu Asp Glu Tyr
610                 615                 620

Ile Lys Asn Gly Ile Thr Ser Ile Gly Gln Arg Ile Leu Leu Leu Ser
625                 630                 635                 640

Gly Val Leu Ile Met Asp Gly Gln Leu Leu Ser Gln Glu Ala Leu Glu
            645                 650                 655

Lys Val Asp Tyr Pro Gly Arg Arg Val Leu Thr Glu Leu Asn Ser Leu
            660                 665                 670

Ile Ser Arg Leu Ala Asp Asp Thr Lys Thr Tyr Lys Ala Glu Lys Ala
            675                 680                 685

Arg Gly Glu Leu Ala Ser Ser Ile Glu Cys Tyr Met Lys Asp His Pro
            690                 695                 700

Glu Cys Thr Glu Glu Glu Ala Leu Asp His Ile Tyr Ser Ile Leu Glu
705                 710                 715                 720

Pro Ala Val Lys Glu Leu Thr Arg Glu Phe Leu Lys Pro Asp Asp Val
```

-continued

```
                        725                 730                 735
Pro Phe Ala Cys Lys Lys Met Leu Phe Glu Glu Thr Arg Val Thr Met
                740                 745                 750

Val Ile Phe Lys Asp Gly Asp Gly Phe Gly Val Ser Lys Leu Glu Val
            755                 760                 765

Lys Asp His Ile Lys Glu Cys Leu Ile Glu Pro Leu Pro Leu
        770                 775                 780

<210> SEQ ID NO 17
<211> LENGTH: 1967
<212> TYPE: DNA
<213> ORGANISM: Abies grandis
<220> FEATURE:
<221> NAME/KEY: CDS
<222> LOCATION: (3)..(1736)
<223> OTHER INFORMATION: Clone AG4.30

<400> SEQUENCE: 17 tt tct gaa tct tcc atc cct cga cgc aca ggg aat cat cac gga aat      47
   Ser Glu Ser Ser Ile Pro Arg Arg Thr Gly Asn His His Gly Asn
     1               5                  10                  15 gtg tgg gac gat gac ctc ata cac tct ctc aac tcg ccc tat ggg gca     95
Val Trp Asp Asp Asp Leu Ile His Ser Leu Asn Ser Pro Tyr Gly Ala
                20                  25                  30 cct gca tat tat gag ctc ctt caa aag ctt att gag gag atc aag cat    143
Pro Ala Tyr Tyr Glu Leu Leu Gln Lys Leu Ile Glu Glu Ile Lys His
            35                  40                  45 tta ctt ttg act gaa atg gaa atg gat gat ggc gat cat gat tta atc    191
Leu Leu Leu Thr Glu Met Glu Met Asp Asp Gly Asp His Asp Leu Ile
        50                  55                  60 aaa cgt ctt cag atc gtt gac act ttg gaa tgc ctg gga atc gat aga    239
Lys Arg Leu Gln Ile Val Asp Thr Leu Glu Cys Leu Gly Ile Asp Arg
    65                  70                  75 cat ttt gaa cac gaa ata caa aca gct gct tta gat tac gtt tac aga    287
His Phe Glu His Glu Ile Gln Thr Ala Ala Leu Asp Tyr Val Tyr Arg
 80                  85                  90                  95 tgg tgg aac gaa aaa ggt atc ggg gag gga tca aga gat tcc ttc agc    335
Trp Trp Asn Glu Lys Gly Ile Gly Glu Gly Ser Arg Asp Ser Phe Ser
                100                 105                 110 aaa gat ctc aac gct aca gct tta gga ttt cgc gct ctc cga ctg cat    383
Lys Asp Leu Asn Ala Thr Ala Leu Gly Phe Arg Ala Leu Arg Leu His
            115                 120                 125 cga tat aac gta tcg tca ggt gtg ttg aag aat ttc aag gat gaa aac    431
Arg Tyr Asn Val Ser Ser Gly Val Leu Lys Asn Phe Lys Asp Glu Asn
        130                 135                 140 ggg aag ttc ttc tgc aac ttt act ggt gaa gaa gga aga gga gat aaa    479
Gly Lys Phe Phe Cys Asn Phe Thr Gly Glu Glu Gly Arg Gly Asp Lys
    145                 150                 155 caa gtg aga agc atg ttg tcg tta ctt cga gct tca gag att tcg ttt    527
Gln Val Arg Ser Met Leu Ser Leu Leu Arg Ala Ser Glu Ile Ser Phe
160                 165                 170                 175 ccc gga gaa aaa gtg atg gaa gag gcc aag gca ttc aca aga gaa tat    575
Pro Gly Glu Lys Val Met Glu Glu Ala Lys Ala Phe Thr Arg Glu Tyr
                180                 185                 190 cta aac caa gtt tta gct gga cac ggg gat gtg act gac gtg gat caa    623
Leu Asn Gln Val Leu Ala Gly His Gly Asp Val Thr Asp Val Asp Gln
            195                 200                 205 agc ctt ttg gag aga ggt gaa gta cgc att gga gtt tcc atg gct tgc    671
Ser Leu Leu Glu Arg Gly Glu Val Arg Ile Gly Val Ser Met Ala Cys
        210                 215                 220
```

-continued

| | | |
|---|---|---|
| agt gtg ccg aga tgg gag gca agg agc ttt ctc gaa ata tat gga cac<br>Ser Val Pro Arg Trp Glu Ala Arg Ser Phe Leu Glu Ile Tyr Gly His<br>225                       230                         235 | 719 |
| aac cat tcg tgg ctc aag tcg aat atc aac caa aaa atg ttg aag tta<br>Asn His Ser Trp Leu Lys Ser Asn Ile Asn Gln Lys Met Leu Lys Leu<br>240                   245                   250                   255 | 767 |
| gcc aaa ttg gac ttc aat att ctg caa tgc aaa cat cac aag gag ata<br>Ala Lys Leu Asp Phe Asn Ile Leu Gln Cys Lys His His Lys Glu Ile<br>                    260                   265                   270 | 815 |
| cag ttt att aca agg tgg tgg aga gac tcg ggt ata tcg cag ctg aat<br>Gln Phe Ile Thr Arg Trp Trp Arg Asp Ser Gly Ile Ser Gln Leu Asn<br>         275                   280                   285 | 863 |
| ttc tat cga aag cga cac gtg gaa tat tat tct tgg gtt gtt atg tgc<br>Phe Tyr Arg Lys Arg His Val Glu Tyr Tyr Ser Trp Val Val Met Cys<br>290                       295                         300 | 911 |
| att ttt gag cca gag ttc tct gaa agt aga att gcc ttc gcc aaa act<br>Ile Phe Glu Pro Glu Phe Ser Glu Ser Arg Ile Ala Phe Ala Lys Thr<br>305                       310                   315 | 959 |
| gct atc cta tgt act gtt cta gat gac ctc tat gat acg cac gca acg<br>Ala Ile Leu Cys Thr Val Leu Asp Asp Leu Tyr Asp Thr His Ala Thr<br>320                       325                   330                   335 | 1007 |
| ttg cat gaa atc aaa atc atg aca gag gga gtg aga cga tgg gat ctt<br>Leu His Glu Ile Lys Ile Met Thr Glu Gly Val Arg Arg Trp Asp Leu<br>                    340                   345                   350 | 1055 |
| tcg ttg aca gat gac ctc cca gac tac att aaa att gca ttc cag ttc<br>Ser Leu Thr Asp Asp Leu Pro Asp Tyr Ile Lys Ile Ala Phe Gln Phe<br>         355                   360                   365 | 1103 |
| ttc ttc aat aca gtg aat gaa ttg ata gtt gaa atc gtg aaa cgg caa<br>Phe Phe Asn Thr Val Asn Glu Leu Ile Val Glu Ile Val Lys Arg Gln<br>                    370                   375                   380 | 1151 |
| ggg cgg gat atg aca acc ata gtt aaa gat tgc tgg aag cga tac att<br>Gly Arg Asp Met Thr Thr Ile Val Lys Asp Cys Trp Lys Arg Tyr Ile<br>385                       390                   395 | 1199 |
| gag tct tat ctg caa gaa gcg gaa tgg ata gca act gga cat att ccc<br>Glu Ser Tyr Leu Gln Glu Ala Glu Trp Ile Ala Thr Gly His Ile Pro<br>400                       405                   410                   415 | 1247 |
| act ttt aac gaa tac ata aag aac ggc atg gct agc tca ggg atg tgt<br>Thr Phe Asn Glu Tyr Ile Lys Asn Gly Met Ala Ser Ser Gly Met Cys<br>                    420                   425                   430 | 1295 |
| att gta aat ttg aat cca ctt ctc ttg ttg ggt aaa ctt ctc ccc gac<br>Ile Val Asn Leu Asn Pro Leu Leu Leu Leu Gly Lys Leu Leu Pro Asp<br>         435                   440                   445 | 1343 |
| aac att ctg gag caa ata cat tct cca tcc aag atc ctg gac ctc tta<br>Asn Ile Leu Glu Gln Ile His Ser Pro Ser Lys Ile Leu Asp Leu Leu<br>450                       455                   460 | 1391 |
| gaa ttg acg ggc aga atc gcc gat gac tta aaa gat ttc gag gac gag<br>Glu Leu Thr Gly Arg Ile Ala Asp Asp Leu Lys Asp Phe Glu Asp Glu<br>465                       470                   475 | 1439 |
| aag gaa cgc ggg gag atg gct tca tct tta cag tgt tat atg aaa gaa<br>Lys Glu Arg Gly Glu Met Ala Ser Ser Leu Gln Cys Tyr Met Lys Glu<br>480                       485                   490                   495 | 1487 |
| aat cct gaa tct aca gtg gaa aat gct tta aat cac ata aaa ggc atc<br>Asn Pro Glu Ser Thr Val Glu Asn Ala Leu Asn His Ile Lys Gly Ile<br>                    500                   505                   510 | 1535 |
| ctt aat cgt tcc ctt gag gaa ttt aat tgg gag ttt atg aag cag gat<br>Leu Asn Arg Ser Leu Glu Glu Phe Asn Trp Glu Phe Met Lys Gln Asp<br>         515                   520                   525 | 1583 |
| agt gtc cca atg tgt tgc aag aaa ttc act ttc aat ata ggt cga gga<br>Ser Val Pro Met Cys Cys Lys Lys Phe Thr Phe Asn Ile Gly Arg Gly<br>530                       535                   540 | 1631 |

```
ctt caa ttc atc tac aaa tac aga gac ggc tta tac att tct gac aag      1679
Leu Gln Phe Ile Tyr Lys Tyr Arg Asp Gly Leu Tyr Ile Ser Asp Lys
        545                 550                 555 gaa gta aag gac cag ata ttc aaa att cta gtc cac caa gtt cca atg      1727
Glu Val Lys Asp Gln Ile Phe Lys Ile Leu Val His Gln Val Pro Met
560                 565                 570                 575 gag gaa tag tgatggtctt ggttgtagtt gtctattatg gtatattgca              1776
Glu Glu ttgacattta tgcttaaagg tgtttcttaa acgtttaggg cggaccgtta aataagttgg    1836
caataattaa tatttagaga ctttgtggaa gtgtttaggg cataaaattg cctatggcct    1896
atggcaagct acaaattgaa attgttgtgt ttataatatt tttattttat ttaaaaaaaa    1956
aaaaaaaaaa a                                                         1967
```

<210> SEQ ID NO 18
<211> LENGTH: 577
<212> TYPE: PRT
<213> ORGANISM: Abies grandis

<400> SEQUENCE: 18

```
Ser Glu Ser Ser Ile Pro Arg Arg Thr Gly Asn His His Gly Asn Val
 1               5                  10                  15

Trp Asp Asp Asp Leu Ile His Ser Leu Asn Ser Pro Tyr Gly Ala Pro
             20                  25                  30

Ala Tyr Tyr Glu Leu Leu Gln Lys Leu Ile Glu Ile Lys His Leu
         35                  40                  45

Leu Leu Thr Glu Met Glu Met Asp Asp Gly Asp His Asp Leu Ile Lys
     50                  55                  60

Arg Leu Gln Ile Val Asp Thr Leu Glu Cys Leu Gly Ile Asp Arg His
 65                  70                  75                  80

Phe Glu His Glu Ile Gln Thr Ala Ala Leu Asp Tyr Val Tyr Arg Trp
                 85                  90                  95

Trp Asn Glu Lys Gly Ile Gly Gly Ser Arg Asp Ser Phe Ser Lys
            100                 105                 110

Asp Leu Asn Ala Thr Ala Leu Gly Phe Arg Ala Leu Arg Leu His Arg
        115                 120                 125

Tyr Asn Val Ser Ser Gly Val Leu Lys Asn Phe Lys Asp Glu Asn Gly
    130                 135                 140

Lys Phe Phe Cys Asn Phe Thr Gly Glu Glu Gly Arg Gly Asp Lys Gln
145                 150                 155                 160

Val Arg Ser Met Leu Ser Leu Leu Arg Ala Ser Glu Ile Ser Phe Pro
                165                 170                 175

Gly Glu Lys Val Met Glu Glu Ala Lys Ala Phe Thr Arg Glu Tyr Leu
            180                 185                 190

Asn Gln Val Leu Ala Gly His Gly Asp Val Thr Asp Val Asp Gln Ser
        195                 200                 205

Leu Leu Glu Arg Gly Glu Val Arg Ile Gly Val Ser Met Ala Cys Ser
    210                 215                 220

Val Pro Arg Trp Glu Ala Arg Ser Phe Leu Glu Ile Tyr Gly His Asn
225                 230                 235                 240

His Ser Trp Leu Lys Ser Asn Ile Asn Gln Lys Met Leu Lys Leu Ala
                245                 250                 255

Lys Leu Asp Phe Asn Ile Leu Gln Cys Lys His His Lys Glu Ile Gln
            260                 265                 270
```

```
Phe Ile Thr Arg Trp Trp Arg Asp Ser Gly Ile Ser Gln Leu Asn Phe
            275                 280                 285

Tyr Arg Lys Arg His Val Glu Tyr Tyr Ser Trp Val Met Cys Ile
        290                 295                 300

Phe Glu Pro Glu Phe Ser Glu Ser Arg Ile Ala Phe Ala Lys Thr Ala
305                 310                 315                 320

Ile Leu Cys Thr Val Leu Asp Asp Leu Tyr Asp Thr His Ala Thr Leu
                325                 330                 335

His Glu Ile Lys Ile Met Thr Glu Gly Val Arg Arg Trp Asp Leu Ser
            340                 345                 350

Leu Thr Asp Asp Leu Pro Asp Tyr Ile Lys Ile Ala Phe Gln Phe Phe
        355                 360                 365

Phe Asn Thr Val Asn Glu Leu Ile Val Glu Ile Val Lys Arg Gln Gly
370                 375                 380

Arg Asp Met Thr Thr Ile Val Lys Asp Cys Trp Lys Arg Tyr Ile Glu
385                 390                 395                 400

Ser Tyr Leu Gln Glu Ala Glu Trp Ile Ala Thr Gly His Ile Pro Thr
                405                 410                 415

Phe Asn Glu Tyr Ile Lys Asn Gly Met Ala Ser Gly Met Cys Ile
            420                 425                 430

Val Asn Leu Asn Pro Leu Leu Leu Gly Lys Leu Leu Pro Asp Asn
                435                 440                 445

Ile Leu Glu Gln Ile His Ser Pro Ser Lys Ile Leu Asp Leu Leu Glu
            450                 455                 460

Leu Thr Gly Arg Ile Ala Asp Asp Leu Lys Asp Phe Glu Asp Glu Lys
465                 470                 475                 480

Glu Arg Gly Glu Met Ala Ser Ser Leu Gln Cys Tyr Met Lys Glu Asn
                485                 490                 495

Pro Glu Ser Thr Val Glu Asn Ala Leu Asn His Ile Lys Gly Ile Leu
                500                 505                 510

Asn Arg Ser Leu Glu Glu Phe Asn Trp Glu Phe Met Lys Gln Asp Ser
            515                 520                 525

Val Pro Met Cys Cys Lys Lys Phe Thr Phe Asn Ile Gly Arg Gly Leu
530                 535                 540

Gln Phe Ile Tyr Lys Tyr Arg Asp Gly Leu Tyr Ile Ser Asp Lys Glu
545                 550                 555                 560

Val Lys Asp Gln Ile Phe Lys Ile Leu Val His Gln Val Pro Met Glu
                565                 570                 575

Glu

<210> SEQ ID NO 19
<211> LENGTH: 1416
<212> TYPE: DNA
<213> ORGANISM: Abies grandis
<220> FEATURE:
<221> NAME/KEY: CDS
<222> LOCATION: (3)..(1199)
<223> OTHER INFORMATION: Clone AG5.9

<400> SEQUENCE: 19 aa aaa gtg atg gaa gag gcg aag gca ttc aca aca aat tat cta aag      47
   Lys Val Met Glu Glu Ala Lys Ala Phe Thr Thr Asn Tyr Leu Lys
     1               5                  10                  15 aaa gtt tta gca gga cgg gag gct acc cac gtc gat gaa agc ctt ttg      95
Lys Val Leu Ala Gly Arg Glu Ala Thr His Val Asp Glu Ser Leu Leu
            20                  25                  30
```

| | | |
|---|---|---|
| gga gag gtg aag tac gca ttg gag ttt cca tgg cat tgc agt gtg cag<br>Gly Glu Val Lys Tyr Ala Leu Glu Phe Pro Trp His Cys Ser Val Gln<br>35                          40                       45 | | 143 |

```
gga gag gtg aag tac gca ttg gag ttt cca tgg cat tgc agt gtg cag        143
Gly Glu Val Lys Tyr Ala Leu Glu Phe Pro Trp His Cys Ser Val Gln
         35                  40                  45 aga tgg gag gca agg agc ttt atc gaa ata ttt gga caa att gat tca        191
Arg Trp Glu Ala Arg Ser Phe Ile Glu Ile Phe Gly Gln Ile Asp Ser
     50                  55                  60 gag ctt aag tcg aat ttg agc aaa aaa atg tta gag ttg gcg aaa ttg        239
Glu Leu Lys Ser Asn Leu Ser Lys Lys Met Leu Glu Leu Ala Lys Leu
 65                  70                  75 gac ttc aat att ctg caa tgc aca cat cag aaa gaa ctg cag att atc        287
Asp Phe Asn Ile Leu Gln Cys Thr His Gln Lys Glu Leu Gln Ile Ile
 80                  85                  90                  95 tca agg tgg ttc gca gac tca agt ata gca tcc ctg aat ttc tat cgg        335
Ser Arg Trp Phe Ala Asp Ser Ser Ile Ala Ser Leu Asn Phe Tyr Arg
                100                 105                 110 aaa tgt tac gtc gaa ttt tac ttt tgg atg gct gca gcc atc tcc gag        383
Lys Cys Tyr Val Glu Phe Tyr Phe Trp Met Ala Ala Ala Ile Ser Glu
            115                 120                 125 ccg gag ttt tct gga agc aga gtt gcc ttc aca aaa att gct ata ctg        431
Pro Glu Phe Ser Gly Ser Arg Val Ala Phe Thr Lys Ile Ala Ile Leu
        130                 135                 140 atg aca atg cta gat gac ctg tac gat act cac gga acc ttg gac caa        479
Met Thr Met Leu Asp Asp Leu Tyr Asp Thr His Gly Thr Leu Asp Gln
    145                 150                 155 ctc aaa atc ttt aca gag gga gtg aga cga tgg gat gtt tcg ttg gta        527
Leu Lys Ile Phe Thr Glu Gly Val Arg Arg Trp Asp Val Ser Leu Val
160                 165                 170                 175 gag ggc ctc cca gac ttc atg aaa att gca ttc gag ttc tgg tta aag        575
Glu Gly Leu Pro Asp Phe Met Lys Ile Ala Phe Glu Phe Trp Leu Lys
                180                 185                 190 aca tct aat gaa ttg att gct gaa gct gtt aaa gcg caa ggg caa gat        623
Thr Ser Asn Glu Leu Ile Ala Glu Ala Val Lys Ala Gln Gly Gln Asp
            195                 200                 205 atg gcg gcc tac ata aga aaa aat gca tgg gag cga tac ctt gaa gct        671
Met Ala Ala Tyr Ile Arg Lys Asn Ala Trp Glu Arg Tyr Leu Glu Ala
        210                 215                 220 tat ctg caa gat gcg gaa tgg ata gcc act gga cat gtc ccc acc ttt        719
Tyr Leu Gln Asp Ala Glu Trp Ile Ala Thr Gly His Val Pro Thr Phe
    225                 230                 235 gat gag tac ttg aat aat ggc aca cca aac act ggg atg tgt gta ttg        767
Asp Glu Tyr Leu Asn Asn Gly Thr Pro Asn Thr Gly Met Cys Val Leu
240                 245                 250                 255 aat ttg att ccg ctt ctg tta atg ggt gaa cat tta cca atc gac att        815
Asn Leu Ile Pro Leu Leu Leu Met Gly Glu His Leu Pro Ile Asp Ile
                260                 265                 270 ctg gag caa ata ttc ttg ccc tcc agg ttc cac cat ctc att gaa ttg        863
Leu Glu Gln Ile Phe Leu Pro Ser Arg Phe His His Leu Ile Glu Leu
            275                 280                 285 gct tcc agg ctc gtc gat gac gcg aga gat ttc cag gcg gag aag gat        911
Ala Ser Arg Leu Val Asp Asp Ala Arg Asp Phe Gln Ala Glu Lys Asp
        290                 295                 300 cat ggg gat tta tcg tgt att gag tgt tat tta aaa gat cat cct gag        959
His Gly Asp Leu Ser Cys Ile Glu Cys Tyr Leu Lys Asp His Pro Glu
    305                 310                 315 tct aca gta gaa gat gct tta aat cat gtt aat ggc ctc ctt ggc aat       1007
Ser Thr Val Glu Asp Ala Leu Asn His Val Asn Gly Leu Leu Gly Asn
320                 325                 330                 335 tgc ctt ctg gaa atg aat tgg aag ttc tta aag aag cag gac agt gtg       1055
Cys Leu Leu Glu Met Asn Trp Lys Phe Leu Lys Lys Gln Asp Ser Val
                340                 345                 350
```

```
cca ctc tcg tgt aag aag tac agc ttc cat gta ttg gca cga agc atc      1103
Pro Leu Ser Cys Lys Lys Tyr Ser Phe His Val Leu Ala Arg Ser Ile
            355                 360                 365 caa ttc atg tac aat caa ggc gat ggc ttc tcc att tcg aac aaa gtg      1151
Gln Phe Met Tyr Asn Gln Gly Asp Gly Phe Ser Ile Ser Asn Lys Val
            370                 375                 380 atc aag gat caa gtg cag aaa gtt ctt att gtc ccc gtg cct att tga      1199
Ile Lys Asp Gln Val Gln Lys Val Leu Ile Val Pro Val Pro Ile
385                 390                 395 tagtagatac tagatagtag attagtagct attagtattt atttcatatc aatatttact    1259
aatgctgatg atggttaaag tccattcaga ccaatctttg gtttattgga cttaaataaa    1319
tgaattaatt agtttgtttt aaaattgtac tatttactgt tggaaataat gttttcatta   1379
ttgaaataac tagcacaact attttagtgt ggttgat                             1416
```

<210> SEQ ID NO 20
<211> LENGTH: 398
<212> TYPE: PRT
<213> ORGANISM: Abies grandis

<400> SEQUENCE: 20

```
Lys Val Met Glu Glu Ala Lys Ala Phe Thr Thr Asn Tyr Leu Lys Lys
  1               5                  10                  15

Val Leu Ala Gly Arg Glu Ala Thr His Val Asp Glu Ser Leu Leu Gly
             20                  25                  30

Glu Val Lys Tyr Ala Leu Glu Phe Pro Trp His Cys Ser Val Gln Arg
         35                  40                  45

Trp Glu Ala Arg Ser Phe Ile Glu Ile Phe Gly Gln Ile Asp Ser Glu
     50                  55                  60

Leu Lys Ser Asn Leu Ser Lys Lys Met Leu Glu Leu Ala Lys Leu Asp
 65                  70                  75                  80

Phe Asn Ile Leu Gln Cys Thr His Gln Lys Glu Leu Gln Ile Ile Ser
                 85                  90                  95

Arg Trp Phe Ala Asp Ser Ser Ile Ala Ser Leu Asn Phe Tyr Arg Lys
            100                 105                 110

Cys Tyr Val Glu Phe Tyr Phe Trp Met Ala Ala Ala Ile Ser Glu Pro
        115                 120                 125

Glu Phe Ser Gly Ser Arg Val Ala Phe Thr Lys Ile Ala Ile Leu Met
    130                 135                 140

Thr Met Leu Asp Asp Leu Tyr Asp Thr His Gly Thr Leu Asp Gln Leu
145                 150                 155                 160

Lys Ile Phe Thr Glu Gly Val Arg Arg Trp Asp Val Ser Leu Val Glu
                165                 170                 175

Gly Leu Pro Asp Phe Met Lys Ile Ala Phe Glu Phe Trp Leu Lys Thr
            180                 185                 190

Ser Asn Glu Leu Ile Ala Glu Ala Val Lys Ala Gln Gly Gln Asp Met
        195                 200                 205

Ala Ala Tyr Ile Arg Lys Asn Ala Trp Glu Arg Tyr Leu Glu Ala Tyr
    210                 215                 220

Leu Gln Asp Ala Glu Trp Ile Ala Thr Gly His Val Pro Thr Phe Asp
225                 230                 235                 240

Glu Tyr Leu Asn Asn Gly Thr Pro Asn Thr Gly Met Cys Val Leu Asn
                245                 250                 255

Leu Ile Pro Leu Leu Leu Met Gly Glu His Leu Pro Ile Asp Ile Leu
            260                 265                 270
```

```
Glu Gln Ile Phe Leu Pro Ser Arg Phe His His Leu Ile Glu Leu Ala
        275                 280                 285

Ser Arg Leu Val Asp Asp Ala Arg Asp Phe Gln Ala Glu Lys Asp His
        290                 295                 300

Gly Asp Leu Ser Cys Ile Glu Cys Tyr Leu Lys Asp His Pro Glu Ser
305                 310                 315                 320

Thr Val Glu Asp Ala Leu Asn His Val Asn Gly Leu Leu Gly Asn Cys
                325                 330                 335

Leu Leu Glu Met Asn Trp Lys Phe Leu Lys Gln Asp Ser Val Pro
            340                 345                 350

Leu Ser Cys Lys Lys Tyr Ser Phe His Val Leu Ala Arg Ser Ile Gln
        355                 360                 365

Phe Met Tyr Asn Gln Gly Asp Gly Phe Ser Ile Ser Asn Lys Val Ile
        370                 375                 380

Lys Asp Gln Val Gln Lys Val Leu Ile Val Pro Val Pro Ile
385                 390                 395
```

```
<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:
      oligonucleotide PCR primer E  wherein the letter
      "n" represents an inosine residue
<220> FEATURE:
<221> NAME/KEY: misc_feature
<222> LOCATION: (1)..(23)
<223> OTHER INFORMATION: PCR primer E wherein the letter n represents
      inosine

<400> SEQUENCE: 21
ggngaramrr tnatggarga rgc                                             23

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: degenerate
      oligonucleotide primer F  wherein the letter "n"
      represents an inosine residue
<220> FEATURE:
<221> NAME/KEY: misc_feature
<222> LOCATION: (1)..(24)
<223> OTHER INFORMATION: PCR primer F wherein the letter n represents
      inosine

<400> SEQUENCE: 22
garytncary tnhbnmgntg gtgg                                            24

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: degenerate
      oligonucleotide PCR primer G  wherein the letter
      "n" represents an inosine residue
<220> FEATURE:
<221> NAME/KEY: misc_feature
<222> LOCATION: (1)..(21)
<223> OTHER INFORMATION: PCR primer G wherein the letter n represents
      inosine

<400> SEQUENCE: 23
```

```
ccarttnarn ccyttnacrt c                                               21
```

<210> SEQ ID NO 24
<211> LENGTH: 533
<212> TYPE: DNA
<213> ORGANISM: Abies grandis

<400> SEQUENCE: 24

```
gggaaaaaa  tgatggagga  agctgaaatc  ttctctacca  aatatttaaa  agaagccctg    60
caaaagattc  cggtctccag  tctttcgcga  gagatcgggg  acgttttgga  atatggttgg   120
cacacatatt  tgccgcgatt  ggaagcaagg  aattacatcc  aagtctttgg  acaggacact   180
gagaacacga  agtcatatgt  gaagagcaaa  aaacttttag  aactcgcaaa  attggagttc   240
aacatctttc  aatccttact  cgcatatccg  cattgcaacc  cattctgaca  atggacatcc   300
cctttcctga  tcatatcctc  aaggaagttg  acttcccatc  aaagcttaac  gacttggcat   360
gtgccatcct  tcgattacga  ggtgatacgc  ggtgctacaa  ggcggacagg  gctcgtggag   420
aagaagcttc  ctctatatca  tgttatatga  aagacaatcc  tggagtatca  gaggaagatg   480
ctctcgatca  tatcaacgcc  atgatcagtg  acgaagtcaa  aggcttcaat  tgg          533
```

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: conserved
      amino acid motif on which the sequence of Primer D
      was based, wherein Xaa at position number 3 represents Thr or
      Ile, Xaa at position number 4 represents Ile or Tyr or Phe, Xaa
      at position number 6 represents Ala or Val and Xaa at position
      number 8 represents Ala or Gly
<220> FEATURE:
<221> NAME/KEY: SITE
<222> LOCATION: (1)..(8)
<223> OTHER INFORMATION: conserved amino acid motif on which sequence of
      primer D was based

<400> SEQUENCE: 25

Asp Asp Xaa Xaa Asp Xaa Tyr Xaa
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: conserved
      amino acid motif on which the sequence of Primer E
      was based wherein Xaa at position 3 represents Lys or Thr, Xaa
      at position 4 represents Val or Ile, Xaa at position 6 represents
      Glu or Asp
<220> FEATURE:
<221> NAME/KEY: SITE
<222> LOCATION: (1)..(8)
<223> OTHER INFORMATION: conserved amino acid sequence on which the
      sequence of primer E was based

<400> SEQUENCE: 26

Gly Glu Xaa Xaa Met Xaa Glu Ala
 1               5

<210> SEQ ID NO 27
<211> LENGTH: 7
<212> TYPE: PRT
<213> ORGANISM: Artificial Sequence -continued

```
<220> FEATURE:
<223> OTHER INFORMATION: Description of Artificial Sequence: conserved
      amino acid sequence on which the sequence of primer F was based
      wherein Xaa at position 2 represents Phe or Tyr or Asp Xaa at
      position 3 represents Ile or Leu, Xaa at position 4 represents
      Thr or or Arg
<220> FEATURE:
<221> NAME/KEY: SITE
<222> LOCATION: (1)..(7)
<223> OTHER INFORMATION: conserved amino acid sequence on which the
      sequence of primer F was based

<400> SEQUENCE: 27

Gln Xaa Xaa Xaa Arg Trp Trp
  1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: conserved
      amino acid motif on which the sequence of primer G
      was based wherein Xaa at position 6 represents Phe or Leu
<220> FEATURE:
<221> NAME/KEY: SITE
<222> LOCATION: (1)..(8)
<223> OTHER INFORMATION: conserved amino acid sequence on which the
      sequence of primer G was based

<400> SEQUENCE: 28

Asp Val Ile Lys Gly Xaa Asn Trp
  1               5

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: T3 primer
      oligonucleotide sequence

<400> SEQUENCE: 29
aattaaccct cactaaaggg                                                 20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: T7
      oligonucleotide primer sequence

<400> SEQUENCE: 30
gtaatacgac tcactatagg gc                                              22

<210> SEQ ID NO 31
<211> LENGTH: 2205
<212> TYPE: DNA
<213> ORGANISM: Abies grandis
<220> FEATURE:
<221> NAME/KEY: CDS
<222> LOCATION: (57)..(1943)
<223> OTHER INFORMATION: Clone AG3.48

<400> SEQUENCE: 31
gttatcttga gcttcctcca tataggccaa cacatatcat atcaaaggga gcaaga atg    59
                                                              Met
                                                                1
```

-continued

| | |
|---|---|
| gct ctg gtt tct atc tca ccg ttg gct tcg aaa tct tgc ctg cgc aag<br>Ala Leu Val Ser Ile Ser Pro Leu Ala Ser Lys Ser Cys Leu Arg Lys<br>       5                 10                15 | 107 |
| tcg ttg atc agt tca att cat gaa cat aag cct ccc tat aga aca atc<br>Ser Leu Ile Ser Ser Ile His Glu His Lys Pro Pro Tyr Arg Thr Ile<br>        20                25              30 | 155 |
| cca aat ctt gga atg cgt agg cga ggg aaa tct gtc acg cct tcc atg<br>Pro Asn Leu Gly Met Arg Arg Arg Gly Lys Ser Val Thr Pro Ser Met<br>35                     40                45 | 203 |
| agc atc agt ttg gcc acc gct gca cct gat gat ggt gta caa aga cgc<br>Ser Ile Ser Leu Ala Thr Ala Ala Pro Asp Asp Gly Val Gln Arg Arg<br>50                 55               60              65 | 251 |
| ata ggt gac tac cat tcc aat atc tgg gac gat gat ttc ata cag tct<br>Ile Gly Asp Tyr His Ser Asn Ile Trp Asp Asp Asp Phe Ile Gln Ser<br>              70                75              80 | 299 |
| cta tca acg cat tat ggg gaa ccc tct tac cag gaa cgt gct gag aga<br>Leu Ser Thr His Tyr Gly Glu Pro Ser Tyr Gln Glu Arg Ala Glu Arg<br>               85                90              95 | 347 |
| tta att gtg gag gta aag aag ata ttc aat tca atg tac ctg gat gat<br>Leu Ile Val Glu Val Lys Lys Ile Phe Asn Ser Met Tyr Leu Asp Asp<br>       100                105              110 | 395 |
| gga aga tta atg agt tcc ttt aat gat ctc atg caa cgc ctt tgg ata<br>Gly Arg Leu Met Ser Ser Phe Asn Asp Leu Met Gln Arg Leu Trp Ile<br>115                   120              125 | 443 |
| gtc gat agc gtt gaa cgt ttg ggg ata gct aga cat ttc aag aac gag<br>Val Asp Ser Val Glu Arg Leu Gly Ile Ala Arg His Phe Lys Asn Glu<br>130                135              140              145 | 491 |
| ata aca tca gct ctg gat tat gtt ttc cgt tac tgg gag gaa aac ggc<br>Ile Thr Ser Ala Leu Asp Tyr Val Phe Arg Tyr Trp Glu Glu Asn Gly<br>               150              155              160 | 539 |
| att gga tgt ggg aga gac agt att gtt act gat ctc aac tca act gcg<br>Ile Gly Cys Gly Arg Asp Ser Ile Val Thr Asp Leu Asn Ser Thr Ala<br>             165              170              175 | 587 |
| ttg ggg ttt cga act ctt cga tta cac ggg tac act gta tct cca gag<br>Leu Gly Phe Arg Thr Leu Arg Leu His Gly Tyr Thr Val Ser Pro Glu<br>180                   185              190 | 635 |
| gtt tta aaa gct ttt caa gat caa aat gga cag ttt gta tgc tcc ccc<br>Val Leu Lys Ala Phe Gln Asp Gln Asn Gly Gln Phe Val Cys Ser Pro<br>       195                200              205 | 683 |
| ggt cag aca gag ggt gag atc aga agc gtt ctt aac tta tat cgg gct<br>Gly Gln Thr Glu Gly Glu Ile Arg Ser Val Leu Asn Leu Tyr Arg Ala<br>210                   215              220              225 | 731 |
| tcc ctc att gcc ttc cct ggt gag aaa gtt atg gaa gaa gct gaa atc<br>Ser Leu Ile Ala Phe Pro Gly Glu Lys Val Met Glu Glu Ala Glu Ile<br>               230              235              240 | 779 |
| ttc tcc aca aga tat ttg aaa gaa gct cta caa aag att cca gtc tcc<br>Phe Ser Thr Arg Tyr Leu Lys Glu Ala Leu Gln Lys Ile Pro Val Ser<br>             245              250              255 | 827 |
| gct ctt tca caa gag ata aag ttt gtt atg gaa tat ggc tgg cac aca<br>Ala Leu Ser Gln Glu Ile Lys Phe Val Met Glu Tyr Gly Trp His Thr<br>260                   265              270 | 875 |
| aat ttg cca aga ttg gaa gca aga aat tac ata gac aca ctt gag aaa<br>Asn Leu Pro Arg Leu Glu Ala Arg Asn Tyr Ile Asp Thr Leu Glu Lys<br>       275                280              285 | 923 |
| gac acc agt gca tgg ctc aat aaa aat gct ggg aag aag ctt tta gaa<br>Asp Thr Ser Ala Trp Leu Asn Lys Asn Ala Gly Lys Lys Leu Leu Glu<br>290                   295              300              305 | 971 |
| ctt gca aaa ttg gag ttc aat ata ttt aac tcc tta caa caa aag gaa<br>Leu Ala Lys Leu Glu Phe Asn Ile Phe Asn Ser Leu Gln Gln Lys Glu<br>             310              315              320 | 1019 |

```
                                                     -continued tta caa tat ctt ttg aga tgg tgg aaa gag tcg gat ttg cct aaa ttg    1067
Leu Gln Tyr Leu Leu Arg Trp Trp Lys Glu Ser Asp Leu Pro Lys Leu
            325                 330                 335 aca ttt gct cgg cat cgt cat gtg gaa ttc tac act ttg gcc tct tgt    1115
Thr Phe Ala Arg His Arg His Val Glu Phe Tyr Thr Leu Ala Ser Cys
        340                 345                 350 att gcc att gac cca aaa cat tct gca ttc aga cta ggc ttc gcc aaa    1163
Ile Ala Ile Asp Pro Lys His Ser Ala Phe Arg Leu Gly Phe Ala Lys
    355                 360                 365 atg tgt cat ctt gtc aca gtt ttg gac gat att tac gac act ttt gga    1211
Met Cys His Leu Val Thr Val Leu Asp Asp Ile Tyr Asp Thr Phe Gly
370                 375                 380                 385 acg att gac gag ctt gaa ctc ttc aca tct gca att aag aga tgg aat    1259
Thr Ile Asp Glu Leu Glu Leu Phe Thr Ser Ala Ile Lys Arg Trp Asn
                390                 395                 400 tca tca gag ata gaa cac ctt cca gaa tat atg aaa tgt gtg tac atg    1307
Ser Ser Glu Ile Glu His Leu Pro Glu Tyr Met Lys Cys Val Tyr Met
            405                 410                 415 gtc gtg ttt gaa act gta aat gaa ctg aca cga gag gcg gag aag act    1355
Val Val Phe Glu Thr Val Asn Glu Leu Thr Arg Glu Ala Glu Lys Thr
        420                 425                 430 caa ggg aga aac act ctc aac tat gtt cga aag gct tgg gag gct tat    1403
Gln Gly Arg Asn Thr Leu Asn Tyr Val Arg Lys Ala Trp Glu Ala Tyr
    435                 440                 445 ttt gat tca tat atg gaa gaa gca aaa tgg atc tct aat ggt tat ctg    1451
Phe Asp Ser Tyr Met Glu Glu Ala Lys Trp Ile Ser Asn Gly Tyr Leu
450                 455                 460                 465 cca acg ttt gaa gag tac cat gag aat ggg aaa gtg agc tct gca tat    1499
Pro Thr Phe Glu Glu Tyr His Glu Asn Gly Lys Val Ser Ser Ala Tyr
                470                 475                 480 cgc gta gca aca ttg caa ccc atc ctc act ttg aat gca tgg ctt cct    1547
Arg Val Ala Thr Leu Gln Pro Ile Leu Thr Leu Asn Ala Trp Leu Pro
            485                 490                 495 gat tac atc ttg aag gga att gat ttt cca tcc agg ttc aat gat ttg    1595
Asp Tyr Ile Leu Lys Gly Ile Asp Phe Pro Ser Arg Phe Asn Asp Leu
        500                 505                 510 gca tcg tcc ttc ctt cgg cta cga ggt gac aca cgc tgc tac aag gcc    1643
Ala Ser Ser Phe Leu Arg Leu Arg Gly Asp Thr Arg Cys Tyr Lys Ala
    515                 520                 525 gat agg gat cgt ggt gaa gaa gct tcg tgt ata tca tgt tat atg aaa    1691
Asp Arg Asp Arg Gly Glu Glu Ala Ser Cys Ile Ser Cys Tyr Met Lys
530                 535                 540                 545 gac aat cct gga tca acc gaa gaa gat gcc ctc aat cat atc aat gcc    1739
Asp Asn Pro Gly Ser Thr Glu Glu Asp Ala Leu Asn His Ile Asn Ala
                550                 555                 560 atg gtc aat gac ata atc aaa gaa tta aat tgg gaa ctt cta aga tcc    1787
Met Val Asn Asp Ile Ile Lys Glu Leu Asn Trp Glu Leu Leu Arg Ser
            565                 570                 575 aac gac aat att cca atg ctg gcc aag aaa cat gct ttt gac ata aca    1835
Asn Asp Asn Ile Pro Met Leu Ala Lys Lys His Ala Phe Asp Ile Thr
        580                 585                 590 aga gct ctc cac cat ctc tac ata tat cga gat ggc ttt agt gtt gcc    1883
Arg Ala Leu His His Leu Tyr Ile Tyr Arg Asp Gly Phe Ser Val Ala
    595                 600                 605 aac aag gaa aca aaa aaa ttg gtt atg gaa aca ctc ctt gaa tct atg    1931
Asn Lys Glu Thr Lys Lys Leu Val Met Glu Thr Leu Leu Glu Ser Met
610                 615                 620                 625 ctt ttt taa cta taaccatatc cataataata agctcataat gctaaattat        1983
Leu Phe
```

-continued

```
tggccttatg acatagttta tgtatgtact tgtgtgaatt caatcatatc gtgtgggtat    2043
gattaaaaag ctagagctta ctaggttagt aacatggtga taaaagttat aaaatgtgag    2103
ttatagagat acccatgttg aataatgaat tacaaaaaga gaaatttatg tagaataaga    2163
ttggaagctt ttcaattgtt ttaaaaaaaa aaaaaaaaa aa                         2205
```

<210> SEQ ID NO 32
<211> LENGTH: 627
<212> TYPE: PRT
<213> ORGANISM: Abies grandis

<400> SEQUENCE: 32

```
Met Ala Leu Val Ser Ile Ser Pro Leu Ala Ser Lys Ser Cys Leu Arg
 1               5                  10                  15

Lys Ser Leu Ile Ser Ser Ile His Glu His Lys Pro Pro Tyr Arg Thr
                20                  25                  30

Ile Pro Asn Leu Gly Met Arg Arg Gly Lys Ser Val Thr Pro Ser
            35                  40                  45

Met Ser Ile Ser Leu Ala Thr Ala Ala Pro Asp Asp Gly Val Gln Arg
 50                  55                  60

Arg Ile Gly Asp Tyr His Ser Asn Ile Trp Asp Asp Phe Ile Gln
 65                  70                  75                  80

Ser Leu Ser Thr His Tyr Gly Glu Pro Ser Tyr Gln Glu Arg Ala Glu
                85                  90                  95

Arg Leu Ile Val Glu Val Lys Lys Ile Phe Asn Ser Met Tyr Leu Asp
                100                 105                 110

Asp Gly Arg Leu Met Ser Ser Phe Asn Asp Leu Met Gln Arg Leu Trp
            115                 120                 125

Ile Val Asp Ser Val Glu Arg Leu Gly Ile Ala Arg His Phe Lys Asn
130                 135                 140

Glu Ile Thr Ser Ala Leu Asp Tyr Val Phe Arg Tyr Trp Glu Glu Asn
145                 150                 155                 160

Gly Ile Gly Cys Gly Arg Asp Ser Ile Val Thr Asp Leu Asn Ser Thr
                165                 170                 175

Ala Leu Gly Phe Arg Thr Leu Arg Leu His Gly Tyr Thr Val Ser Pro
            180                 185                 190

Glu Val Leu Lys Ala Phe Gln Asp Gln Asn Gly Gln Phe Val Cys Ser
        195                 200                 205

Pro Gly Gln Thr Glu Gly Glu Ile Arg Ser Val Leu Asn Leu Tyr Arg
210                 215                 220

Ala Ser Leu Ile Ala Phe Pro Gly Glu Lys Val Met Glu Glu Ala Glu
225                 230                 235                 240

Ile Phe Ser Thr Arg Tyr Leu Lys Glu Ala Leu Gln Lys Ile Pro Val
                245                 250                 255

Ser Ala Leu Ser Gln Glu Ile Lys Phe Val Met Glu Tyr Gly Trp His
            260                 265                 270

Thr Asn Leu Pro Arg Leu Glu Ala Arg Asn Tyr Ile Asp Thr Leu Glu
        275                 280                 285

Lys Asp Thr Ser Ala Trp Leu Asn Lys Asn Ala Gly Lys Lys Leu Leu
290                 295                 300

Glu Leu Ala Lys Leu Glu Phe Asn Ile Phe Asn Ser Leu Gln Gln Lys
305                 310                 315                 320

Glu Leu Gln Tyr Leu Leu Arg Trp Trp Lys Glu Ser Asp Leu Pro Lys
                325                 330                 335
```

-continued

```
Leu Thr Phe Ala Arg His Arg His Val Glu Phe Tyr Thr Leu Ala Ser
            340                 345                 350
Cys Ile Ala Ile Asp Pro Lys His Ser Ala Phe Arg Leu Gly Phe Ala
            355                 360                 365
Lys Met Cys His Leu Val Thr Val Leu Asp Asp Ile Tyr Asp Thr Phe
370                 375                 380
Gly Thr Ile Asp Glu Leu Glu Leu Phe Thr Ser Ala Ile Lys Arg Trp
385                 390                 395                 400
Asn Ser Ser Glu Ile Glu His Leu Pro Glu Tyr Met Lys Cys Val Tyr
                405                 410                 415
Met Val Val Phe Glu Thr Val Asn Glu Leu Thr Arg Glu Ala Glu Lys
            420                 425                 430
Thr Gln Gly Arg Asn Thr Leu Asn Tyr Val Arg Lys Ala Trp Glu Ala
            435                 440                 445
Tyr Phe Asp Ser Tyr Met Glu Glu Ala Lys Trp Ile Ser Asn Gly Tyr
            450                 455                 460
Leu Pro Thr Phe Glu Glu Tyr His Glu Asn Gly Lys Val Ser Ser Ala
465                 470                 475                 480
Tyr Arg Val Ala Thr Leu Gln Pro Ile Leu Thr Leu Asn Ala Trp Leu
                485                 490                 495
Pro Asp Tyr Ile Leu Lys Gly Ile Asp Phe Pro Ser Arg Phe Asn Asp
                500                 505                 510
Leu Ala Ser Ser Phe Leu Arg Leu Arg Gly Asp Thr Arg Cys Tyr Lys
            515                 520                 525
Ala Asp Arg Asp Arg Gly Glu Glu Ala Ser Cys Ile Ser Cys Tyr Met
530                 535                 540
Lys Asp Asn Pro Gly Ser Thr Glu Glu Asp Ala Leu Asn His Ile Asn
545                 550                 555                 560
Ala Met Val Asn Asp Ile Ile Lys Glu Leu Asn Trp Glu Leu Leu Arg
                565                 570                 575
Ser Asn Asp Asn Ile Pro Met Leu Ala Lys Lys His Ala Phe Asp Ile
            580                 585                 590
Thr Arg Ala Leu His His Leu Tyr Ile Tyr Arg Asp Gly Phe Ser Val
            595                 600                 605
Ala Asn Lys Glu Thr Lys Lys Leu Val Met Glu Thr Leu Leu Glu Ser
610                 615                 620
Met Leu Phe
625

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: PCR
      oligonucleotide primer 2.2 BamHI

<400> SEQUENCE: 33
caaagggatc cagaatggct ctgg                                        24

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: PCR
      oligonucleotide primer 2.2 Not I
```

```
<400> SEQUENCE: 34
agtaagcggc cgcttttaa tcatacccac                              30

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: PCR
      oligonucleotide primer 3.18 EcoRI

<400> SEQUENCE: 35
ctgcaggaat tcggcacgag c                                      21

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: PCR
      oligonucleotide primer 3.18 SmaI

<400> SEQUENCE: 36
catagccccg ggcatagatt tgagctg                                27

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: PCR
      oligonucleotide primer 10 NdeI

<400> SEQUENCE: 37
ggcaggaaca tatggctctc ctttctatcg                             30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: PCR
      oligonucleotide primer 10 BamHI

<400> SEQUENCE: 38
tctagaacta gtggatcccc cgggctgcag                             30

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: PCR
      oligonucleotide primer JB29

<400> SEQUENCE: 39
ctaccattcc aatatctg                                          18

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: PCR
      oligonucleotide primer 2-8
```

```
<400> SEQUENCE: 40
gttggatctt agaagttccc                                                    20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: PCR
      oligonucleotide primer 3-9

<400> SEQUENCE: 41
tttccattcc aacctctggg                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: PCR
      oligonucleotide primer 3-11

<400> SEQUENCE: 42
cgtaatggaa agctctggcg                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: PCR
      oligonucleotide primer 7-1

<400> SEQUENCE: 43
ccttacacgc ctttggatgg                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: PCR
      oligonucleotide sequence 7-3

<400> SEQUENCE: 44
tctgttgatc caggatggtc                                                    20

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: conserved
      amino acid motif common to all prenyl transferases wherein Xaa
      at position 3 and 4 represents any amino acid

<400> SEQUENCE: 45

Asp Asp Xaa Xaa Asp
  1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: amino acid
      motif from which oligonucleotide primers can be
```

```
        synthesized that hybridize to the monoterpene
        synthases of the present invention, wherein Xaa at position 4
        represents Leu or Ile or Val

<400> SEQUENCE: 46

His Ser Asn Xaa Trp Asp Asp Asp
  1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: amino acid
        motif from which degenerate oligonucleotides can
        be constructed that hybridize to the monoterpene
        synthases of the present invention

<400> SEQUENCE: 47

Ala Leu Asp Tyr Val Tyr
  1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: amino acid
        motif from which degenerate oligonucleotide
        sequences can be constructed that hybridize to the
        monoterpene synthases of the present invention

<400> SEQUENCE: 48

Glu Leu Ala Lys Leu Glu Phe
  1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: amino acid
        motif from which degenerate oligonucleotide
        sequences can be constructed that hybridize to
        monoterpene synthase clones of the present
        invention

<400> SEQUENCE: 49

Arg Trp Trp Lys Glu Ser
  1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: amino acid
        motif from which oligonucleotide sequences can be
        constructed that hybridize to monoterpene synthase
        clones of the present invention, wherein Xaa at position 1
        represents Val or Ile or Leu

<400> SEQUENCE: 50

Xaa Leu Asp Asp Met Tyr Asp
  1               5

<210> SEQ ID NO 51
<211> LENGTH: 7
<212> TYPE: PRT
```

```
<213> ORGANISM: Artificial Sequence
<220> FEATURE:
<223> OTHER INFORMATION: Description of Artificial Sequence: amino acid
      motif from which oligonucleotide sequences can be
      constructed that hybridize to monoterpene synthase
      clones of the present invention wherein Xaa at position 1
      reperesents Val or Ile or Leu

<400> SEQUENCE: 51

Xaa Leu Asp Asp Leu Tyr Asp
  1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: amino acid
      motif from which oligonucleotide sequences can be
      constructed that hybridize to the monoterpene
      synthase clones of the present invention, wherein Xaa at
      position 1 represents Val or Ile or Leu

<400> SEQUENCE: 52

Xaa Leu Asp Asp Ile Tyr Asp
  1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: amino
      acid motif from which oligonucleotide sequences can be
      constructed that hybridize to the monoterpene
      synthase clones of the present invention, wherein Xaa at
      position 6 represents Asn or His

<400> SEQUENCE: 53

Cys Tyr Met Lys Asp Xaa Pro
  1               5

<210> SEQ ID NO 54
<211> LENGTH: 9
<212> TYPE: DNA
<213> ORGANISM: Artificial Sequence
<220> FEATURE:
<223> OTHER INFORMATION: Description of Artificial Sequence: exemplary
      oligonucleotide that corresponds to peptide
      sequence MetMetMet

<400> SEQUENCE: 54 atgatgatg                                                              9

<210> SEQ ID NO 55
<211> LENGTH: 9
<212> TYPE: DNA
<213> ORGANISM: Artificial Sequence
<220> FEATURE:
<223> OTHER INFORMATION: Description of Artificial Sequence: exemplary
      oligonucleotide sequence that corresponds to
      peptide sequence MetMetMet

<400> SEQUENCE: 55 tactactac                                                              9

<210> SEQ ID NO 56
<211> LENGTH: 9
<212> TYPE: DNA
```

```
<213> ORGANISM: Artificial Sequence
<220> FEATURE:
<223> OTHER INFORMATION: Description of Artificial Sequence: exemplary
      oligonucleotide that corresponds to peptide
      sequence MetMetMet, n is inosine

<400> SEQUENCE: 56 nacnacnac                                                              9

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence:
      oligonucleotide corresponding to amino acid
      sequence set forth in SEQ ID NO:46
<220> FEATURE:
<221> NAME/KEY: misc_feature
<222> LOCATION: (1)..(24)
<223> OTHER INFORMATION: Oligonucleotide that corresponds to the
      conserved amino acid sequence set forth in SEQ ID NO:46

<400> SEQUENCE: 57
gtgtcgttgg agaccctgct gctg                                            24

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence:
      oligonucleotide sequence corresponding to amino
      acid sequence set forth in SEQ ID NO:47
<220> FEATURE:
<221> NAME/KEY: misc_feature
<222> LOCATION: (1)..(18)
<223> OTHER INFORMATION: Oligonucleotide corresponding to amino acid
      sequence set forth in SEQ ID NO:47

<400> SEQUENCE: 58
cgggagctga tgcagatg                                                   18

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence:
      oligonucleotide that corresponds to amino acid
      sequence set forth in SEQ ID NO:48
<220> FEATURE:
<221> NAME/KEY: misc_feature
<222> LOCATION: (1)..(21)
<223> OTHER INFORMATION: Oligonucleotide that corresponds to conserved
      amino acid sequence set forth in SEQ ID NO:48

<400> SEQUENCE: 59
ctcgagcggt tcgagctcaa g                                               21

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence:
      oligonucleotide that corresponds to amino acid
      sequence set forth in SEQ ID NO:49
<220> FEATURE:
<221> NAME/KEY: misc_feature
<222> LOCATION: (1)..(18)
```

<223> OTHER INFORMATION: Oligonucleotide that corresponds to conserved
     amino acid sequence set forth in SEQ ID NO:49

<400> SEQUENCE: 60
gccaccacct tcctctcg                                                      18

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence:
     oligonucleotide sequence corresponding to amino
     acid sequence set forth in SEQ ID NO:50
<220> FEATURE:
<221> NAME/KEY: misc_feature
<222> LOCATION: (1)..(21)
<223> OTHER INFORMATION: Oligonucleotide sequence corresponding to amino
     acid sequence set forth in SEQ ID NO:50

<400> SEQUENCE: 61
gaggagctgc tgtacatgct g                                                  21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence:
     oligonucleotide corresponding to amino acid
     sequence set forth in SEQ ID NO:51
<220> FEATURE:
<221> NAME/KEY: misc_feature
<222> LOCATION: (1)..(21)
<223> OTHER INFORMATION: Oligonucleotide corresponding to conserved
     amino acid sequence set forth in SEQ ID NO:51

<400> SEQUENCE: 62
gaggagctgc tggagatgct g                                                  21

<210> SEQ ID NO 63
<211> LENGTH: 293
<212> TYPE: DNA
<213> ORGANISM: Abies grandis

<400> SEQUENCE: 63
cttaatgaat tggcgcaaga ggctgagaag actcaaggca gagatacgct caactatatt        60
cgcaatgctt atgagtctca tttgattcg tttatgcacg aagcaaaatg gatctcaagt        120
ggttatctcc caacgtttga ggagtacttg aagaatggga agttagttc cggttctcgc        180 acagccactt tacaacccat actcaccttg gatgtaccac ttcctaatta catactgcaa        240
gaaattgatt atccatctag gttcaatgac ttggcttcgt ccctccttcg cta              293

<210> SEQ ID NO 64
<211> LENGTH: 2013
<212> TYPE: DNA
<213> ORGANISM: Abies grandis
<220> FEATURE:
<221> NAME/KEY: CDS
<222> LOCATION: (36)..(1889)

<400> SEQUENCE: 64
ttttgacgtg ccttcttatc tgatagcaag ctgaa atg gct ctt ctt tct att           53
                                      Met Ala Leu Leu Ser Ile
                                        1               5 act ccg ctg gtt tcc agg tcg tgc ctc agt tct tct cat gag att aag         101

```
Thr Pro Leu Val Ser Arg Ser Cys Leu Ser Ser His Glu Ile Lys
            10                  15                  20 gct ctc cgt aga aca atc cca act ctt gga atc tgc agg ccg ggg aaa      149
Ala Leu Arg Arg Thr Ile Pro Thr Leu Gly Ile Cys Arg Pro Gly Lys
            25                  30                  35 tcc gtc gcg cat tcc ata aac atg tgt ttg aca agc gtc gca tct act      197
Ser Val Ala His Ser Ile Asn Met Cys Leu Thr Ser Val Ala Ser Thr
        40                  45                  50 gat tct gta cag aga cgc gtg ggc aac tat cat tcc aac ctg tgg gac      245
Asp Ser Val Gln Arg Arg Val Gly Asn Tyr His Ser Asn Leu Trp Asp
 55                  60                  65                  70 gat gat ttc ata cag tct ctg atc tca acg cct tat gga gca cct gat      293
Asp Asp Phe Ile Gln Ser Leu Ile Ser Thr Pro Tyr Gly Ala Pro Asp
                75                  80                  85 tac cgg gaa cgt gct gac aga ctt att ggg gaa gta aag gat ata atg      341
Tyr Arg Glu Arg Ala Asp Arg Leu Ile Gly Glu Val Lys Asp Ile Met
            90                  95                 100 ttc aat ttc aag tcg ctg gaa gat gga ggc aat gat ctc ctt caa cga      389
Phe Asn Phe Lys Ser Leu Glu Asp Gly Gly Asn Asp Leu Leu Gln Arg
            105                 110                 115 ctt ttg ctg gtc gat gac gtt gaa cgt ttg gga atc gac agg cat ttc      437
Leu Leu Leu Val Asp Asp Val Glu Arg Leu Gly Ile Asp Arg His Phe
        120                 125                 130 aaa aaa gag ata aaa acg gca ctc gat tat gtt aac agt tat tgg aac      485
Lys Lys Glu Ile Lys Thr Ala Leu Asp Tyr Val Asn Ser Tyr Trp Asn
135                 140                 145                 150 gaa aaa ggc att gga tgt ggg agg gag agt gtt gtg act gac ctc aac      533
Glu Lys Gly Ile Gly Cys Gly Arg Glu Ser Val Val Thr Asp Leu Asn
                155                 160                 165 tca acc gcc ttg ggg ctt cga act ctc cga cta cac gga tac act gtg      581
Ser Thr Ala Leu Gly Leu Arg Thr Leu Arg Leu His Gly Tyr Thr Val
            170                 175                 180 tct tca gat gtt ttg aac gtt ttt aaa gac aaa aat ggg caa ttt tcc      629
Ser Ser Asp Val Leu Asn Val Phe Lys Asp Lys Asn Gly Gln Phe Ser
            185                 190                 195 tcc act gcc aat att cag ata gag gga gag att aga ggc gtt ctc aat      677
Ser Thr Ala Asn Ile Gln Ile Glu Gly Glu Ile Arg Gly Val Leu Asn
    200                 205                 210 tta ttc agg gcc tcc ctc gtc gcc ttt ccc ggc gag aaa gtt atg gat      725
Leu Phe Arg Ala Ser Leu Val Ala Phe Pro Gly Glu Lys Val Met Asp
215                 220                 225                 230 gaa gct gaa aca ttc tct aca aaa tat tta aga gaa gcc ctg caa aag      773
Glu Ala Glu Thr Phe Ser Thr Lys Tyr Leu Arg Glu Ala Leu Gln Lys
                235                 240                 245 att ccg gca tcc agt ata ctt tca cta gag ata cgg gac gtt ctg gaa      821
Ile Pro Ala Ser Ser Ile Leu Ser Leu Glu Ile Arg Asp Val Leu Glu
            250                 255                 260 tat ggt tgg cac acc aat ttg cca cgc ttg gaa gca agg aat tac atg      869
Tyr Gly Trp His Thr Asn Leu Pro Arg Leu Glu Ala Arg Asn Tyr Met
            265                 270                 275 gac gtc ttt gga cag cac act aaa aat aag aac gcc gcc gag aaa ctt      917
Asp Val Phe Gly Gln His Thr Lys Asn Lys Asn Ala Ala Glu Lys Leu
        280                 285                 290 tta gaa ctt gca aaa ttg gaa ttc aat ata ttt cac tcc tta caa gag      965
Leu Glu Leu Ala Lys Leu Glu Phe Asn Ile Phe His Ser Leu Gln Glu
295                 300                 305                 310 aga gag tta aaa cat gtt tcc cga tgg tgg aaa gac tcg ggt tct cct     1013
Arg Glu Leu Lys His Val Ser Arg Trp Trp Lys Asp Ser Gly Ser Pro
                315                 320                 325
```

-continued

```
gag atg acc ttc tgt cga cat cgt cac gtg gaa tac tac gct ttg gct       1061
Glu Met Thr Phe Cys Arg His Arg His Val Glu Tyr Tyr Ala Leu Ala
        330                 335                 340 tcc tgc att gcg ttc gag cct caa cat tct gga ttc aga ctc ggc ttt       1109
Ser Cys Ile Ala Phe Glu Pro Gln His Ser Gly Phe Arg Leu Gly Phe
            345                 350                 355 acc aag atg tct cat ctt atc acg gtt ctt gac gac atg tac gac gtc       1157
Thr Lys Met Ser His Leu Ile Thr Val Leu Asp Asp Met Tyr Asp Val
    360                 365                 370 ttc ggc aca gta gac gag ctg gaa ctc ttc aca gcg aca att aag aga       1205
Phe Gly Thr Val Asp Glu Leu Glu Leu Phe Thr Ala Thr Ile Lys Arg
375                 380                 385                 390 tgg gat ccg tcc gcg atg gaa tgc ctt cca gaa tat atg aaa gga gtg       1253
Trp Asp Pro Ser Ala Met Glu Cys Leu Pro Glu Tyr Met Lys Gly Val
                395                 400                 405 tac atg atg gtt tat cac acc gta aat gaa atg gct cga gtg gca gag       1301
Tyr Met Met Val Tyr His Thr Val Asn Glu Met Ala Arg Val Ala Glu
            410                 415                 420 aag gct caa ggc cga gac acg ctc aac tat gca aga cag gct tgg gag       1349
Lys Ala Gln Gly Arg Asp Thr Leu Asn Tyr Ala Arg Gln Ala Trp Glu
    425                 430                 435 gcg tgt ttt gat tcg tat atg cag gaa gca aag tgg atc gcc act ggt       1397
Ala Cys Phe Asp Ser Tyr Met Gln Glu Ala Lys Trp Ile Ala Thr Gly
440                 445                 450 tat ctg ccc acg ttt gag gag tac ttg gag aac ggg aaa gtt agc tct       1445
Tyr Leu Pro Thr Phe Glu Glu Tyr Leu Glu Asn Gly Lys Val Ser Ser
455                 460                 465                 470 gct cat cgc cca tgc gca ctg caa ccc att ctg acg ttg gac atc ccc       1493
Ala His Arg Pro Cys Ala Leu Gln Pro Ile Leu Thr Leu Asp Ile Pro
                475                 480                 485 ttt cct gat cac atc ctc aag gaa gtt gac ttc cca tcg aag ctc aat       1541
Phe Pro Asp His Ile Leu Lys Glu Val Asp Phe Pro Ser Lys Leu Asn
            490                 495                 500 gac ttg ata tgt atc atc ctt cga tta aga ggt gat aca cgg tgc tac       1589
Asp Leu Ile Cys Ile Ile Leu Arg Leu Arg Gly Asp Thr Arg Cys Tyr
    505                 510                 515 aag gca gac agg gcc cgt gga gaa gaa gct tcg tct ata tca tgt tat       1637
Lys Ala Asp Arg Ala Arg Gly Glu Glu Ala Ser Ser Ile Ser Cys Tyr
520                 525                 530 atg aaa gac aat cct gga tta acg gaa gaa gat gct ctg aat cat atc       1685
Met Lys Asp Asn Pro Gly Leu Thr Glu Glu Asp Ala Leu Asn His Ile
535                 540                 545                 550 aac ttc atg atc agg gac gca atc aga gaa tta aat tgg gag ctt cta       1733
Asn Phe Met Ile Arg Asp Ala Ile Arg Glu Leu Asn Trp Glu Leu Leu
                555                 560                 565 aag cca gac aac agt gtt ccc atc act tcc aag aaa cac gca ttt gac       1781
Lys Pro Asp Asn Ser Val Pro Ile Thr Ser Lys Lys His Ala Phe Asp
            570                 575                 580 ata agc aga gtt tgg cat cac ggt tac aga tac cga gat ggc tac agc       1829
Ile Ser Arg Val Trp His His Gly Tyr Arg Tyr Arg Asp Gly Tyr Ser
    585                 590                 595 ttt gcc aac gtt gaa aca aag agt ttg gtg atg aga acc gtc att gaa       1877
Phe Ala Asn Val Glu Thr Lys Ser Leu Val Met Arg Thr Val Ile Glu
600                 605                 610 cct gtg cct ttg taacaacact tcaaatctac aatattaact gaggatgccc          1929
Pro Val Pro Leu
615 tatgggtgta tagggcac acaaaaataa atatggttgt gttagtaaag ctgtaattta      1989 tgaaaaaaaa aaaaaaaaaa aaaa                                            2013
```

<210> SEQ ID NO 65
<211> LENGTH: 618
<212> TYPE: PRT
<213> ORGANISM: Abies grandis

<400> SEQUENCE: 65

```
Met Ala Leu Leu Ser Ile Thr Pro Leu Val Ser Arg Ser Cys Leu Ser
 1               5                  10                  15

Ser Ser His Glu Ile Lys Ala Leu Arg Arg Thr Ile Pro Thr Leu Gly
            20                  25                  30

Ile Cys Arg Pro Gly Lys Ser Val Ala His Ser Ile Asn Met Cys Leu
        35                  40                  45

Thr Ser Val Ala Ser Thr Asp Ser Val Gln Arg Arg Val Gly Asn Tyr
 50                  55                  60

His Ser Asn Leu Trp Asp Asp Phe Ile Gln Ser Leu Ile Ser Thr
 65                  70                  75                  80

Pro Tyr Gly Ala Pro Asp Tyr Arg Glu Arg Ala Asp Arg Leu Ile Gly
                85                  90                  95

Glu Val Lys Asp Ile Met Phe Asn Phe Lys Ser Leu Glu Asp Gly Gly
            100                 105                 110

Asn Asp Leu Leu Gln Arg Leu Leu Leu Val Asp Asp Val Glu Arg Leu
        115                 120                 125

Gly Ile Asp Arg His Phe Lys Lys Glu Ile Lys Thr Ala Leu Asp Tyr
130                 135                 140

Val Asn Ser Tyr Trp Asn Glu Lys Gly Ile Gly Cys Gly Arg Glu Ser
145                 150                 155                 160

Val Val Thr Asp Leu Asn Ser Thr Ala Leu Gly Leu Arg Thr Leu Arg
                165                 170                 175

Leu His Gly Tyr Thr Val Ser Ser Asp Val Leu Asn Val Phe Lys Asp
            180                 185                 190

Lys Asn Gly Gln Phe Ser Ser Thr Ala Asn Ile Gln Ile Glu Gly Glu
        195                 200                 205

Ile Arg Gly Val Leu Asn Leu Phe Arg Ala Ser Leu Val Ala Phe Pro
210                 215                 220

Gly Glu Lys Val Met Asp Glu Ala Glu Thr Phe Ser Thr Lys Tyr Leu
225                 230                 235                 240

Arg Glu Ala Leu Gln Lys Ile Pro Ala Ser Ser Ile Leu Ser Leu Glu
                245                 250                 255

Ile Arg Asp Val Leu Glu Tyr Gly Trp His Thr Asn Leu Pro Arg Leu
            260                 265                 270

Glu Ala Arg Asn Tyr Met Asp Val Phe Gly Gln His Thr Lys Asn Lys
        275                 280                 285

Asn Ala Ala Glu Lys Leu Leu Glu Leu Ala Lys Leu Glu Phe Asn Ile
290                 295                 300

Phe His Ser Leu Gln Glu Arg Glu Leu Lys His Val Ser Arg Trp Trp
305                 310                 315                 320

Lys Asp Ser Gly Ser Pro Glu Met Thr Phe Cys Arg His Arg His Val
                325                 330                 335

Glu Tyr Tyr Ala Leu Ala Ser Cys Ile Ala Phe Glu Pro Gln His Ser
            340                 345                 350

Gly Phe Arg Leu Gly Phe Thr Lys Met Ser His Leu Ile Thr Val Leu
        355                 360                 365

Asp Asp Met Tyr Asp Val Phe Gly Thr Val Asp Glu Leu Glu Leu Phe
```

-continued

```
                370                 375                 380
Thr Ala Thr Ile Lys Arg Trp Asp Pro Ser Ala Met Glu Cys Leu Pro
385                 390                 395                 400

Glu Tyr Met Lys Gly Val Tyr Met Val Tyr His Thr Val Asn Glu
                405                 410                 415

Met Ala Arg Val Ala Glu Lys Ala Gln Gly Arg Asp Thr Leu Asn Tyr
                420                 425                 430

Ala Arg Gln Ala Trp Glu Ala Cys Phe Asp Ser Tyr Met Gln Glu Ala
                435                 440                 445

Lys Trp Ile Ala Thr Gly Tyr Leu Pro Thr Phe Glu Glu Tyr Leu Glu
                450                 455                 460

Asn Gly Lys Val Ser Ser Ala His Arg Pro Cys Ala Leu Gln Pro Ile
465                 470                 475                 480

Leu Thr Leu Asp Ile Pro Phe Pro Asp His Ile Leu Lys Glu Val Asp
                485                 490                 495

Phe Pro Ser Lys Leu Asn Asp Leu Ile Cys Ile Ile Leu Arg Leu Arg
                500                 505                 510

Gly Asp Thr Arg Cys Tyr Lys Ala Asp Arg Ala Arg Gly Glu Glu Ala
                515                 520                 525

Ser Ser Ile Ser Cys Tyr Met Lys Asp Asn Pro Gly Leu Thr Glu Glu
530                 535                 540

Asp Ala Leu Asn His Ile Asn Phe Met Ile Arg Asp Ala Ile Arg Glu
545                 550                 555                 560

Leu Asn Trp Glu Leu Leu Lys Pro Asp Asn Ser Val Pro Ile Thr Ser
                565                 570                 575

Lys Lys His Ala Phe Asp Ile Ser Arg Val Trp His His Gly Tyr Arg
                580                 585                 590

Tyr Arg Asp Gly Tyr Ser Phe Ala Asn Val Glu Thr Lys Ser Leu Val
                595                 600                 605

Met Arg Thr Val Ile Glu Pro Val Pro Leu
610                 615
```

<210> SEQ ID NO 66
<211> LENGTH: 2186
<212> TYPE: DNA
<213> ORGANISM: Abies grandis
<220> FEATURE:
<221> NAME/KEY: CDS
<222> LOCATION: (34)..(1923)

<400> SEQUENCE: 66

```
cccaaatcct atatccgtta taagcgagca gga atg gct ctg gtt tct tcc gca      54
                                    Met Ala Leu Val Ser Ser Ala
                                      1               5 ccc aaa tcc tgc ctg cac aaa tcg ttg atc agg tct act cat cat gag     102
Pro Lys Ser Cys Leu His Lys Ser Leu Ile Arg Ser Thr His His Glu
            10                  15                  20 ctc aag cct ctg cgc aga acc atc cca act ctt gga atg tgt agg cga     150
Leu Lys Pro Leu Arg Arg Thr Ile Pro Thr Leu Gly Met Cys Arg Arg
        25                  30                  35 ggg aaa tct ttc aca cct tct gtg agc atg agt ttg acc acc gct gta     198
Gly Lys Ser Phe Thr Pro Ser Val Ser Met Ser Leu Thr Thr Ala Val
40                  45                  50                  55 tct gat gat ggt cta caa aga cgc ata ggt gac tat cat tcc aat ctc     246
Ser Asp Asp Gly Leu Gln Arg Arg Ile Gly Asp Tyr His Ser Asn Leu
                60                  65                  70 tgg gac gac gat ttc ata cag tct cta tca acg cct tat ggg gag cct     294
```

```
                                                            -continued

Trp Asp Asp Phe Ile Gln Ser Leu Ser Thr Pro Tyr Gly Glu Pro
         75                  80                  85 tct tac cga gaa cgt gct gag aaa ctg att ggg gaa gtg aag gag atg        342
Ser Tyr Arg Glu Arg Ala Glu Lys Leu Ile Gly Glu Val Lys Glu Met
         90                  95                 100 ttc aat tca atg cca tcg gaa gat gga gaa tca atg agt ccc ctc aat        390
Phe Asn Ser Met Pro Ser Glu Asp Gly Glu Ser Met Ser Pro Leu Asn
        105                 110                 115 gat ctt att gaa cga ctt tgg atg gtc gat agc gtt gaa cgt ttg ggg        438
Asp Leu Ile Glu Arg Leu Trp Met Val Asp Ser Val Glu Arg Leu Gly
120                 125                 130                 135 att gat aga cat ttc aaa aaa gag ata aaa tca gcc ctt gat tat gtt        486
Ile Asp Arg His Phe Lys Lys Glu Ile Lys Ser Ala Leu Asp Tyr Val
                140                 145                 150 tac agt tat tgg aac gaa aaa ggt att gga tgc ggt aga gat agt gtt        534
Tyr Ser Tyr Trp Asn Glu Lys Gly Ile Gly Cys Gly Arg Asp Ser Val
                155                 160                 165 ttt cct gat gtc aac tcg act gcc tcg ggg ttt cga act ctt cgc cta        582
Phe Pro Asp Val Asn Ser Thr Ala Ser Gly Phe Arg Thr Leu Arg Leu
                170                 175                 180 cac gga tac agt gtc tct tca gag gtt ttg aaa gta ttt caa gac caa        630
His Gly Tyr Ser Val Ser Ser Glu Val Leu Lys Val Phe Gln Asp Gln
        185                 190                 195 aat ggg cag ttt gca ttc tct cct agt aca aaa gag aga gac atc aga        678
Asn Gly Gln Phe Ala Phe Ser Pro Ser Thr Lys Glu Arg Asp Ile Arg
200                 205                 210                 215 acc gtt ctg aat tta tat cgg gct tct ttc att gcc ttt cct ggg gag        726
Thr Val Leu Asn Leu Tyr Arg Ala Ser Phe Ile Ala Phe Pro Gly Glu
                220                 225                 230 aaa gtt atg gaa gag gct gaa att ttc tct tca aga tat ttg aaa gaa        774
Lys Val Met Glu Glu Ala Glu Ile Phe Ser Ser Arg Tyr Leu Lys Glu
                235                 240                 245 gcc gtg caa aag att ccg gtc tcc agt ctt tca caa gaa ata gac tac        822
Ala Val Gln Lys Ile Pro Val Ser Ser Leu Ser Gln Glu Ile Asp Tyr
        250                 255                 260 act ttg gaa tat ggt tgg cac aca aat atg cca aga ttg gaa aca agg        870
Thr Leu Glu Tyr Gly Trp His Thr Asn Met Pro Arg Leu Glu Thr Arg
        265                 270                 275 aat tac tta gat gta ttt gga cat cct acc agt cca tgg ctc aag aag        918
Asn Tyr Leu Asp Val Phe Gly His Pro Thr Ser Pro Trp Leu Lys Lys
280                 285                 290                 295 aaa agg acg caa tat ctg gac agc gaa aag ctt tta gaa ctc gca aaa        966
Lys Arg Thr Gln Tyr Leu Asp Ser Glu Lys Leu Leu Glu Leu Ala Lys
                300                 305                 310 ttg gag ttc aac atc ttt cac tcc ctt caa cag aag gag tta cag tat       1014
Leu Glu Phe Asn Ile Phe His Ser Leu Gln Gln Lys Glu Leu Gln Tyr
                315                 320                 325 ctc tcc aga tgg tgg ata cat tcg ggt ttg cct gaa ctg acc ttt ggt       1062
Leu Ser Arg Trp Trp Ile His Ser Gly Leu Pro Glu Leu Thr Phe Gly
        330                 335                 340 cgg cat cgt cac gtg gaa tac tac acc ctg agc tct tgc att gcg act       1110
Arg His Arg His Val Glu Tyr Tyr Thr Leu Ser Ser Cys Ile Ala Thr
        345                 350                 355 gag ccc aaa cat tct gca ttc aga ttg ggc ttt gcc aaa acg tgt cat       1158
Glu Pro Lys His Ser Ala Phe Arg Leu Gly Phe Ala Lys Thr Cys His
360                 365                 370                 375 ctt atc acg gtt ctg gac gat atc tac gac act ttc gga acg atg gat       1206
Leu Ile Thr Val Leu Asp Asp Ile Tyr Asp Thr Phe Gly Thr Met Asp
                380                 385                 390
```

```
gaa atc gaa ctc ttc aac gag gca gtt agg aga tgg aat ccg tcg gag      1254
Glu Ile Glu Leu Phe Asn Glu Ala Val Arg Arg Trp Asn Pro Ser Glu
        395                 400                 405 aaa gaa cgc ctc cca gaa tat atg aaa gaa atc tac atg gca ctc tac      1302
Lys Glu Arg Leu Pro Glu Tyr Met Lys Glu Ile Tyr Met Ala Leu Tyr
410                 415                 420 gaa gcc tta act gac atg gcg cga gag gca gag aag aca caa ggc cga      1350
Glu Ala Leu Thr Asp Met Ala Arg Glu Ala Glu Lys Thr Gln Gly Arg
    425                 430                 435 gac acg ctc aat tat gct aga aag gct tgg gaa gtt tat ctt gat tcg      1398
Asp Thr Leu Asn Tyr Ala Arg Lys Ala Trp Glu Val Tyr Leu Asp Ser
440                 445                 450                 455 tat aca caa gaa gca aag tgg atc gcc agc ggt tat ctg cca act ttc      1446
Tyr Thr Gln Glu Ala Lys Trp Ile Ala Ser Gly Tyr Leu Pro Thr Phe
                460                 465                 470 gag gag tac tta gag aac gcg aag gtt agc tct ggt cat cgt gca gcg      1494
Glu Glu Tyr Leu Glu Asn Ala Lys Val Ser Ser Gly His Arg Ala Ala
            475                 480                 485 gca ttg aca ccc ctc ctg aca ttg gac gta ccg ctt cct gat gac gtc      1542
Ala Leu Thr Pro Leu Leu Thr Leu Asp Val Pro Leu Pro Asp Asp Val
        490                 495                 500 ttg aag gga ata gat ttt cca tcg aga ttt aat gat ttg gca tct tcc      1590
Leu Lys Gly Ile Asp Phe Pro Ser Arg Phe Asn Asp Leu Ala Ser Ser
505                 510                 515 ttc ctt aga cta aga ggt gac aca cga tgc tac aag gca gac agg gac      1638
Phe Leu Arg Leu Arg Gly Asp Thr Arg Cys Tyr Lys Ala Asp Arg Asp
520                 525                 530                 535 cga gga gaa gaa gcg tca agc ata tcg tgt tac atg aaa gac aat ccc      1686
Arg Gly Glu Glu Ala Ser Ser Ile Ser Cys Tyr Met Lys Asp Asn Pro
                540                 545                 550 gga tta aca gag gaa gat gct ctc aat cat atc aat gcc atg atc aac      1734
Gly Leu Thr Glu Glu Asp Ala Leu Asn His Ile Asn Ala Met Ile Asn
            555                 560                 565 gac ata atc aaa gaa tta aat tgg gaa ctt ctc aaa ccc gat agc aat      1782
Asp Ile Ile Lys Glu Leu Asn Trp Glu Leu Leu Lys Pro Asp Ser Asn
        570                 575                 580 att cca atg act gca cgg aaa cat gct tat gag ata acc aga gct ttc      1830
Ile Pro Met Thr Ala Arg Lys His Ala Tyr Glu Ile Thr Arg Ala Phe
585                 590                 595 cac caa ctt tac aaa tat aga gat ggc ttc agc gtt gcc act caa gaa      1878
His Gln Leu Tyr Lys Tyr Arg Asp Gly Phe Ser Val Ala Thr Gln Glu
600                 605                 610                 615 acg aaa agt ttg gtg agg aga acg gtc ctt gaa cca gtg cct ctt           1923
Thr Lys Ser Leu Val Arg Arg Thr Val Leu Glu Pro Val Pro Leu
                620                 625                 630 taacaattta aaccttctat aataaattgg tgtaggctcc gctatgcgtt tatgcatgtg     1983
catgtctctc tatgtaacta gttgtatgcg tggtatgatt ataaaattgg aggttactcg     2043
gtcctcacat ggtaatatgt gagttgtgaa attctcaaaa aaaaaaaaaa aaaaaaaaaa     2103
aaaaaaaaaa aaaaaaaaaa aaaaaaaaaa aaaaaaaaaa aaaaaaaaaa aaaaaaaaaa     2163
aaaaaaaaaa aaaaaaaaaa aaa                                             2186

<210> SEQ ID NO 67
<211> LENGTH: 630
<212> TYPE: PRT
<213> ORGANISM: Abies grandis

<400> SEQUENCE: 67

Met Ala Leu Val Ser Ser Ala Pro Lys Ser Cys Leu His Lys Ser Leu
```

-continued

```
  1               5                   10                  15
Ile Arg Ser Thr His His Glu Leu Lys Pro Leu Arg Arg Thr Ile Pro
                20                  25                  30
Thr Leu Gly Met Cys Arg Arg Gly Lys Ser Phe Thr Pro Ser Val Ser
                35                  40                  45
Met Ser Leu Thr Thr Ala Val Ser Asp Asp Gly Leu Gln Arg Arg Ile
                50                  55                  60
Gly Asp Tyr His Ser Asn Leu Trp Asp Asp Phe Ile Gln Ser Leu
 65                 70                  75                  80
Ser Thr Pro Tyr Gly Glu Pro Ser Tyr Arg Glu Arg Ala Glu Lys Leu
                    85                  90                  95
Ile Gly Glu Val Lys Glu Met Phe Asn Ser Met Pro Ser Glu Asp Gly
                    100                 105                 110
Glu Ser Met Ser Pro Leu Asn Asp Leu Ile Glu Arg Leu Trp Met Val
                    115                 120                 125
Asp Ser Val Glu Arg Leu Gly Ile Asp Arg His Phe Lys Lys Glu Ile
                    130                 135                 140
Lys Ser Ala Leu Asp Tyr Val Tyr Ser Tyr Trp Asn Glu Lys Gly Ile
 145                150                 155                 160
Gly Cys Gly Arg Asp Ser Val Phe Pro Asp Val Asn Ser Thr Ala Ser
                    165                 170                 175
Gly Phe Arg Thr Leu Arg Leu His Gly Tyr Ser Val Ser Ser Glu Val
                    180                 185                 190
Leu Lys Val Phe Gln Asp Gln Asn Gly Gln Phe Ala Phe Ser Pro Ser
                    195                 200                 205
Thr Lys Glu Arg Asp Ile Arg Thr Val Leu Asn Leu Tyr Arg Ala Ser
                    210                 215                 220
Phe Ile Ala Phe Pro Gly Glu Lys Val Met Glu Glu Ala Glu Ile Phe
 225                230                 235                 240
Ser Ser Arg Tyr Leu Lys Glu Ala Val Gln Lys Ile Pro Val Ser Ser
                    245                 250                 255
Leu Ser Gln Glu Ile Asp Tyr Thr Leu Glu Tyr Gly Trp His Thr Asn
                    260                 265                 270
Met Pro Arg Leu Glu Thr Arg Asn Tyr Leu Asp Val Phe Gly His Pro
                    275                 280                 285
Thr Ser Pro Trp Leu Lys Lys Lys Arg Thr Gln Tyr Leu Asp Ser Glu
                    290                 295                 300
Lys Leu Leu Glu Leu Ala Lys Leu Glu Phe Asn Ile Phe His Ser Leu
 305                310                 315                 320
Gln Gln Lys Glu Leu Gln Tyr Leu Ser Arg Trp Trp Ile His Ser Gly
                    325                 330                 335
Leu Pro Glu Leu Thr Phe Gly Arg His Arg His Val Glu Tyr Tyr Thr
                    340                 345                 350
Leu Ser Ser Cys Ile Ala Thr Glu Pro Lys His Ser Ala Phe Arg Leu
                    355                 360                 365
Gly Phe Ala Lys Thr Cys His Leu Ile Thr Val Leu Asp Asp Ile Tyr
                    370                 375                 380
Asp Thr Phe Gly Thr Met Asp Glu Ile Glu Leu Phe Asn Glu Ala Val
 385                390                 395                 400
Arg Arg Trp Asn Pro Ser Glu Lys Glu Arg Leu Pro Glu Tyr Met Lys
                    405                 410                 415
Glu Ile Tyr Met Ala Leu Tyr Glu Ala Leu Thr Asp Met Ala Arg Glu
                    420                 425                 430
```

-continued

```
Ala Glu Lys Thr Gln Gly Arg Asp Thr Leu Asn Tyr Ala Arg Lys Ala
        435                 440                 445

Trp Glu Val Tyr Leu Asp Ser Tyr Thr Gln Glu Ala Lys Trp Ile Ala
    450                 455                 460

Ser Gly Tyr Leu Pro Thr Phe Glu Glu Tyr Leu Glu Asn Ala Lys Val
465                 470                 475                 480

Ser Ser Gly His Arg Ala Ala Leu Thr Pro Leu Leu Thr Leu Asp
                485                 490                 495

Val Pro Leu Pro Asp Asp Val Leu Lys Gly Ile Asp Phe Pro Ser Arg
            500                 505                 510

Phe Asn Asp Leu Ala Ser Ser Phe Leu Arg Leu Arg Gly Asp Thr Arg
                515                 520                 525

Cys Tyr Lys Ala Asp Arg Asp Arg Gly Glu Glu Ala Ser Ser Ile Ser
        530                 535                 540

Cys Tyr Met Lys Asp Asn Pro Gly Leu Thr Glu Asp Ala Leu Asn
545                 550                 555                 560

His Ile Asn Ala Met Ile Asn Asp Ile Ile Lys Glu Leu Asn Trp Glu
                565                 570                 575

Leu Leu Lys Pro Asp Ser Asn Ile Pro Met Thr Ala Arg Lys His Ala
            580                 585                 590

Tyr Glu Ile Thr Arg Ala Phe His Gln Leu Tyr Lys Tyr Arg Asp Gly
        595                 600                 605

Phe Ser Val Ala Thr Gln Glu Thr Lys Ser Leu Val Arg Arg Thr Val
    610                 615                 620

Leu Glu Pro Val Pro Leu
625                 630

<210> SEQ ID NO 68
<211> LENGTH: 2429
<212> TYPE: DNA
<213> ORGANISM: Abies grandis
<220> FEATURE:
<221> NAME/KEY: CDS
<222> LOCATION: (35)..(1945)

<400> SEQUENCE: 68
attaaagaag ctaccatagt ttaggcagga atgc atg gct ctc ctt tct atc gta      55
                                    Met Ala Leu Leu Ser Ile Val
                                    1               5 tct ttg cag gtt ccc aaa tcc tgc ggg ctg aaa tcg ttg atc agt tcc       103
Ser Leu Gln Val Pro Lys Ser Cys Gly Leu Lys Ser Leu Ile Ser Ser
        10                  15                  20 agc aat gtg cag aag gct ctc tgt atc tct aca gca gtc cca act ctc      151
Ser Asn Val Gln Lys Ala Leu Cys Ile Ser Thr Ala Val Pro Thr Leu
    25                  30                  35 aga atg cgt agg cga cag aaa gct ctg gtc atc aac atg aaa ttg acc      199
Arg Met Arg Arg Arg Gln Lys Ala Leu Val Ile Asn Met Lys Leu Thr
40                  45                  50                  55 act gta tcc cat cgt gat gat aat ggt ggt ggt gta ctg caa aga cgc      247
Thr Val Ser His Arg Asp Asp Asn Gly Gly Gly Val Leu Gln Arg Arg
                60                  65                  70 ata gcc gat cat cat ccc aac ctg tgg gaa gat gat ttc ata caa tca      295
Ile Ala Asp His His Pro Asn Leu Trp Glu Asp Asp Phe Ile Gln Ser
            75                  80                  85 ttg tcc tca cct tat ggg gga tct tcg tac agt gaa cgt gct gtg aca      343
Leu Ser Ser Pro Tyr Gly Gly Ser Ser Tyr Ser Glu Arg Ala Val Thr
        90                  95                  100
```

| | | |
|---|---|---|
| gtg gtt gag gaa gta aaa gag atg ttc aat tca ata cca aat aat aga<br>Val Val Glu Glu Val Lys Glu Met Phe Asn Ser Ile Pro Asn Asn Arg<br>105 110 115 | | 391 |
| gaa tta ttt ggt tcc caa aat gat ctc ctt aca cgc ctt tgg atg gtg<br>Glu Leu Phe Gly Ser Gln Asn Asp Leu Leu Thr Arg Leu Trp Met Val<br>120 125 130 135 | | 439 |
| gat agc att gaa cgt ctg ggg ata gat aga cat ttc caa aat gag ata<br>Asp Ser Ile Glu Arg Leu Gly Ile Asp Arg His Phe Gln Asn Glu Ile<br>140 145 150 | | 487 |
| aga gta gcc ctc gat tat gtt tac agt tat tgg aag gaa aag gaa ggc<br>Arg Val Ala Leu Asp Tyr Val Tyr Ser Tyr Trp Lys Glu Lys Glu Gly<br>155 160 165 | | 535 |
| att ggg tgt ggc aga gat tct act ttt cct gat ctc aac tcg act gct<br>Ile Gly Cys Gly Arg Asp Ser Thr Phe Pro Asp Leu Asn Ser Thr Ala<br>170 175 180 | | 583 |
| ctg gcg ctt cga act ctt cga ctg cac gga tac aat gtg tct tca gat<br>Leu Ala Leu Arg Thr Leu Arg Leu His Gly Tyr Asn Val Ser Ser Asp<br>185 190 195 | | 631 |
| gtg ctg gaa tac ttc aaa gat caa aag ggg cat ttt gcc tgc cct gca<br>Val Leu Glu Tyr Phe Lys Asp Gln Lys Gly His Phe Ala Cys Pro Ala<br>200 205 210 215 | | 679 |
| atc cta acc gag gga cag atc act aga agt gtt cta aat tta tat cgg<br>Ile Leu Thr Glu Gly Gln Ile Thr Arg Ser Val Leu Asn Leu Tyr Arg<br>220 225 230 | | 727 |
| gct tcc ctg gtc gcc ttt ccg ggg gag aaa gtt atg gaa gag gct gaa<br>Ala Ser Leu Val Ala Phe Pro Gly Glu Lys Val Met Glu Glu Ala Glu<br>235 240 245 | | 775 |
| atc ttc tcg gca tct tat ttg aaa gaa gtc tta caa aag att cca gtc<br>Ile Phe Ser Ala Ser Tyr Leu Lys Glu Val Leu Gln Lys Ile Pro Val<br>250 255 260 | | 823 |
| tcc agt ttt tca cga gag ata gaa tac gtt ttg gaa tat ggt tgg cac<br>Ser Ser Phe Ser Arg Glu Ile Glu Tyr Val Leu Glu Tyr Gly Trp His<br>265 270 275 | | 871 |
| aca aat ttg cca aga ttg gaa gca aga aat tat atc gac gtc tac ggg<br>Thr Asn Leu Pro Arg Leu Glu Ala Arg Asn Tyr Ile Asp Val Tyr Gly<br>280 285 290 295 | | 919 |
| cag gac agc tat gaa agt tca aac gag atg cca tat gtg aat acg cag<br>Gln Asp Ser Tyr Glu Ser Ser Asn Glu Met Pro Tyr Val Asn Thr Gln<br>300 305 310 | | 967 |
| aag ctt tta aaa ctt gca aaa ttg gag ttt aat atc ttt cac tct ttg<br>Lys Leu Leu Lys Leu Ala Lys Leu Glu Phe Asn Ile Phe His Ser Leu<br>315 320 325 | | 1015 |
| caa cag aaa gag ttg caa tat atc tct aga tgg tgg aaa gat tcg tgt<br>Gln Gln Lys Glu Leu Gln Tyr Ile Ser Arg Trp Trp Lys Asp Ser Cys<br>330 335 340 | | 1063 |
| tca tct cat ctg act ttt act cga cac cgt cac gtg gaa tac tac aca<br>Ser Ser His Leu Thr Phe Thr Arg His Arg His Val Glu Tyr Tyr Thr<br>345 350 355 | | 1111 |
| atg gca tct tgc att tct atg gag ccg aaa cac tcc gct ttc aga ttg<br>Met Ala Ser Cys Ile Ser Met Glu Pro Lys His Ser Ala Phe Arg Leu<br>360 365 370 375 | | 1159 |
| ggg ttt gtc aaa aca tgt cat ctt cta aca gtt ctg gat gat atg tat<br>Gly Phe Val Lys Thr Cys His Leu Leu Thr Val Leu Asp Asp Met Tyr<br>380 385 390 | | 1207 |
| gac act ttt gga aca ctg gac gaa ctc caa ctt ttt acg act gcc ttt<br>Asp Thr Phe Gly Thr Leu Asp Glu Leu Gln Leu Phe Thr Thr Ala Phe<br>395 400 405 | | 1255 |
| aag aga tgg gat ttg tca gag aca aag tgt ctt cca gaa tat atg aaa<br>Lys Arg Trp Asp Leu Ser Glu Thr Lys Cys Leu Pro Glu Tyr Met Lys<br>410 415 420 | | 1303 |

```
gca gtg tac atg gac ttg tat caa tgt ctt aat gaa ttg gcg caa gag   1351
Ala Val Tyr Met Asp Leu Tyr Gln Cys Leu Asn Glu Leu Ala Gln Glu
    425                 430                 435 gct gag aag act caa ggc aga gat acg ctc aac tat att cgc aat gct   1399
Ala Glu Lys Thr Gln Gly Arg Asp Thr Leu Asn Tyr Ile Arg Asn Ala
440                 445                 450                 455 tat gag tct cat ttt gat tcg ttt atg cac gaa gca aaa tgg atc tca   1447
Tyr Glu Ser His Phe Asp Ser Phe Met His Glu Ala Lys Trp Ile Ser
                460                 465                 470 agt ggt tat ctc cca acg ttt gag gag tac ttg aag aat ggg aaa gtt   1495
Ser Gly Tyr Leu Pro Thr Phe Glu Glu Tyr Leu Lys Asn Gly Lys Val
            475                 480                 485 agt tcc ggt tct cgc aca gcc act tta caa ccc ata ctc acc ttg gat   1543
Ser Ser Gly Ser Arg Thr Ala Thr Leu Gln Pro Ile Leu Thr Leu Asp
        490                 495                 500 gta cca ctt cct aat tac ata ctg caa gaa att gat tat cca tct agg   1591
Val Pro Leu Pro Asn Tyr Ile Leu Gln Glu Ile Asp Tyr Pro Ser Arg
505                 510                 515 ttc aat gac ttg gct tcg tcc ctc ctt cgg cta cgt ggt gac acg cgc   1639
Phe Asn Asp Leu Ala Ser Ser Leu Leu Arg Leu Arg Gly Asp Thr Arg
520                 525                 530                 535 tgc tac aag gcg gat agg gct cgt gga gaa gaa gct tca gct ata tcg   1687
Cys Tyr Lys Ala Asp Arg Ala Arg Gly Glu Glu Ala Ser Ala Ile Ser
                540                 545                 550 tgt tat atg aaa gac cat cct gga tca aca gag gaa gat gct ctc aat   1735
Cys Tyr Met Lys Asp His Pro Gly Ser Thr Glu Glu Asp Ala Leu Asn
            555                 560                 565 cat atc aac gtc atg atc agt gat gca atc aga gaa tta aat tgg gag   1783
His Ile Asn Val Met Ile Ser Asp Ala Ile Arg Glu Leu Asn Trp Glu
        570                 575                 580 ctt ctc aga cca gat agc aaa agt ccc atc tct tcc aag aaa cat gct   1831
Leu Leu Arg Pro Asp Ser Lys Ser Pro Ile Ser Ser Lys Lys His Ala
585                 590                 595 ttt gac atc acc aga gct ttc cat cac ctc tac aag tac cga gat ggt   1879
Phe Asp Ile Thr Arg Ala Phe His His Leu Tyr Lys Tyr Arg Asp Gly
600                 605                 610                 615 tac act gtt gcg agt agt gaa aca aag aat ttg gtg atg aaa aca gtt   1927
Tyr Thr Val Ala Ser Ser Glu Thr Lys Asn Leu Val Met Lys Thr Val
                620                 625                 630 ctt gaa cct gtg gca ttg taaaaaaata tcaaccgcat caaaatgcac          1975
Leu Glu Pro Val Ala Leu
            635 ggagtttgta atttaatgca cttctcttat aatacacttc tctttagacc tgtagtgaag  2035 ccgatgcacc attacagtgt atatgggagc cagtctagtc tcaaaaagtt tgtaaatgtt  2095 attctatgat atactcttta gaccaaaagc tagatgccca tgaaaagcaa gtgttttaga  2155 attgcttctg gatttgctta aatttctcc atgattcttt agaatgttg catccccaaa    2215 cttcactgcc atataagata acgggagtga caaggatttt aaagaggatt tttttttatg  2275 tcccgcatca caaggtttgt cgatttacag ttgttttcaa gactgaagta ggatttccac  2335 cctccattaa tcctcttctc gatgttatag tttcacttga gcttgtgatg gaagtcaatt  2395 cctagatatt tataagaaaa aaaaaaaaaa aaaa                              2429
```

<210> SEQ ID NO 69
<211> LENGTH: 637
<212> TYPE: PRT
<213> ORGANISM: Abies grandis

<400> SEQUENCE: 69

| | | | | | | | | | | | | | | |
|---|---|---|---|---|---|---|---|---|---|---|---|---|---|---|
|Met|Ala|Leu|Leu|Ser|Ile|Val|Ser|Leu|Gln|Val|Pro|Lys|Ser|Cys|Gly|
|1| | | |5| | | | |10| | | | |15| |
|Leu|Lys|Ser|Leu|Ile|Ser|Ser|Asn|Val|Gln|Lys|Ala|Leu|Cys|Ile|
| | | |20| | | | |25| | | | |30| |
|Ser|Thr|Ala|Val|Pro|Thr|Leu|Arg|Met|Arg|Arg|Gln|Lys|Ala|Leu|
| | |35| | | | |40| | | | |45| | |
|Val|Ile|Asn|Met|Lys|Leu|Thr|Thr|Val|Ser|His|Arg|Asp|Asp|Asn|Gly|
| |50| | | | |55| | | | |60| | | | |
|Gly|Gly|Val|Leu|Gln|Arg|Arg|Ile|Ala|Asp|His|His|Pro|Asn|Leu|Trp|
|65| | | | |70| | | | |75| | | | |80|
|Glu|Asp|Asp|Phe|Ile|Gln|Ser|Leu|Ser|Ser|Pro|Tyr|Gly|Gly|Ser|Ser|
| | | | |85| | | | |90| | | | |95| |
|Tyr|Ser|Glu|Arg|Ala|Val|Thr|Val|Val|Glu|Glu|Val|Lys|Glu|Met|Phe|
| | | | |100| | | | |105| | | | |110| |
|Asn|Ser|Ile|Pro|Asn|Asn|Arg|Glu|Leu|Phe|Gly|Ser|Gln|Asn|Asp|Leu|
| | | | |115| | | | |120| | | | |125| |
|Leu|Thr|Arg|Leu|Trp|Met|Val|Asp|Ser|Ile|Glu|Arg|Leu|Gly|Ile|Asp|
| | |130| | | | |135| | | | |140| | | |
|Arg|His|Phe|Gln|Asn|Glu|Ile|Arg|Val|Ala|Leu|Asp|Tyr|Val|Tyr|Ser|
|145| | | | |150| | | | |155| | | | |160|
|Tyr|Trp|Lys|Glu|Lys|Glu|Gly|Ile|Gly|Cys|Gly|Arg|Asp|Ser|Thr|Phe|
| | | | |165| | | | |170| | | | |175| |
|Pro|Asp|Leu|Asn|Ser|Thr|Ala|Leu|Ala|Leu|Arg|Thr|Leu|Arg|Leu|His|
| | | | |180| | | | |185| | | | |190| |
|Gly|Tyr|Asn|Val|Ser|Ser|Asp|Val|Leu|Glu|Tyr|Phe|Lys|Asp|Gln|Lys|
| | | | |195| | | | |200| | | | |205| |
|Gly|His|Phe|Ala|Cys|Pro|Ala|Ile|Leu|Thr|Glu|Gly|Gln|Ile|Thr|Arg|
| | |210| | | | |215| | | | |220| | | |
|Ser|Val|Leu|Asn|Leu|Tyr|Arg|Ala|Ser|Leu|Val|Ala|Phe|Pro|Gly|Glu|
|225| | | | |230| | | | |235| | | | |240|
|Lys|Val|Met|Glu|Glu|Ala|Glu|Ile|Phe|Ser|Ala|Ser|Tyr|Leu|Lys|Glu|
| | | | |245| | | | |250| | | | |255| |
|Val|Leu|Gln|Lys|Ile|Pro|Val|Ser|Ser|Phe|Ser|Arg|Glu|Ile|Glu|Tyr|
| | | |260| | | | |265| | | | |270| | |
|Val|Leu|Glu|Tyr|Gly|Trp|His|Thr|Asn|Leu|Pro|Arg|Leu|Glu|Ala|Arg|
| | |275| | | | |280| | | | |285| | | |
|Asn|Tyr|Ile|Asp|Val|Tyr|Gly|Gln|Asp|Ser|Tyr|Glu|Ser|Ser|Asn|Glu|
| |290| | | | |295| | | | |300| | | | |
|Met|Pro|Tyr|Val|Asn|Thr|Gln|Lys|Leu|Leu|Lys|Leu|Ala|Lys|Leu|Glu|
|305| | | | |310| | | | |315| | | | |320|
|Phe|Asn|Ile|Phe|His|Ser|Leu|Gln|Gln|Lys|Glu|Leu|Gln|Tyr|Ile|Ser|
| | | | |325| | | | |330| | | | |335| |
|Arg|Trp|Trp|Lys|Asp|Ser|Cys|Ser|Ser|His|Leu|Thr|Phe|Thr|Arg|His|
| | | |340| | | | |345| | | | |350| | |
|Arg|His|Val|Glu|Tyr|Tyr|Thr|Met|Ala|Ser|Cys|Ile|Ser|Met|Glu|Pro|
| | |355| | | | |360| | | | |365| | | |
|Lys|His|Ser|Ala|Phe|Arg|Leu|Gly|Phe|Val|Lys|Thr|Cys|His|Leu|Leu|
| |370| | | | |375| | | | |380| | | | |
|Thr|Val|Leu|Asp|Asp|Met|Tyr|Asp|Thr|Phe|Gly|Thr|Leu|Asp|Glu|Leu|
|385| | | | |390| | | | |395| | | | |400|
|Gln|Leu|Phe|Thr|Thr|Ala|Phe|Lys|Arg|Trp|Asp|Leu|Ser|Glu|Thr|Lys|
| | | | |405| | | | |410| | | | |415| |

```
Cys Leu Pro Glu Tyr Met Lys Ala Val Tyr Met Asp Leu Tyr Gln Cys
            420                 425                 430
Leu Asn Glu Leu Ala Gln Glu Ala Glu Lys Thr Gln Gly Arg Asp Thr
            435                 440                 445
Leu Asn Tyr Ile Arg Asn Ala Tyr Glu Ser His Phe Asp Ser Phe Met
        450                 455                 460
His Glu Ala Lys Trp Ile Ser Ser Gly Tyr Leu Pro Thr Phe Glu Glu
465                 470                 475                 480
Tyr Leu Lys Asn Gly Lys Val Ser Ser Gly Ser Arg Thr Ala Thr Leu
                485                 490                 495
Gln Pro Ile Leu Thr Leu Asp Val Pro Leu Pro Asn Tyr Ile Leu Gln
            500                 505                 510
Glu Ile Asp Tyr Pro Ser Arg Phe Asn Asp Leu Ala Ser Ser Leu Leu
        515                 520                 525
Arg Leu Arg Gly Asp Thr Arg Cys Tyr Lys Ala Asp Arg Ala Arg Gly
        530                 535                 540
Glu Glu Ala Ser Ala Ile Ser Cys Tyr Met Lys Asp His Pro Gly Ser
545                 550                 555                 560
Thr Glu Glu Asp Ala Leu Asn His Ile Asn Val Met Ile Ser Asp Ala
                565                 570                 575
Ile Arg Glu Leu Asn Trp Glu Leu Leu Arg Pro Asp Ser Lys Ser Pro
            580                 585                 590
Ile Ser Ser Lys Lys His Ala Phe Asp Ile Thr Arg Ala Phe His His
                595                 600                 605
Leu Tyr Lys Tyr Arg Asp Gly Tyr Thr Val Ala Ser Ser Glu Thr Lys
        610                 615                 620
Asn Leu Val Met Lys Thr Val Leu Glu Pro Val Ala Leu
625                 630                 635
```

<210> SEQ ID NO 70
<211> LENGTH: 696
<212> TYPE: DNA
<213> ORGANISM: Abies grandis

<400> SEQUENCE: 70

```
gcatttaaga gatgggatcc gtctgccaca gatttgcttc cagagtatat gaaagggttg      60
tacatggtgg tttacgaaac cgtaaatgaa attgctcgag aggcagacaa gtctcaaggc     120
cgagagacgc tcaacgatgc tcgacgagct tgggaggcct atcttgattc gtatatgaaa     180
gaagctgagt ggatctccag tggttatctg ccaacgtttg aggagtacat ggagaccagc     240
aaagttagtt ttggttatcg catattcgca ttgcaaccca tcctcactat ggatgttccc     300
cttactcacc acatcctgca ggaaatagac tttccattga ggtttaatga cttaatatgt     360
tccatccttc gacttaaaaa tgacactcgc tgctacaagg cggacagggc cgtggagaa      420
gaagcttcgt gtatatcgtg ttatatgaaa gagaatcctg atcaacaga ggaagatgct      480
atcaatcata tcaacgctat ggtcaataac ttaatcaaag aagtgaattg ggagcttctc     540
cgacaggacg gcaccgctca tattgcttgc aagaaacacg cttttgacat cctcaaaggt     600
tcccttcacg gctacaaata ccgagatggg ttcagcgttg ccaacaagga aaccaagaat     660
tgggtgagga gaacagtcct tgagtctgtg cctttg                                696
```

<210> SEQ ID NO 71
<211> LENGTH: 20
<212> TYPE: DNA

<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(20)
<223> OTHER INFORMATION: Reverse RACE primer 10-2

<400> SEQUENCE: 71
acgaagcttc ttctccacgg                                              20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(20)
<223> OTHER INFORMATION: Reverse RACE primer 10-4

<400> SEQUENCE: 72
ggatcccatc tcttaactgc                                              20

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(27)
<223> OTHER INFORMATION: PCR primer AP1

<400> SEQUENCE: 73
ccatcctaat acgactcact atagggc                                      27

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(23)
<223> OTHER INFORMATION: PCR primer AP2

<400> SEQUENCE: 74
actcactata gggctcgagc ggc                                          23

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(24)
<223> OTHER INFORMATION: PCR primer AG9F

<400> SEQUENCE: 75

-continued

```
atggctcttg tttctatctt gccc                                              24
```

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(24)
<223> OTHER INFORMATION: PCR primer AG9R

<400> SEQUENCE: 76

```
ttacaaaggc acagactcaa ggac                                              24
```

<210> SEQ ID NO 77
<211> LENGTH: 1890
<212> TYPE: DNA
<213> ORGANISM: Abies grandis
<220> FEATURE:
<221> NAME/KEY: CDS
<222> LOCATION: (1)..(1890)

<400> SEQUENCE: 77

```
atg gct ctt gtt tct atc ttg ccc ttg tct tcc aaa tcg gtc ctg cac        48
Met Ala Leu Val Ser Ile Leu Pro Leu Ser Ser Lys Ser Val Leu His
 1               5                  10                  15 aaa tcg tgg atc gtt tct act tat gag cat aag gct atc agt aga aca        96
Lys Ser Trp Ile Val Ser Thr Tyr Glu His Lys Ala Ile Ser Arg Thr
             20                  25                  30 atc cca aat ctt gga ttg cgt ggg cga ggg aaa tct gtg aca cat tcc       144
Ile Pro Asn Leu Gly Leu Arg Gly Arg Gly Lys Ser Val Thr His Ser
         35                  40                  45 ctg aga atg agt ttg agc acc gca gtc tct gat gat cat ggt gta caa       192
Leu Arg Met Ser Leu Ser Thr Ala Val Ser Asp Asp His Gly Val Gln
     50                  55                  60 aga cgc ata gtc gag ttt cat tcc aat ctg tgg gac gac gat ttc ata       240
Arg Arg Ile Val Glu Phe His Ser Asn Leu Trp Asp Asp Asp Phe Ile
 65                  70                  75                  80 caa tct cta tca acg cct tat ggg gca cct tca tac cgt gaa cgt gct       288
Gln Ser Leu Ser Thr Pro Tyr Gly Ala Pro Ser Tyr Arg Glu Arg Ala
                 85                  90                  95 gat aga ctt att gtg gaa gta aag ggt ata ttc act tca att tca gcg       336
Asp Arg Leu Ile Val Glu Val Lys Gly Ile Phe Thr Ser Ile Ser Ala
            100                 105                 110 gaa gat gga gaa cta atc act ccc ctc aat gat ctc att caa cgc ctt       384
Glu Asp Gly Glu Leu Ile Thr Pro Leu Asn Asp Leu Ile Gln Arg Leu
        115                 120                 125 tta atg gtc gat aac gtt gaa cgt tta ggg att gat aga cat ttc aaa       432
Leu Met Val Asp Asn Val Glu Arg Leu Gly Ile Asp Arg His Phe Lys
    130                 135                 140 aat gag ata aaa gca gca cta gac tat gtt tac agt tat tgg aac gaa       480
Asn Glu Ile Lys Ala Ala Leu Asp Tyr Val Tyr Ser Tyr Trp Asn Glu
145                 150                 155                 160 aaa ggc att ggc agt gga agt gat agt ggt gtt gct gat ctc aac tca       528
Lys Gly Ile Gly Ser Gly Ser Asp Ser Gly Val Ala Asp Leu Asn Ser
                165                 170                 175 act gcc ctg ggg ttt cga att ctt cga cta cac gga tac agt gtt tct       576
Thr Ala Leu Gly Phe Arg Ile Leu Arg Leu His Gly Tyr Ser Val Ser
            180                 185                 190 tca gat gtg ttg gaa cac ttc aaa gag gag aag gag aag ggg cag ttt       624
```

```
                                                        -continued

Ser Asp Val Leu Glu His Phe Lys Glu Glu Lys Glu Lys Gly Gln Phe
        195                 200                 205 gta tgt tcg gcc atc caa aca gag gaa gag ata aaa agc gtt ctg aat      672
Val Cys Ser Ala Ile Gln Thr Glu Glu Glu Ile Lys Ser Val Leu Asn
210                 215                 220 tta ttt cgg gcc tcc ctc att gcc ttt cct ggg gag aaa gtt atg gaa      720
Leu Phe Arg Ala Ser Leu Ile Ala Phe Pro Gly Glu Lys Val Met Glu
225                 230                 235                 240 gag gct gaa atc ttc tct aaa ata tat tta aaa gaa gcc tta caa aat      768
Glu Ala Glu Ile Phe Ser Lys Ile Tyr Leu Lys Glu Ala Leu Gln Asn
            245                 250                 255 att gct gtc tcc agt ctt tca cga gag ata gag tac gtt ctg gag gat      816
Ile Ala Val Ser Ser Leu Ser Arg Glu Ile Glu Tyr Val Leu Glu Asp
                260                 265                 270 ggt tgg caa aca aat atg cca aga ttg gaa aca agg aac tac atc gat      864
Gly Trp Gln Thr Asn Met Pro Arg Leu Glu Thr Arg Asn Tyr Ile Asp
            275                 280                 285 gta ttg gga gag aac gat cgt gat gag acg tta tat atg aac atg gag      912
Val Leu Gly Glu Asn Asp Arg Asp Glu Thr Leu Tyr Met Asn Met Glu
        290                 295                 300 aaa ctt tta gaa att gca aaa ttg gag ttc aat att ttt cac tcc tta      960
Lys Leu Leu Glu Ile Ala Lys Leu Glu Phe Asn Ile Phe His Ser Leu
305                 310                 315                 320 caa cag aga gag cta aaa gac ctc tcc aga tgg tgg aaa gat tcg ggt     1008
Gln Gln Arg Glu Leu Lys Asp Leu Ser Arg Trp Trp Lys Asp Ser Gly
            325                 330                 335 ttc tct cac ctg aca ttt tct cgg cat cgt cat gtg gaa ttc tac gct     1056
Phe Ser His Leu Thr Phe Ser Arg His Arg His Val Glu Phe Tyr Ala
        340                 345                 350 ctg gca tct tgc att gaa act gat cgc aaa cat tcc gga ttc aga ctc     1104
Leu Ala Ser Cys Ile Glu Thr Asp Arg Lys His Ser Gly Phe Arg Leu
    355                 360                 365 ggc ttt gcc aaa atg tgt cat ctt atc acg gtt ttg gac gat ata tac     1152
Gly Phe Ala Lys Met Cys His Leu Ile Thr Val Leu Asp Asp Ile Tyr
370                 375                 380 gac acc ttt gga aca atg gag gag ctg gaa ctc ttc act gca gca ttt     1200
Asp Thr Phe Gly Thr Met Glu Glu Leu Glu Leu Phe Thr Ala Ala Phe
385                 390                 395                 400 aag aga tgg gat ccg tct gcc aca gat ttg ctt cca gag tat atg aaa     1248
Lys Arg Trp Asp Pro Ser Ala Thr Asp Leu Leu Pro Glu Tyr Met Lys
            405                 410                 415 ggg ttg tac atg gtg gtt tac gaa acc gta aat gaa att gct cga gag     1296
Gly Leu Tyr Met Val Val Tyr Glu Thr Val Asn Glu Ile Ala Arg Glu
        420                 425                 430 gca gac aag tct caa ggc cga gag acg ctc aac gat gct cga cga gct     1344
Ala Asp Lys Ser Gln Gly Arg Glu Thr Leu Asn Asp Ala Arg Arg Ala
    435                 440                 445 tgg gag gcc tat ctt gat tcg tat atg aaa gaa gct gag tgg atc tcc     1392
Trp Glu Ala Tyr Leu Asp Ser Tyr Met Lys Glu Ala Glu Trp Ile Ser
450                 455                 460 agt ggt tat ctg cca acg ttt gag gag tac atg gag acc agc aaa gtt     1440
Ser Gly Tyr Leu Pro Thr Phe Glu Glu Tyr Met Glu Thr Ser Lys Val
465                 470                 475                 480 agt ttt ggt tat cgc ata ttc gca ttg caa ccc atc ctc act atg gat     1488
Ser Phe Gly Tyr Arg Ile Phe Ala Leu Gln Pro Ile Leu Thr Met Asp
            485                 490                 495 gtt ccc ctt act cac cac atc ctg cag gaa ata gac ttt cca ttg agg     1536
Val Pro Leu Thr His His Ile Leu Gln Glu Ile Asp Phe Pro Leu Arg
        500                 505                 510
```

```
ttt aat gac tta ata tgt tcc atc ctt cga ctt aaa aat gac act cgc    1584
Phe Asn Asp Leu Ile Cys Ser Ile Leu Arg Leu Lys Asn Asp Thr Arg
    515                 520                 525 tgc tac aag gcg gac agg gcc cgt gga gaa gaa gct tcg tgt ata tcg    1632
Cys Tyr Lys Ala Asp Arg Ala Arg Gly Glu Glu Ala Ser Cys Ile Ser
530                 535                 540 tgt tat atg aaa gag aat cct gga tca aca gag gaa gat gct atc aat    1680
Cys Tyr Met Lys Glu Asn Pro Gly Ser Thr Glu Glu Asp Ala Ile Asn
545                 550                 555                 560 cat atc aac gct atg gtc aat aac tta atc aaa gaa gtg aat tgg gag    1728
His Ile Asn Ala Met Val Asn Asn Leu Ile Lys Glu Val Asn Trp Glu
            565                 570                 575 ctt ctc cga cag gac ggc acc gct cat att gct tgc aag aaa cac gct    1776
Leu Leu Arg Gln Asp Gly Thr Ala His Ile Ala Cys Lys Lys His Ala
        580                 585                 590 ttt gac atc ctc aaa ggt tcc ctt cac ggc tac aaa tac cga gat ggg    1824
Phe Asp Ile Leu Lys Gly Ser Leu His Gly Tyr Lys Tyr Arg Asp Gly
    595                 600                 605 ttc agc gtt gcc aac aag gaa acc aag aat tgg gtg agg aga aca gtc    1872
Phe Ser Val Ala Asn Lys Glu Thr Lys Asn Trp Val Arg Arg Thr Val
610                 615                 620 ctt gag tct gtg cct ttg                                            1890
Leu Glu Ser Val Pro Leu
625             630
```

<210> SEQ ID NO 78
<211> LENGTH: 630
<212> TYPE: PRT
<213> ORGANISM: Abies grandis

<400> SEQUENCE: 78

```
Met Ala Leu Val Ser Ile Leu Pro Leu Ser Ser Lys Ser Val Leu His
1               5                   10                  15

Lys Ser Trp Ile Val Ser Thr Tyr Glu His Lys Ala Ile Ser Arg Thr
            20                  25                  30

Ile Pro Asn Leu Gly Leu Arg Gly Arg Gly Lys Ser Val Thr His Ser
        35                  40                  45

Leu Arg Met Ser Leu Ser Thr Ala Val Ser Asp Asp His Gly Val Gln
    50                  55                  60

Arg Arg Ile Val Glu Phe His Ser Asn Leu Trp Asp Asp Phe Ile
65                  70                  75                  80

Gln Ser Leu Ser Thr Pro Tyr Gly Ala Pro Ser Tyr Arg Glu Arg Ala
            85                  90                  95

Asp Arg Leu Ile Val Glu Val Lys Gly Ile Phe Thr Ser Ile Ser Ala
        100                 105                 110

Glu Asp Gly Glu Leu Ile Thr Pro Leu Asn Asp Leu Ile Gln Arg Leu
    115                 120                 125

Leu Met Val Asp Asn Val Glu Arg Leu Gly Ile Asp Arg His Phe Lys
130                 135                 140

Asn Glu Ile Lys Ala Ala Leu Asp Tyr Val Tyr Ser Tyr Trp Asn Glu
145                 150                 155                 160

Lys Gly Ile Gly Ser Gly Ser Asp Ser Gly Val Ala Asp Leu Asn Ser
            165                 170                 175

Thr Ala Leu Gly Phe Arg Ile Leu Arg Leu His Gly Tyr Ser Val Ser
        180                 185                 190

Ser Asp Val Leu Glu His Phe Lys Glu Glu Lys Glu Lys Gly Gln Phe
    195                 200                 205
```

-continued

```
Val Cys Ser Ala Ile Gln Thr Glu Glu Ile Lys Ser Val Leu Asn
    210                 215                 220
Leu Phe Arg Ala Ser Leu Ile Ala Phe Pro Gly Lys Val Met Glu
225                 230                 235                 240
Glu Ala Glu Ile Phe Ser Lys Ile Tyr Leu Lys Glu Ala Leu Gln Asn
                    245                 250                 255
Ile Ala Val Ser Ser Leu Ser Arg Glu Ile Glu Tyr Val Leu Glu Asp
                260                 265                 270
Gly Trp Gln Thr Asn Met Pro Arg Leu Glu Thr Arg Asn Tyr Ile Asp
                275                 280                 285
Val Leu Gly Glu Asn Asp Arg Asp Glu Thr Leu Tyr Met Asn Met Glu
    290                 295                 300
Lys Leu Leu Glu Ile Ala Lys Leu Glu Phe Asn Ile Phe His Ser Leu
305                 310                 315                 320
Gln Gln Arg Glu Leu Lys Asp Leu Ser Arg Trp Trp Lys Asp Ser Gly
                    325                 330                 335
Phe Ser His Leu Thr Phe Ser Arg His Arg His Val Glu Phe Tyr Ala
                340                 345                 350
Leu Ala Ser Cys Ile Glu Thr Asp Arg Lys His Ser Gly Phe Arg Leu
            355                 360                 365
Gly Phe Ala Lys Met Cys His Leu Ile Thr Val Leu Asp Asp Ile Tyr
370                 375                 380
Asp Thr Phe Gly Thr Met Glu Glu Leu Glu Leu Phe Thr Ala Ala Phe
385                 390                 395                 400
Lys Arg Trp Asp Pro Ser Ala Thr Asp Leu Leu Pro Glu Tyr Met Lys
                405                 410                 415
Gly Leu Tyr Met Val Val Tyr Glu Thr Val Asn Glu Ile Ala Arg Glu
                420                 425                 430
Ala Asp Lys Ser Gln Gly Arg Glu Thr Leu Asn Asp Ala Arg Arg Ala
            435                 440                 445
Trp Glu Ala Tyr Leu Asp Ser Tyr Met Lys Glu Ala Glu Trp Ile Ser
    450                 455                 460
Ser Gly Tyr Leu Pro Thr Phe Glu Glu Tyr Met Glu Thr Ser Lys Val
465                 470                 475                 480
Ser Phe Gly Tyr Arg Ile Phe Ala Leu Gln Pro Ile Leu Thr Met Asp
                485                 490                 495
Val Pro Leu Thr His Ile Leu Gln Glu Ile Asp Phe Pro Leu Arg
                500                 505                 510
Phe Asn Asp Leu Ile Cys Ser Ile Leu Arg Leu Lys Asn Asp Thr Arg
    515                 520                 525
Cys Tyr Lys Ala Asp Arg Ala Arg Gly Glu Glu Ala Ser Cys Ile Ser
    530                 535                 540
Cys Tyr Met Lys Glu Asn Pro Gly Ser Thr Glu Glu Asp Ala Ile Asn
545                 550                 555                 560
His Ile Asn Ala Met Val Asn Asn Leu Ile Lys Glu Val Asn Trp Glu
                565                 570                 575
Leu Leu Arg Gln Asp Gly Thr Ala His Ile Ala Cys Lys Lys His Ala
                580                 585                 590
Phe Asp Ile Leu Lys Gly Ser Leu His Gly Tyr Lys Tyr Arg Asp Gly
            595                 600                 605
Phe Ser Val Ala Asn Lys Glu Thr Lys Asn Trp Val Arg Arg Thr Val
610                 615                 620
Leu Glu Ser Val Pro Leu
```

```
625             630
```

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence:
    oligonucleotide
<220> FEATURE:
<221> NAME/KEY: misc_feature
<222> LOCATION: (1)..(30)
<223> OTHER INFORMATION: Mutagenesis primer 6eBamHIF

<400> SEQUENCE: 79
caattaagag atgggacccg tccgcgatgg                                    30

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence:
    oligonucleotide
<220> FEATURE:
<221> NAME/KEY: misc_feature
<222> LOCATION: (1)..(30)
<223> OTHER INFORMATION: Mutagenesis primer 6eBamHIR

<400> SEQUENCE: 80
ccatcgcgga cgggtcccat ctcttaattg                                    30

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence:
    oligonucleotide
<220> FEATURE:
<221> NAME/KEY: misc_feature
<222> LOCATION: (1)..(30)
<223> OTHER INFORMATION: Mutagenesis primer 9eBamHIF

<400> SEQUENCE: 81
gcatttaaga gatgggaccc gtctgccaca                                    30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence:
    oligonucleotide
<220> FEATURE:
<221> NAME/KEY: misc_feature
<222> LOCATION: (1)..(30)
<223> OTHER INFORMATION: Mutagenesis primer 9eBamHIR

<400> SEQUENCE: 82
ctgtggcaga cgggtcccat ctcttaaatg                                    30

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence:
    oligonucleotide
<220> FEATURE:

<221> NAME/KEY: misc_feature
<222> LOCATION: (1)..(25)
<223> OTHER INFORMATION: Mutagenesis primer 732eNdeIF

<400> SEQUENCE: 83
cgagatgcca tacgtgaata cgcag                                    25

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(25)
<223> OTHER INFORMATION: mutagenesis primer 732eNde1R

<400> SEQUENCE: 84
ctgcgtattc acgtatggca tctcg                                    25

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(30)
<223> OTHER INFORMATION: PCR primer 6-Nde1-M

<400> SEQUENCE: 85
ctgatagcaa gctcatatgg ctcttctttc                               30

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(34)
<223> OTHER INFORMATION: PCR primer 6-NdeI-R

<400> SEQUENCE: 86
gcccacgcgt tcatatgag aatcagtaga tgcg                           34

<210> SEQ ID NO 87
<211> LENGTH: 29
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(29)
<223> OTHER INFORMATION: PCR primer 6-BamHI

<400> SEQUENCE: 87
cacccatagg ggatcctcag ttaatattg                                29

<210> SEQ ID NO 88
<211> LENGTH: 30

```
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(30)
<223> OTHER INFORMATION: PCR primer 8-NdeI-M

<400> SEQUENCE: 88
taagcgagca catatggctc tggtttcttc                                30

<210> SEQ ID NO 89
<211> LENGTH: 29
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(29)
<223> OTHER INFORMATION: PCR primer 8-BamHI

<400> SEQUENCE: 89
gcataaacgc atagcggatc ctacaccaa                                 29

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(29)
<223> OTHER INFORMATION: PCR primer 9-NdeI-M

<400> SEQUENCE: 90
cccggggatc ggacatatgg ctcttgtttc                                30

<210> SEQ ID NO 91
<211> LENGTH: 34
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(34)
<223> OTHER INFORMATION: PCR primer 9_BamHI

<400> SEQUENCE: 91
ggtcgactct agaggatcca ctagtgatat ggat                           34

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(27)
<223> OTHER INFORMATION: PCR primer 11-NdeI-M

<400> SEQUENCE: 92
```
gaacatatgg ctctcctttc tatcgta            27

<210> SEQ ID NO 93
<211> LENGTH: 31
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(31)
<223> OTHER INFORMATION: PCR primer 11-NdeI-R

<400> SEQUENCE: 93
ggtggtggtg tacatatgag acgcatacgg g            31

<210> SEQ ID NO 94
<211> LENGTH: 34
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(34)
<223> OTHER INFORMATION: PCR primer 11-BamHI

<400> SEQUENCE: 94
gagactagac tggatcccat atacactgta atgg            34

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(24)
<223> OTHER INFORMATION: PCR primer 2-NdeI-M

<400> SEQUENCE: 95
caaagggagc acatatggct ctgg            24

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(30)
<223> OTHER INFORMATION: PCR primer 2-NdeI-R

<400> SEQUENCE: 96
ctgatgatgg tcatatgaga cgcataggtg            30

<210> SEQ ID NO 97
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

```
<220> FEATURE:
<221> NAME/KEY: misc_feature
<222> LOCATION: (1)..(28)
<223> OTHER INFORMATION: PCR primer 2-BamHI

<400> SEQUENCE: 97
gaccttatta ttatggatcc ggttatag                                    28

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(30)
<223> OTHER INFORMATION: PCR primer 3-NdeI-R

<400> SEQUENCE: 98
ccgatgatgg tcatatgaga cgcatgggcg                                  30

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(30)
<223> OTHER INFORMATION: PCR primer 3-BamHI

<400> SEQUENCE: 99
gggcatagat ttgagcggat cctacaaagg                                  30

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(24)
<223> OTHER INFORMATION: Mutagenesis primer 3e1BamHIF

<400> SEQUENCE: 100
cgtttgggaa tccatagaca tttc                                        24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(24)
<223> OTHER INFORMATION: Mutagenesis primer 3e1BamHIR

<400> SEQUENCE: 101
gaaatgtcta tggattccca aacg                                        24

<210> SEQ ID NO 102
```

```
<211> LENGTH: 26
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(26)
<223> OTHER INFORMATION: PCR primer 3e2BamHIF

<400> SEQUENCE: 102
gaagagatgg gacccgtcct cgatag                                    26

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(26)
<223> OTHER INFORMATION: Mutagenesis primer 3e2BamHIR

<400> SEQUENCE: 103
ctatcgagga cgggtcccat ctcttc                                    26

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(25)
<223> OTHER INFORMATION: Mutagenesis primer 3e1NdeIF

<400> SEQUENCE: 104
gaacacgaag tcctatgtga agagc                                     25

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(25)
<223> OTHER INFORMATION: Mutagenesis primer 3e1NdeIR

<400> SEQUENCE: 105
gctcttcaca taggacttcg tgttc                                     25

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(25)
<223> OTHER INFORMATION: Mutagenesis primer 3e3NdeIF
```

```
<400> SEQUENCE: 106
gatacgctca cttatgctcg ggaag                                         25

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(25)
<223> OTHER INFORMATION: Mutagenesis primer 3e2NdeIR

<400> SEQUENCE: 107
cttcccgagc ataagtgagc gtatc                                         25
```

US 6,429,014 B1

MONOTERPENE SYNTHASES FROM GRAND FIR (ABIES GRANDIS)

RELATED APPLICATIONS

The present application is a continuation-in-part of international application serial number US98/14528, filed on Jul. 10, 1998, which claims benefit of priority from United States provisional application serial No. 60/052,249 filed on Jul. 11, 1997.

This invention was funded in part by grant GM-3135A from the National Institutes of Health and by grant 97-35302-4432 from the United States Department of Agriculture. The government has certain rights in this invention.

FIELD OF THE INVENTION

The present invention relates to nucleic acid sequences which code for monoterpene synthases from gymnosperm plant species, in particular from Grand fir (Abies grandis), including (−)-camphene synthase, (−)-β-phellandrene synthase, terpinolene synthase, (−)-limonene/(−)-α-pinene synthase, limonene synthase, myrcene synthase, and pinene synthase, to vectors containing the sequences, to host cells containing the sequences, to plant seeds expressing the sequences and to methods of producing recombinant monoterpene synthases and their mutants.

BACKGROUND OF THE INVENTION

Chemical defense of conifer trees against bark beetles and their associated fungal pathogens relies primarily upon constitutive and inducible oleoresin biosynthesis (Johnson, M. A., and Croteau, R. (1987) in *Ecology and Metabolism of Plant Lipids* (Fuller, G., and Nes, W. D., eds.) pp. 76–91, American Chemical Society Symposium Series 325, Washington, D.C.; Gijzen, M., Lewinsohn, E., Savage, T. J., and Croteau, R. B. (1993) in *Bioactive Volatile Compounds from Plants* (Teranishi, R., Buttery, R. G., and Sugisawa, H., eds.) pp. 8–22, American Chemical Society Symposium Series 525, Washington, D.C.). This defensive secretion is a complex mixture of monoterpene and sesquiterpene olefins (turpentine) and diterpene resin acids (rosin) that is synthesized constitutively in the epithelial cells of specialized structures, such as resin ducts and blisters or, in the case of induced oleoresin formation, in undifferentiated cells surrounding wound sites (Lewinsohn, E., Gijzen, M., Savage, T. J., and Croteau, R. (1991) *Plant Physiol.* 96:38–43). The volatile fraction of conifer oleoresin, which is toxic to both bark beetles and their fungal associates (Raffa, K. F., Berryman, A. A., Simasko, J., Teal, W., and Wong, B. L. (1985) *Environ. Entomol.* 14:552–556), may consist of up to 30 different monoterpenes (Lewinsohn, E., Savage, T. J., Gijzen, M., and Croteau, R. (1993) *Phytochem. Anal.* 4:220–225), including acyclic types (e.g., myrcene), monocyclic types (e.g., limonene) and bicyclic types (e.g., pinenes) (FIG. 1). Although the oleoresin is toxic, many bark beetle species nevertheless employ turpentine volatiles in host selection and can convert various monoterpene components into aggregation or sex pheromones to promote coordinated mass attack of the host (Gijzen, M., Lewinsohn, E., Savage, T. J., and Croteau, R. B. (1993) in *Bioactive Volatile Compounds from Plants* (Teranishi, R., Buttery, R. G., and Sugisawa, H., eds.) pp. 8–22, American Chemical Society Symposium Series 525, Washington, D.C.; Byers, J. A. (1995) in *Chemical Ecology of Insects* 2 (Cardé, R. T., and Bell, W. J., eds.) pp. 154–213, Chapman and Hall, New York). In Grand fir (Abies grandis), increased formation of oleoresin monoterpenes, sesquiterpenes and diterpenes is induced by bark beetle attack (Lewinsohn, E., Gijzen, M., Savage, T. J., and Croteau, †R. (1991) *Plant Physiol.* 96:38–43; Raffa, K. F., and Berryman, A. A. (1982) *Can. Etomol.* 114:797–810; Lewinsohn, E., Gijzen, M., and Croteau, R. (1991) *Plant Physiol.* 96:44–49), and this inducible defense response is mimicked by mechanically wounding sapling stems (Lewinsohn, E., Gijzen, M., Savage, T. J., and Croteau, R. (1991) *Plant Physiol.* 96:38–43; Lewinsohn, E., Gijzen, M., and Croteau, R. (1991) *Plant Physiol.* 96:44–49; Funk, C., Lewinsohn, E., Stofer Vogel, B., Steele C., and Croteau, R. (1994) *Plant Physiol.* 106:999–1005). Therefore, Grand fir has been developed as a model system to study the biochemical and molecular genetic regulation of constitutive and inducible terpene biosynthesis in conifers (Steele, C., Lewinsohn, E., and Croteau, R. (1995) *Proc. Natl. Acad Sci. USA* 92:4164–4168).

Most monoterpenes are derived from geranyl diphosphate, the ubiquitous $C_{10}$ intermediate of the isoprenoid pathway, by synthases which catalyze the divalent metal ion-dependent ionization (to 1, FIG. 1) and isomerization of this substrate to enzyme-bound linalyl diphosphate which, following rotation about C2–C3, undergoes a second ionization (to 2, FIG. 1) followed by cyclization to the α-terpinyl cation, the first cyclic intermediate en route to both monocyclic and bicyclic products (Croteau, R., and Cane, D. E. (1985) *Methods Enzymol.* 110:383–405; Croteau, R. (1987) *Chem. Rev.* 87:929–954) (FIG. 1). Acyclic monoterpenes, such as myrcene, may arise by deprotonation of carbocations 1 or 2, whereas the isomerization step to linalyl diphosphate is required in the case of cyclic types, such as limonene and pinenes, which cannot be derived from geranyl diphosphate directly because of the geometric impediment of the trans-double bond at C2–C3 (Croteau, R., and Cane, D. E. (1985) *Methods Enzymol* 110:383–405; Croteau, R. (1987) *Chem. Rev.* 87:929–954). Many monoterpene synthases catalyze the formation of multiple products, including acyclic, monocyclic and bicyclic types, by variations on this basic mechanism (Gambliel, H., and Croteau, R. (1984) *J. Biol. Chem.* 259:740–748; Croteau, R., Satterwhite, D. M., Cane, D. E., and Chang, C. C. (1988) *J. Biol. Chem.* 263:10063–10071; Croteau, R., and Satterwhite, D. M. (1989) *J. Biol. Chem.* 264:15309–15315). For example, (−)-limonene synthase, the principal monoterpene synthase of spearmint (Mentha spicata) and peppermint (M. x piperita), produces small amounts of myrcene, (−)-α-pinene and (−)-β-pinene in addition to the monocyclic product (Rajaonarivony, J. I. M., Gershenzon, J., and Croteau, R. (1992) *Arch. Biochem. Biophys.* 296:49–57; Colby, S. M., Alonso, W. R., Katahira, E. J., McGarvey, D. J., and Croteau, R. (1993) *J. Biol. Chem.* 268:23016–23024. Conversely, six different inducible monoterpene synthase activities have been demonstrated in extracts of wounded Grand fir stem (Gijzen, M., Lewinsohi, E., and Croteau, R. (1991) *Arch. Biochem. Biophys.* 289:267–273) indicating that formation of acyclic, monocyclic and bicyclic monoterpenes in this species involves several genes encoding distinct catalysts. The inducible (−)-pinene synthase has been purified (Lewinsohn, E., Gijzen, M., and Croteau, R. (1992) *Arch. Biochem. Biophys.* 293:167–173), and isotopically sensitive branching experiments employed to demonstrate that this enzyme synthesizes both (−)-α- and (−)-β-pinene (Wagschal, K., Savage, T. J., and Croteau, R. (1991) *Tetraheadon* 47:5933–5944).

Deciphering the molecular genetic control of oleoresinosis and examining structure-function relationships among the monoterpene synthases of Grand fir requires isolation of the cDNA species encoding these key enzymes. Although a protein-based cloning strategy was recently employed to acquire a cDNA for the major wound-inducible diterpene synthase from Grand fir, abietadiene synthase (Funk, C., Lewinsohn, E., Stofer Vogel, B., Steele C., and Croteau, R. (1994) *Plant Physiol.* 106:999–1005; LaFever, R. E., Stofer Vogel, B., and Croteau, R. (1994) *Arch. Biochem. Biophys.* 313:139–149; Stofer Vogel, B., Wildung, M. R., Vogel, G., and Croteau, R. (1996) *J. Biol. Chem.* 271:23262–23268), all attempts at the reverse genetic approach to cloning of Grand fir monoterpene synthases have failed (Steele, C., Lewinsohn, E., and Croteau, R. (1995) *Proc. Natl. Acad Sci. USA* 92:4164–4168). As an alternative, a similarity-based PCR strategy was developed (Steele, C., Lewinsohn, E., and Croteau, R. (1995) *Proc. Natl. Acad Sci. USA* 92:4164–4168) that employed sequence information from terpene synthases of angiosperm origin, namely a monoterpene synthase, (−)-4S-limonene synthase, from spearmint (*Mentha spicata*, Lamiaceae) (Colby, S. M., Alonso, W. R., Katahira, E. J., McGarvey, D. J., and Croteau, R. (1993) *J. Biol. Chem.* 268:23016–23024), a sesquiterpene synthase, 5-epi-aristolochene synthase, from tobacco (*Nicotiana tabacum*, Solanaceae) (Facchini, P. J., and Chappell, J. (1992) *Proc. Natl. Acad. Sci. USA* 89:11088–11092), and a diterpene synthase, casbene synthase, from castor bean (*Ricinus communis*, Euphorbiaceae) (Mau, C. J. D., and West, C. A. (1994) *Proc. Natl. Acad. Sci. USA* 91:8497–8501).

Monoterpenes have significant potential for cancer prevention and treatment. Monoterpenes such as limonene, perillyl alcohol, carvone, geraniol and farnesol not only reduce tumor incidence and slow tumor proliferation, but have also been reported to cause regression of established solid tumors by initiating apoptosis (Mills J. J., Chari R. S., Boyer I. J., Gould M. N., Jirtle R. L., *Cancer Res.,* 55:979–983, 1995). Terpenes have activity against cancers such as mammary, colon, and prostate. Clinical trials are being pursued (Seachrist L, *J. NIH Res.* 8:43) in patients with various types of advanced cancers to validate the health benefits of dietary terpenes for humans. However, terpenes are present in Western diets at levels that are probably inadequate for any significant preventive health benefits. Daily supplementation of the diet with a terpene concentrate (10–20 g/day) would appear to be the most rational strategy for dietary therapy of diagnosed cases of cancer. This invention envisages the production of such nutritionally beneficial terpenes in, for example, vegetable oils consumed daily via the engineering of relevant genes from Grand fir into oil seed crop plants such as oil seed brassica (canola), soybean and corn.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

SUMMARY OF THE INVENTION

Figure 1:
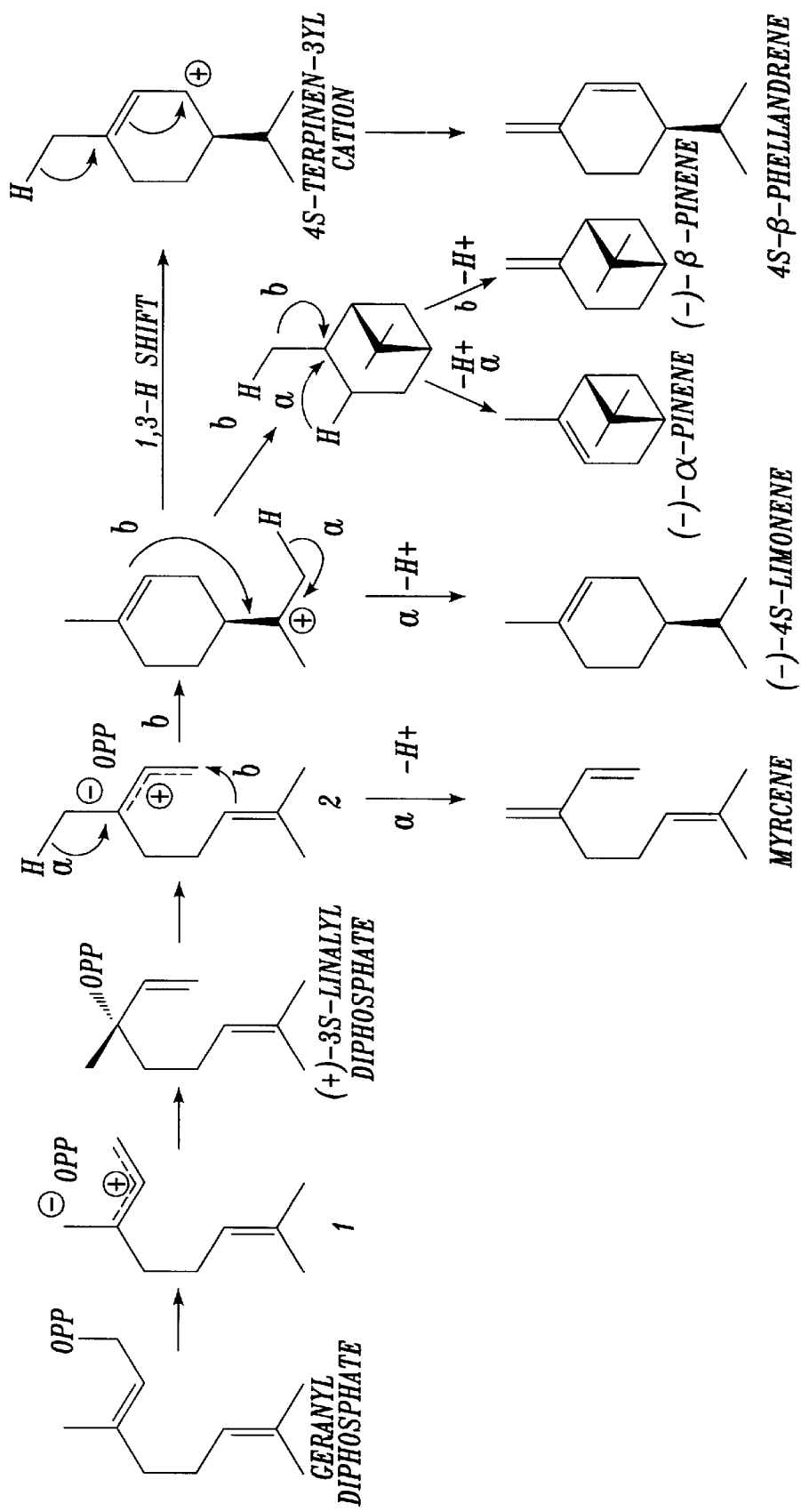
FIG. 1 is a schematic representation depicting the mechanism for the conversion of geranyl diphosphate to myrcene, (−)-limonene, β-phellandrene, (−)-α-pinene and (−)-β-pinene by monoterpene synthases from Grand fir. Formation of the monocyclic and bicyclic products requires preliminary isomerization of geranyl diphosphate to linalyl diphosphate. The acyclic product could be formed from either geranyl diphosphate or linalyl diphosphate via carbocations 1 or 2. OPP denotes the diphosphate moiety.
Figure 2:
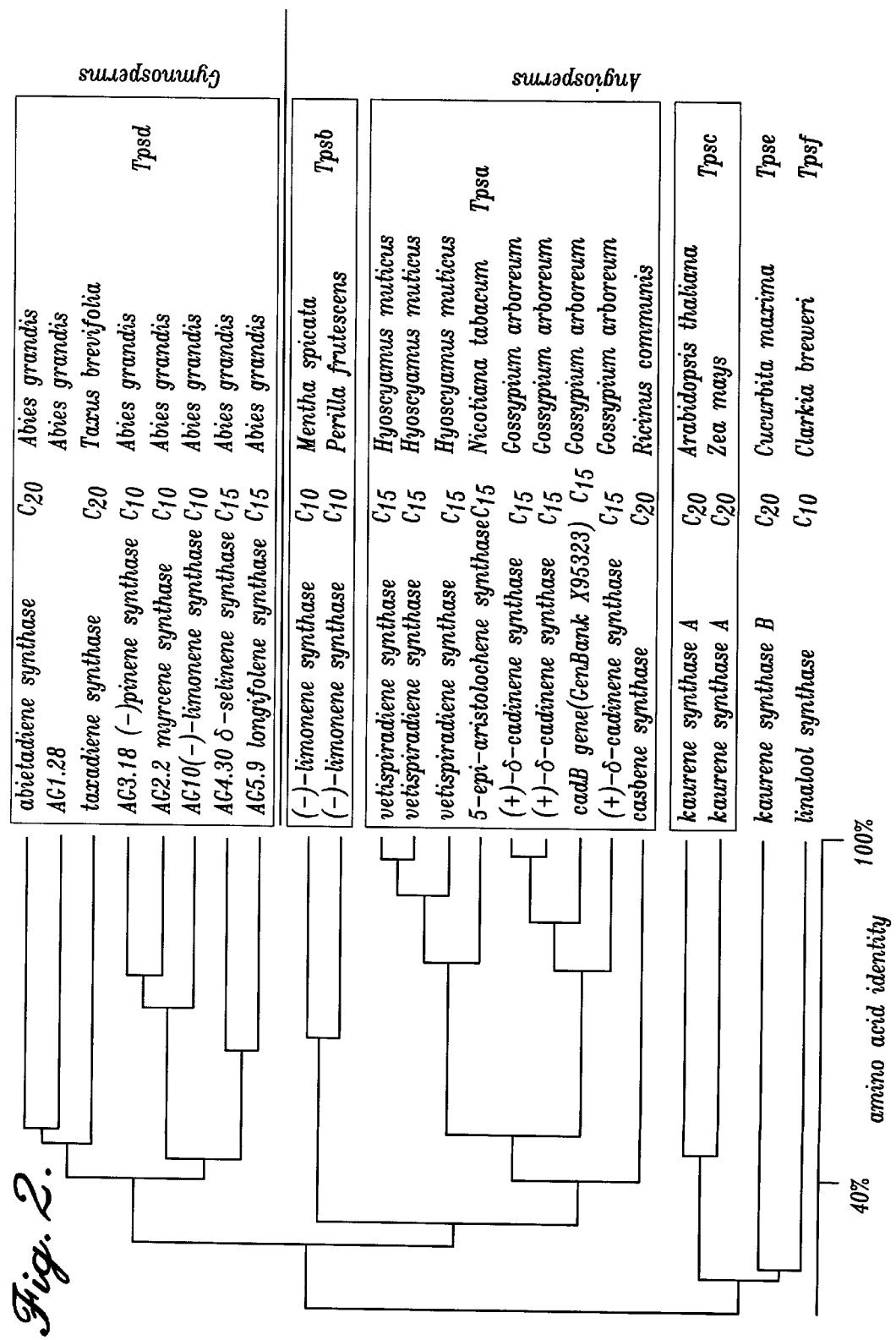
FIG. 2 is a sequence comparison of plant terpene synthases. A three-letter designation (Tps) for the gene family is proposed with sub-groups (Tpsa through Tpsf) defined by a minimum of 40% amino acid identity between members.

In accordance with the foregoing, cDNAs encoding (−)-camphene synthase, (−)-β-phellandrene synthase, terpinolene synthase, (−)-limonene/(−)-α-pinene synthase, myrcene synthase, (−)-limonene synthase and (−)-pinene synthase from Grand fir (*Abies grandis*) have been isolated and sequenced, and the corresponding amino acid sequences have been deduced. Accordingly, the present invention relates to isolated DNA sequences which code for the expression of monoterpene synthases, including (−)-camphene synthase, (−)-β-phellandrene synthase, terpinolene synthase, (−)-limonene/(−)-α-pinene synthase, myrcene synthase, (−)-limonene synthase and (−)-pinene synthase, and to isolated nucleic acid molecules that hybridize to portions of Grand fir monoterpene synthase cDNAs, as described more fully herein. In another aspect, the present invention relates to isolated monoterpene synthases, including isolated (−)-camphene synthase, (−)-β-phellandrene synthase, terpinolene synthase and (−)-limonene/(−)-α-pinene synthase. In other aspects, the present invention is directed to replicable recombinant cloning vehicles comprising a nucleic acid sequence, e.g., a DNA sequence which codes for a monoterpene synthase such as (−)-camphene synthase, (−)-β-phellandrene synthase, terpinolene synthase, (−)-limonene/(−)-α-pinene synthase, myrcene synthase, (−)-limonene synthase or (−)-pinene synthase, or for a base sequence sufficiently complementary to at least a portion of DNA or RNA encoding a monoterpene synthase such as (−)-camphene synthase, (−)-β-phellandrene synthase, terpinolene synthase, (−)-limonene/(−)-α-pinene synthase, myrcene synthase, (−)-limonene synthase or (−)-pinene synthase to enable hybridization therewith (e.g., antisense RNA or fragments of DNA complementary to a portion of DNA or RNA molecules encoding (−)-camphene synthase, (−)-β-phellandrene synthase, terpinolene synthase, (−)-limonene/(−)-α-pinene synthase, myrcene synthase, (−)-limonene synthase or (−)-pinene synthase which are useful as polymerase chain reaction primers or as probes for any of the foregoing synthases or related genes). In yet other aspects of the invention, modified host cells are provided that have been transformed, transfected, infected and/or injected with a recombinant cloning vehicle and/or DNA sequence of the invention. Thus, the present invention provides for the recombinant expression of (−)-camphene synthase, (−)-β-phellandrene synthase, terpinolene synthase, (−)-limonene/(−)-α-pinene synthase, myrcene synthase, (−)-limonene synthase and (−)-pinene synthase, and the inventive concepts may be used to facilitate the production, isolation and purification of significant quantities of recombinant (−)-camphene synthase, (−)-β-phellandrene synthase, terpinolene synthase, (−)-limonene/(−)-α-pinene synthase, myrcene synthase, (−)-limonene synthase and (−)-pinene synthase (or of their primary enzyme products) for subsequent use, to obtain expression or enhanced expression of (−)-camphene synthase, (−)-β-phellandrene synthase, terpinolene synthase, (−)-limonene/(−)-α-pinene synthase, myrcene synthase, (−)-limonene synthase and (−)-pinene synthase in microorganisms, animals or plants (including, but not limited to, Brassica, cotton, soybean, safflower, sunflower, coconut, palm, wheat, barley, rice, corn, oats, amaranth, pumpkin, squash, sesame, poppy, grape, mung beans, peanut, peas, beans, broad beans, chick peas, lentils, radish, alfalfa, cocoa, coffee, tree nuts, spinach, culinary herbs, berries, stone fruit and citrus), or may be otherwise employed in an environment where the regulation or expression of the foregoing monoterpene synthases is desired for the production of these synthases, or their enzyme products, or derivatives thereof. In another aspect, the present invention relates to manipulation of monoterpene production to enhance resistance to insects and/or accumulate nutritionally beneficial monoterpenes in oil seeds (such as seeds from Brassica, cotton, soybean, safflower, sunflower, coconut, palm, wheat, barley, rice, corn, oats, amaranth, pumpkin, squash, sesame, poppy, grape, mung beans, peanut, peas, beans, broad beans, chick peas, lentils, radish, alfalfa, cocoa, coffee and tree nuts) and other food stuffs.

DETAILED DESCRIPTION OF THE PREFERRED EMBODIMENT

As used herein, the terms "amino acid" and "amino acids" refer to all naturally occurring L-α-amino acids or their residues. The amino acids are identified by either the single-letter or three-letter designations:

| Asp | D | aspartic acid |
|-----|---|---------------|
| Thr | T | threonine |
| Ser | S | serine |
| Glu | E | glutamic acid |
| Pro | P | proline |
| Gly | G | glycine |
| Ala | A | alanine |
| Cys | C | cysteine |
| Val | V | valine |
| Met | M | methionine |
| Ile | I | isoleucine |
| Leu | L | leucine |
| Tyr | Y | tyrosine |
| Phe | F | phenylalanine |
| His | H | histidine |
| Lys | K | lysine |
| Arg | R | arginine |
| Trp | W | tryptophan |
| Gln | Q | glutamine |
| Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally-occurring bases (A, C, G or T). The four RNA bases are A,G,C and uracil ("U"). The nucleotide sequences described herein comprise a linear array of nucleotides connected by phosphodiester bonds between the 3' and 5' carbons of adjacent pentoses.

The term "percent identity" means the percentage of amino acids or nucleotides that occupy the same relative position when two amino acid sequences, or two nucleic acid sequences are aligned side by side.

The term "percent similarity" is a statistical measure of the degree of relatedness of two compared protein sequences. The percent similarity is calculated by a computer program that assigns a numerical value to each compared pair of amino acids based on chemical similarity (e.g., whether the compared amino acids are acidic, basic, hydrophobic, aromatic, etc.) and/or evolutionary distance as measured by the minimum number of base pair changes that would be required to convert a codon encoding one member of a pair of compared amino acids to a codon encoding the other member of the pair. Calculations are made after a best fit alignment of the two sequences have been made empirically by iterative comparison of all possible alignments. (Henikoff, S. and Henikoff, J. G., *Proc. Nat'l. Acad. Sci. USA* 89:10915–10919, 1992).

"Oligonucleotide" refers to short length single or double stranded sequences of deoxyribonucleotides linked via phosphodiester bonds. The oligonucleotides are chemically synthesized by known methods and purified, for example, on polyacrylamide gels.

The term "myrcene synthase" is used herein to mean an enzyme capable of generating multiple monoterpenes from geranyl diphosphate. The principal and characteristic monoterpene synthesized by myrcene synthase is myrcene, which constitutes at least about 50% of the monoterpene mixture synthesized by myrcene synthase from geranyl diphosphate.

The term "(−)-limonene synthase" is used herein to mean an enzyme capable of generating multiple monoterpenes from geranyl diphosphate. The principal and characteristic monoterpene synthesized by (−)-limonene synthase is (−)-limonene, which constitutes at least about 60% of the monoterpene mixture synthesized by (−)-limonene synthase from geranyl diphosphate.

The term "(−)-pinene synthase" is used herein to mean an enzyme capable of generating multiple monoterpenes from geranyl diphosphate. The principal and characteristic monoterpene synthesized by (−)-pinene synthase is (−)-pinene, which comprises at least about 50% of the monoterpene mixture synthesized by (−)-pinene synthase from geranyl diphosphate.

The term "(−)-camphene synthase" is used herein to mean an enzyme capable of generating multiple monoterpenes from geranyl diphosphate. The principal and characteristic monoterpene synthesized by (−)-camphene synthase is (−)-camphene, which comprises at least about 50% of the monoterpene mixture synthesized by (−)-camphene synthase from geranyl diphosphate.

The term "(−)-β-phellandrene synthase" is used herein to mean an enzyme capable of generating multiple monoterpenes from geranyl diphosphate. The principal and characteristic monoterpene synthesized by (−)-β-phellandrene synthase is (−)-β-phellandrene, which comprises at least about 50% of the monoterpene mixture synthesized by (−)-β-phellandrene synthase from geranyl diphosphate.

The term "terpinolene synthase" is used herein to mean an enzyme capable of generating multiple monoterpenes from geranyl diphosphate. The principal and characteristic monoterpene synthesized by terpinolene synthase is terpinolene which comprises at least about 40% of the monoterpene mixture synthesized by terpinolene synthase from geranyl diphosphate.

The term (−)-limonene/(−)-α-pinene synthase is used herein to mean an enzyme capable of generating multiple monoterpenes from geranyl diphosphate. The principal and characteristic monoterpenes synthesized by (−)-limonene/(−)-α-pinene synthase are (−)-limonene and (−)-α-pinene which comprise at least about 35% and 25%, respectively, of the monoterpene mixture synthesized by (−)-limonene/(−)-α-pinene synthase from geranyl diphosphate.

The abbreviation "SSPE" refers to a buffer used in nucleic acid hybridization solutions. The 20× (twenty times concentrate) stock SSPE buffer solution is prepared as follows: dissolve 175.3 grams of NaCl, 27.6 grams of $NaH_2PO_4H_2O$ and 7.4 grams of EDTA in 800 milliliters of $H_2O$. Adjust the pH to pH 7.4 with NaOH. Adjust the volume to one liter with $H_2O$.

The abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

The terms "alteration", "amino acid sequence alteration", "variant" and "amino acid sequence variant" refer to monoterpene synthase molecules with some differences in their amino acid sequences as compared to the corresponding, native, i.e., naturally-occurring, monoterpene synthases. Ordinarily, the variants will possess at least about 70% homology with the corresponding native monoterpene synthases, and preferably, they will be at least about 80% homologous with the corresponding, native monoterpene synthases. The amino acid sequence variants of the monoterpene synthases falling within this invention possess substitutions, deletions, and/or insertions at certain positions. Sequence variants of monoterpene synthases may be used to attain desired enhanced or reduced enzrymatic activity, modified regiochemistry or stereochemistry, or altered substrate utilization or product distribution.

Substitutional monoterpene synthase variants are those that have at least one amino acid residue in the native monoterpene synthase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the monoterpene synthase molecules of the present invention may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the monoterpene synthase molecules of the present invention would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional monoterpene synthase variants are those with one or more amino acids inserted immediately adjacent to an amino acid at a particular position in the native monoterpene synthase molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native monoterpene synthase molecules have been removed. Ordinarily, deletional variants will have one or two amino acids deleted in a particular region of the monoterpene synthase molecule.

The terms "biological activity", "biologically active", "activity" and "active" refer to the ability of the monoterpene synthases of the present invention to convert geranyl diphosphate to a group of monoterpenes, of which myrcene is the principal and characteristic monoterpene synthesized by myrcene synthase, (−)-limonene is the principal and characteristic monoterpene synthesized by (−)-limonene synthase, (−)-pinene is the principal and characteristic monoterpene synthesized by (−)-pinene synthase, (−)-camphene is the principal and characteristic monoterpene synthesized by (−)-camphene synthase, (−)-β-phellandrene is the principal and characteristic monoterpene synthesized by (−)-β-phellandrene synthase, terpinolene is the principal and characteristic monoterpene synthesized by terpinolene synthase, and (−)-limonene and (−)-α-pinene are the principal and characteristic monoterpenes synthesized by (−)-limonene/(−)-α-pinene synthase. The monoterpenes produced by the monoterpene synthases of the present invention are as measured in an enzyme activity assay, such as the assay described in Example 3. Amino acid sequence variants of the monoterpene synthases of the present invention may have desirable altered biological activity including, for example, altered reaction kinetics, substrate utilization product distribution or other characteristics such as regiochemistry and stereochemistry.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host. The vector is used to transport the foreign or heterologous DNA into a suitable host cell. Once in the host cell, the vector can replicate independently of or coincidental with the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of E. coli. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

In accordance with the present invention, cDNAs encoding myrcene synthase (SEQ ID NO:1), (−)-pinene synthase (SEQ ID NO:3) and (−)-limonene synthase (SEQ ID NO:5) from Grand fir (Abies grandis) were isolated and sequenced in the following manner. Based on comparison of sequences of limonene synthase from spearmint (Colby, S. M., Alonso, W. R., Katahira, E. J., McGarvey, D. J., and Croteau, R. (1993) J. Biol. Chem. 268:23016–23024), 5-epi-aristolochene synthase from tobacco (Facchini, P. J., and Chappell, J. (1992) Proc. Natl. Acad Sci. USA 89:11088–11092), and casbene synthase from castor bean (Mau, C. J. D., and West, C. A. (1994) Proc. Natl. Acad Sci. USA 91:8497–8501), four conserved regions were identified for which a set of consensus, degenerate primers were synthesized: Primer A (SEQ ID NO:7), Primer B (SEQ ID NO:8), Primer C (SEQ ID NO:9) and Primer D (SEQ ID NO:10). Primers A (SEQ ID NO:7), B (SEQ ID NO:8), and D (SEQ ID NO:10) were sense primers, while Primer C (SEQ ID NO:9), was an antisense primer. Each of the sense primers, A (SEQ ID NO:7), B (SEQ ID NO:8) and D (SEQ ID NO:10), was used for PCR in combination with antisense primer C (SEQ ID NO:9) by employing a broad range of amplification conditions. Analysis of the PCR reaction products by agarose gel electrophoresis revealed that only the combination of primers C (SEQ ID NO:9) and D (SEQ ID NO:10) generated a specific PCR product of approximately 110 bps.

The 110 bps PCR product was gel purified, ligated into a plasmid, and transformed into E. coli XL1-Blue cells. Plasmid DNA was prepared from 41 individual transformants and the inserts were sequenced. Four different insert sequences were identified, and were designated as probes 1 (SEQ ID NO:11), 2 (SEQ ID NO:12), 4 (SEQ ID NO:13) and 5 (SEQ ID NO:14). Probes 1 (SEQ ID NO:1), 2 (SEQ ID NO:12), 4 (SEQ ID NO:13) and 5 (SEQ ID NO:14) were used to screen a cDNA library made from mRNA extracted from wounded Grand fir stems, and the longest clone that hybridized to each of these probes was isolated and sequenced. Thus, clone AG1.28 (SEQ ID NO:15) is the longest cDNA clone that hybridized to probe 1 (SEQ ID NO:11), clone AG2.2 (SEQ ID NO:1) is the longest cDNA clone that hybridized to probe 2 (SEQ ID NO:12), clone AG4.30 (SEQ ID NO:17) is the longest cDNA clone that hybridized to probe 4 (SEQ ID NO:13), and clone AG5.9 (SEQ ID NO:19) is the longest cDNA clone that hybridized to probe 5 (SEQ ID NO:14).

Truncated clone AG1.28 (SEQ ID NO:15) resembled most closely in size and sequence (72% similarity, 49% identity) a diterpene cyclase, abietadiene synthase, from Grand fir. Clones AG4.30 (SEQ ID NO:17) and AG5.9 (SEQ ID NO:19) encode sesquiterpene synthases. Sequence and functional analysis of clone AG2.2 (SEQ ID NO:1) revealed that it encoded the monoterpene synthase, myrcene synthase.

Alignment of the four new terpene synthase cDNA sequences AG1.28 (SEQ ID NO:15), AG2.2 (SEQ ID NO:1), AG4.30 (SEQ ID NO:17) and AG5.9 (SEQ ID NO:19) with that for abietadiene synthase (Stofer Vogel, B., Wildung, M. R., Vogel, G., and Croteau, R. (1996) J. Biol. Chem. 271:23262–23268) allowed the identification of several, conserved sequence motifs. Two new sense PCR primers, primer E (SEQ ID NO:21) and primer F (SEQ ID NO:22) were designed based on the sequence of the conserved protein sequence motifs. A new antisense PCR primer, primer G (SEQ ID NO:23), was designed based on limited sequence information available from pinene synthase. The combination of primer E (SEQ ID NO:21) and primer G (SEQ ID NO:23) amplified a cDNA product of 1022 bps, which was designated as probe 3 (SEQ ID NO:24).

Probe 3 (SEQ ID NO:24) was used to screen a cDNA library made from mRNA extracted from wounded Grand fir stems. Hybridization of $10^5$ Grand fir λZAP II cDNA clones with probe 3 (SEQ ID NO:24) yielded two types of signals comprised of about 400 strongly positive clones and an equal number of weak positives, indicating that the probe recognized more than one type of cDNA. Thirty-four of the former clones and eighteen of the latter were purified, the inserts were selected by size (2.0–2.5 kb), and the in vivo excised clones were partially sequenced from both ends. Those clones which afforded weak hybridization signals were shown to contain inserts that were either identical to myrcene synthase clone A G2.2 (SEQ ID NO:1) or exhibited no significant sequence similarity to terpene synthases.

Clones which gave strong hybridization signals segregated into distinct sequence groups represented by clone AG3.18 (SEQ ID NO:3) and clone AG10 (SEQ ID NO:5). Both AG3.18 (SEQ ID NO:3) and AG10 (SEQ ID NO:5) were subcloned into plasmid expression vectors and expressed in E. coli. When extracts of the induced cells were tested for terpene synthase activity with all of the potential prenyl diphosphate substrates, only geranyl diphosphate was utilized. Extracts from E. coli containing the AG10 (SEQ ID NO:5) expression construct converted geranyl diphosphate to the (−)-4S enantiomer of limonene as the major product, indicating that AG10 (SEQ ID NO:5) encodes (−)-limonene synthase. Similar analysis of the monoterpene products generated from geranyl diphosphate by cell-free extracts of E. coli containing the AG3.18 (SEQ ID NO:3) insert ligated into an expression vector revealed the presence of a 42:58% mixture of α-pinene and β-pinene, the same product ratio previously described for the purified, native (−)-pinene synthase from Grand fir. These data indicate that AG3.18 (SEQ ID NO:3) encodes (−)-pinene synthase.

Additionally, cDNA molecules encoding (−)-camphene synthase, (−)-β-phellandrene synthase, terpinolene synthase, (−)-limonene/(−)-α-pinene synthase were isolated and characterized as described in Example 11.

The isolation of cDNAs encoding (−)-camphene synthase, (−)-,β-phellandrene synthase, terpinolene synthase, (−)-limonene/(−)-α-pinene synthase, (−)-limonene synthase, (−)-pinene synthase and myrcene synthase permits the development of efficient expression systems for these functional enzymes; provides useful tools for examining the developmental regulation of monoterpene biosynthesis; permits investigation of the reaction mechanism(s) of these unusual, multiproduct enzymes, and permits the isolation of other monoterpene synthases including (−)-camphene synthases, (−)-β-phellandrene synthases, terpinolene synthases, (−)-limonene/(−)-α-pinene synthases, (−)-limonene synthases, (−)-pinene synthases and myrcene synthases. The isolation of the (−)-camphene synthase, (−)-β-phellandrene synthase, terpinolene synthase, (−)-limonene/(−)-α-pinene synthase, (−)-limonene synthase, (−)-pinene synthase and myrcene synthase cDNAs also permits the transformation of a wide range of organisms in order to introduce monoterpene biosynthesis de novo, or to modify endogenous monoterpene biosynthesis.

Substitution of the presumptive targeting sequence of the cloned monoterpene synthases (e.g., SEQ ID NO:2, amino acids 1 to 61; SEQ ID NO:4, amino acids 1 to 61; SEQ ID NO:6, amino acids 1 to 66) with other transport sequences well known in the art (see, e.g., von Heijne et al., *Eur. J. Biochem.* 180:535–545, 1989; Stryer, *Biochemistry*, W.H. Freeman and Company, New York, N.Y., p. 769 [1988]) may be employed to direct the cloned monoterpene synthases of the invention to other cellular or extracellular locations.

In addition to the native monoterpene synthase amino acid sequences, sequence variants produced by deletions, substitutions, mutations and/or insertions are intended to be within the scope of the invention except insofar as limited by the prior art. The monoterpene synthase amino acid sequence variants of this invention may be constructed by mutating the DNA sequences that encode the wild-type synthases, such as by using techniques commonly referred to as site-directed mutagenesis. Nucleic acid molecules encoding the monoterpene synthases of the present invention can be mutated by a variety of PCR techniques well known to one of ordinary skill in the art. See, e.g., "PCR Strategies", M. A. Innis, D. H. Gelfand and J. J. Sninsky, eds., 1995, Academic Press, San Diego, Calif. (Chapter 14); "PCR Protocols: A Guide to Methods and Applications", M. A. Innis, D. H. Gelfand, J. J. Sninsky and T. J. White, eds., Academic Press, NY (1990).

By way of non-limiting example, the two primer system utilized in the Transformer Site-Directed Mutagenesis kit from Clontech, may be employed for introducing site-directed mutants into the monoterpene synthase genes of the present invention. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of E. coli. Plasmid DNA is isolated from the transformed bacteria, restricted with the relevant restriction enzyme (thereby linearizing the unmutated plasmids), and then retransformed into E. coli. This system allows for generation of mutations directly in an expression plasmid, without the necessity of subjoining or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis on Mutation Detection Enhancement gel (J. T. Baker) to confirm that no other alterations in the sequence have occurred (by band shift comparison to the unmutagenized control).

The verified mutant duplexes in the pET (or other) overexpression vector can be employed to transform E. coli such as strain E. coli BL21(DE3)pLysS, for high level production of the mutant protein, and purification by standard protocols. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutagenesis, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native enzyme. If the residue is by this means demonstrated to be important by activity impairment, or knockout, then conservative substitutions can be made, such as Asp for Glu to alter side chain length, Ser for Cys, or Arg for His. For hydrophobic segments, it is largely size that is usefully altered, although aromatics can also be substituted for alkyl side chains. Changes in the normal product distribution can indicate which step(s) of the reaction sequence have been altered by the mutation. Modification of the hydrophobic pocket can be employed to change binding conformations for substrates and result in altered regiochemistry and/or stereochemistry.

Other site directed mutagenesis techniques may also be employed with the nucleotide sequences of the invention. For example, restriction endonuclease digestion of DNA followed by ligation may be used to generate deletion variants of (−)-camphene synthase, (−)-β-phellandrene synthase, terpinolene synthase, (−)-limonene/(−)-α-pinene synthase, (−)-limonene synthase, (−)-pinene synthase and myrcene synthase, as described in section 15.3 of Sambrook et al. (*Molecular Cloning: A Laboratory Manual,* 2nd Ed., Cold Spring Harbor Laboratory Press, New York, N.Y. [1989]). A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (DNA 2:183 [1983]); Sambrook et al., supra; "Current Protocols in Molecular Biology", 1991, Wiley (NY), F. T. Ausubel, R. Brent, R. E. Kingston, D. D. Moore, J. D. Seidman, J. A. Smith and K. Struhl, eds.

Generally, oligonucleotides of at least 25 nucleotides in length are used to insert, delete or substitute two or more nucleotides in the nucleic acid molecules encoding monoterpene synthases of the invention. An optimal oligonucleotide will have 12 to 15 perfectly matched nucleotides on either side of the nucleotides coding for the mutation. To mutagenize nucleic acids encoding wild-type monoterpene synthases of the invention, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type synthase inserted in the vector, and the second strand of DNA encodes the mutated form of the synthase inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type monoterpene synthase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

A gene encoding (−)-camphene synthase, (−)-β-phellandrene synthase, terpinolene synthase, (−)-limonene/(−)-α-pinene synthase, (−)-limonene synthase, (−)-pinene synthase or myrcene synthase may be incorporated into any organism (intact plant, animal, microbe, etc.), or cell culture derived therefrom, that produces geranyl diphosphate. A (−)-camphene synthase, (−)-β-phellandrene synthase, terpinolene synthase, (−)-limonene/(−)-α-pinene synthase, (−)-limonene synthase, (−)-pinene synthase or myrcene synthase gene may be introduced into any organism for a variety of purposes including, but not limited to: production of (−)-camphene synthase, (−)-β-phellandrene synthase, terpinolene synthase, (−)-limonene/(−)-α-pinene synthase, (−)-limonene synthase, (−)-pinene synthase or myrcene synthase, or their products; production or modification of flavor and aroma properties; improvement of defense capability, and the alteration of other ecological interactions mediated by (−)-camphene, (−)-β-phellandrene, terpinolene, myrcene, (−)-limonene, (−)-pinene, or their derivatives.

Eukaryotic expression systems may be utilized for the production of (−)-camphene synthase, (−)-β-phellandrene synthase, terpinolene synthase, (−)-limonene/(−)-α-pinene synthase, (−)-limonene synthase, (−)-pinene synthase and myrcene synthase since they are capable of carrying out any required posttranslational modifications and of directing the enzymes to the proper membrane location. A representative eukaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* [1986]; Luckow et al., *Biotechnology* 6:47–55 [1987]) for expression of the terpenoid synthases of the invention. Infection of insect cells (such as cells of the species *Spodoptera frugiperda*) with the recombinant baculoviruses allows for the production of large amounts of the monoterpene synthase proteins. In addition, the baculovirus system has other important advantages for the production of recombinant monoterpene synthases. For example, baculoviruses do not infect humans and can therefore be safely handled in large quantities. In the baculovirus system, a DNA construct is prepared including a DNA segment encoding (−)-camphene synthase, (−)-β-phellandrene synthase, terpinolene synthase, (−)-limonene/(−)-α-pinene synthase, (−)-limonene synthase, (−)-pinene synthase or myrcene synthase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoter/monoterpene synthase combination is flanked on both sides by200–300 base pairs of baculovirus DNA (the flanking sequences).

To produce the monoterpene synthase DNA construct, a cDNA clone encoding the full length (−)-camphene synthase, (−)-β-phellandrene synthase, terpinolene synthase, (−)-limonene/(−)-α-pinene synthase, (−)-limonene synthase, (−)-pinene synthase or myrcene synthase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full (−)-camphene synthase, (−)-β-phellandrene synthase, terpinolene synthase, (−)-limonene/(−)-α-pinene synthase, (−)-limonene synthase, (−)-pinene synthase or myrcene synthase. For example, an insect host cell can be cotransfected or transfected separately with the DNA construct and a functional baculovirus. Resulting recombinant baculoviruses can then be isolated and used to infect cells to effect production of the monoterpene synthase. Host insect cells include, for example, *Spodoptera frugiperda* cells, that are capable of producing a baculovirus-expressed monoterpene synthase. Insect host cells infected with a recombinant baculovirus of the present invention are then cultured under conditions allowing expression of the baculovirus-encoded (−)-camphene synthase, (−)-β-phellandrene synthase, terpinolene synthase, (−)-limonene/(−)-α-pinene synthase, (−)-limonene synthase, (−)-pinene synthase or myrcene synthase. Monoterpene synthases thus produced are then extracted from the cells using methods known in the art.

Other eukaryotic microbes such as yeasts may also be used to practice this invention. The baker's yeast *Saccharomyces cerevisiae,* is a commonly used yeast, although several other strains are available. The plasmid YRp7 (Stinchcomb et al., *Nature* 282:39 [1979]; Kingsman et al., *Gene* 7:141 [1979]; Tschemper et al., *Gene* 10:157 [1980]) is commonly used as an expression vector in Saccharomyces. This plasmid contains the trp1 gene that provides a selection marker for a mutant strain of yeast lacking the ability to grow in tryptophan, such as strains ATCC No. 44,076 and PEP4-1 (Jones, *Genetics* 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA* 75:1929 [1978]). Additional yeast transformation protocols are set forth in Gietz et al., *N.A.R* 20(17) 1425(1992); Reeves et al., *FEMS* 99(2–3):193–197, (1992).

Suitable promoting sequences in yeast vectors include the promoters for 3-phosphoglycerate kinase (Hitzeman et al., *J. Biol. Chem.* 255:2073 [1980]) or other glycolytic enzymes (Hess et al., *J. Adv. Enzyme Reg.* 7:149 [1968]; Holland et al., *Biochemistry* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms, such as plants, may be used as hosts to practice this invention. Transgenic plants can be obtained, for example, by transferring plasmids that encode (−)-camphene synthase, (−)-β-phellandrene synthase, terpinolene synthase, (−)-limonene/(−)-α-pinene synthase, (−)-limonene synthase, (−)-pinene synthase and/or myrcene synthase and a selectable marker gene, e.g., the kan gene encoding resistance to kanamycin, into *Agrobacterium tumifaciens* containing a helper Ti plasmid as described in Hoeckema et al., *Nature* 303:179–181 [1983] and culturing the Agrobacterium cells with leaf slices of the plant to be transformed as described by An et al., *Plant Physiology* 81:301–305 [1986]. Transformation of cultured plant host cells is normally accomplished through *Agrobacterium tumifaciens,* as described above. Cultures of mammalian host cells and other host cells that do not have rigid cell membrane barriers are usually transformed using the calcium phosphate method as originally described by Graham and Van der Eb (*Virology* 52:546 [1978]) and modified as described in sections 16.32–16.37 of Sambrook et al., supra. However, other methods for introducing DNA into cells such as Polybrene (Kawai and Nishizawa, *Mol. Cell. Biol.* 4:1172 [1984]), protoplast fusion (Schaffner, *Proc. Natl. Acad. Sci. USA* 77:2163 [1980]), electroporation (Neumann et al., *EMBO J.* 1:841 [1982]), and direct microinjection into nuclei (Capecchi, *Cell* 22:479 [1980]) may also be used. Additionally, animal transformation strategies are reviewed in Monastersky G. M. and Robl, J. M., *Strategies in Transgenic Animal Science,* ASM Press, Washington, D.C., 1995. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating (−)-camphene synthase, (−)-β-phellandrene synthase, terpinolene synthase, (−)-limonene/(−)-α-pinene synthase, (−)-limonene synthase, (−)-pinene synthase or myrcene synthase production can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product is not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology* 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a (−)-camphene synthase, (−)-β-phellandrene synthase, terpinolene synthase, (−)-limonene/(−)-α-pinene synthase, (−)-limonene synthase, (−)-pinene synthase or myrcene synthase gene that previously has had its native promoter removed. This engineered gene is the combination of a promoter that responds to an external chemical stimulus and a gene responsible for successful production of (−)-camphene synthase, (−)-β-phellandrene synthase, terpinolene synthase, (−)-limonene/(−)-α-pinene synthase, (−)-limonene synthase, (−)-pinene synthase or myrcene synthase.

In addition to the methods described above, several methods are known in the art for transferring cloned DNA into a wide variety of plant species, including gymnosperms, angiosperms, monocots and dicots (see, e.g., Glick and Thompson, eds., *Methods in Plant Molecular Biology*, CRC Press, Boca Raton, Fla. [1993]). Representative examples include electroporation-facilitated DNA uptake by protoplasts (Rhodes et al., *Science* 240(4849):204–207 [1988]); treatment of protoplasts with polyethylene glycol (Lyznik et al., *Plant Molecular Biology* 13:151–161 [1989]); and bombardment of cells with DNA laden microprojectiles (Klein et al., *Plant Physiol.* 91:440–444 [1989] and Boynton et al., *Science* 240(4858):1534–1538 [1988]). Additionally, plant transformation strategies and techniques are reviewed in Birch, R. G., *Ann Rev Plant Phys Plant Mol Biol* 48:297 (1997); Forester et al., *Exp. Agric.* 33:15–33 (1997). Minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J. Gen. Virol* 36:59 [1977]); baby hamster kidney cells (BHK, ATCC CCL 10); Chinese hamster ovary cells (Urlab and Chasin, *Proc. Natl. Acad. Sci USA* 77:4216 [1980]); mouse sertoli cells (TM4, Mather, *Biol. Reprod.* 23:243 [1980]); monkey kidney cells (CVI-76, ATCC CCL 70); African green monkey kidney cells (VERO-76, ATCC CRL-1587); human cervical carcinoma cells HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.* 85:1 [1980]); and TRI cells (Mather et al., *Annals N.Y. Acad. Sci.* 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus 2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature* 273:113 [1978]). Smaller or larger SV40 DNA fragments may also be used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels of (−)-camphene synthase, (−)-β-phellandrene synthase, terpinolene synthase, (−)-limonene/(−)-α-pinene synthase, (−)-limonene synthase, (−)-pinene synthase and myrcene synthase in transformed cell lines. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-Kl cell line (ATCC No. CL 61) possesses these characteristics, and is thus a useful cell line for this purpose. The addition of MTX to the cell culture medium will permit only those cells transformed with the DNA encoding the MTX-resistant DHFk to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include E. coli K12 strain 94 (ATCC No. 31,446), E. coli strain W3110 (ATCC No. 27,325) E. coli X1776 (ATCC No. 31,537), and E. coli B; however many other strains of E. coli, such as HB101, JM101, NM522, NM538, NM539, and many other species and genera of prokaryotes including bacilli such as *Bacillus subtilis,* other enterobacteriaceae such as *Salmonella typhimurium* or *Serratia marcesans,* and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275–296, Plenum Publishing Corp., 1990; Hanahan et al., *Meth. Enxymol.,* 204:63 (1991).

As a representative example, cDNA sequences encoding (−)-camphene synthase, (−)-β-phellandrene synthase, terpinolene synthase, (−)-limonene/(−)-α-pinene synthase, (−)-limonene synthase, (−)-pinene synthase or myrcene synthase may be transferred to the $(His)_6$.Tag pET vector commercially available (from Novagen) for overexpression in *E. coli* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein with thrombin, and the (−)-camphene synthase, (−)-β-phellandrene synthase, terpinolene synthase, (−)-limonene/(−)-α-pinene synthase, (−)-limonene synthase, (−)-pinene synthase and myrcene synthase again purified by immobilized metal ion affinity chromatography, this time using a shallower imidazole gradient to elute the recombinant synthases while leaving the histidine block still adsorbed. This overexpression-purification system has high capacity, excellent resolving power and is fast, and the chance of a contaminating *E. coli* protein exhibiting similar binding behavior (before and after thrombin proteolysis) is extremely small.

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI18, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature* 375:615 [1978]; Itakura et al., *Science* 198:1056 [1977]; Goeddel et al., *Nature* 281:544 [1979]) and a tryptophan (trp) promoter system (Goeddel et al., *Nucl. Acids Res.* 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell* 20:269 [1980]).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, *Biochemistry* W.H. Freeman and Company, New York, N.Y., p. 769 [1988]), and can be used as signal sequences in appropriate eukaryotic host cells. Yeast signal sequences, as for example acid phosphatase (Arima et al., *Nuc. Acids Res.* 11:1657 [1983]), α-factor, alkaline phosphatase and invertase may be used to direct secretion from yeast host cells. Prokaryotic signal sequences from genes encoding, for example, LamB or OmpF (Wong et al., *Gene* 68:193 [1988]), MalE, PhoA, or beta-lactamase, as well as other genes, may be used to target proteins from prokaryotic cells into the culture medium.

Trafficking sequences from plants, animals and microbes can be employed in the practice of the invention to direct the monoterpene synthase proteins of the present invention to the cytoplasm, endoplasmic reticulum, mitochondria or other cellular components, or to target the protein for export to the medium. These considerations apply to the overexpression of (−)-camphene synthase, (−)-β-phellandrene synthase, terpinolene synthase, (−)-limonene/(−)-α-pinene synthase, (−)-limonene synthase, (−)-pinene synthase and myrcene synthase, and to direction of expression within cells or intact organisms to permit gene product function in any desired location.

The construction of suitable vectors containing DNA encoding replication sequences, regulatory sequences, phenotypic selection genes and the monoterpene synthase DNA of interest are prepared using standard recombinant DNA procedures. Isolated plasmids and DNA fragments are cleaved, tailored, and ligated together in a specific order to generate the desired vectors, as is well known in the art (see, for example, Maniatis, supra, and Sambrook et al., supra).

As discussed above, (−)-camphene synthase, (−)-β-phellandrene synthase, terpinolene synthase, (−)-limonene/(−)-α-pinene synthase, (−)-limonene synthase, (−)-pinene synthase and myrcene synthase variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also sections 1.60–1.61 and sections 3.38–3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (*Nucleic Acids Res.* 9:6103–6114 [1982]), and Goeddel et al. (*Nucleic Acids Res.*, supra).

The following examples merely illustrate the best mode now contemplated for practicing the invention, but should not be construed to limit the invention.

EXAMPLE 1

PCR-Based Generation of Probes for Cloning Certain Monoterpene Synthases from Grand fir (*Abies grandis*)

Substrates, Reagents and cDNA Library—[1-$^3$H]Geranyl diphosphate (250 Ci/mol) (Croteau, R., Alonso, W. R., Koepp, A. E., and Johnson, M. A. (1994) *Arch. Biochem. Biophys.* 309:184–192), [1-$^3$H]farnesyl diphosphate (125 Ci/mol) (Dehal, S. S., and Croteau, R. (1988) *Arch. Biochem. Biophys.* 261:346–356) and [1-$^3$ H]geranylgeranyl diphosphate (120 Ci/mol) (LaFever, R. E., Stofer Vogel, B., and Croteau, R. (1994) *Arch. Biochem. Biophys.* 313:139–149) were prepared as described previously. Terpenoid standards were from our own collection. All other biochemicals and reagents were purchased from Sigma Chemical Co. or Aldrich Chemical Co., unless otherwise noted. Construction of the λZAP II cDNA library, using mRNA isolated from wounded Grand fir sapling stems, was described previously (Stofer Vogel, B., Wildung, M. R., Vogel, G., and Croteau, R. (1996) *J. Biol. Chem.* 271:23262–23268).

PCR-Based Probe Generation—Based on comparison of sequences of limonene synthase from spearmint (Colby, S. M., Alonso, W. R., Katahira, E. J., McGarvey, D. J., and Croteau, R. (1993) *J. Biol. Chem.* 268:23016–23024), 5-epi-aristolochene synthase from tobacco (Facchini, P. J., and Chappell, J. (1992) *Proc. Natl. Acad. Sci. USA* 89:11088–11092), and casbene synthase from castor bean (Mau, C. J. D., and West, C. A. (1994) *Proc. Natl. Acad. Sci. USA* 91:8497–8501), four conserved regions were identified for which a set of consensus degenerate primers were synthesized: Primer A (SEQ ID NO:7); Primer B (SEQ ID NO:8); Primer C (SEQ ID NO:9); Primer D (SEQ ID NO:10). Primers A (SEQ ID NO:7), B (SEQ ID NO:8) and C (SEQ ID NO:9) have been described previously (Steele, C., Lewinsohn, E. and Croteau, R., *Proc. Nat'l. Acad. Sci. USA*, 92: 4164–4168 (1995)); primer D (SEQ ID NO:10) was designed based on the conserved amino acid sequence motif DD(T/I)(I/Y/F)D(A/V)Y(A/G)(SEQ ID NO:25) of the above noted terpene synthases (Colby, S. M., Alonso, W. R., Katahira, E. J., McGarvey, D. J., and Croteau, R. (1993) *J. Biol. Chem.* 268:23016–23024; Facchini, P. J., and Chappell, J. (1992) *Proc. Natl. Acad. Sci. USA* 89:11088–11092; Mau, C. J. D., and West, C. A. (1994) *Proc. Natl. Acad. Sci. USA* 91:8497–8501).

Each of the sense primers, A (SEQ ID NO:7), B (SEQ ID NO:8) and D (SEQ ID NO:10), was used for PCR in combination with antisense primer C (SEQ ID NO:9) by employing a broad range of amplification conditions. PCR was performed in a total volume of 50 μl containing 20 mM Tris/HCl (tris(hydroxymethyl) aminomethane/HCl, pH 8.4), 50 mM KCl, 5 mM MgCl$_2$, 200 μM of each dNTP, 1–5 μM of each primer, 2.5 units of Taq polymerase (BRL) and 5 μl of purified Grand fir stem cDNA library phage as template (1.5×10$^9$ pfu/ml). Analysis of the PCR reaction products by agarose gel electrophoresis (Sambrock, J., Fritsch, E. F., and Maniatis, T. (1989) *Molecular Cloning: A Laboratory Manual*, 2nd Ed., Cold Spring Harbor Laboratory, Cold Spring Harbor, N.Y.) revealed that only the combination of primers C and D generated a specific PCR product of approximately 110 bps (base pairs). This PCR product was gel purified, ligated into pT7Blue (Novagen), and transformed into *E. coli* XL1-Blue cells. Plasmid DNA was prepared from 41 individual transformants and the inserts were sequenced (DyeDeoxy Terminator Cycle Sequencing, Applied Biosystems). Four different insert sequences were identified, and were designated as probes 1 (SEQ ID NO:11), 2 (SEQ ID NO:12), 4 (SEQ ID NO:13) and 5 (SEQ ID NO:14).

Subsequent isolation of four new cDNA species (AG1.28 (SEQ ID NO:15); AG2.2 (SEQ ID NO:1); AG4.30 (SEQ ID NO:17) and AG5.9 (SEQ ID NO:19)), encoding terpene synthases from Grand fir corresponding to probes 1 (SEQ ID NO:11), 2 (SEQ ID NO:12), 4 (SEQ ID NO:13) and 5 (SEQ ID NO:14), respectively, allowed the identification of three additional conserved sequence elements which were used to design a set of three new PCR primers: Primer E (5'-GGI GA(A/G) A(A/C)(A/G) (A/G)TI ATG GA(A/G) GA(A/G) GC-3')(SEQ ID NO:21); Primer F (5'-GA(A/G) (C/T)TI CA(G/A) (C/T)TI (A/C/T)(C/G/T)I (A/C)GI TGG TGG-3') (SEQ ID NO:22) and Primer G (5'-CCA (A/G)TT IA(A/G) ICC (C/T)TT IAC (A/G)TC-3')(SEQ ID NO:23).

Degenerate primer E (SEQ ID NO:21) was designed to conserved element GE(K/T)(V/I)M(E/D)EA (SEQ ID NO:26) and degenerate primer F (SEQ ID NO:22) was designed to conserved element QF/Y/D)(I/L)(T/L/R)RWW (SEQ ID NO:27) by comparing the sequences of five cloned terpene synthases from Grand fir: a monoterpene synthase corresponding to probe 2 (SEQ ID NO:12), two sesquiterpene synthases corresponding to probe 4 (SEQ ID NO:13) and probe 5 (SEQ ID NO:14), respectively, a previously described diterpene synthase (Stofer Vogel, B., Wildung, M. R., Vogel, G., and Croteau, R. (1996) *J. Biol. Chem.* 271:23262–23268), and a truncated terpene synthase corresponding to probe 1 (SEQ ID NO:11). Degenerate primer G (SEQ ID NO:23) was designed according to the amino acid sequence DVIKG(FAL)NW (SEQ ID NO:28) obtained from a peptide generated by trypsin digestion of purified (–)-pinene synthase from Grand fir. Primers E (SEQ ID NO:21) and F (SEQ ID NO:22) were independently used for PCR amplification in combination with primer G (SEQ ID NO:23), with Grand fir stem cDNA library as template. The combination of primers E (SEQ ID NO:21) and G (SEQ ID NO:23) yielded a specific PCR product of approximately 1020 bps. This PCR product was ligated into pT7Blue and transformed into *E. coli* XL1-Blue. Plasmid DNA was prepared from 20 individual transformants and inserts were sequenced from both ends. The sequence of this 1022 bp insert was identical for all 20 plasmids and was designated as probe 3 (SEQ ID NO:24).

EXAMPLE 2

Screening a Wounded Grand fir Stem cDNA Library

For library screening, 100 ng of each probe was amplified by PCR, gel purified, randomly labeled with [α-$^{32}$P]dATP (Feinberg, A. P., and Vogelstein, B. (1984) *Anal. Biochem.* 137:266–267), and used individually to screen replica filters of $10^5$ plaques of the wound-induced Grand fir stem cDNA library plated on *E. coli* LE392. Hybridization with probes 1 (SEQ ID NO:11), 2 (SEQ ID NO:12), 4 (SEQ ID NO:13) and 5 (SEQ ID NO:14) was performed for 14 h at 65° C. in 3×SSPE and 0.1% SDS. Filters were washed three times for 10 min at 55° C. in 3×SSPE with 0.1% SDS and exposed for 12 h to Kodak XAR film at –70° C. All of the λZAPII clones yielding positive signals were purified through a second round of hybridization (probe 1 (SEQ ID NO:11) gave 25 positives, probe 2 (SEQ ID NO:12) gave 16 positives, probe 4 (SEQ ID NO:13) gave 49 positives and probe 5 (SEQ ID NO:14) gave 12 positives).

Hybridization with probe 3 (SEQ ID NO:24) was performed as before, but the filters were washed three times for 10 min at 65° C. in 3×SSPE and 0.1% SDS before exposure. Approximately 400 λZAPII clones yielded strong positive signals, and 34 of these were purified through a second round of hybridization at 65° C. Approximately 400 additional clones yielded weak positive signals with probe 3 (SEQ ID NO:24), and 18 of these were purified through a second round of hybridization for 20 h at 45° C. Purified λZAP II clones isolated using all five probes were in vivo excised as Bluescript II SK(–) phagemids and transformed into *E. coli* XLOLR according to the manufacturer's instructions (Stratagene). The size of each cDNA insert was determined by PCR using T3 (SEQ ID NO:29) and T7 (SEQ ID NO:30) promoter primers and selected inserts (>1.5 kb) were partially sequenced from both ends.

EXAMPLE 3

Grand Fir Monoterpene Synthase cDNA Expression in *E. coli* and Enzyme Assays

Except for cDNA clones AG3.18 (SEQ ID NO:3) and AG3.48 (SEQ ID NO:3 1), all of the partially sequenced inserts were either truncated at the 5'-end, or were out of frame, or bore premature stop codons upstream of the presumptive methionine start codon. For the purpose of functional expression, a 2023 bp insert fragment, extending from nucleotides 75 to 2097 of the sequence set forth in SEQ ID NO:1, and a 1911 bp insert fragment, extending from nucleotide 1 to nucleotide 1910 of the sequence set forth in SEQ ID NO:3, were subcloned in frame into pGEX vectors (Pharmacia). A 2016 bp fragment extending from nucleotide 73 to nucleotide 2088 of the sequence set forth in SEQ ID NO:5 was subcloned in frame into the pSBETa vector (Schenk, P. M., Baumann, S., Mattes, R., and Steinbiss, H.-H. (1995) *Biotechniques* 19, 196–200). To introduce suitable restriction sites for subcloning, fragments were amplified by PCR using primer combinations 2.2-BamHI (5-'CAA A<u>GG GAT CC</u>A GAA TGG CTC TGG-3')(SEQ ID NO:33) and 2.2-NotI (5'-AGT AAG <u>CGG CCG C</u>TT TTT AAT CAT ACC CAC-3')(SEQ ID NO:34) with pAG2.2 insert (SEQ ID NO:1) as template, 3.18-EcoRI (5-'CTG CAG <u>GAA TTC</u> GGC ACG AGC-3')(SEQ ID NO:35) and 3.18-SmaI (5-'CAT AG<u>C CCC GGG</u> CAT AGA TTT GAG CTG-3')(SEQ ID NO:36) with pAG3.18 insert (SEQ ID NO:3) as template, and 10-NdeI (5-GGC AGG AAC <u>ATA TGG</u> CTC TCC TTT CTA TCG-3')(SEQ ID NO:37) and 10-BamHI (5-'TCT AGA ACT AGT <u>GGATCC</u> CCC GGG CTG CAG-3')(SEQ ID NO:38) with pAG10 insert (SEQ ID NO:5) as template.

PCR reactions were performed in volumes of 50 μl containing 20 mM Tris/HCl (pH 8.8), 10 mM KCl, 10 mM $(NH_4)_2SO_4$, 2 mM $MgSO_4$, 0.1% Triton X-100, 5 μg bovine serum albumin (BSA), 200 μM of each dNTP, 0.1 μM of each primer, 2.5 units of recombinant Pfu polymerase (Stratagene) and 100 ng plasmid DNA with the following program: denaturation at 94° C., 1 min; annealing at 60° C., 1 min; extension at 72° C., 3.5 min; 35 cycles with final extension at 72° C., 5 min. The PCR products were purified by agarose gel electrophoresis and used as template for a secondary PCR amplification with the identical conditions in total volumes of 250 μl each. Products from this secondary amplification were digested with the above indicated restriction enzymes, purified by ultrafiltration and then ligated, respectively, into BamHI/NotI-digested pGEX4T-2 to yield plasmid pGAG2.2, into EcoRI/SmaI-digested pGEX-4T-3 to yield plasmid pGAG3.18, and into NdeI/BamHI-digested pSBETa to yield plasmid pSBAG10; these plasmids were then transformed into *E. coli* XL1-Blue or *E. coli* BL21I(DE3).

For expression, bacterial strains *E. coil* XLOLR/pAG3.18, *E. coil* XLOLR/pAG3.48, *E. coli* XL1-Blue/pGAG2.2, *E. coli* XL1-Blue/pGAG3.18, and *E. coil* BL21 (DE3)/pSBAG10were grown to $A_{600}$=0.5 at 37° C. in 5 ml of LB medium (Sambrock, J., Fritsch, E. F., and Maniatis, T. (1989) *Molecular Cloning: A Laboratory Manual,* 2d Ed., Cold Spring Harbor Laboratory, Cold Spring Harbor, N.Y.) supplemented with 100 μg ampicillin/ml or 30 μg kanamycin/ml as determined by the vector. Cultures were then induced by addition of 1 mM isopropyl-1-thio-β-D-galactopyranoside and grown for another 12 h at 20° C. Cells were harvested by centrifugation (2000×g, 10 min) and resuspended in either 1 ml monoterpene synthase assay buffer [50 mM Tris/HCl (pH 7.5), 500 mM KCl, 1 mM $MnCl_2$, 5 mM dithiothreitol, 0.05% (w/v) $NaHSO_3$ and 10% (v/v) glycerol], 1 ml sesquiterpene synthase assay buffer [10 mM dibasic potassium phosphate, 1.8 mM monobasic potassium phosphate (pH 7.3), 140 mM NaCl, 10 mM $MgCl_2$, 5 mM dithiothreitol, 0.05% (w/v) $NaHSO_3$ and 10% (v/v) glycerol], or 1 ml diterpene synthase assay buffer [30 mM Hepes (N-2-hydroxyethylpiperazine-N-'2-ethanesulfonic acid, pH 7.2), 7.5 mM $MgCl_2$, 5 mM dithiothreitol, 10 gM $MnCl_2$, 0.05% (w/v) $NaHSO_3$ and 10% (v/v) glycerol].

Cells were disrupted by sonication (Braun-Sonic 2000 with microprobe at maximum power for 15 seconds at 0–4° C.), the homogenates were cleared by centrifugation (18,000×g, 10 min), and 1 ml of the resulting supernatant was assayed for monoterpene synthase activity with 2.5 μM of $[1-^3H]$geranyl diphosphate, for sesquiterpene synthase activity with 3.5 μM $[1-^3H]$farnesyl diphosphate, or for diterpene synthase activity with 5 μM $[1-^3H]$geranylgeranyl diphosphate following standard protocols (Croteau, R., and Cane, D. E. (1985) *Methods Enzymol.* 110:383–405; LaFever, R. E., Stofer Vogel, B., and Croteau, R. (1994) *Arch. Biochem. Biophys.* 313:139–149; Dehal, S. S., and Croteau, R. (1988) *Arch. Biochem. Biophys.* 261:346–356). In the case of the monoterpene synthase and sesquiterpene synthase assays, the incubation mixture was overlaid with 1 ml pentane to trap volatile products. In all cases, after incubation at 31° C. for 2 h, the reaction mixture was extracted with pentane (3×1 ml) and the combined extract was passed through a 1.5 ml column of anhydrous $MgSO_4$ and silica gel (Mallinckrodt 60 Å) to provide the terpene hydrocarbon fraction free of oxygenated metabolites. The columns were subsequently eluted with 3×1 ml of ether to collect any oxygenated products, and an aliquot of each fraction was taken for liquid scintillation counting to determine conversion rate.

Product Identification—To obtain sufficient product for analysis by radio-GLC (gas liquid chromatography), chiral capillary GLC and GLC-MS (mass spectrum/spectrometry), preparative-scale enzyme incubations were carried out. Thus, the enzyme was prepared from 50 ml of cultured bacterial cells by extraction with 3 ml of assay buffer as above, and the extracts were incubated with excess substrate overnight at 31° C. The hydrocarbon fraction was isolated by elution through $MgSO_4$-silica gel as before, and the pentane eluate was concentrated for evaluation by capillary radio-GLC as described (Croteau, R., and Satterwhite, D. M. (1990) *J. Chromatogr.* 500:349–354), by chiral column capillary GLC (Lewinsohn, E., Savage, T. J., Gijzen, M., and Croteau, R. (1993) *Phytochem. Anal.* 4:220–225), and by combined GLC-MS [Hewlett-Packard 6890 GC-MSD with cool (40° C.) on-column injection, detection via electron impact ionization (70 eV), He carrier at 0.7 psi., column:0.25 mm i.d.×30 m fused silica with 0.25 μm film of 5MS (Hewlett-Packard) programmed from 35° C. (5 min hold) to 230° C. at 5° C./min].

EXAMPLE 4

Sequence Analysis

Inserts of all recombinant bluescript plasmids and pGEX plasmids were completely sequenced on both strands via primer walking and nested deletions (Sambrock, J., Fritsch, E. F., and Maniatis, T. (1989) *Molecular Cloning: A Laboratory Manual,* 2d Ed., Cold Spring Harbor Laboratory, Cold Spring Harbor, N.Y.) using the DyeDeoxy Terminator Cycle Sequencing method (Applied Biosystems). Sequence analysis was done using the Wisconsin Package Version 9.0, Genetics Computer Group (GCG), Madison, Wis.

EXAMPLE 5

RNA Extraction and Northern Blotting

Grand fir sapling stem tissue was harvested prior to wounding or two days after wounding by a standard procedure (Gijzen, M., Lewinsohn, E., and Croteau, R. (1991) *Arch. Biochem. Biophys.* 289:267–273). Total RNA was isolated (Lewinsohn, E., Steele, C. L., and Croteau, R. (1994) *Plant Mol. Biol. Rep.* 12:20–25) and 20 μg of RNA per gel lane was separated under denaturing conditions (Sambrock, J., Fritsch, E. F., and Maniatis, T. (1989) *Molecular Cloning: A Laboratory Manual,* 2d Ed., Cold Spring Harbor Laboratory, Cold Spring Harbor, N.Y.) and transferred to nitrocellulose membranes (Schleicher and Schuell) according to the manufacturer's protocol. To prepare hybridization probes, cDNA fragments of 1.4–1.5 kb were amplified by PCR from AG2.2 (SEQ ID NO:1) with primer JB29 (5-'CTA CCA TTC CAA TAT CTG-3')(SEQ ID NO:39) and primer 2-8 (5-'GTT GGA TCT TAG AAG TTC CC-3')(SEQ ID NO:40), from AG3.18 (SEQ ID NO:3) with primer 3-9 (5-'TTT CCA TTC CAA CCT CTG GG-3')(SEQ ID NO:41) and primer 3-11 (5-'CGT AAT GGA AAG CTC TGG CG-3')(SEQ ID NO:42), and from AG10 (SEQ ID NO:5) with primer 7-1 (5-'CCT TAC ACG CCT TTG GAT GG-3')(SEQ ID NO:43) and primer 7-3 (5-'TCT GTT GAT CCA GGA TGG TC-3')(SEQ ID NO:44). The probes were randomly labeled with $[\alpha-^{32}P]dATP$ (Feinberg, A. P., and Vogelstein, B. (1984) *Anal. Biochem.* 137:266–267). Blots were hybridized for 24 h at 55° C. in 3×SSPE and 0.1% SDS, washed at 55° C. in 1×SSPE and 0.1%, SDS and subjected to autoradiography as described above at −80° C. for 24 h.

EXAMPLE 6

Cloning and Characterization of Clones AG1.28 (SEQ ID NO:15). AG2.2 (SEQ ID NO:1), AG4.30 (SEQ ID NO:17) and AG 5.9 (SEQ ID NO:19)

Similarity-Based Cloning of Grand fir Terpene Synthases—Grand fir has been developed as a model system for the study of induced oleoresin production in conifers in response to wounding and insect attack (Johnson, M. A., and Croteau, R. (1987) in *Ecology and Metabolism of Plant Lipids* (Fuller, G., and Nes, W. D., eds) pp. 76–91, American Chemical Society Symposium Series 325, Washington, D.C.; Gijzen, M., Lewinsohn, E., Savage, T. J., and Croteau, R. B. (1993) in *Bioactive Volatile Compounds from Plants* (Teranishi, R., Buttery, R. G., and Sugisawa, H., eds) pp. 8–22, American Chemical Society Symposium Series 525, Washington, D.C.; Raffa, K. F., and Berryman, A. A. (1982) *Can. Entomol.* 114:797–810; Steele, C., Lewinsohn, E., and Croteau, R. (1995) *Proc. Natl. Acad Sci. USA* 92:4164–4168; Lewinsohn, E., Gijzen, M., and Croteau, R. (1992) in Regulation of *Isopentenoid Metabolism* (Nes, W. D., Parish, E. J., and Trzaskos, J. M., eds) pp. 8–17, American Chemical Society Symposium Series 497, Washington, D.C.). The chemistry and biosynthesis of the oleoresin monoterpenes, sesquiterpenes and diterpenes have been well defined (Lewinsohn, E., Savage, T. J., Gijzen, M., and Croteau, R. (1993) *Phytochem. Anal.* 4:220–225; Lewinsohn, E., Gijzen, M., and Croteau, R. (1991) *Plant Physiol.* 96:44–49; Funk, C., Lewinsohn, E., Stofer Vogel, B., Steele C., and Croteau, R. (1994) *Plant Physiol.* 106:999–1005; Gijzen, M., Lewinsohn, E., and Croteau, R. (1991) *Arch. Biochem. Biophys.* 289:267–273; Lewinsohn, E., Gijzen, M., and Croteau, R. (1992) *Arch. Biochem. Biophys.* 293:167–173; LaFever, R. E., Stofer Vogel, B., and Croteau, R. (1994) Arch. Biochem. Biophys. 313:139–149; Funk, C., and Croteau, R. (1994) *Arch. Biochem. Biophys.* 308:258–266); however, structural analysis of the responsible terpene synthases as well as studies on the regulation of oleoresinosis require the isolation of cDNA species encoding the terpene synthases. Protein purification from conifers, as the basis for cDNA isolation, has been of limited success (Stofer Vogel, B., Wildung, M. R., Vogel, G., and Croteau, R. (1996) J. Biol. Chem. 271:23262–23268) and thus far has not permitted cloning of any of the monoterpene synthases from these species (Steele, C., Lewinsohn, E., and Croteau, R. (1995) *Proc. Natl. Acad Sci. USA* 92:4164–4168).

As a possible alternative to protein-based cloning of terpene synthases, a homology-based PCR strategy was proposed (Steele, C., Lewinsohn, E., and Croteau, R. (1995) *Proc. Natl. Acad. Sci. USA* 92:4164–4168) that was founded upon the three terpene synthases of plant origin then available, a monoterpene synthase, (−)-4S-limonene synthase, from spearmint (Mentha spicata, Lamiaceae) (Colby, S. M., Alonso, W. R., Katahira, E. J., McGarvey, D. J., and Croteau, R. (1993) *J. Biol. Chem.* 268:23016–23024), a sesquiterpene synthase, 5-epi-aristolochene synthase, from tobacco (*Nicotiana tabacum*, Solanaceae) (Facchini, P. J., and Chappell, J. (1992) *Proc. Natl. Acad Sci. USA* 89:11088–11092), and a diterpene synthase, casbene synthase, from castor bean (*Ricinus communis*, Euphorbiaceae) (Mau, C. J. D., and West, C. A. (1994) *Proc. Natl. Acad. Sci. USA* 91:8497–8501). Despite the taxonomic distances between these three angiosperm species and the differences in substrate utilized, reaction mechanism and product type of the three enzymes, a comparison of the deduced amino acid sequences identified several conserved regions that appeared to be useful for the design of degenerate PCR primers (see Example 1). Using cDNA from a wound-induced Grand fir stem library as template, PCR primers C (SEQ ID NO:9) and D (SEQ ID NO:10) amplified products corresponding to four distinct sequence groups, all of which showed significant similarity to sequences of cloned terpene synthases of plant origin. The four different inserts were designated as probes 1 (SEQ ID NO:11), 2 (SEQ ID NO:12), 4 (SEQ ID NO:13) and 5 (SEQ ID NO:14), and were employed for isolation of the corresponding cDNA clones by plaque hybridization.

Screening of $10^5$ cDNA phage plaques from the wounded Grand fir stem library, with each of the four probes, yielded a four-fold difference in the number of positives, most likely reflecting different levels of expression of the corresponding genes. Size selected inserts (>1.5 kb) of purified and in vivo excised clones were partially sequenced from both ends, and were shown to segregate into four distinct groups corresponding to the four hybridization probes. Since all cDNAs corresponding to probes 1 (SEQ ID NO:11), 4 (SEQ ID NO:13) and 5 (SEQ ID NO:14) were truncated at their 5'-ends, only inserts of the largest representatives of each group, clone AG1.28 (SEQ ID NO:15), clone AG2.2 (SEQ ID NO:1) (apparently full length), clone AG4.30 (SEQ ID NO:17) and clone AG5.9 (SEQ ID NO:19), were completely sequenced. Clone AG1.28 (SEQ ID NO:15)(2424 bps) includes an open reading frame (ORF) of 2350 nucleotides (nts) encoding 782 amino acids (SEQ ID NO:16); clone AG2.2 (SEQ ID NO:1)(2196 bps), includes an ORF of 1881 nts encoding 627 amino acids (SEQ ID NO:2); clone AG4.30 (SEQ ID NO:17)(1967 bps) includes an ORF of 1731 nts encoding 577 amino acids (SEQ ID NO:18) and clone AG5.9 (SEQ ID NO:19)(1416 bps) includes an ORF of 1194 nucleotides encoding 398 amino acids (SEQ ID NO:20).

cDNA clones AG1.28 (SEQ ID NO:15), AG2.2 (SEQ ID NO:1), AG4.30 (SEQ ID NO:17) and AG5.9 (SEQ ID NO:19) were compared pairwise with each other and with other cloned plant terpene synthases. Truncated clone AG1.28 (SEQ ID NO:15) resembled most closely in size and sequence (72% similarity, 49% identity) a diterpene cyclase, abietadiene synthase, from Grand fir (Stofer Vogel, B., Wildung, M. R., Vogel, G., and Croteau, R. (1996) *J. Biol. Chem.* 271:23262–23268). Clones AG4.30 (SEQ ID NO:17) and AG5.9 (SEQ ID NO:19) share approximately 80% similarity (60% identity) at the amino acid level, and are almost equally distant from both clone AG1.28 (SEQ ID NO:15) and full-length clone AG2.2 (SEQ ID NO:1)(range of 65–70% similarity and 45–47% identity); the amino acid sequence similarity between AG1.28 (SEQ ID NO:15) and AG2.2 (SEQ ID NO:1) is 65% (41% identity). Considering the high level of homology between AG4.30 (SEQ ID NO:17) and AG5.9 (SEQ ID NO:19), these comparisons suggest that the four new cDNAs, AG1.28 (SEQ ID NO:15), AG2.2 (SEQ ID NO:1), AG4.30 (SEQ ID NO:17) and AG5.9 (SEQ ID NO:19), represent the three major subfamilies of Grand fir terpene synthase genes encoding monoterpene synthases, sesquiterpene synthases and diterpene synthases.

Identification of cDNA Clone AG2.2 (SEQ ID NO:1) as Myrcene Synthase—The pAG2.2 insert (SEQ ID NO:1) appeared to be a full-length clone encoding a protein of molecular weight 72,478 with a calculated pI at 6.5. The size of the translated protein encoded by AG2.2 (SEQ ID NO:1) (627 residues)(SEQ ID NO:2) is in the range of the monoterpene synthase preproteins for limonene synthase from spearmint (Colby, S. M., Alonso, W. R., Katahira, E. J., McGarvey, D. J., and Croteau, R. (1993) *J. Biol. Chem.* 268:23016–23024) and *Perilla frutescens* (Yuba, A., Yazaki, K., Tabata, M., Honda, G., and Croteau, R. (1996) *Arch. Biochem. Biophys.* 332:280–287), but is about 240 amino acids shorter than the two gymnosperm diterpene synthase preproteins for abietadiene synthase (Stofer Vogel, B., Wildung, M. R., Vogel, G., and Croteau, R. (1996) *J. Biol. Chem.* 271:23262–23268) and taxadiene synthase (Wildung, M. R., and Croteau, R. (1996) *J. Biol. Chem.* 271:9201–9204). Monoterpene and diterpene biosynthesis are compartmentalized in plastids whereas sesquiterpene biosynthesis is cytosolic (reviewed in Kleinig, H. (1989) *Annu. Rev. Plant Physiol Plant Mol. Biol.* 40:39–53; Gershenzon, J., and Croteau, R. (1993) in *Lipid Metabolism in Plants* (Moore, T. S. Jr., ed) pp. 339–388, CRC Press, Boca Raton, Fla.; McGarvey, D. J., and Croteau, R. (1995) *Plant Cell* 7, 1015–1026); thus, monoterpene and diterpene synthases are encoded as preproteins bearing an amino-terminal transit peptide for import of these nuclear gene products into plastids where they are proteolytically processed to the mature forms (Keegstra, K., Olsen, J. J., and Theg, S. M. (1989) *Annu. Rev. Plant Physiol. Plant Mol. Biol.* 40:471–501; von Heijne, G., Stepphuhn, J., and Herrmann (1989) *Eur. J Biochem.* 180:535–545). Both the size of the deduced protein and the presence of an N-terminal domain (of 60 to 70 amino acids) with features characteristic of a targeting sequence [rich in serine residues (16–18%) and low in acidic residues (four Asp or Glu) (Keegstra, K., Olsen, J. J., and Theg, S. M. (1989) *Annu. Rev. Plant Physiol Plant Mol Biol.* 40:471–501; von Heijne, G., Stepphuhn, J., and Herrmann (1989) *Eur. J Biochem.* 180:535–545)] suggest that AG2.2 (SEQ ID NO:1) encodes a monoterpene synthase rather than a sesquiterpene synthase or a diterpene synthase.

Figure 3A:
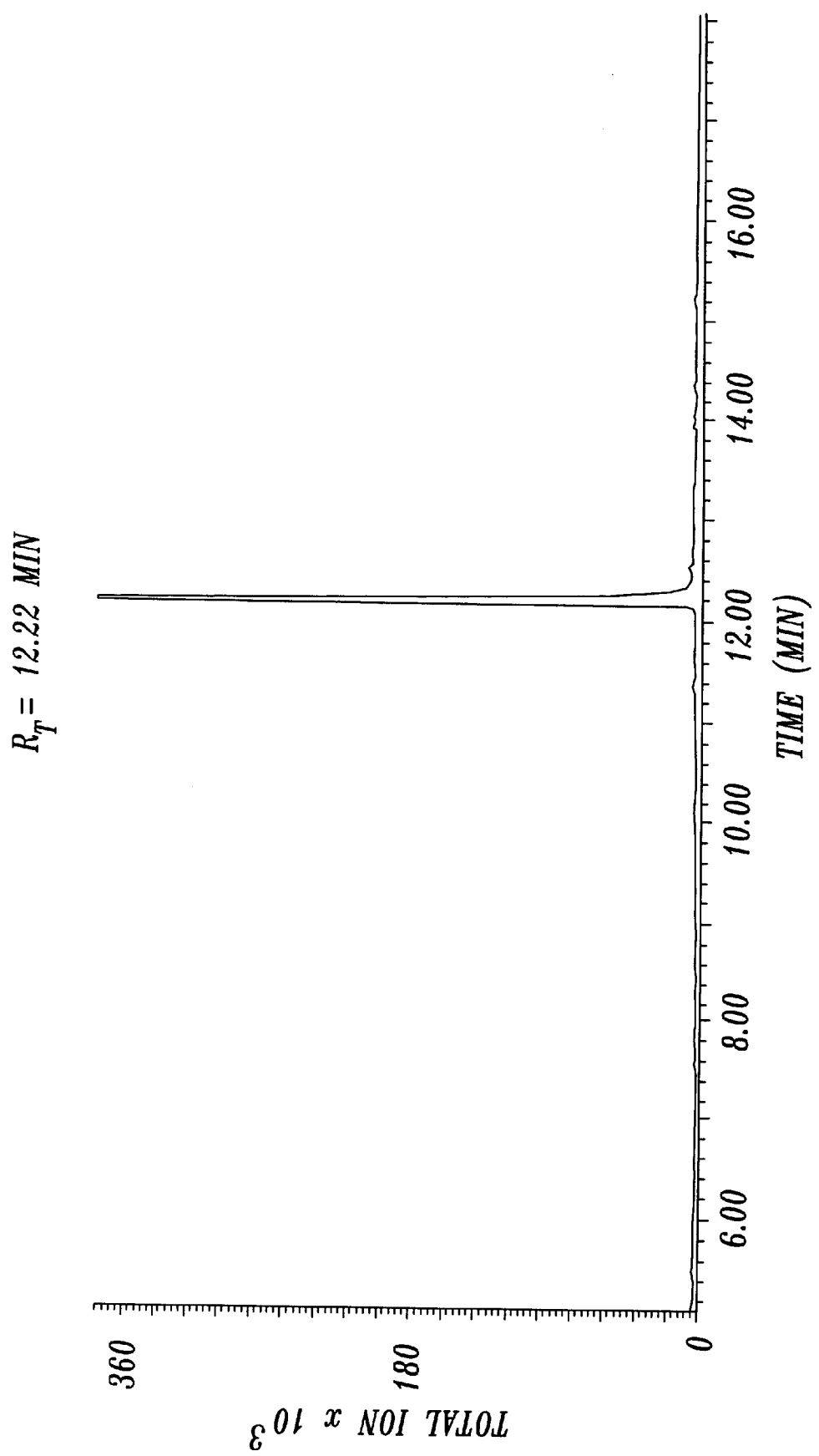
FIG. 3 depicts a GLC-MS analysis of the products of the recombinant protein encoded by AG2.2 (SEQ ID NO:1), the sequence of the protein encoded by clone AG2.2 being set forth in SEQ ID NO:2. The GLC profile of the total pentane-soluble products generated from geranyl diphosphate when incubated with a cell-free extract of *E. coli* XL1-Blue/pGAG2.2 is illustrated (FIG. 3A), as are the mass fragmentation patterns for the monoterpene product with $R_t$=12.22 min (FIG. 3B) and for authentic myrcene FIG. 3C).
Figure 3B:
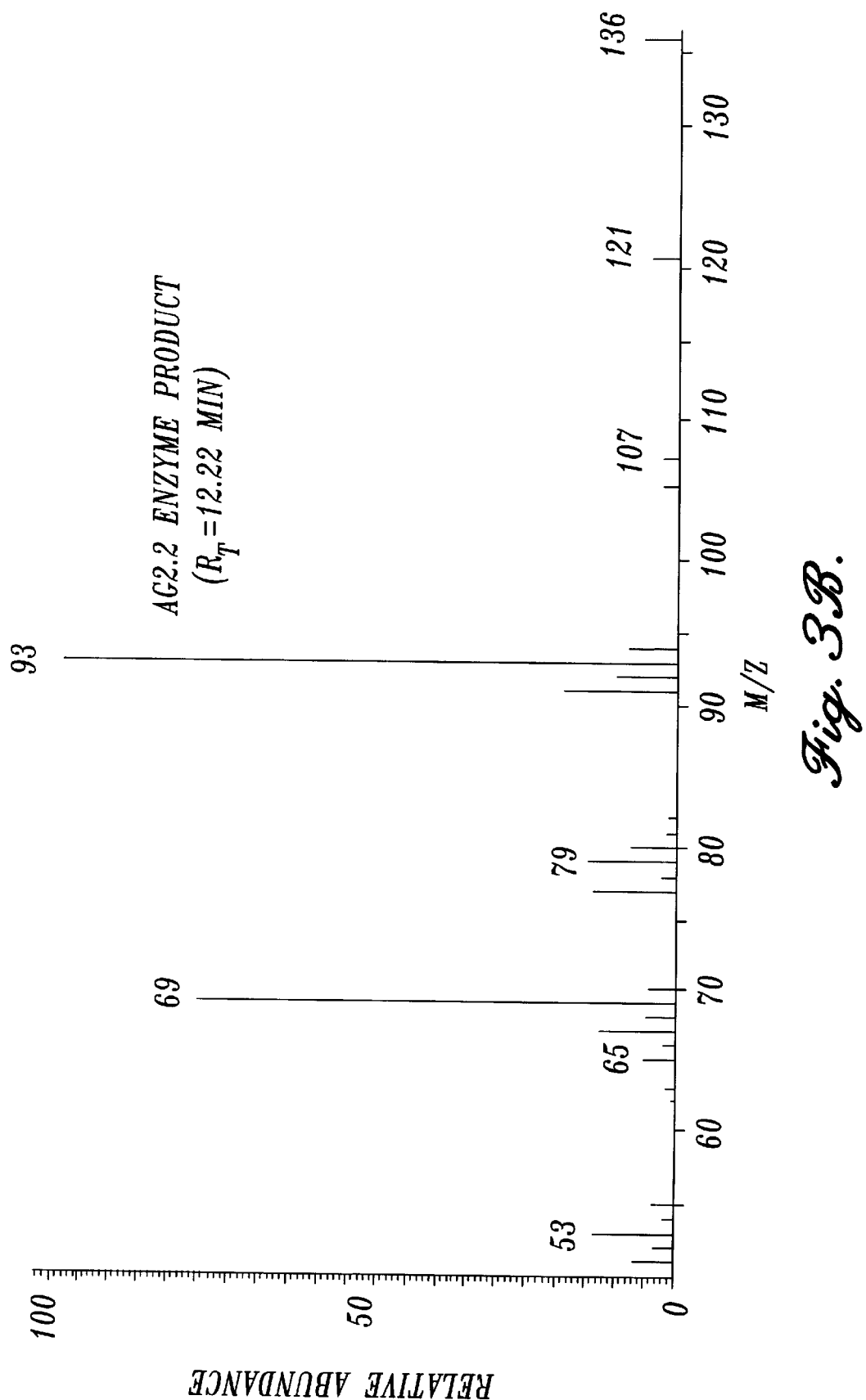
Figure 3C:
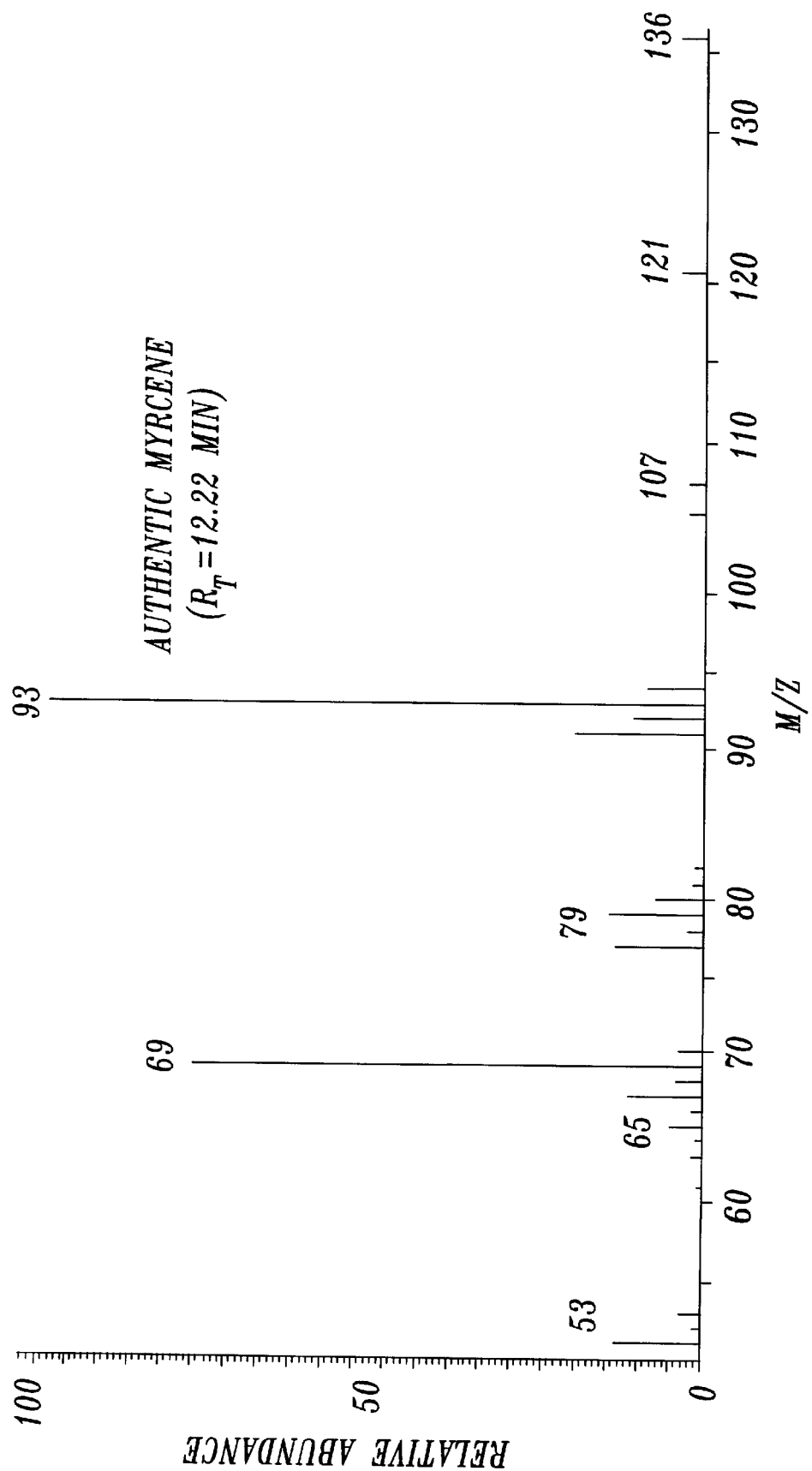
Figure 4A:
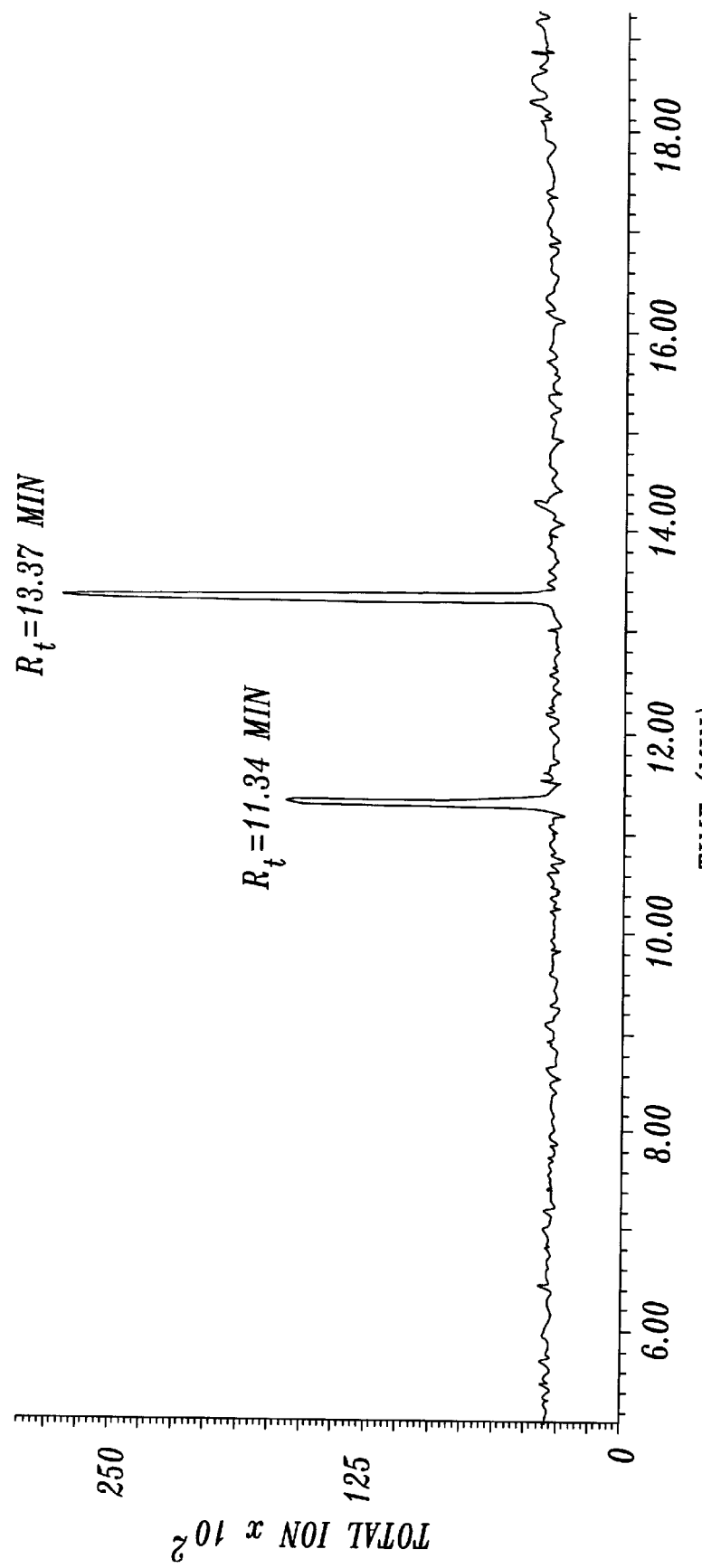
FIG. 4 depicts a GLC-MS analysis of the products of the recombinant protein encoded by AG3.18 (SEQ ID NO:3), the sequence of the protein encoded by clone AG3.18 (SEQ ID NO:3) being set forth in SEQ ID NO:4. The GLC profile of the total pentane-soluble products generated from geranyl diphosphate when incubated with a cell-free extract of *E. coli* XL1-Blue/pGAG3.18 is illustrated (FIG. 4A), as are the mass fragmentation patterns (selected ion mode) for the monoterpene products with $R_t$=11.34 min (FIG. 4B), and $R_t$=13.37 min (FIG. 4D), and for authentic α-pinene (FIG. 4C) and authentic β-pinene (FIG. 4E).
Figure 4B:
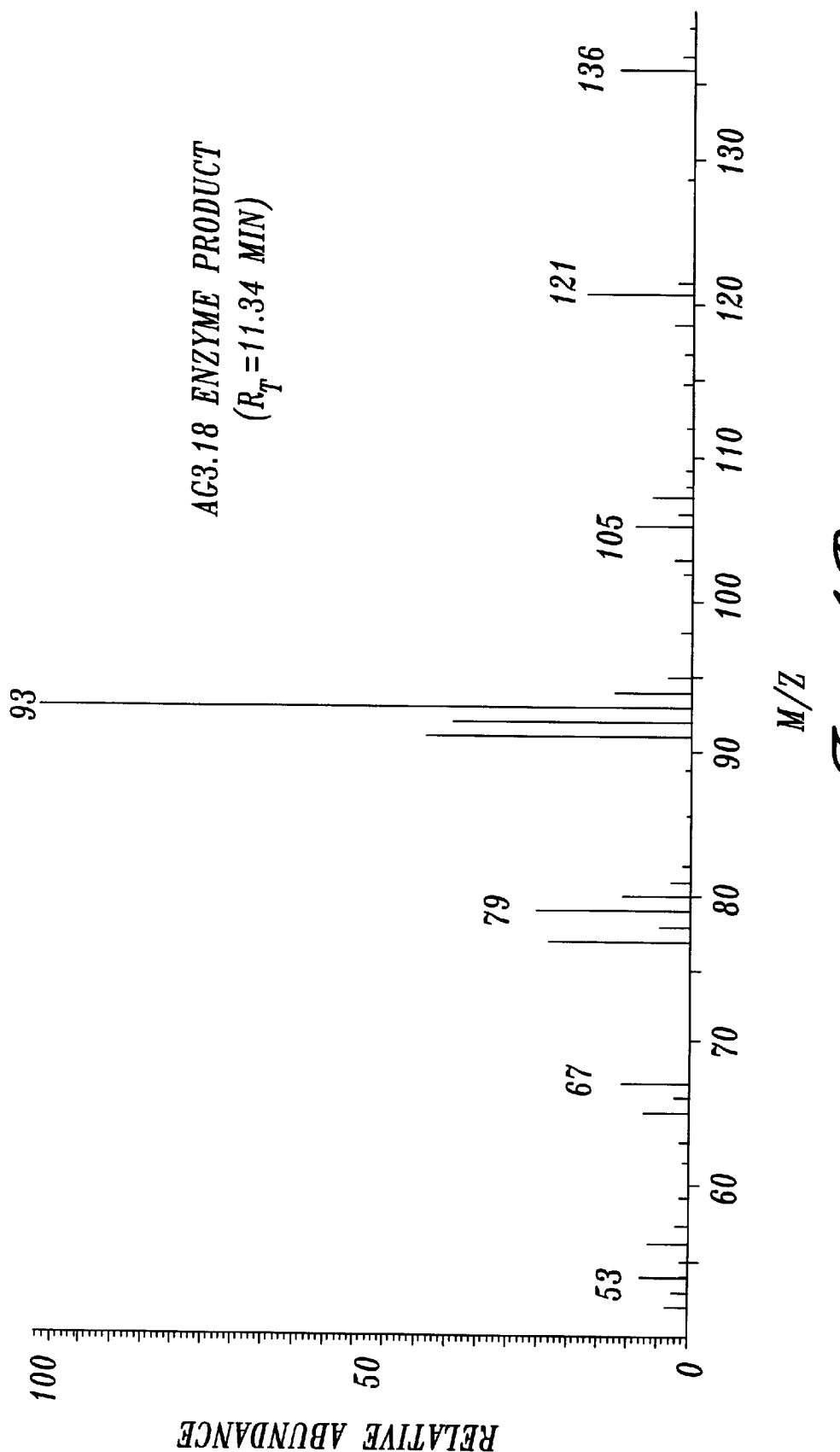
Figure 4C:
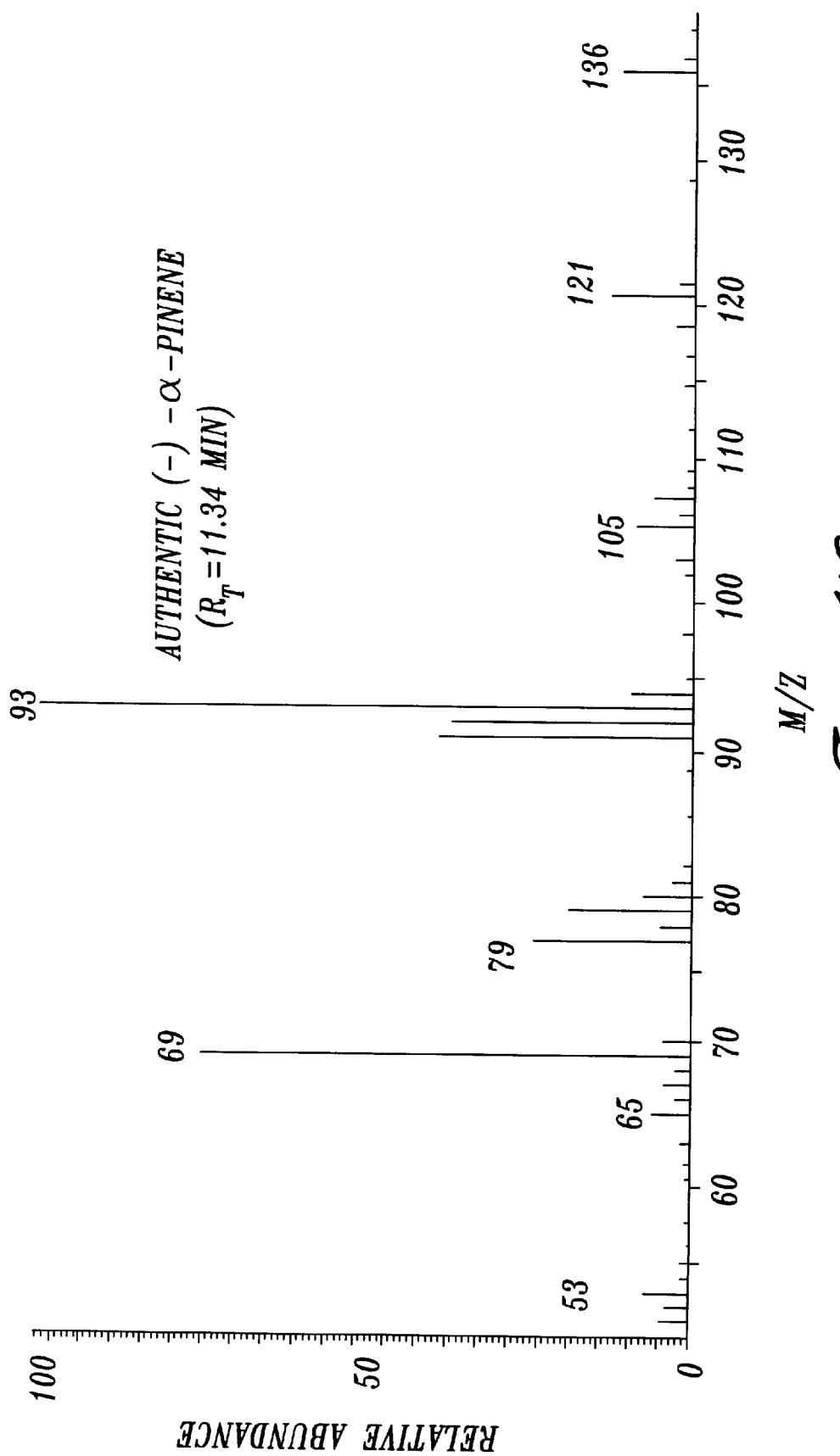
Figure 4D:
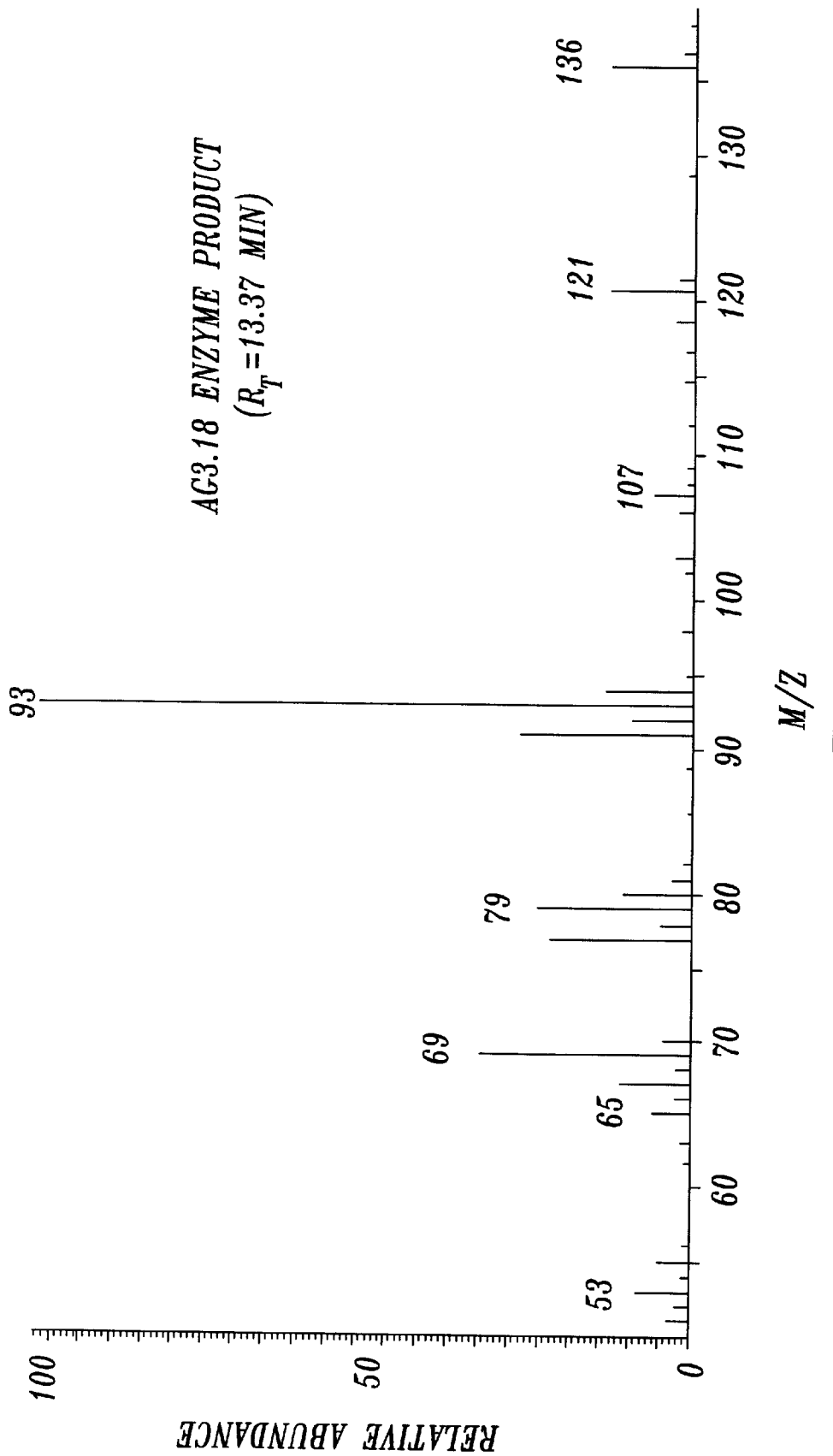
Figure 4E:
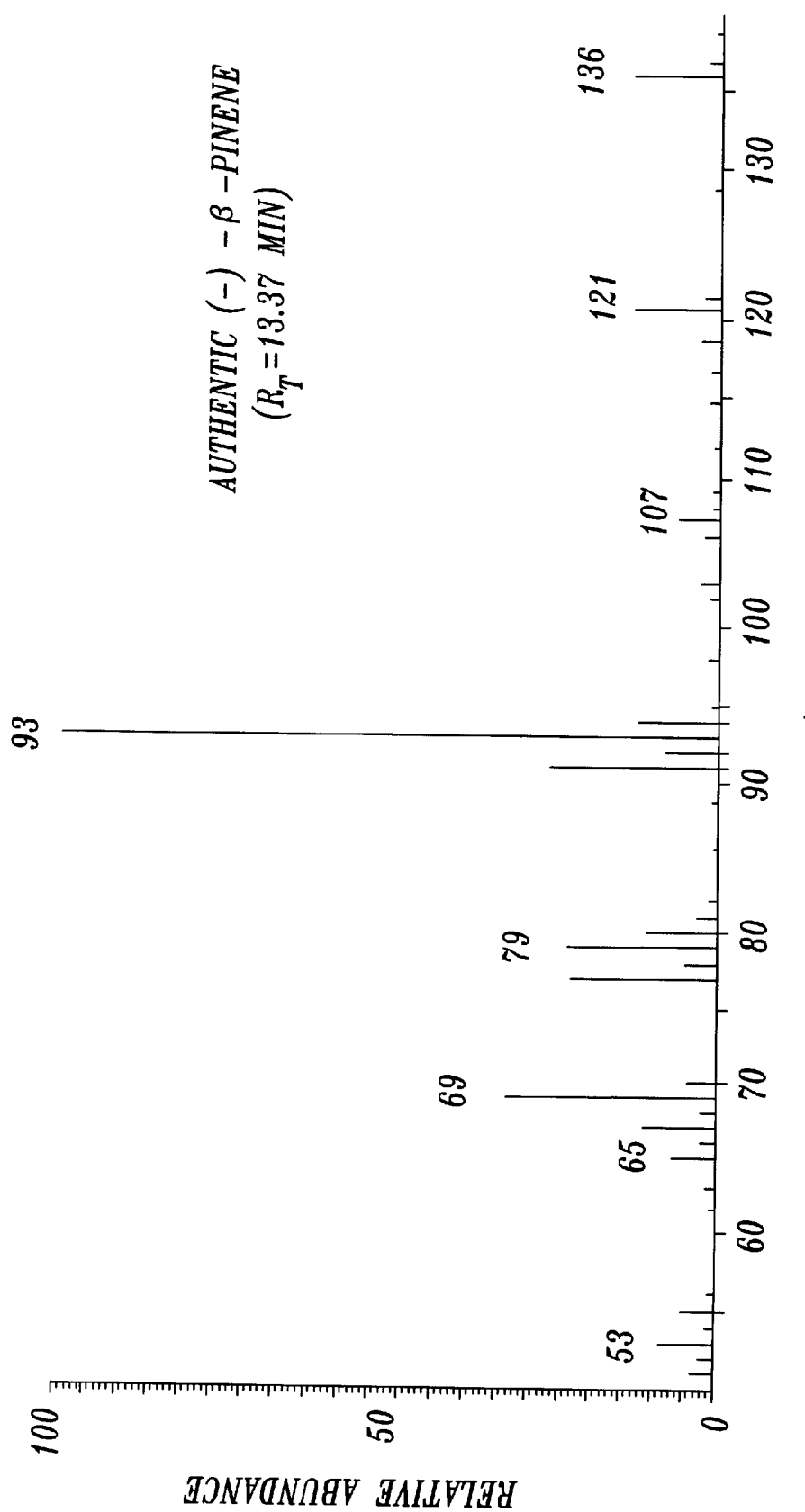

Since pAG2.2 contained the terpene synthase insert in reversed orientation, the ORF was subcloned in frame with glutathione S-transferase, for ultimate ease of purification (Bohlmann, J., DeLuca, V., Eilert, U., and Martin, W. (1995) *Plant J.* 7:491–501; Bohlmann, J., Lins, T., Martin, W., and Eilert, U. (1996) Plant Physiol. 111:507–514), into pGEX-4T-2, yielding plasmid pGAG2.2. The recombinant fusion protein was expressed in *E. coli* strain XL1-Blue/pGAG2.2, then extracted and assayed for monoterpene synthase, sesquiterpene synthase and diterpene synthase activity using tritium labeled geranyl diphosphate, farnesyl diphosphate and geranylgeranyl diphosphate as the respective substrate. Enzymatic production of a terpene olefin was observed only with geranyl diphosphate as substrate, and the only product was shown to be myrcene by radio-GLC and GLC-MS comparison to an authentic standard (FIG. 3). Bacteria transformed with pGEX vector containing the AG2.2 insert (SEQ ID NO:1) in antisense orientation did not afford detectable myrcene synthase activity when induced, and the protein isolated and assayed as above. A myrcene synthase cDNA has not been obtained previously from any source, although myrcene is a minor co-product (2%) of the native and recombinant limonene synthase from spearmint (Rajaonarivony, J. I. M., Gershenzon, J., and Croteau, R. (1992) *Arch. Biochem. Biophys.* 296:49–57; Colby, S. M., Alonso, W. R., Katahira, E. J., McGarvey, D. J., and Croteau, R. (1993) *J. Biol. Chem.* 268:23016–23024) and of several enzymes from sage (Croteau, R., and Satterwhite, D. M. (1989) *J. Biol. Chem.* 264:15309–15315). cDNA cloning and functional expression of myrcene synthase, which is one of several wound-inducible monoterpene synthase activities of Grand fir (Gijzen, M., Lewinsohn, E., and Croteau, R. (1991) *Arch. Biochem. Biophys.* 289:267–273), demonstrates that this acyclic monoterpene is formed by a distinct enzyme and is not a co-product of another synthase.

EXAMPLE 7

Cloning and Characterization of Clones AG3.18 (SEQ ID NO:3) Encoding (−)-Pinene Synthase and cDNA Clone AG10 (SEQ ID NO:5) Encoding (−)-Limonene Synthase Identification of cDNA Clone AG3.18 (SEQ ID NO:3) as (−)-Pinene Synthase and cDNA Clone AG10 (SEQ ID NO:5) as (−)-Limonene Synthase—Alignment of the four new terpene synthase cDNA sequences (AG1.28 (SEQ ID NO:15), AG2.2 (SEQ ID NO:1), AG4.30 (SEQ ID NO:17) and AG5.9 (SEQ ID NO:19)), and that for abietadiene synthase (Stofer Vogel, B., Wildung, M. R., Vogel, G., and Croteau, R. (1996) *J. Biol. Chem.* 271:23262–23268), allowed the identification of several conserved sequence motifs among this enzyme family from Grand fir, which provided the foundation for an extended similarity-based cloning approach. Two new sense primers E (SEQ ID NO:21) and F (SEQ ID NO:22) were designed according to conserved sequence elements, whereas a degenerate antisense primer G (SEQ ID NO:23) was designed based upon very limited amino acid sequence information from pinene synthase (see Example 1). Only the combination of primers E (SEQ ID NO:21) and G (SEQ ID NO:23) amplified a specific product of 533 bps, which was designated as probe 3 (SEQ ID NO:24).

Hybridization of 10 Grand fir λZAP II cDNA clones with probe 3 (SEQ ID NO:24) yielded two types of signals comprised of about 400 strongly positive clones and an equal number of weak positives, indicating that the probe recognized more than one type of cDNA. Thirty-four of the former clones and 18 of the latter were purified, the inserts were selected by size (2.0–2.5 kb), and the in vivo excised clones were partially sequenced from both ends. Those clones which afforded weak hybridization signals were shown to contain inserts that were either identical to myrcene synthase clone AG2.2 (SEQ ID NO:1) or exhibited no significant sequence similarity to terpene synthases. Clone AG3.48 (SEQ ID NO:3 1) contained the myrcene synthase ORF in the correct orientation and in frame for expression from the Bluescript plasmid vector. This cDNA was functionally expressed in *E. coli* and the resulting enzyme was shown to accept only geranyl diphosphate as the prenyl diphosphate substrate and to produce myrcene as the exclusive reaction product. This finding with AG3.48 (SEQ ID NO:31) confirms that expression of AG2.2 (SEQ ID NO:1) as the glutathione S-transferase fusion protein from pGAG2.2 does not influence substrate utilization or product outcome of the myrcene synthase.

Clones which gave strong hybridization signals segregated into distinct sequence groups represented by clone AG3.18 (SEQ ID NO:3)(2018 bp insert with ORF of 1884 nt; encoded protein of 628 residues at 71,505 Da and pI of 5.5) and AG10 (SEQ ID NO:5)(2089 bp insert with ORF of 1911 nt; encoded protein of 637 residues at 73,477 Da and pI of 6.4). AG3.18 (SEQ ID NO:3) and AG10 (SEQ ID NO:5) form a subfamily together with the myrcene synthase clone AG2.2 (SEQ ID NO:1) that is characterized by a minimum of 79% pairwise similarity (64% identity) at the amino acid level. Like myrcene synthase, both AG3.18 (SEQ ID NO:3) and AG10 (SEQ ID NO:5) encode N-terminal sequences of 60 to 70 amino acids which are rich in serine (19–22% and 11–15%, respectively) and low in acidic residues (4 and 2, respectively) characteristic of plastid transit peptides (Keegstra, K., Olsen, J. J., and Theg, S. M. (1989) *Annu. Rev. Plant Physiol. Plant Mol. Biol.* 40:471–501; von Heijne, G., Stepphuhn, J., and Herrmann (1989) *Eur. J Biochem.* 180:535–545).

Figure 5A:
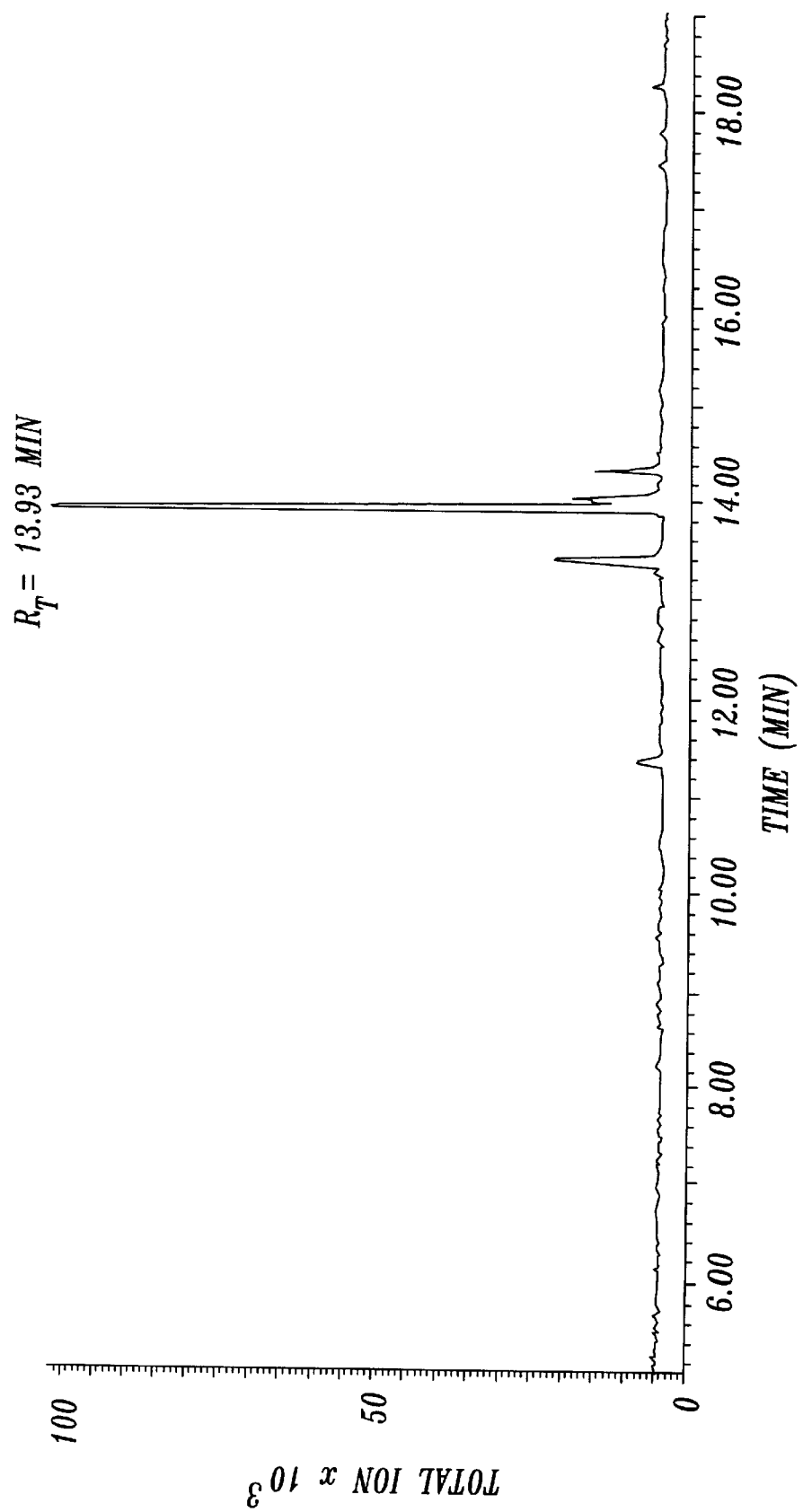
FIG. 5 depicts a GLC-MS analysis of the products of the recombinant protein encoded by AG10 (SEQ ID NO:5), the sequence of the protein encoded by clone AG10 (SEQ ID NO:5) being set forth in SEQ ID NO:6. The GLC profile of the total pentane-soluble products generated from geranyl diphosphate when incubated with a cell-free extract of *E. coli* BL21(DE3)/pSBAG10 is illustrated (FIG. 5A), as are the mass fragmentation patterns for the principal monoterpene product with $R_t$=13.93 min (FIG. 5B) and for authentic limonene (FIG. 5C).
Figure 5B:
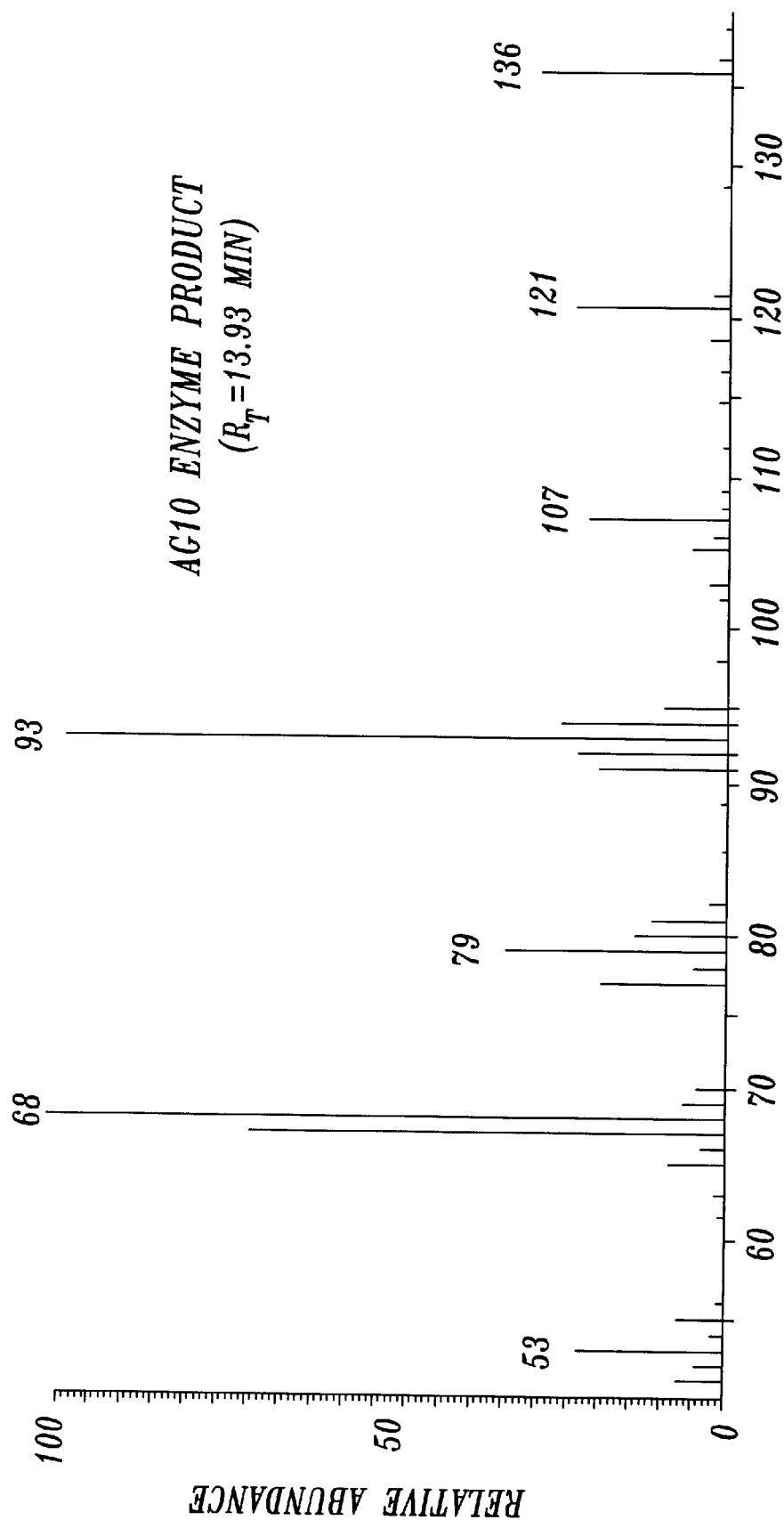
Figure 5C:
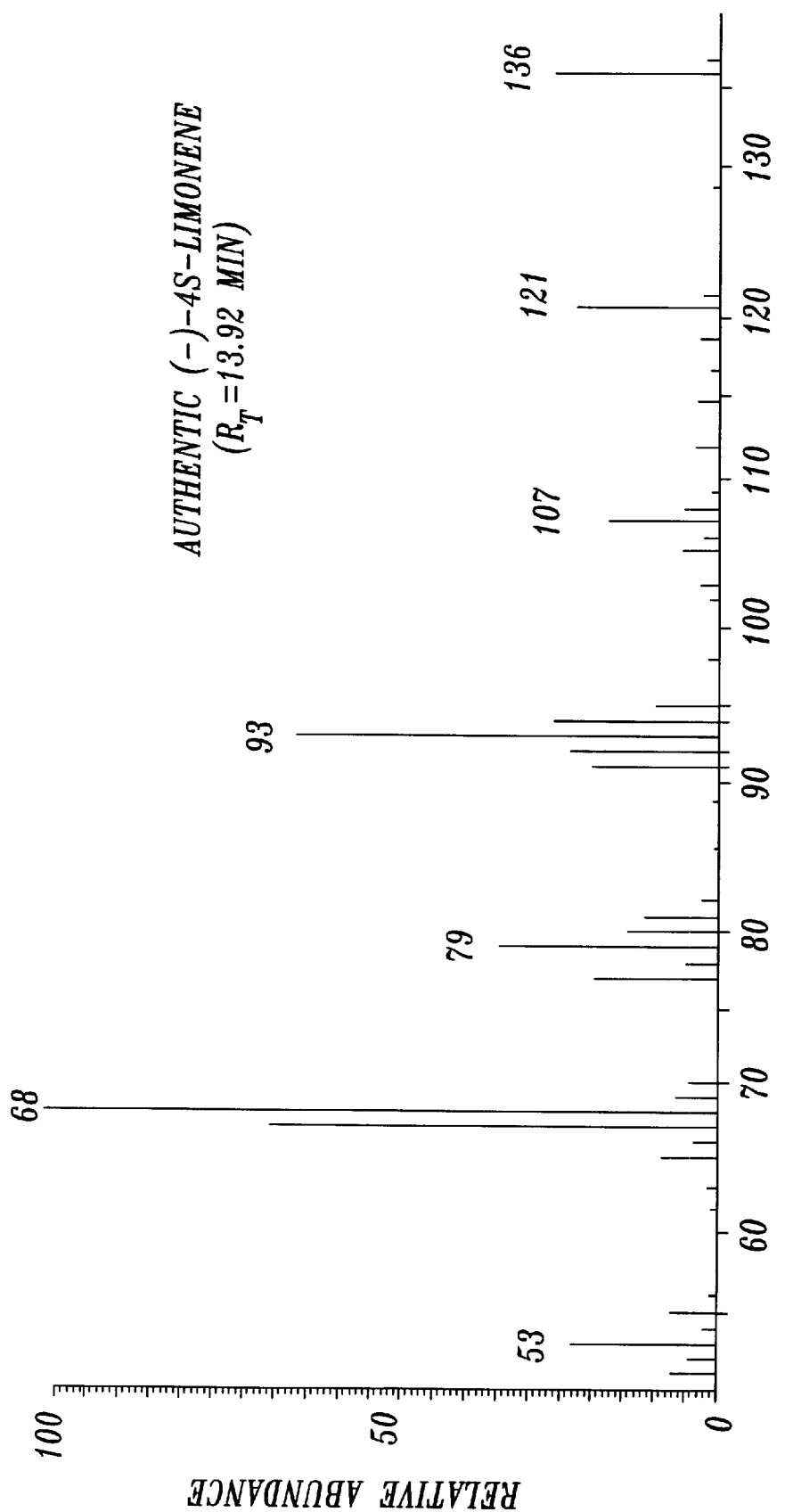

Plasmid pAG3.18 (SEQ ID NO:3) contained the presumptive terpene synthase ORF in frame for direct expression from the bluescript plasmid, whereas the AG10 (SEQ ID NO:5) ORF was in reversed orientation. Both AG3.18 (SEQ ID NO:3) and AG10 (SEQ ID NO:5) were subdloned into expression vectors yielding plasmids pGAG3.18 and pSBAG10. Recombinant proteins were expressed in bacterial strain *E. coli* XLOLR/pAG3.18, *E. coli* XL1-Blue/pGAG3.18 and *E. coli* BL21(DE3)/pSBAG10. When extracts of the induced cells were tested for terpene synthase activity with all of the potential prenyl diphosphate substrates, only geranyl diphosphate was utilized. Extracts from *E. coli* BL21(DE3)/pSBAG10 converted geranyl diphosphate to limonene as the major product with lesser amounts of α-pinene, β-pinene and β-phellandrene, as determined by radio-GLC and combined GLC-MS (FIG. 5). Chiral phase capillary GLC on β-cyclodextrin revealed the limonene product to be the (−)-4S-enantiomer and the pinene products to be the related (−)-(1S:5S)-enantiomers. Although optically pure standards were not available for the analysis, stereochemical considerations suggest that the minor product β-phellandrene is also the mechanistically related (−)-(4S)-antipode (Gambliel, H., and Croteau, R. (1984) J. Biol.Chem. 259:740–748; Croteau, R., Satterwhite, D. M., Cane, D. E., and Chang, C. C. (1988) J. Biol. Chem. 263:10063–10071; Wagschal, K., Savage, T. J., and Croteau, R. (1991) Tetrahedron 47:5933–5944; Croteau, R., Satterwhite, D. M., Wheeler, C. J., and Felton, N. M. (1989) J. Biol. Chem. 264:2075–2080; LaFever, R. E., and Croteau, R. (1993) Arch. Biochem. Biophys. 301:361–366). Similar analysis of the monoterpene products generated from geranyl diphosphate by cell-free extracts of E. coli XLOLR/pAG3.18 and E. coli XL1-Blue/pGAG3.18 demonstrated the presence of a 42:58% mixture of α-pinene and β-pinene (FIG. 4), the same product ratio previously described for the purified, native (−)-pinene synthase from Grand fir (Lewinsohn, E., Gijzen, M., and Croteau, R. (1992) Arch. Biochem. Biophys. 293:167–173). Chiral phase capillary GLC confirmed the products of the recombinant pinene synthase to be the (−)-(1S:5S)-enantiomers, as expected. No other monoterpene co-products were detected with the recombinant (−)-pinene synthase, as observed previously for the native enzyme (Lewinsohn, E., Gijzen, M., and Croteau, R. (1992) Arch. Biochem. Biophys. 293:167–173).

Evidence for the formation of both α- and β-pinene by a single enzyme has been previously provided through co-purification studies, and differential inhibition and inactivation studies, as well as by isotopically sensitive branching experiments (Gambliel, H., and Croteau, R. (1984) J. Biol. Chem. 259:740–748; Wagschal, K. C., Pyun, H.-J., Coates, R. M., and Croteau, R. (1994) Arch. Biochem. Biophys. 308:477–487; Wagschal, K., Savage, T. J., and Croteau, R. (1991) Tetrahedron 47:5933–5944; 5944; Croteau, R., Wheeler, C. J., Cane, D. E., Ebert, R., and Ha, H.-J. (1987) Biochemistry 26:5383–5389). The cDNA cloning of pinene synthase provides the ultimate proof that a single enzyme forms both products. The calculated molecular weight of the (−)-pinene synthase deduced from AG3.18 (SEQ ID NO:3) is approximately 64,000 (excluding the putative transit peptide), which agrees well with the molecular weight of 63,000 established for the native enzyme from Grand fir by gel permeation chromatography and SDS-PAGE (Lewinsohn, E., Gijzen, M., and Croteau, R. (1992) Arch. Biochem. Biophys. 293:167–173).

Figure 6A:
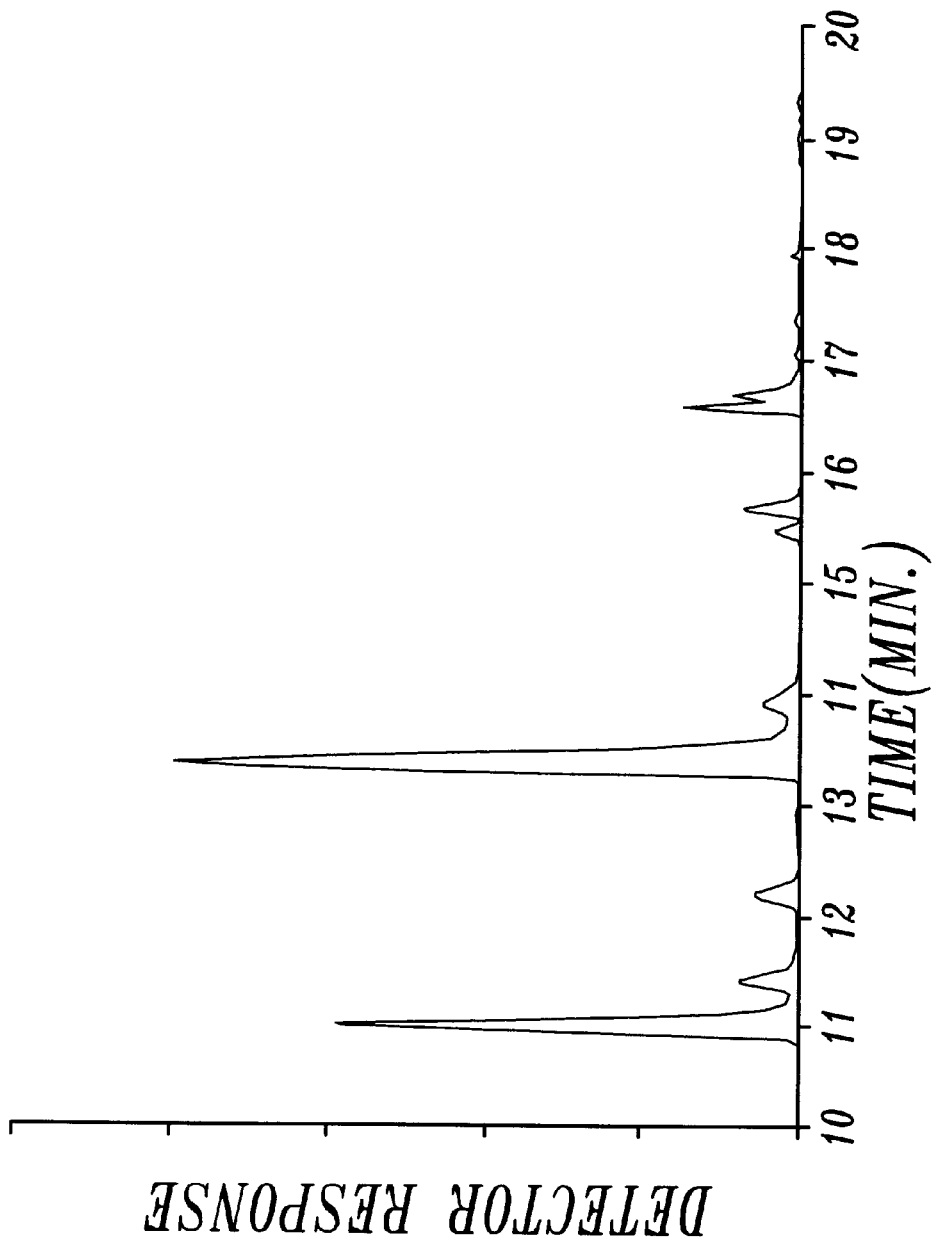
FIG. 6A depicts a total ion chromatogram of monoterpene products derived from geranyl diphosphate by a (−)-camphene synthase of the invention.
Figure 6B:
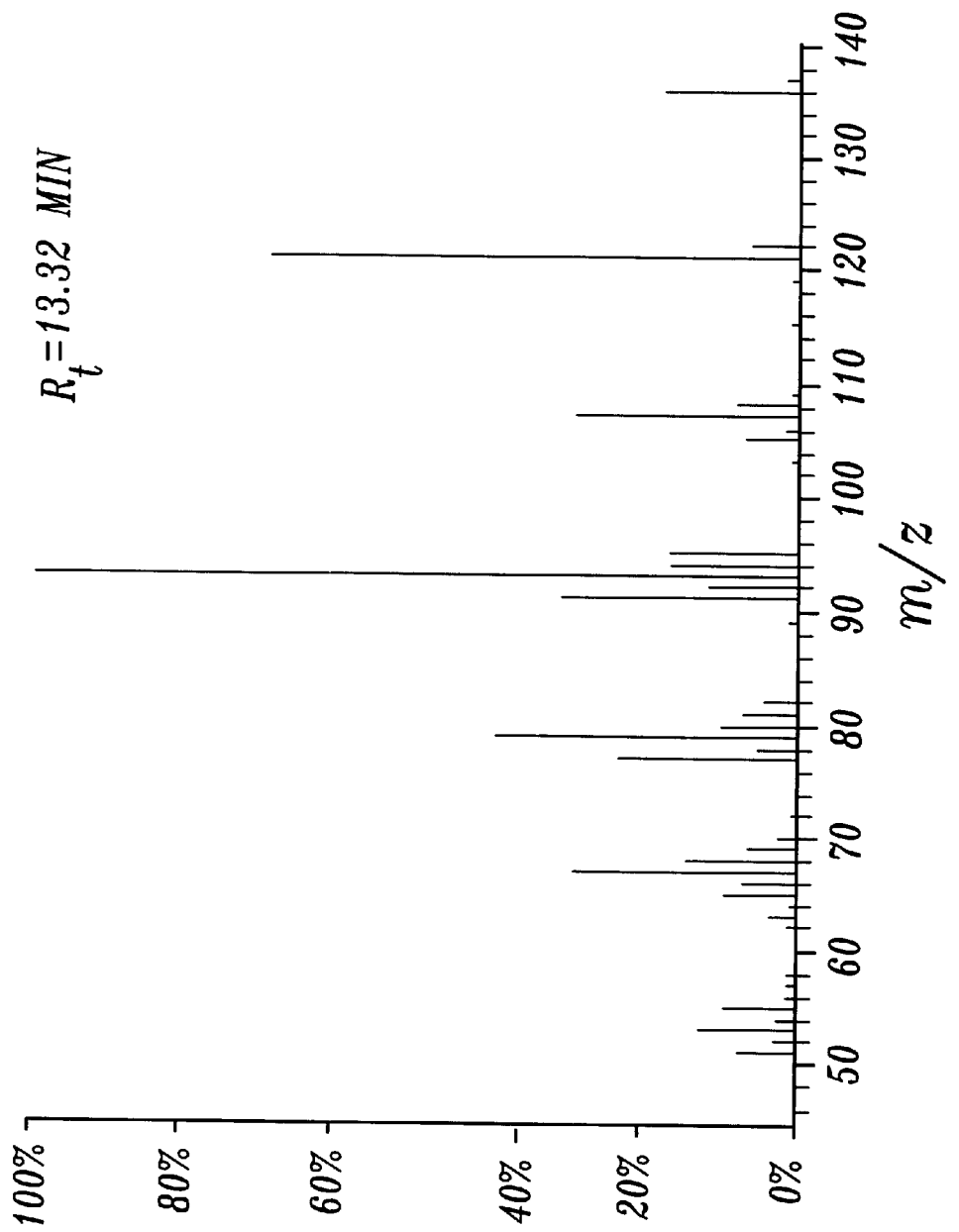
FIG. 6B depicts the mass spectrum and retention time for the principal enzyme product shown in FIG. 6A.
Figure 6C:
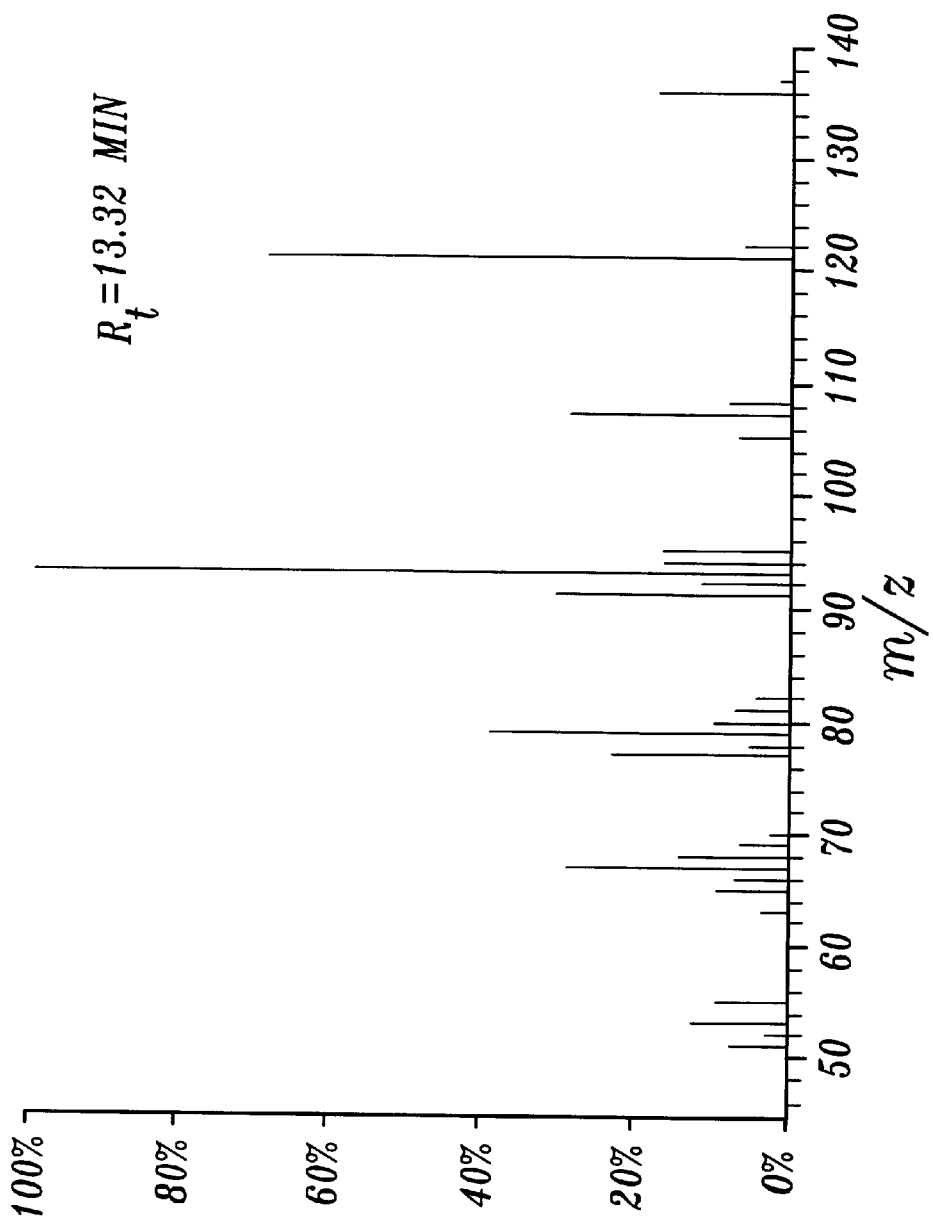
FIG. 6C depicts the mass spectrum and retention time for the authentic camphene standard.
Figure 7A:
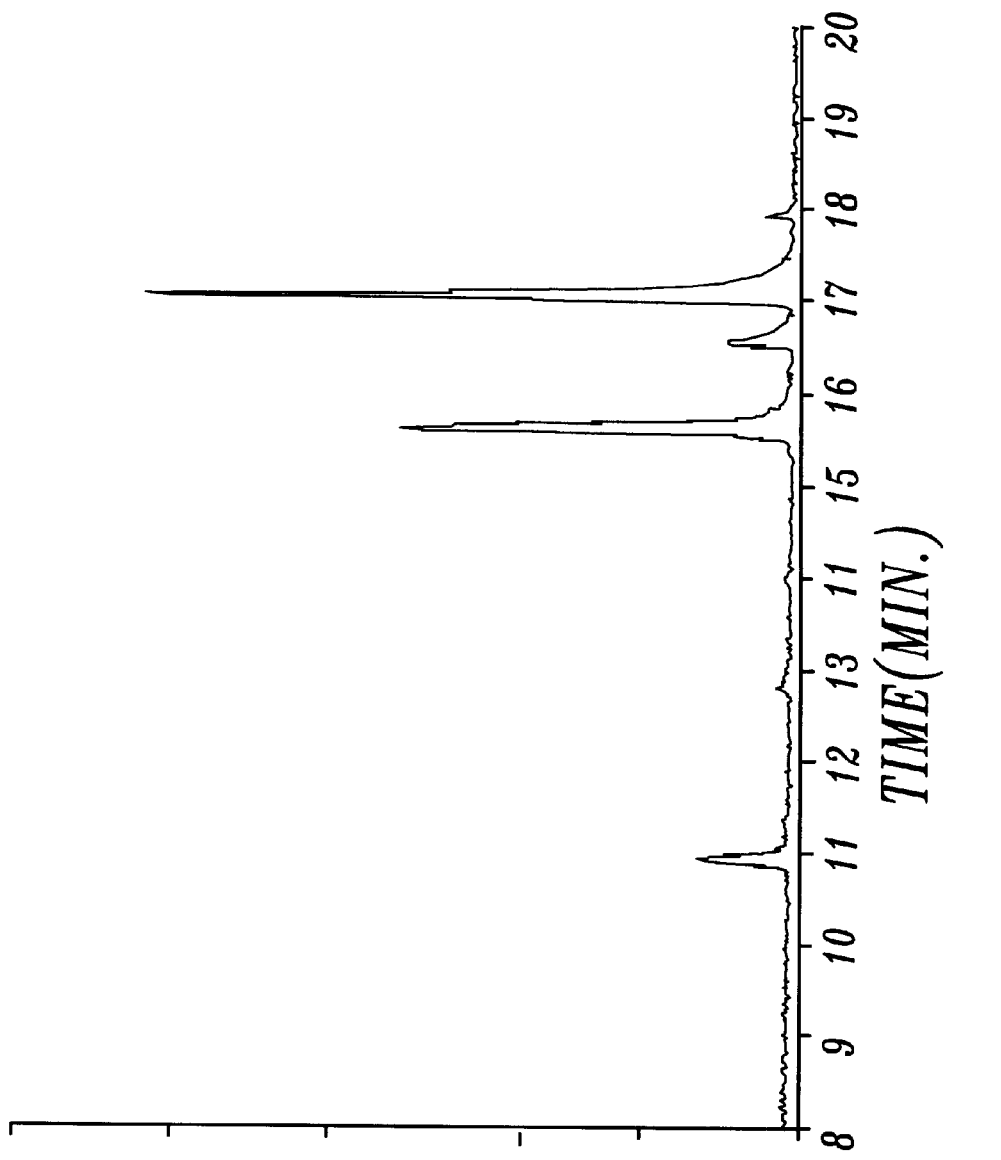
FIG. 7A depicts a total ion chromatogram of monoterpene products derived from geranyl diphosphate by a (−)-β-phellandrene synthase of the invention.
Figure 7B:
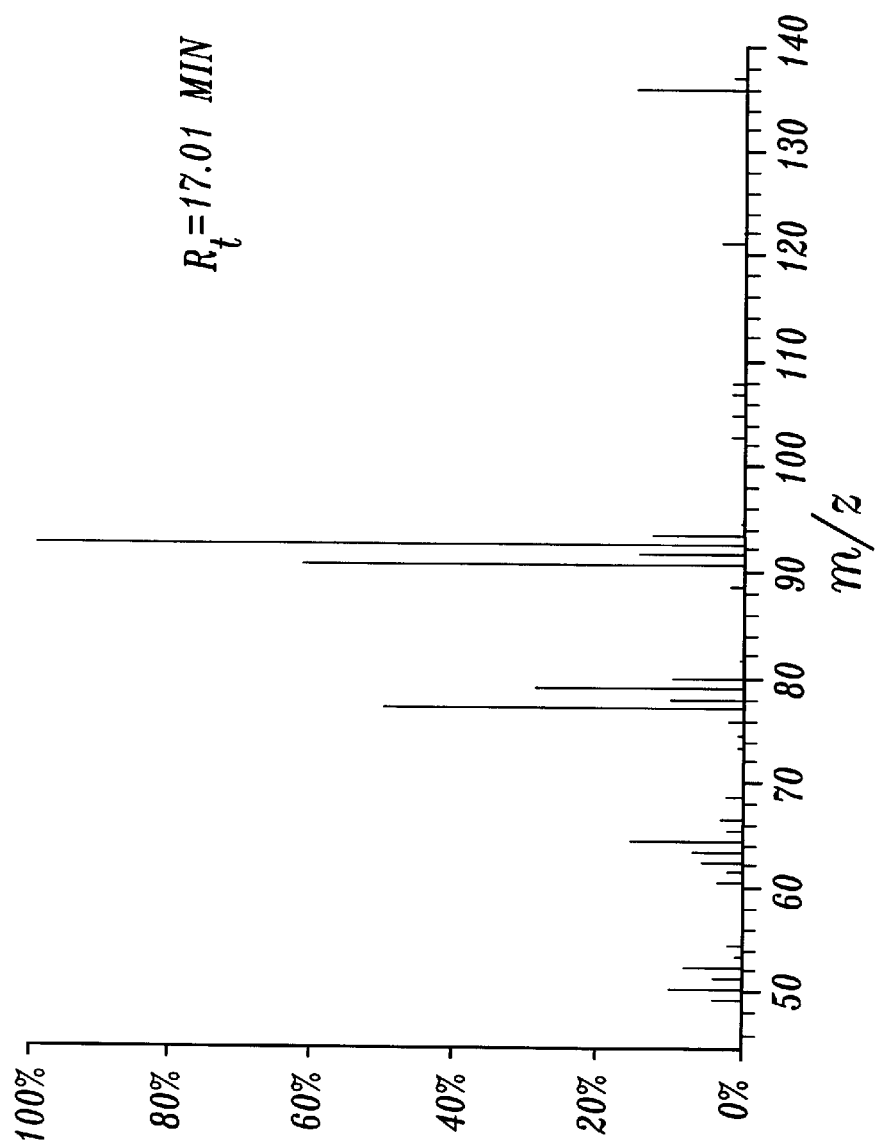
FIG. 7B depicts the mass spectrum and retention time for the principal enzyme product shown in FIG. 7A.
Figure 7C:
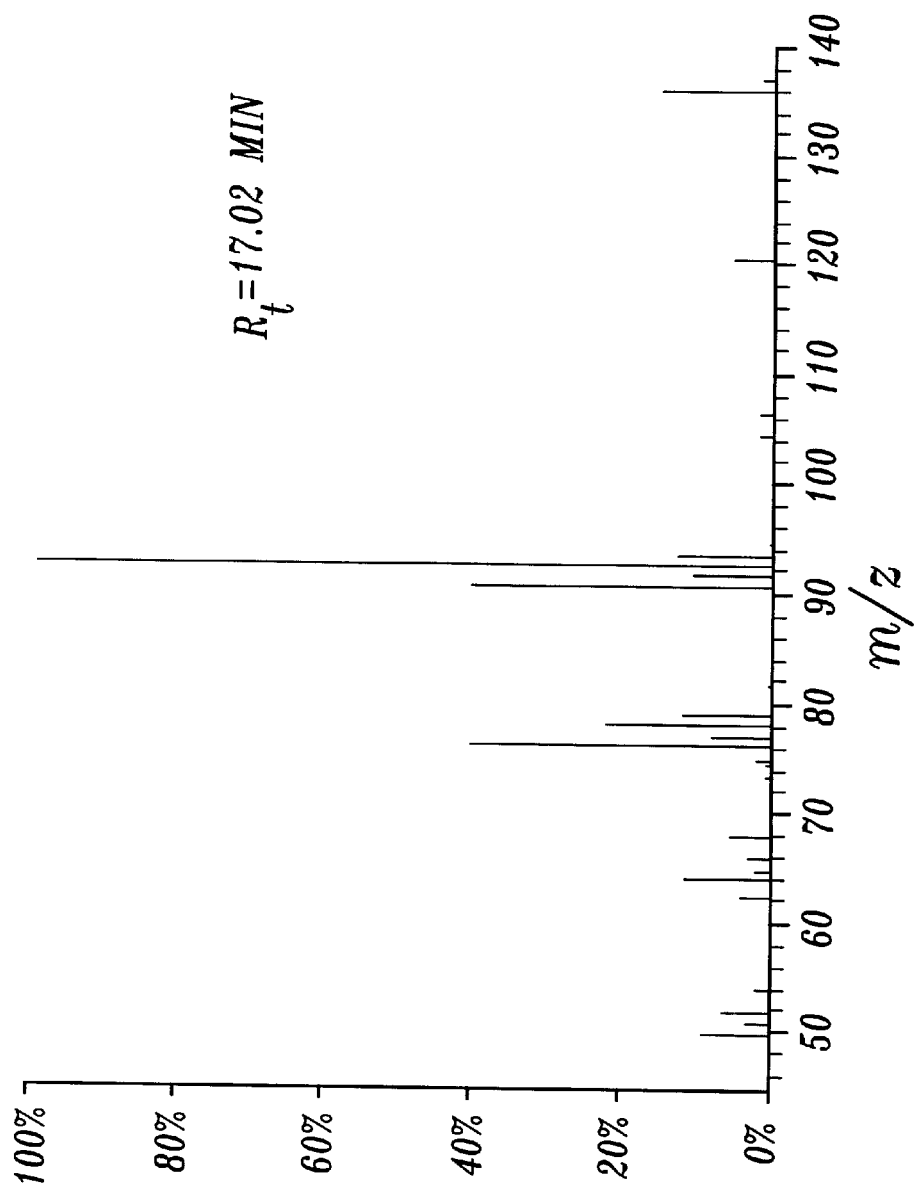
FIG. 7C depicts the mass spectrum and retention time for the authentic β-phellandrene standard.

A limonene synthase cDNA has thus far been cloned only from two very closely related angiosperm species (Colby, S. M., Alonso, W. R., Katahira, E. J., McGarvey, D. J., and Croteau, R. (1993) J. Biol. Chem. 268:23016–23024; Yuba, A., Yazaki, K., Tabata, M., Honda, G., and Croteau, R. (1996) Arch. Biochem. Biophys. 332:280–287), and the isolation of a pinene synthase cDNA has not been reported before. Pinene synthase has previously received considerable attention as a major defense-related monoterpene synthase in conifers (Gijzen, M., Lewinsohn, E., and Croteau, R. (1991) Arch. Biochem. Biophys. 289:267–273; Lewinsohn, E., Gijzen, M., and Croteau, R. (1992) Arch. Biochem. Biophys. 293:167–173). In the Grand fir cDNA library, which was synthesized from mRNA obtained from wound-induced sapling stems, clones corresponding to pinene synthase are at least ten times more abundant than clones for myrcene synthase. This finding reflects the relative proportions of the induced levels of activities of these enzymes in Grand fir saplings; pinene synthase and limonene synthase are the major monoterpene synthase activities whereas the induced level of myrcene synthase activity is relatively low (Gijzen, M., Lewinsohn, E., and Croteau, R. (1991) Arch. Biochem. Biophys. 289:267–273). The cDNAs for inducible monoterpene synthases provide probes for genetic and molecular analysis of oleoresin-based defense in conifers. Northern blots (FIG. 6) of total RNA extracted from non-wounded sapling stems and from stems two days after wounding (when enzyme activity first appears) were probed with cDNA fragments for AG2.2 (SEQ ID NO:1), AG3.18 (SEQ ID NO:3) and AG10 (SEQ ID NO:5), and thus demonstrated that increased mRNA accumulation for monoterpene synthases is responsible for this induced, defensive response in Grand fir. The availability of cloned, defense-related monoterpene synthases presents several possible avenues for transgenic manipulation of oleoresin composition to improve tree resistance to bark beetles and other pests. For example, altering the monoterpene content of oleoresin may chemically disguise the host and decrease insect aggregation by changing the levels of pheromone precursors or predator attractants, or lower infestation by increasing toxicity toward beetles and their pathogenic fungal associates (Johnson, M. A., and Croteau, R. (1987) in Ecology and Metabolism of Plant Lipids (Fuller, G., and Nes, W. D., eds) pp. 76–91, American Chemical Society Symposium Series 325, Washington, D.C.; Gijzen, M., Lewinsohn, E., Savage, T. J., and Croteau, R. B. (1993) in Bioactive Volatile Compounds from Plants (Teranishi, R., Buttery, R. G., and Sugisawa, H., eds) pp. 8–22, American Chemical Society Symposium Series 525, Washington, D.C.; Byers, J. A. (1995) in Chemical Ecology of Insects 2 (Cardé, R. T., and Bell, W. J., eds) pp. 154–213, Chapman and Hall, New York).

EXAMPLE 8

Properties of the Recombinant Monoterpene Synthases Encoded by cDNA Clones AG2.2 (SEQ ID NO:1), AG3.18 (SEQ ID NO:3) and AG10 (SEO ID NO:5)

All three recombinant enzymes require $Mn^{2+}$ for activity, and $Mg^{2+}$ is essentially ineffective as the divalent metal ion cofactor. This finding confirms earlier results obtained with the native monoterpene synthases of Grand fir and lodgepole pine (Pinus contorta) (Lewinsohn, E., Gijzen, M., and Croteau, R. (1992) Arch. Biochem. Biophys. 293:167–173; Savage, T. J., Hatch, M. W., and Croteau, R. (1994) J. Biol. Chem. 269:4012–4020). All terpene synthases and prenyltransferases are thought to employ a divalent metal ion, usually $Mg^{2+}$ or $Mn^{2+}$, in the ionization steps of the reaction sequence to neutralize the negative charge of the diphosphate leaving group (Croteau, R. (1987) Chem. Rev. 87:929–954; Cane, D. E. (1992) Ciba Found. Symp. Ser. 171:163–167; Poulter, C. D., and Rilling, H. C. (1981) in Biosynthesis of Isoprenoid Compounds (Porter, J. W., and Spurgeon, S. L., eds) Vol. 1, pp. 161–224, Wiley & Sons, New York), and all relevant sequences thus far obtained bear a conserved aspartate rich element (DDXXD)(SEQ ID NO:45) considered to be involved in divalent metal ion binding (Stofer Vogel, B., Wildung, M. R., Vogel, G., and Croteau, R. (1996) J. Biol. Chem. 271:23262–23268; Ashby, M. N., and Edwards, P. A. (1990) J. Biol. Chem. 265:13157–13164; Chen, A., Kroon, P. A., and Poulter, D. C. (1994) Protein Sci. 3:600–607; Tarshis, L. C., Yan, M., Poulter, C. D., and Sacchettini, J. C. (1994) Biochemistry 33:10871–10877; Cane, D. E., Sohng, J. K., Lamberson, C. R., Rudnicki, S. M., Wu, Z., Lloyd, M. D., Oliver, J. S., and Hubbard, B. R. (1994) Biochemistry 33:5846–5857; Proctor, R. H., and Hohn, T. M. (1993) J. Biol. Chem. 268:4543–4548). In addition to this strict, general dependence on a divalent metal ion, the monoterpene synthases of conifers are unique in their further requirement for a monovalent cation (K⁺), a feature that distinguishes the gymnosperm monoterpene synthases from their counterparts from angiosperm species and implies a fundamental structural and/or mechanistic difference between these two families of catalysts (Savage, T. J., Hatch, M. W., and Croteau, R. (1994) *J. Biol. Chem.* 269:4012–4020). All three recombinant monoterpene synthases depend upon K⁺, with maximum activity achieved at approximately 500 mM KCl. A requirement for K⁺ has been reported for a number of different types of enzymes, including those that catalyze phosphoryl cleavage or transfer reactions (Suelter, C. H. (1970) *Science* 168:789–794) such as Hsc70 ATPase (Wilbanks, S. M., and McKay, D. B. (1995) *J. Biol. Chem.* 270:2251–2257). The crystal structure of bovine Hsc70 ATPase indicates that both $Mg^{2+}$ and K⁺ interact directly with phosphate groups of the substrate and implicates three active site aspartate residues in $Mg^{2+}$ and K⁺ binding (Wilbanks, S. M., and McKay, D. B. (1995) *J. Biol. Chem.* 270:2251–2257), reminiscent of the proposed role of the conserved DDXXD (SEQ ID NO:45) motif of the terpene synthases and prenyltransferases in divalent cation binding, a function also supported by recent site directed mutagenesis (Marrero, P. F., Poulter, C. D., and Edwards, P. A. (1992) *J. Biol. Chem.* 267:21873–21878; Joly, A., and Edwards, P. A. (1993) *J. Biol. Chem.* 268: 26983–26989; Song, L., and Poulter, C. D. (1994) *Proc. Natl. Acad Sci. U.S.A.* 91:3044–3048; Koyama, T., Tajima, M., Sano, H., Doi, T., Koike-Takeshita, A., Obata, S., Nishino, T., and Ogura, K. (1996) *Biochemistry* 35:9533–9538) and by X-ray structural analysis (Tarshis, L. C., Yan, M., Poulter, C. D., and Sacchettini, J. C. (1994) *Biochemistry* 33:10871–10877) of farnesyl diphosphate synthase.

cDNA cloning and functional expression of the myrcene, limonene and pinene synthases from Grand fir represent the first example of the isolation of multiple synthase genes from the same species, and provide tools for evaluation of structure-function relationships in the construction of acyclic, monocyclic and bicyclic monoterpene products and for detailed comparison to catalysts from phylogenetically distant plants that carry out ostensibly identical reactions (Gambliel, H., and Croteau, R. (1984) *J. Biol. Chem.* 259:740–748; Rajaonarivony, J. I. M., Gershenzon, J., and Croteau, R. (1992) *Arch. Biochem. Biophys.* 296:49–57; Colby, S. M., Alonso, W. R., Katahira, E. J., McGarvey, D. J., and Croteau, R. (1993) *J. Biol. Chem.* 268:23016–23024; Adam, K.-P., Crock, J., and Croteau, R. (1996) *Arch. Biochem. Biophys.* 332:352–356). The recent acquisition of cDNA isolates encoding sesquiterpene synthases and diterpene synthases (Stofer Vogel, B., Wildung, M. R., Vogel, G., and Croteau, R. (1996) *J. Biol. Chem.* 271:23262–23268) from Grand fir should, together with the monoterpene synthases, also permit addressing the structural basis of chain-length specificity for prenyl diphosphate substrates in this family of related enzymes.

EXAMPLE 9

Sequence Comparison of Certain Cloned Monoterpene Synthases

Previous studies based on substrate protection from inactivation with selective amino acid modifying reagents have implicated functionally important cysteine, histidine and arginine residues in a range of different monoterpene synthases (Rajaonarivony, J. I. M., Gershenzon, J., and Croteau, R. (1992) *Arch. Biochem. Biophys.* 296:49–57; Lewinsohn, E., Gijzen, M., and Croteau, R. (1992) *Arch. Biochem. Biophys.* 293:167–173; Savage, T. J., Hatch, M. W., and Croteau, R. (1994) *J. Biol. Chem.* 269:4012–4020; Rajaonarivony, J. I. M., Gershenzon, J., Miyazaki, J., and Croteau, R. (1992) *Arch. Biochem. Biophys.* 299:77–82; Savage, T. J., Ichii, H., Hume, S. D., Little, D. B., and Croteau, R. (1994) *Arch. Biochem. Biophys.* 320:257–265). Sequence alignment of 21 terpene synthases of plant origin (Colby, S. M., Alonso, W. R., Katahira, E. J., McGarvey, D. J., and Croteau, R. (1993) *J. Biol. Chem.* 268:23016–23024; Stofer Vogel, B., Wildung, M. R., Vogel, G., and Croteau, R. (1996) *J. Biol. Chem.* 271:23262–23268; Facchini, P. J., and Chappell, J. (1992) *Proc. Natl. Acad Sci. USA* 89:11088–11092; Mau, C. J. D., and West, C. A. (1994) *Proc. Nati. Acad Sci. USA* 91:8497–8501; Yuba, A., Yazaki, K., Tabata, M., Honda, G., and Croteau, R. (1996) *Arch. Biochem. Biophys.* 332:280–287; Wildung, M. R., and Croteau, R. (1996) *J. Biol. Chem.* 271:9201–9204; Yamaguchi, S., Saito, T., Abe, H., Yamane, H., Murofushi, N., and Kamiya, Y. (1996) *Plant J.* 10:203–213; Dudareva, N., Cseke, L., Blanc, V. M., and Pichersky, E. (1996) *Plant Cell* 8:1137–1148; Chen, X.-Y., Chen, Y., Heinstein, P., and Davisson, V. J. (1995) *Arch. Biochem. Biophys.* 324:255–266; Chen, X.-Y., Wang, M., Chen, Y., Davisson, J., and Heinstein, P. (1996) *J. Nat. Prod.* 59:944–951; Back, K., and Chappell, J. (1995) *J. Biol. Chem.* 270:7375–7381) reveals two absolutely conserved arginine residues, corresponding to $Arg^{184}$ and $Arg^{365}$ of pinene synthase (SEQ ID NO:4), one highly conserved cysteine residue (pinene synthase $Cys^{543}$)(SEQ ID NO:4), and one highly conserved histidine residue (pinene synthase $His^{186}$)(SEQ ID NO:4). The DDXXD (SEQ ID NO:45) sequence motif (pinene synthase $Asp^{379}$, $Asp^{380}$ and $Asp^{383}$) (SEQ ID NO:4) is absolutely conserved in all relevant plant terpene synthases, as are several other amino acid residues corresponding to $Phe^{198}$, $Leu^{248}$, $Glu^{322}$, $Trp^{329}$, $Trp^{460}$ and $Pro^{467}$ of pinene synthase (SEQ ID NO:4).

Amino acid sequences of the plant terpene synthases were compared with each other and with the deduced sequences of several sesquiterpene synthases cloned from microorganisms (Proctor, R. H., and Hohn, T. M. (1993) *J. Biol. Chem.* 268:4543–4548; Back, K., and Chappell, J. (1995) *J. Biol. Chem.* 270:7375–7381; Hohn, T. M., and Desjardins, A. E. (1992) *Mol. Plant-Microbe Interactions* 5:249–256). As with all other plant terpene synthases, no significant conservation in primary sequence exists between the monoterpene synthases from Grand fir and the terpene synthases of microbial origin, except for the DDXXD (SEQ ID NO:45) sequence motif previously identified as a common element of all terpene synthases, and prenyltransferases which employ a related electrophilic reaction mechanism (Croteau, R., Wheeler, C. J., Cane, D. E., Ebert, R., and Ha, H.-J. (1987) *Biochemistry* 26:5383–5389; Chen, A., Kroon, P. A., and Poulter, D. C. (1994) *Protein Sci.* 3:600–607; McCaskill, D., and Croteau, R. (1997) *Adv. Biochem. Engineering Biotech.* 55:108–146). The evidence is presently insufficient to determine whether extant plant and microbial terpene synthases represent divergent evolution from a common ancestor, which may also have given rise to the prenyltransferases, or whether these similar catalysts evolved convergently.

EXAMPLE 10

A Strategy For Cloning Certain Gymnosperm Monoterpene Synthases

The present invention includes myrcene synthase, (−)-limonene synthase and (−)-pinene synthase proteins, and nucleic acid molecules that encode myrcene synthase, (−)- limonene synthase and (−)-pinene synthase proteins. The amino acid sequence of each of the myrcene synthase, (−)-limonene synthase and (−)-pinene synthase proteins of the present invention each includes at least one of the amino acid sequence elements disclosed in Table 1.

orientation) (SEQ ID NO:54); 3'TACTACTAC5' (antisense orientation) (SEQ ID NO:55) and 3'IACIACIAC5' (SEQ ID NO:56).

One or more oligonucleotide sequence(s), corresponding to at least a portion of at least one of the amino acid

TABLE 1

| Amino Acids | Sequence | Orientation | Comments |
|---|---|---|---|
| 1. 70–77 | H S N (L,I,V) W D D D (SEQ ID NO: 46) | F only | HS makes a poor reverse primer |
| 2. 148–153 | A L D Y V Y (SEQ ID NO: 47) | F and R | |
| 3. 306–312 | E L A K L E F (SEQ ID NO: 48) | F and R | |
| 4. 328–333 | R W W K E S (SEQ ID NO: 49) | F and R | F primer uses 1$^{st}$nt of Ser codon; R uses 1$^{st}$two nts of Arg codon (rare only) |
| 5. 377–383 | (V,I,L)L D D M Y D (SEQ ID NO: 50) | F and R | |
| 6. 377–383 | (V,I,L) L D D L Y D (SEQ ID NO: 51) | F and R | Degeneracy of V/I/L at 377 too high for single primer |
| 7. 377–383 | (V,I,L)L D D I Y D (SEQ ID NO: 52). | F and R | |
| 8. 543–549 | C Y M K D (N,H) P (SEQ ID NO: 53) | R | F primer can also be constructed with this peptide but is too close to the 3' end to be useful |

The numbers set forth in Table 1 for the first and last amino acid residue of each of the peptide sequences is the number of the corresponding amino acid residue in the amino acid sequence of the (−)-pinene synthase (SEQ ID NO:4) isolated from *Abies grandis*. Where a sequence of amino acid residues appears in brackets, e.g., (L,I,V) in Table 1, the first amino acid residue within the brackets is the residue that appears in the (−)-pinene synthase amino acid sequence set forth in SEQ ID NO:4. The subsequent amino acid residues within the brackets represent other amino acid residues that commonly occur at the corresponding position in the amino acid sequence of other *Abies grandis* enzymes involved in terpene synthesis.

In Table 1, the letter "F" refers to the forward PCR reaction, i.e., the PCR reaction which synthesizes the sense nucleic acid strand that encodes a gymnosperm monoterpene synthase. The letter "R" refers to the reverse PCR reaction, i.e., the PCR reaction that synthesizes the antisense nucleic acid molecule that is complementary to the sense nucleic acid strand synthesized in the forward PCR reaction.

In order to clone nucleic acid molecules encoding myrcene synthase, (−)-limonene synthase and (−)-pinene synthase of the present invention, one or more oligonucleotide molecules corresponding to at least a portion of one of the amino acid sequences set forth in Table 1 can be used as a probe or probes with which to screen a genomic or cDNA library derived from one or more gymnosperm species. In this context, the term "corresponding," or "correspond" or "corresponds," means that the oligonucleotide base sequence either a) encodes all or part of at least one of the amino acid sequences set forth in Table 1, or b) is complementary to a base sequence that encodes all or part of at least one of the amino acid sequences set forth in Table 1. The oligonucleotide probe(s) may contain a synthetic base, such as inosine, which can be substituted for one or more of the four, naturally-occurring bases, i.e., adenine ("A"), guanine ("G"), cytosine ("C") and thymine ("T"). Thus, for example, the following oligonucleotide sequences "correspond" to the tripeptide sequence M M M: 5'ATGATGATG3' (sense sequences set forth in Table 1, can be used to screen a nucleic acid library in order to identify myrcene synthase, (−)-limonene synthase and (−)-pinene synthase clones of the present invention, according to methods well known to one of ordinary skill in the art. See, e.g., Sambrook et al, supra. The stringency of the hybridization and wash conditions during library screening in accordance with the present invention, utilizing one or more oligonucleotide sequence(s) corresponding to at least a portion of at least one of the amino acid sequences set forth in Table 1, is at least: for the hybridization step, 6×SSPE, 40–45° C., for 36 hours; for the wash step, 3×SSPE, 45° C., 3×15 minute washes. The presently preferred hybridization and wash conditions during library screening, utilizing one or more oligonucleotide sequence(s) corresponding to at least a portion of at least one of the amino acid sequences set forth in Table 1, in accordance with the present invention are: for the hybridization step, 6×SSPE, 40–45° C., for 36 hours; for the wash step, 0.1×SSPE, 65° C.–70° C., 3×15 minute washes.

Examples of oligonucleotide sequences, corresponding to at least one of the amino acid sequences set forth in Table 1, that hybridize, under the foregoing hybridization and wash conditions, to the sense strands of the nucleic acid sequences of the present invention that encode myrcene synthase, (−)-limonene synthase or (−)-pinene synthase proteins are set forth in Table 2.

TABLE 2

| Nucleic Acid Sequence | Corresponds to: |
|---|---|
| GTG TCG TTG GAG ACC CTG CTG CTG (SEQ ID NO:57) | SEQ ID No. 46 |
| CGG GAG CTG ATG CAG ATG (SEQ ID NO:58) | SEQ ID No. 47 |

TABLE 2-continued

| Nucleic Acid Sequence | Corresponds to: |
|---|---|
| CTC GAG CGG TTC GAG CTC AAG (SEQ ID NO:59) | SEQ ID No. 48 |
| GCC ACC ACC TTC CTC TCG (SEQ ID NO:60) | SEQ ID No. 49 |
| GAG GAG CTG CTG TAC ATG CTG (SEQ ID NO:61) | SEQ ID No. 50 |
| GAG GAG CTG CTG GAG ATG CTQ (SEQ ID NO:62) | SEQ ID No. 51 |

Similarly, each of the myrcene synthase, (−)-limonene synthase and (−)-pinene synthase clones set forth in SEQ ID NO:1, SEQ ID NO:3 and SEQ ID NO:5, or a portion thereof, may be used as a probe to screen a nucleic acid library in order to isolate monoterpene synthase clones of the present invention, according to methods well known to one of ordinary skill in the art. See, e.g., Sambrook et al, supra. The stringency of the hybridization and wash conditions during library screening in accordance with the present invention is at least: for the hybridization step, 6×SSPE buffer at 45° C. to 50° C. for 36 hours; for the wash step, 3×SSPE buffer at 50° C. (three, fifteen minute washes). In accordance with the present invention, the presently preferred hybridization and wash conditions during library screening utilizing any of the gymnosperm monoterpene synthase clones set forth in SEQ ID NO: 1, SEQ ID NO:3 and SEQ ID NO:5, or a portion thereof, as probe are: for the hybridization step, 6×SSPE, 40–45° C., for 36 hours; for the wash step, 0.1×SSPE, 70° C.–75° C., 3×15 minute washes.

Additionally, at least two oligonucleotide sequence(s), each corresponding to at least a portion of at least one of the amino acid sequences set forth in Table 1, can be used in a PCR reaction to generate a portion of a myrcene synthase, (−)-limonene synthase or (−)-pinene synthase clone of the present invention, which can be used as a probe to isolate a full-length clone of a myrcene synthase, (−)-limonene synthase or (−)-pinene synthase clone of the present invention. Thus, oligonucleotides that are useful as probes in the forward PCR reaction correspond to at least a portion of at least one of the amino acid sequences disclosed in Table 1 as having the "F" orientation. Conversely, oligonucleotides that are useful as probes in the reverse PCR reaction correspond to at least a portion of at least one of the amino acid sequences disclosed in Table 1 as having the "R" orientation. PCR reactions can be carried out according to art-recognized PCR reaction conditions, such as the PCR reaction conditions set forth in Example 1 herein and as set forth in "PCR Strategies", M. A. Innis, D. H. Gelfand and J. J. Sninsky, eds., 1995, Academic Press, San Diego, Calif. (Chapter 14); "PCR Protocols: A Guide to Methods and Applications", M. A. Innis, D. H. Gelfand, J. J. Sninsky and T. J. White, eds., Academic Press, NY (1990). The presently preferred PCR reaction conditions are:

| | |
|---|---|
| dNTPs | 200 μM each |
| MgCl$_2$ | 5–7 mM |
| F and R primers | 100 nM–1 μM each |
| Taq polymerase | 1–2 units/reaction |
| cDNA template | 10–100 ng/reaction |
| Buffers, PCR grade water, and Chill-out wax or mineral oil | |

The presently preferred thermocycler conditions are:

| | | |
|---|---|---|
| Denaturation | 94° × 2 min | 1 cycle |
| Denaturation | 94° × 45 s | 35 cycles |
| Annealing | 42°–55° × 45 s - 1 min | 35 cycles |
| Polymerization | 72° × 1–2 min | 35 cycles |
| Adenylation | 72° × 10 min | 1 cycle |

EXAMPLE 11

Cloning and Characterization of cDNA Clones Encoding (−)-Camphene Synthase (−)-β-Phellandrene Synthase, Terpinolene Synthase and (−)-limonene/(−)-α-pinene Synthase Comparison of resin analysis and the products generated by in vitro assay of the corresponding native enzymes (Lewinsohn, E., Savage, T. J., Gijzen, M., and Croteau, R. (1993) *Phytochem. Anal.* 4, 220–225; Gijzen, M., Lewinsohn, E., and Croteau, R. (1991) *Arch. Biochem. Biophys.* 289, 267–273.), with the products of the available recombinant monoterpene synthases (Bohlmann, J., Steele, C. L., and Croteau, R. (1997) *J. Biol. Chem.* 272, 21784–21792), reveals that myrcene synthase, limonene synthase and pinene synthase do not account for all of the monoterpene synthases of grand fir. Molecular cloning of the complete family of grand fir monoterpene synthases is essential for evaluation of the regulatory role of each gene in constitutive and induced resin formation, can lead to the identification of useful genetic markers for resistance, provide the tools for engineering improved defense, and yield a more diverse set of recombinant catalysts for comparative mechanistic and structural study. Consequently, cDNA molecules encoding additional monoterpene synthases were isolated from a Grand fir cDNA library as described in this Example.

Additional Grand fir monoterpene synthases were cloned and analyzed as follows.

Substrates, Reagents and cDNA library. [1-$^3$H]Geranyl diphosphate (250 Ci/mol) (Croteau, R., Alonso, W. R., Koepp, A E., and Johnson, M. A. (1994) *Arch. Biochem. Biophys.* 309, 184–192), [1-$^3$H]farnesyl diphosphate (125 Ci/mol) (Dehal, S. S., and Croteau, R. (1988) *Arch. Biochem. Biophys.* 261, 346–356) and [1-$^3$H]geranylgeranyl diphosphate (120 Ci/mol) (LaFever, R. E., Stofer Vogel, B., and Croteau, R. (1994) *Arch. Biochem. Biophys.* 313, 139–149) were prepared as described in the foregoing publications. Terpenoid standards were from the inventors' own collection. All other biochemicals and reagents were purchased from Sigma Chemical Co. or Aldrich Chemical Co., unless otherwise noted. Construction of the λZAP II cDNA library, using mRNA isolated from wounded grand fir sapling stems (Lewinsohn, E., Steele, C. L., and Croteau, R. (1994) *Plant Mol. Biol. Rep.* 12, 20–25), was described previously in (Stofer Vogel, B., Wildung, M., Vogel, G., and Croteau, R. (1996) *J. Biol. Chem.* 271, 23262–23268).

PCR-based probe generation. PCR was performed in a total buffer volume of 50 μl containing 20 mM Tris-HCl (pH 8.4), 50 mM KCl, 5 mM MgCl$_2$, 200 μM of each dNTP, 2.5 units of Taq polymerase (BRL) and 5 μl of purified grand fir stem cDNA library phage as template (1.5×10$^9$ pfu/ml). Three different PCR mixtures were evaluated containing either 1–5 μM of each primer, 1–5 μM of primer E (SEQ ID NO:21) only, or 1–5 μM of primer G (SEQ ID NO:23) only. After a denaturing step at 94° C. for 2 min, 35 cycles of amplification were performed employing the following temperature program using a Gradient 96 Robocycler (Stratagene): one min at 94° C., one min at each 2° C. increment from 44 to 66° C., and two min at 72° C. The amplicons were analyzed by agarose gel electrophoresis (Sambrook, J., Fritsch, E. F., and Maniatis, T. (1989) Molecular Cloning: A Laboratory Manual, 2nd Ed., pp. 7.20–7.43, Cold Spring Harbor, N.Y.), and the products were extracted from the gel, ligated into pT7Blue (Novagen) and transformed into E. coli XL1-Blue cells. Plasmid DNA was prepared from individual transformants and the inserts were fully sequenced (DyeDeoxy Terminator Cycle Sequencing, Applied Biosystems). In addition to previously described DNA fragments (Bohlmann, J., Steele, C. L., and Croteau, R. (1997) J. Biol. Chem. 272, 21784–21792), a new insert sequence was identified and was designated as probe 7 (SEQ ID NO:63).

Library screening. For library screening, 200 ng of probe 7 (SEQ ID NO:63) was amplified by PCR, and the resulting amplicon was gel purified, randomly labeled with [$\alpha$-$^{32}$P] dATP (Feinberg, A. P., and Vogelstein, B. (1984) Anal. Biochem. 137, 216–267) and used to screen replica filters of $5 \times 10^4$ plaques from the wound-induced grand fir stem cDNA library plated on E. coli LE392. Hybridization was performed for 20 h at 55° C. in 3×SSPE and 0.1% SDS. Filters were washed three times for 10 min at 55° C. in 3×SSPE with 0.1% SDS and exposed for 17 h to Kodak XAR film at −70° C. (Sambrook, J., Fritsch, E. F., and Maniatis, T. (1989) Molecular Cloning: A Laboratory Manual, 2nd Ed., pp. 7.20–7.43, Cold Spring Harbor, N.Y.). Forty λZAPII clones yielding positive signals with probe 7 (SEQ ID NO:63) were purified through a second round of hybridization. Purified λZAPII clones were excised in vivo as Bluescript II SK⁻ phagemids and transformed into E. coli XLOLR according to the manufacturer's instructions (Stratagene). The size of each cDNA insert was determined by PCR using T3 (SEQ ID NO:29) and T7 (SEQ ID NO:30) promoter primers, and size-selected inserts (>1.5 kb) were partially sequenced from both ends to reveal several acquisitions of four unique clones, including apparent full-length versions of three (designated 7.30 (ag6) (SEQ ID NO:64), 7.36 (ag8) (SEQ ID NO:66) and 7.32 (ag11) (SEQ ID NO:68)), and a fourth (7.31) (SEQ ID NO:70) that was clearly 5'-truncated.

Rapid amplification of cDNA ends. To acquire the 5'-terminus corresponding to truncated cDNA clone ag7.31 (SEQ ID NO:70), 5'-rapid amplification of cDNA ends (RACE) was carried out using the Marathon cDNA amplification system (Clontech) and the manufacturer's protocol. Nested reverse RACE primers specific for ag7.31 (SEQ ID NO:70), designated 10-2 (5'-ACG AAG CTT CTT CTC CAC GG-3')(SEQ ID NO:71) and 10-4 (5'-GGA TCC CAT CTC TTA ACT GC-3')(SEQ ID NO:72), were used in combination with primer AP1 (SEQ ID NO:73) and AP2 (SEQ ID NO:74) (Clontech), respectively. The resulting amplicon was cloned into vector pT7Blue (Novagen) and completely sequenced on both strands. The full length cDNA corresponding to clone ag7.31 (SEQ ID NO:70) was then amplified by PCR using primers AG9F (5'-ATG GCT CTT GTT TCT ATC TTG CCC-3') (SEQ ID NO:75) and AG9R (5'-TTA CAA AGG CAC AGA CTC AAG GAC-3') (SEQ ID NO:76), ligated into pT7Blue and the resulting plasmid was designated pAG9 (SEQ ID NO:77).

The foregoing similarity based cloning approach was designed to employ PCR primers E (SEQ ID NO:21) and G (SEQ ID NO:23) to generate new terpenoid synthase cDNA fragments for isolation and deployment as hybridization probes in screening an enriched library. By using wound-induced grand fir stem library cDNA as template, the combination of primers E (SEQ ID NO:21) and G (SEQ ID NO:23) amplified primarily a 1022 bp PCR product identical to probe 3 (SEQ ID NO:24) and an additional, very minor product of 296 bp. This very low abundance 296 bp product was also amplified when only primer E (SEQ ID NO:21) was used in the PCR reaction with the Grand fir cDNA library template in the absence of a second primer. Cloning and sequencing of this PCR product (designated probe 7) (SEQ ID NO:63) unexpectedly revealed significant deduced sequence similarity with previously cloned grand fir terpene synthases in the region corresponding to amino acid Val$^{424}$-Leu$^{521}$ of (−)-pinene synthase (SEQ ID NO:4). The highest levels of identity were observed at the nucleic acid level with monoterpene synthase clones ag2.2 (SEQ ID NO:1) (myrcene synthase, 74%), ag3.18 (SEQ ID NO:3) (−)-pinene synthase, 69%) and ag10 (SEQ ID NO:5) (−)-limonene synthase, 83%). Lower levels of similarity were noted with the sesquiterpene synthases ag1 (50%), ag4 (54%) and ag5 (57%), and still less with the diterpene synthase abietadiene synthase (46%), suggesting that this PCR product represented a fragment of a new monoterpene synthase. In retrospect, generation of this fragment can be explained based on two unexpected annealing events of primer E (SEQ ID NO:21) to a monoterpene synthase cDNA in the regions corresponding to amino acids Val$^{424}$-Ala$^{432}$ and Leu$^{513}$-Leu$^{521}$ of (−)-pinene synthase (SEQ ID NO:4). These binding sites for primer E (SEQ ID NO:21) are significantly different from the amino acid sequence GE(K/T)(V/I)M(E/D)EA (SEQ ID NO:26) to which the degenerate primer was designed. With nucleic acid sequence identities between primer E (SEQ ID NO:21) (23 nucleotides) and the corresponding two sites of recognition in previously acquired grand fir monoterpene synthases in the range of 44–57% and 48–56%, respectively, amplification of probe 7 (SEQ ID NO:63) would not be predicted. Probe 7 (SEQ ID NO:63) was subsequently employed for filter hybridization of the wound induced grand fir phage cDNA library.

Screening of 10$^5$ cDNA phage plaques from the wounded grand fir stem library with probe 7 (SEQ ID NO:63) yielded 40 positives of which 37 were isolated by one additional round of filter hybridization, excised in vivo and partially sequenced from both ends. Sequence analysis revealed four new, unique cDNA fragments represented by phage clones 7.30 (SEQ ID NO:64), 7.36 (SEQ ID NO:66) 7.31 (SEQ ID NO:70) and 7.32 (SEQ ID NO:68), of which clone 7.32 (SEQ ID NO:68) was identical to probe 7 (SEQ ID NO:63). Complete sequencing of these inserts and sequence comparison placed these genes into the gymnosperm Tpsd subfamily of plant terpenoid synthases (Bohlmann, J., Meyer-Gauen, G., and Croteau. R. (1998) Proc. Natl. Acad Sci. USA 95, 4126–4133) with closest relationship to previously acquired grand fir monoterpene synthases. Alignment of the deduced amino acid sequences of the four new, presumptive terpene synthase fragments with extant monoterpene synthases indicated that clones 7.30 (SEQ ID NO:64), 7.36 (SEQ ID NO:66) and 7.32 (SEQ ID NO:68) represented full-length versions, whereas clone 7.31 (SEQ ID NO:70) was truncated at the 5'-terminus. A full-length clone corresponding to truncated cDNA 7.31 (SEQ ID NO:70) was obtained by a 5'-RACE method. These full-length clones were designated ag6 (7.30) (SEQ ID NO:64), ag8 (7.36) (SEQ ID NO:66), ag9 (7.31) (SEQ ID NO:77) and ag11 (7.32) (SEQ ID NO:68), consistent with the nomenclature for other terpenoid synthases from grand fir (Bohlmann, J., Meyer-Gauen, G., and Croteau. R. (1998) Proc. Natl. Acad. Sci. USA 95, 4126–4133).

Sequence analysis. Inserts of all recombinant Bluescript plasmids and pSBET plasmids were completely sequenced on both strands via primer walking using the DyeDeoxy Terminator Cycle Sequencing method (Applied Biosystems). Sequence analysis was conducted using programs from the Genetics Computer Group (Genetics Computer Group (1996) Program Manual for the Wisconsin Package, Version 9.0, Genetics Computer Group, Madison, Wis.).

The sequences of clone ag6 (2013 bp with ORF of 1854 nt encoding 618 amino acids) (SEQ ID NO:64), clone ag8(2186 bp with ORF of 1890 nt encoding 630 amino acids) (SEQ ID NO:66), clone ag9 (1893 bp with ORF of 1890 nt encoding 630 amino acids) (SEQ ID NO:77) and clone ag11 (2429 bp with ORF of 1911 nt encoding 637 amino acids) (SEQ ID NO:68) revealed, in addition to overall similarities, other features characteristic of monoterpene synthases. The lengths of the deduced proteins (618–637 amino acids) and the predicted molecular weights (71,000–73,000) are in the range of other monoterpene synthases. The deduced proteins are larger than the sesquiterpene synthases, δ-selinene synthase (581 amino acids) and γ-humulene synthases (593 amino acids) (Steele, C. L., Crock, J., Bohlmann, J., and Croteau, R. (1998) *J. Biol. Chem.* 273, 2078–2089) but smaller than abietadiene synthase (868 amino acids) (Stofer Vogel, B., Wildung, M., Vogel, G., and Croteau, R. (1996) *J. Biol. Chem.* 271, 23262–23268) and (E)-α-bisabolene synthase (817 amino acids) (Bohlmann, J., Crock, J., Jetter, R., and Croteau, R. (1998) *Proc. Natl. Acad Sci.* USA 95, 6756–6761) from grand fir. As with other monoterpene synthases (Bohlmann, J., Meyer-Gauen, G., and Croteau. R. (1998) *Proc. Natl. Acad Sci.* USA 95, 4126–4133), ag6 (SEQ ID NO:64), ag8 (SEQ ID NO:66), ag9 (SEQ ID NO:77) and ag11 (SEQ ID NO:68) appear to encode preproteins bearing an amino-terminal transit peptide for plastidial import of these nuclear gene products (Williams, D. C., McGarvey, D. J., Katahira, E. J., and Croteau, R. (1998) *Biochemisiry* 37, 12213–12220; Turner, G., Gershenzon, J., Nielson, E. E., Froehlich, J. E., and Croteau, R. (1999) *Plant Physiol.,* in press). In all cases, the amino-terminal 50–60 residues of the deduced sequences are rich in serine (15–21%) but have few acidic residues, consistent with such targeting peptides (Keegstra, K., Olsen, J. J., and Theg, S. M. (1989) *Annu. Rev. Plant Physiol. Plant Mol. Biol.* 40, 471–501; von Heijne, G., Steppuhn, J., and Herrmann, R. G. (1989) *Eur. J. Biochem.* 180, 535–545). A tandem arginine element has recently been demonstrated to approximate the putative amino-terminus of mature monoterpene synthases, and to be involved in the initial diphosphate migration step of the coupled monoterpene cyclization reaction sequence in which geranyl diphosphate is isomerized to enzyme-bound linalyl diphosphate (Williams, D. C., McGarvey, D. J., Katahira, E. J., and Croteau, R. (1998) *Biochemisiry* 37, 12213–12220). The position of the tandem arginines is similar in ag6 (SEQ ID NO:65) ($R^{59}R^{60}$), ag8 (SEQ ID NO:67) ($R^{62}R^{63}$), ag9 (SEQ ID NO:78) ($R^{65}R^{66}$) and ag11 (SEQ ID NO:69) ($R^{71}R^{72}$), and is conserved in all monoterpene synthases of angiosperm and gymnosperm origin in a position nine amino acids upstream of an absolutely conserved tryptophan residue (Bohlmann, J., Meyer-Gauen, G., and Croteau. R. (1998) *Proc. Natl. Acad Sci.* USA 95, 4126–4133). All other previously described motifs of plant terpene synthases of the tpsa tpsb and tpsd subfamilies (Bohlmann, J., Meyer-Gauen, G., and Croteau. R. (1998) *Proc. Natl. Acad Sci.* USA 95, 4126–4133), including the aspartate-rich DDXXD (SEQ ID NO:45) element involved in coordinating the divalent metal ion for substrate binding (Ashby, M. N., and Edwards, P. A. (1 990) *J. Biol. Chem.* 265, 13157–13164; Marrero, P. F., Poulter, C. D., and Edwards, P. A. (1992) *J. Biol. Chem.* 267, 21873–21878; Tarshis, L. C., Yan, M., Poulter, C. D., and Sacchettini, J. C. (1994) *Biochemistry* 33, 10871–10877; Cane, D. E., Sohng, J. K., Lamberson, C. R., Rudnicki, S. M., Wu, Z., Lloyd, M. D., Oliver, J. S., and Hubbard, B. R. (1994) *Biochemistry* 33, 5846–5857), are also found in the enzymes encoded by ag6 (SEQ ID NO:65), ag8 (SEQ ID NO:70), ag9 (SEQ ID NO:78) and ag11 (SEQ ID NO:69).

cDNA expression in *E. coli* and enzyme assays. The fully sequenced insert fragments of plasmids pAG6 (SEQ ID NO:64), pAG8 (SEQ ID NO:66), pAG9 (SEQ ID NO:77) and pAG11 (SEQ ID NO:68) were subcloned in-frame into the expression vector pSBETa (Schenk, P. M., Baumann, S., Mattes, R., and Steinbiss, H. (1995) *BioTechniques* 19, 196–200). First, internal NdeI sites and internal BamHI sites in cDNA clones pAG6 (SEQ ID NO:64), pAG9 (SEQ ID NO:77) and pAGl11 (SEQ ID NO:68) were eliminated by site directed mutagenesis using the Quick Change Mutagenesis system (Stratagene). Mutagenesis primers designated 6eBamHIF (5'-CAA TTA AGA GAT GGG ACC CGT CCG CGA TGG-3') (SEQ ID NO:79) and 6eBamHIR (5'-CCA TCG CGG ACG GGT CCC ATC TCT TAA TTG-3') (SEQ ID NO:80) were used to eliminate an internal BamHI site in pAG6 (SEQ ID NO:64), 9eBamHIF (5'-GCA TTT AAG AGA TGG GAC CCG TCT GCC ACA G-3') (SEQ ID NO:81) and 9eBamHIR (5'-CTG TGG CAG ACG GGT CCC ATC TCT TAA ATG C-3') (SEQ ID NO:82) to eliminate an internal BamHI site in pAG9 (SEQ ID NO:77), and 732eNdeIF (5'-CGA GAT GCC ATA CGT GAA TAC GCA G-3') (SEQ ID NO:83) and 732eNde1R (5'-CTG CGT ATT CAC GTA TGG CAT CTC G-3') (SEQ ID NO:84) to eliminate an internal NdeI site in pAG11 (SEQ ID NO:68).

To introduce suitable restriction sites for subcloning full-length versions and versions truncated to remove the presumptive plastidial targeting peptide of these enzymes (Bohlmann, J., Meyer-Gauen, G., and Croteau. R. (1998) *Proc. Natl. Acad. Sci.* USA 95, 4126–4133; Williams, D. C., McGarvey, D. J., Katahira, E. J., and Croteau, R. (1998) *Biochemisiry* 37, 12213–12220), fragments were amplified by PCR using primer 6-NdeI-M (5'-CTG ATA GCA AGC TCA TAT GGC TCT TCT TTC-3') (SEQ ID NO:85) or primer 6-NdeI-R (5'-GCC CAC GCG TCT CAT ATG AGA ATC AGT AGA TGC G-3') (SEQ ID NO:86) individually in combination with primer 6-BamHI (5'-CAC CCA TAG GGG ATC CTC AGT TAA TAT TG-3') (SEQ ID NO:87) for pAG6 (SEQ ID NO:64), primer 8-NdeI-M (5'-TAA GCG AGC ACA TAT GGC TCT GGT TTC TTC-3') (SEQ ID NO:88) in combination with primer 8-BamHI (5'-GCA TAA ACG CAT AGC GGA TCC TAC ACC AA-3') (SEQ ID NO:89) for pAG8 (SEQ ID NO:66), primer 9-NdeI-M (5'-CCC GGG GAT CGG ACA TAT GGC TCT TGT TTC-3') (SEQ ID NO:90) in combination with primer 9-BamHI (5'-GGT CGA CTC TAG AGG ATC CAC TAG TGA TAT GGA T-3') (SEQ ID NO:91) for pAG9 (SEQ ID NO:77), and primer 11-NdeI-M (5'-GAA CAT ATG GCT CTC CTT TCT ATC GTA-3') (SEQ ID NO:92) or primer 11-NdeI-R (5'-GGT GGT GGT GTA CAT ATG AGA CGC ATA CGG G-3') (SEQ ID NO:93) in combination with primer 11-BamHI (5'-GAG ACT AGA CTG GAT CCC ATA TAC ACT GTA ATG G-3') (SEQ ID NO:94) for pAG11 (SEQ ID NO:68). PCR reactions were performed in volumes of 50 μl containing 20 mM Tris-HCl (pH 8.8), 10 mM KCl, 10 mM $(NH_4)_2SO_4$, 2 mM $MgSO_4$, 0.1% Triton X-100, 5 μg bovine serum albumin, 200 μM of each dNTP, 0.1 μM of each primer, 2.5 units of recombinant Pfu DNA polymerase (Stratagene) and 100 ng plasmid DNA using the following program: denaturation at 94° C. for 1 min, annealing at 60° C. for 1 min, extension at 72° C. for 3.5 min; 35 cycles with final extension at 72° C. for 5 min. The resulting PCR products were purified by agarose gel electrophoresis and employed as templates for a second PCR amplification under the identical conditions but in a total volume of 250 μl each. Products from this secondary amplification were digested with the above indicated restriction enzymes, purified by ultrafiltration, and then ligated into NdeI/BamHI-digested pSBETa to yield the respective plasmids pSAG6 (M), pSAG6(R), pSAG8(M), pSAG9(M), pSAG11(M) and pSAG11(R).

For use as controls in the expression of full-length and truncated forms, inserts of the previously described (Bohlmann, J., Steele, C. L., and Croteau, R. (1997) *J. Biol. Chem.* 272, 21784–21792) plasmids pGAG2.2 (myrcene synthase) (SEQ ID NO:1) and pGAG3.18 ((−)-pinene synthase) (SEQ ID NO:3) were prepared for subcloning into pSBETa by PCR amplification using primer 2-NdeI-M (5'-CAA AGG GAG CAC ATA TGG CTC TGG-3') (SEQ ID NO:95) or primer 2-NdeI-R (5'-CTG ATG ATG GTC ATA TGA GAC GCA TAG GTG-3') (SEQ ID NO:96) in combination with primer 2-BamHI (5'-GAC CTT ATT ATT ATG GAT CCG GTT ATA G-3') (SEQ ID NO:97) for pGAG2.2 (SEQ ID NO:1), and primer 3-NdeI-R (5'-CCG ATG ATG GTC ATA TGA GAC GCA TGG GCG-3') (SEQ ID NO:98) in combination with primer 3-BamHI (5'-GGG CAT AGA TTT GAG CGG ATC CTA CAA AGG-3') (SEQ ID NO:99) for pGAG3.18 (SEQ ID NO:3). Prior to insert subcloning, two internal BamHI sites and two internal NdeI sites were eliminated from the insert of pGAG3.18 (SEQ ID NO3:) by site directed mutagenesis using primers 3e1BamHIF (5'-CGT TTG GGA ATC CAT AGA CAT TTC-3') (SEQ ID NO:100), 3e1BamHIR (5'-GAA ATG TCT ATG GAT TCC CAA ACG-3') (SEQ ID NO:101), 3e2BamHIF (5'-GAA GAG ATG GGA CCC GTC CTC GAT AG-3') (SEQ ID NO:102), 3e2BamHIR (5'-CTA TCG AGG ACG GGT CCC ATC TCT TC-3') (SEQ ID NO:103), 3e1NdeIF (5'-GAA CAC GAA GTC CTA TGT GAA GAG C-3') (SEQ ID NO:104), 3e1NdeIR (5'-GCT CTT CAC ATA GGA CTT CGT GTT C-3') (SEQ ID NO:105), 3e3NdeIF (5'-GAT ACG CTC ACT TAT GCT CGG GAA G-3') (SEQ ID NO:106) and 3e2NdeIR (5'-CTT CCC GAG CAT AAG TGA GCG TAT C-3') (SEQ ID NO: 107). Subcloning into pSBETa yielded pSAG2(M) and pSAG2(R) for myrcene synthase, and pSAG3(R) for (−)-pinene synthase. All recombinant pSBETa plasmids were confirmed by sequencing to insure that no errors had been introduced by the polymerase reactions, and were then transformed into *E. coli* BL21 (DE3) by standard methods.

For functional expression, bacterial strains *E. coli* BL21 (DE3)/pSAG2(M), *E. coli* BL21(DE3)/pSAG2(R), *E. coli* BL21(DE3)/pSAG3(R), *E. coli* BL21(DE3)/pSAG6(M), *E. coli* BL21(DE3/pSAG6(R), *E. coli* BL21(DE3)/pSAG8(M), *E. coli* BL21(DE3)/pSAG9(M), *E. coli* BL21(DE3)/pSAG11(M) and *E. coli* BL21(DE3)/SAG11(R) were grown to $A_{600}$=0.5 at 37° C. in 5 ml of Luria-Bertani medium (Sambrook, J., Fritsch, E. F., and Maniatis, T. (1989) Molecular Cloning: A Laboratory Manual, 2nd Ed., pp. 7.20–7.43, Cold Spring Harbor, N.Y.) supplemented with 30 μg kanamycin/ml. Cultures were then induced by addition of 1 mM isopropyl-1-thio-β-D-galactopyranoside and grown for another 12 h at 20° C. Cells were harvested by centrifugation and disrupted by sonication followed by centrifugation, and the resulting soluble enzyme preparations were assayed for monoterpene, sesquiterpene and diterpene synthase activity using the appropriate radiolabeled substrate as described previously (Bohlmann, J., Steele, C. L., and Croteau, R. (1997) *J. Biol. Chem.* 272, 21784–21792). This assay involves the isolation and separation of terpene olefins and oxygenated terpenes by column chromatography on silica, followed by scintillation counting to determine conversion rate. GC-MS analysis is employed for product identification, by comparison of retention times and mass spectra to those of authentic standards (Bohlmann, J., Steele, C. L., and Croteau, R. (1997) *J. Biol Chem.* 272, 21784–21792); assignment of absolute configuration is based upon chiral column capillary GC and matching of retention time to that of the corresponding enantiomer (Lewinsohn, E., Savage, T. J., Gijzen, M., and Croteau, R. (1993) *Phytochem. Anal.* 4, 220–225). To insure production of sufficient material for identification, the standard assay (Bohlmann, J., Steele, C. L., and Croteau, R. (1997) *J. Biol. Chem.* 272, 21784–21792) was scaled up by a factor of 20.

For functional characterization, cDNAs ag6 (SEQ ID NO:64), ag8 (SEQ ID NO:66), ag9 (SEQ ID NO:77) and ag11 (SEQ ID NO:68) were subcloned into the bacterial expression vector pSBET (Schenk, P. M., Baumann, S., Mattes, R., and Steinbiss, H. (1995) *BioTechniques* 19, 196–200). This vector employs the T7 RNA polymerase promoter and contains the argU gene for expression in *E. coli* of the tRNA using the rare arginine codons AGA and AGG that are commonly found in plant genes. pSBET constructs have been employed previously for successful bacterial expression of terpene synthases from gymnosperms and angiosperms (Steele, C. L., Crock, J., Bohlmann, J., and Croteau, R. (1998) *J. Biol. Chem.* 273, 2078–2089; Bohlmann, J., Steele, C. L., and Croteau, R. (1997) *J. Biol. Chem.* 272, 21784–21792; Williams, D. C., McGarvey, D. J., Katahira, E. J., and Croteau, R. (1998) *Biochemisiry* 37, 12213–12220).

Initially, the four pSBET plasmids pSAG6(M), pSAG8 (M), pSAG9(M) and pSAG11(M), containing the full-length cDNA inserts of ag6 (SEQ ID NO:64), ag8 (SEQ ID NO:66), ag9 (SEQ ID NO:77) and ag11 (SEQ ID NO:68), respectively, were expressed in *E. coli* BL21(DE3). Extracts of the induced, transformed bacterial cells were assayed for monoterpene, sesquiterpene and diterpene synthase activity using the corresponding labeled $C_{10}$, $C_{15}$ and $C_{20}$ prenyl diphosphate substrates (Bohlmann, J., Steele, C. L., and Croteau, R. (1997) *J. Biol. Chem.* 272, 21784–21792). Enzymatic production of terpene olefin(s) was observed only with *E. coli* strains BL21(DE3)/pSAG8(M) and BL21 (DE3)/pSAG9(M) using [1-H$^3$]geranyl diphosphate as substrate. Since it is known that the relatively large amino-terminal transit peptide of plant terpene synthases can impair expression of the functional preprotein in *E. coli* and promote the formation of intractable inclusion bodies (Williams, D. C., McGarvey, D. J., Katahira, E. J., and Croteau, R. (1998) *Biochemisiry* 37, 12213–12220), the "pseudomature" forms of ag6 (SEQ ID NO:64) and ag11 (SEQ ID NO:68) were prepared by truncation of the cDNAs to insert a starting methionine immediately upstream of their tandem arginine elements (R59R 60 for ag6 (SEQ ID NO:64), $R^{71}R^{72}$ for ag11 (SEQ ID NO:68)) for expression in *E. coli* BL21(DE3)/pSAG6(R) and *E. coli* BL21(DE3)/ pSAG11(R). Similar truncations of previously characterized ag2.2 (SEQ ID NO:1) (myrcene synthase, $R^{64}R^{65}$) and ag3.18 (SEQ ID NO:3) ((−)-pinene synthase, (SEQ ID NO:5) $R^{64}R^{65}$) (Bohlmann, J., Steele, C. L., and Croteau, R. (1997) *J. Biol. Chem.* 272, 21784–21792) were prepared for expression from pSBET as controls for the possible alteration of product yield and distribution resulting from truncation. These three latter constructs, pSAG2(M), pSAG2(R) and pSAG3(R), afforded high level expression of activity in BL21(DE3) cells, and revealed the identical product patterns previously observed for the myrcene synthase and pinene synthase preprotein forms expressed from pBluescript and pGEX vectors (Bohlmann, J., Steele, C. L., and Croteau, R. (1997) *J. Biol. Chem.* 272, 21784–21792). Thus, truncation directly upstream of the arginine pair does not alter product formation of these recombinant monoterpene synthases. When ag6 (SEQ ID NO:64) and ag11 (SEQ ID NO:68) were expressed as their truncated forms pSAG6(R) and pSAG11 (R) in *E. coli* BL21(DE3), and the extracts assayed for all three terpene synthase activities, only geranyl diphosphate yielded high levels of terpene olefin products.

Monoterpenes generated at preparative scale from geranyl diphosphate by the recombinant enzymes encoded by ag6 (SEQ ID NO:64), ag8 (SEQ ID NO:66), ag9 (SEQ ID NO:77) and ag11 (SEQ ID NO:68) were analyzed by GC-MS and chiral phase (β-cyclodextrin) capillary GC, and identified by comparison of retention times and mass spectra to authentic standards (FIGS. 6–9). The synthase encoded by ag6 (SEQ ID NO:65) was shown to produce three principal products FIG. 6A), the major one of which was identified as (−)-1S,4R-camphene (54%) (FIGS. 6B and C), followed by (−)-1S,5S-α-pinene (32%) and (−)-4S-limonene (7%) which were identified by similar means (data not shown (These additional data may be accessed at website www.wsu.edu/~ibc/faculty/rc.html)). The enzyme encoded by ag6 (SEQ ID NO:65) is therefore designated as (−)-1S,4R-camphene synthase. Interestingly, the (−)-camphene synthase (SEQ ID NO:65) is not as stereoselective as other monoterpene synthases in producing both (−)-α-pinene and (+)-α-pinene as coproducts in a ratio of 95:5; the (−)-enantiomer dominates to the extent of more than 99% in this pinene isomer formed by (−)-pinene synthase from grand fir (Bohlmann, J., Steele, C. L., and Croteau, R. (1997) *J. Biol. Chem.* 272, 21784–21792). Soluble enzyme preparations from *E. coli* BL21(DE3)/pSAG8(M) converted geranyl diphosphate to four products (FIG. 7A) with β-phellandrene (52%) as the major olefin (FIGS. 7B and C), and lesser amounts of (−)-1S,5S-β-pinene (34%), (−)-1S,5S-α-pinene (8.5%) and (−)-4S-limonene (6%) identified by similar means (data not shown (these additional data may be accessed at website www.wsu.edu/~ibc/faculty/rc.html)). The stereochemistry of β-phellandrene was not confirmed directly, since only the authentic (+)-enantiomer was available as a standard for chiral phase GC analysis. Nevertheless, stereochemical considerations based on the established absolute configuration of the co-products, and the natural occurrence of (−)-4S-β-phellandrene in the turpentine (Lewinsohn, E., Savage, T. J., Gijzen, M., and Croteau, R. (1993) *Phytochem. Anal.* 4, 220–225), suggest that the biosynthetic product is the mechanistically related (−)-4S-antipode derived via the (+)-3S-linalyl diphosphate intermediate (Croteau, R. (1987) *Chem. Rev.* 87, 929–954; Wise, M. L., and Croteau, R. (1998) in Comprehensive Natural Products Chemistry: Isoprenoids (Cane, D. E., Ed.), Vol. 2, pp. 97–153, Elsevier Science, Oxford). The product of the ag8 gene (SEQ ID NO:67) is therefore designated (−)-4S-β-phellandrene synthase.

Figure 8A:
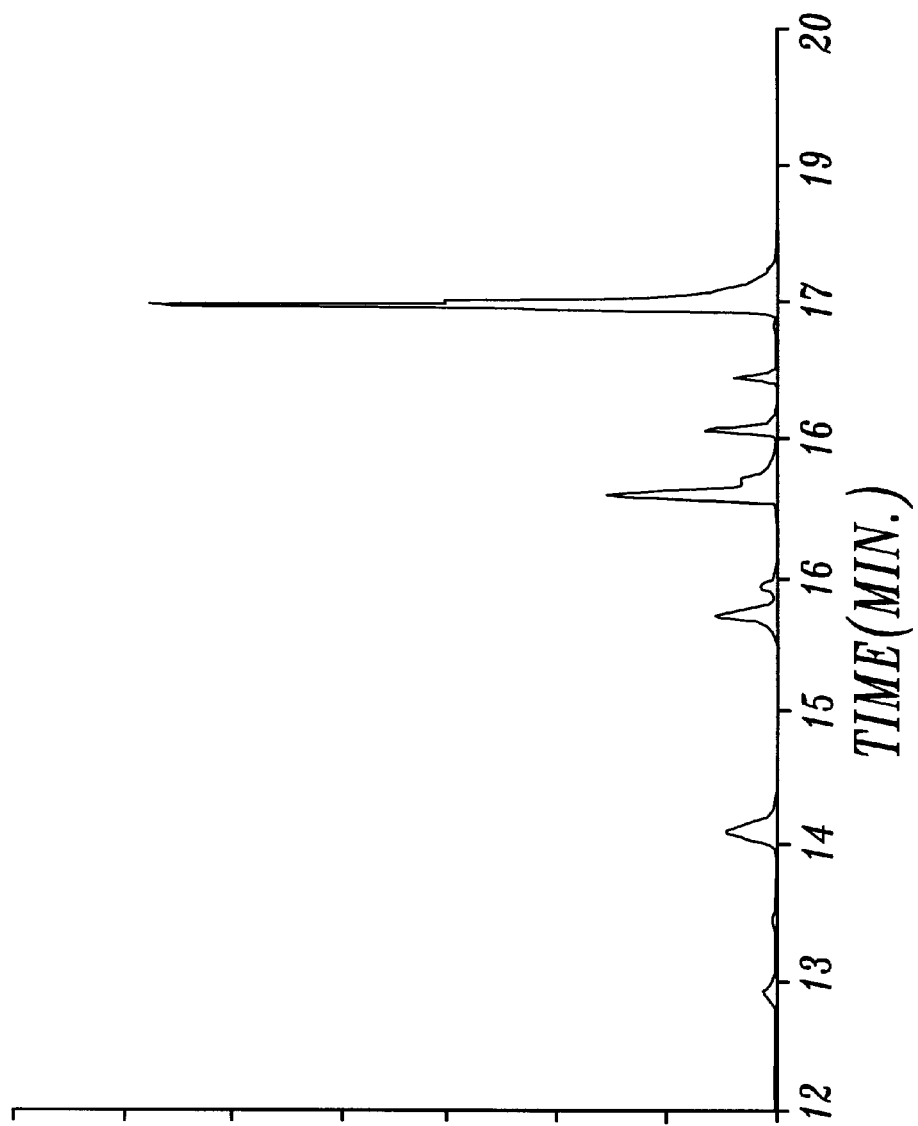
FIG. 8A depicts a total ion chromatogram of monoterpene products derived from geranyl diphosphate by a terpinolene synthase of the invention.
Figure 8B:
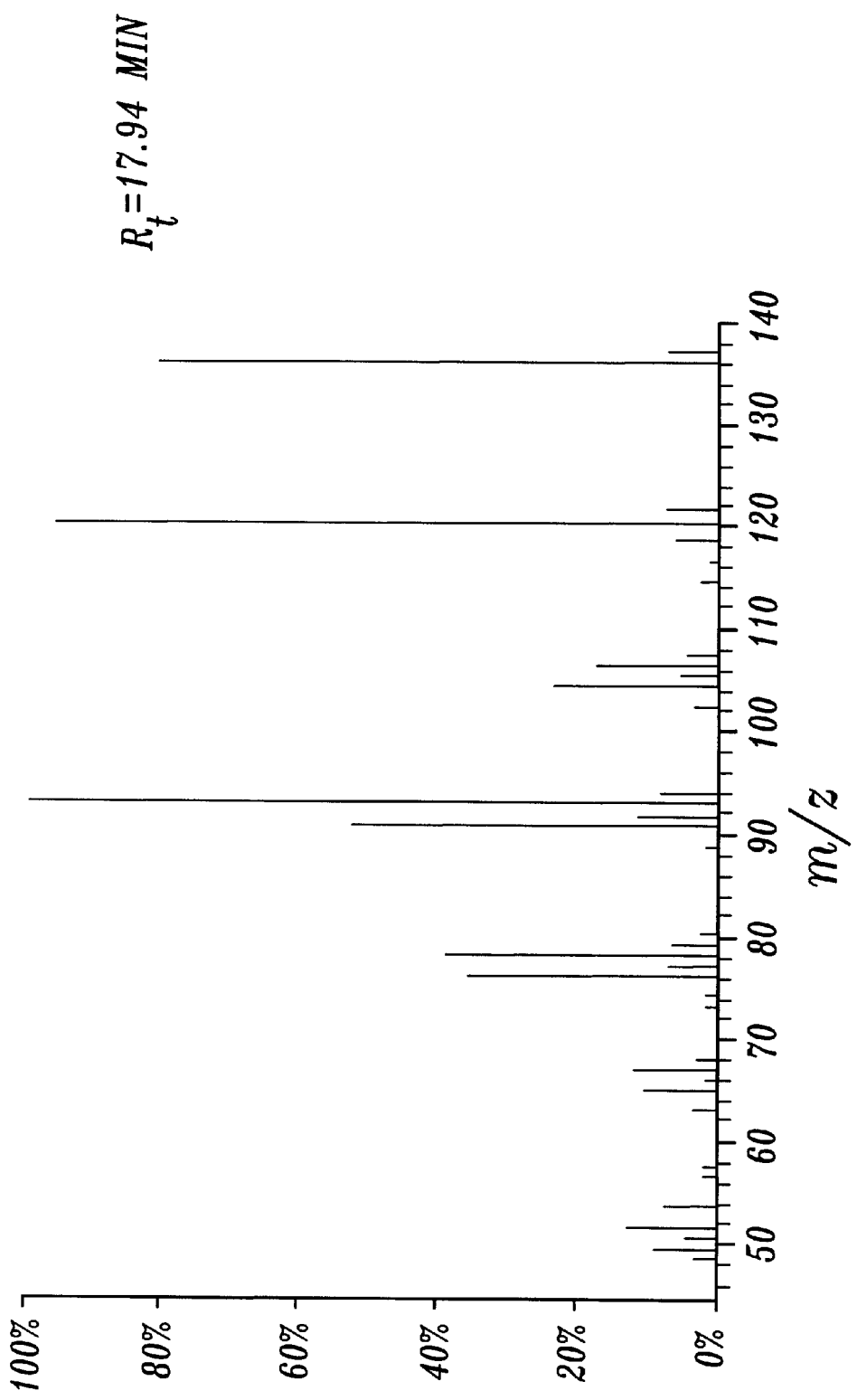
FIG. 8B depicts the mass spectrum and retention time for the principal enzyme product shown in FIG. 8A.
Figure 8C:
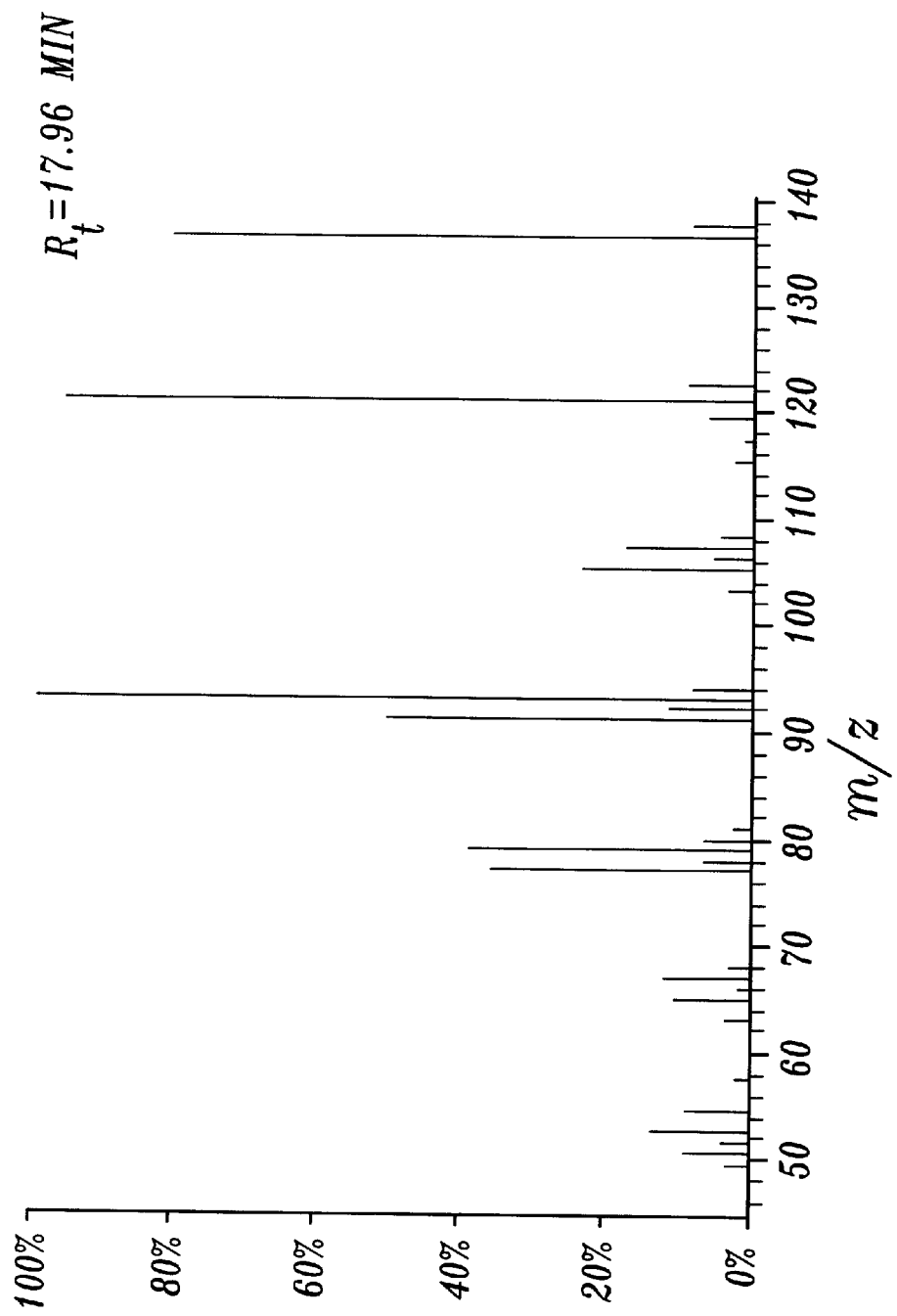
FIG. 8C depicts the mass spectrum and retention time for the authentic terpinolene standard.
Figure 9A:
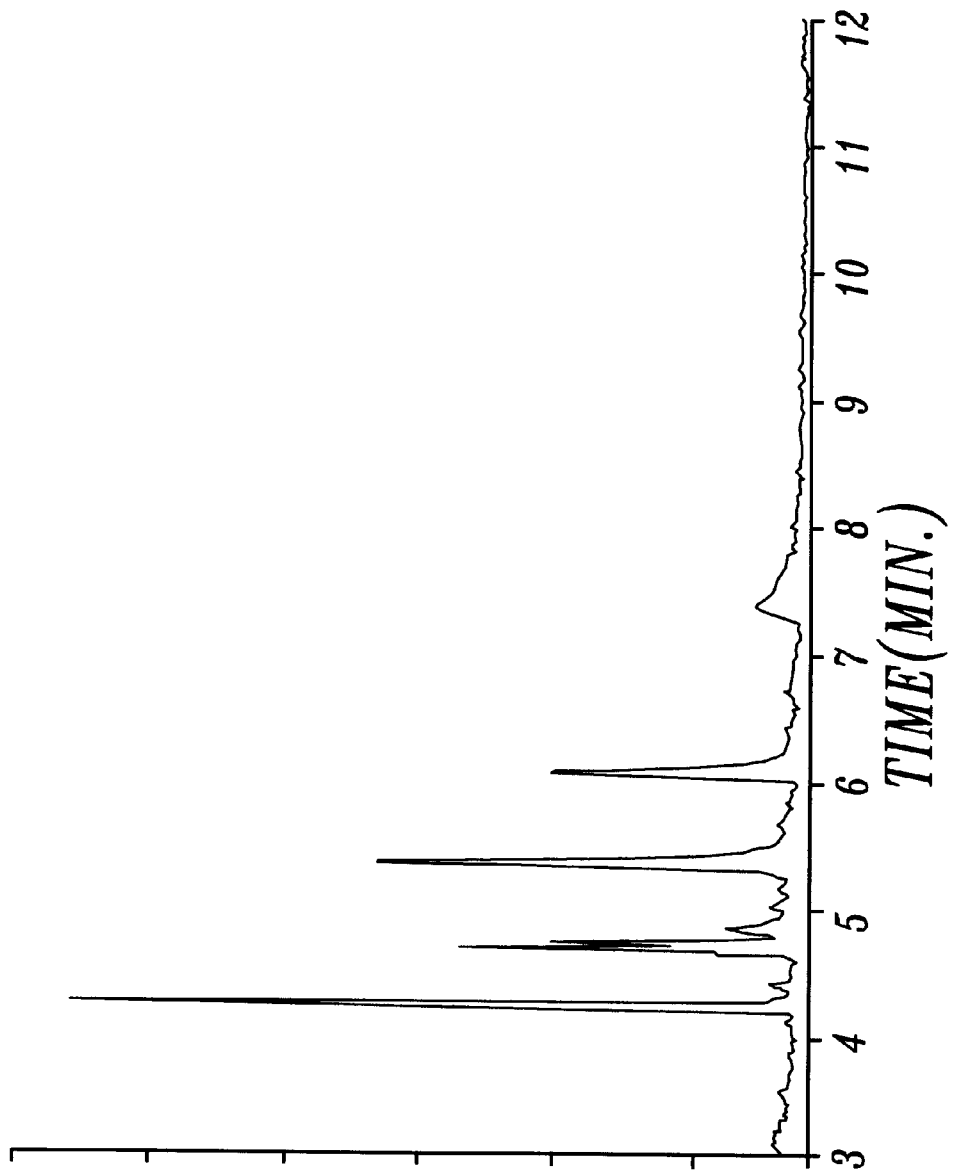
FIG. 9A depicts a total ion chromatogram of monoterpene products derived from geranyl diphosphate by a (−)-limonene/(−)-α-pinene synthase of the invention.
Figure 9B:
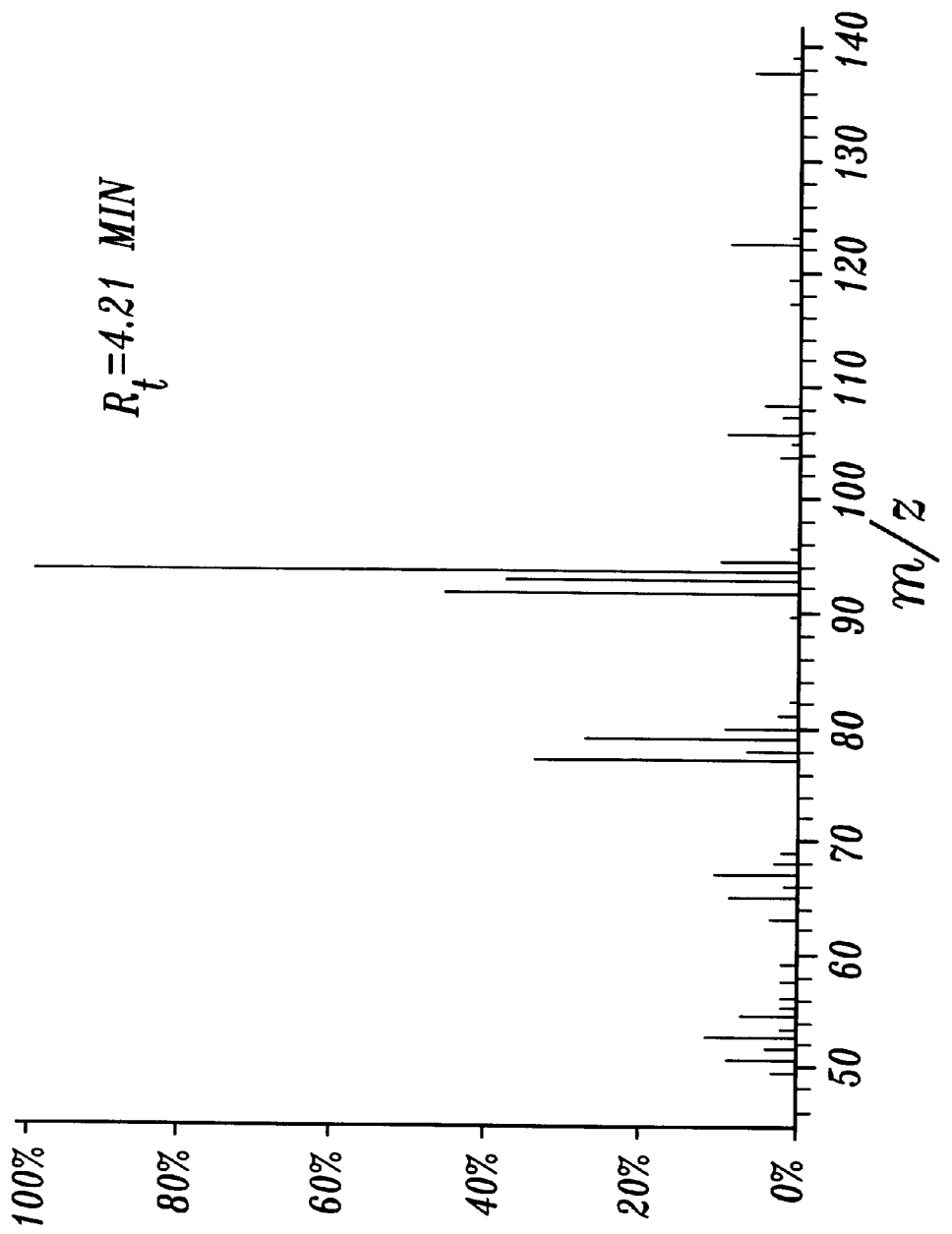
FIG. 9B depicts the mass spectrum and retention time for the principal enzyme product shown in FIG. 9A.
Figure 9E:
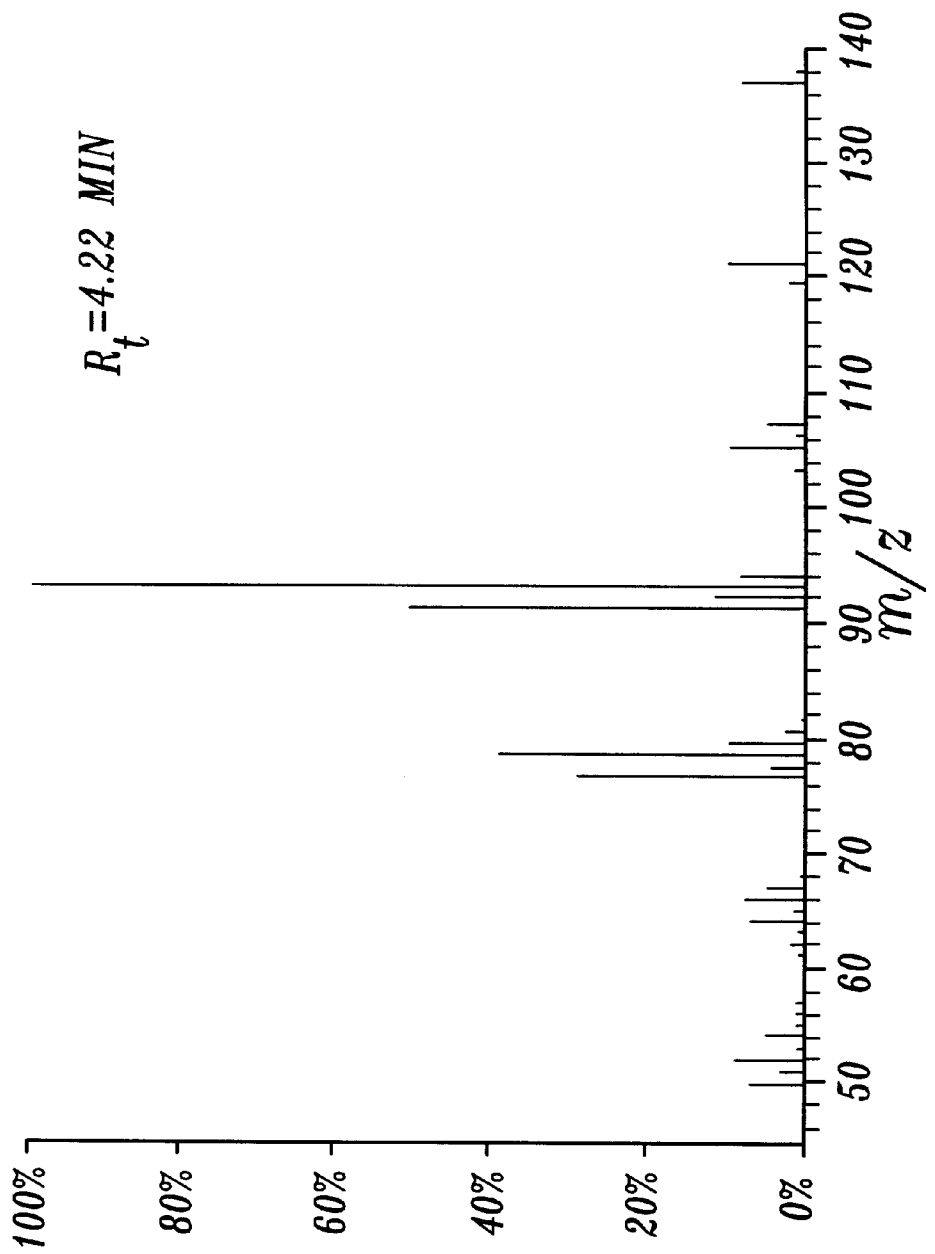
FIG. 9C depicts the mass spectrum and retention time for the authentic α-pinene standard.

The enzyme encoded by cDNA clone ag9 (SEQ ID NO:78) also produced several monoterpenes from geranyl diphosphate (FIG. 8), with the achiral olefin terpinolene identified as the major product (42%) (FIGS. 8B and C). In addition to minor amounts of four unidentified olefins (FIG. 8A), (−)-α-pinene (18%), (−)-limonene (11%) and (−)-β-pinene (10%) were also identified as significant biosynthetic products by mass spectrometric and chromatographic analysis (data not shown (These additional data may be accessed at website www.wsu.edu/~ibc/faculty/rc.html)), indicating that the entire product set was derived in stereochemically consistent fashion via (+)-3S-linalyl diphosphate as intermediate (Croteau, R. (1987) *Chem. Rev.* 87, 929–954; Wise, M. L., and Croteau, R. (1998) in Comprehensive Natural Products Chemistry: Isoprenoids (Cane, D. E., Ed.), Vol. 2, pp. 97–153, Elsevier Science, Oxford). The enzyme encoded by ag9 (SEQ ID NO:78) is designated terpinolene synthase based on the principal olefinic product. cDNA clone ag11 (SEQ ID NO:68) also encodes a multiple product monoterpene synthase (FIG. 9) with the two most abundant products identified as (−)-4S-limonene (35%) and (−)-1,5S-α-pinene (24%) (FIGS. 9B and C), with lesser amounts of β-phellandrene (20%, presumably also the (−)-antipode), (−)-1S,5S-β-pinene (11%), and (−)-1S,5S-sabinene (10%) (data not shown (These additional data may be accessed at website www.wsu.edu/~ibc/faculty/rc.html)). This is the first recombinant monoterpene synthase to produce such a range of cyclic olefins, none of which truly dominate the profile (FIG. 9A). Based on the close sequence relatedness between clone ag11 (SEQ ID NO:68) and the previously described (−)-limonene synthase of grand fir (ag10 (SEQ ID NO:5), which produces about 80% (−)-limonene (Bohlmann, J., Steele, C. L., and Croteau, R. (1997) *J. Biol. Chem.* 272, 21784–21792)), ag11 (SEQ ID NO:69) was previously considered to be a likely (−)-limonene synthase. However, given the significant production of (−)-α-pinene by this cyclase, unlike the ag10 (−)-limonene synthase (SEQ ID NO:6), it seems appropriate to designate the product of the ag11 gene (SEQ ID NO:69) as (−)-limonene/(−)-α-pinene synthase to clearly distinguish the two. The (−)-limonene/(−)-α-pinene synthase (ag 11) (SEQ ID NO:69) and the (−)-limonene synthase (ag10) (SEQ ID NO:6) share 93% similarity and 91% identity at the deduced amino acid level, demonstrating that less than 10% sequence divergence is sufficient to result in a significantly different product outcome. Interestingly, all sequence differences between ag11 (SEQ ID NO:69) and ag10 (SEQ ID NO:6) are confined to the carboxy-terminal half of these proteins, which is thought to comprise the active site region involved in the cyclization step(s) catalyzed by sesquiterpene synthases and presumably other terpene synthases as well (Starks, C. M., Back, K., Chappell, J., and Noel, J. P. (1997) *Science* 277, 1815–1820). This finding is relevant to the rational redesign of terpene synthases, and to the evolution of these catalysts which almost certainly involves gene duplication and modification as the basis for generating new terpenoid synthase function (Bohlmann, J., Meyer-Gauen, G., and Croteau. R. (1998) *Proc. Natl. Acad Sci.* USA 95, 4126–4133).

cDNAs encoding (−)-camphene synthase, (−)-β-phellandrene synthase, terpinolene synthase and (−)-limonene/(−)-α-pinene synthase have not been described previously from any source. Together with the cloned myrcene synthase (SEQ ID NO:1), (−)-limonene synthase (SEQ ID NO:5) and (−)-pinene synthase (SEQ ID NO:3), these seven enzymes account for the production of most, but not all, monoterpenes of the constitutive turpentine (Lewinsohn, E., Savage, T. J., Gijzen, M., and Croteau, R. (1993) *Phytochem. Anal.* 4, 220–225) and wound-induced resin (Gijzen, M., Lewinsohn, E., and Croteau, R. (1991) *Arch. Biochem. Biophys.* 289, 267–273) of grand fir. The cDNA encoding a constitutive and/or inducible (+)-3-carene synthase (Gijzen, M., Lewinsohn, E., and Croteau, R. (1991)

Arch. Biochem. Biophys. 289, 267–273; Savage, T. J., and Croteau, R. (1993) *Arch Biochem. Biophys.* 305, 581–587) has thus far eluded detection. Based on analytical results (Lewinsohn, E., Savage, T. J., Gijzen, M., and Croteau, R. (1993) *Phytochem. Anal.* 4, 220–225) and in vitro assays (Gijzen, M., Lewinsohn, E., and Croteau, R. (1991) *Arch. Biochem. Biophys.* 289, 267–273), the β-phellandrene synthase (SEQ ID NO:67) contributes principally to production of the constitutive turpentine. The terpinolene synthase (SEQ ID NO:78) may also represent a primarily constitutive enzyme; however, the complex and overlapping product profiles of these synthases do not allow unambiguous assignment of their functional role(s) in constitutive resin synthesis or the induced response without more detailed RNA blot analysis. A recent analytical survey of a small grand fir population for different chemotypes in both constitutive resin production and the induced response indicates considerable variation in the constitutive and inducible deployment of the members of this tsd multiple gene family (Katoh, S., and Croteau, R. (1998) *Phytochemistry* 47, 577–582).

EXAMPLE 12

Hybridization Conditions

Presently preferred nucleic acid molecules of the present invention hybridize under stringent conditions to either one or both of hybridization probe A and hybridization probe B (or to their complementary antisense sequences). Hybridization probe A has the nucleic acid sequence of the portion of SEQ ID NO:3 extending from nucleotide 1560 to nucleotide 1694. Hybridization probe B has the nucleic acid sequence of the portion of SEQ ID NO:5 extending from nucleotide 1180 to nucleotide 1302. High stringency conditions are defined as hybridization in 5×SSC at 65° C. for 16 hours, followed by two washes in 2×SSC at 20° C. to 26° C. for fifteen minutes per wash, followed by two washes in 0.2×SSC at 65° C. for twenty minutes per wash. Moderate stringency conditions are defined as hybridization in 3×SSC at 65° C. for 16 hours, followed by two washes in 2×SSC at 20° C. to 26° C. for twenty minutes per wash, followed by one wash in 0.5×SSC at 55° C. for thirty minutes. Low stringency conditions are defined as hybridization in 3×SSC at 65° C. for 16 hours, followed by two washes in 2×SSC at 20° C. to 26° C. for twenty minutes per wash.

EXAMPLE 13

Characteristics of Presently Preferred Monoterpene Synthase Proteins of the Invention Presently preferred monoterpene synthase proteins of the present invention have the following characteristics: a preprotein molecular weight of from about 71 kiloDaltons (kDa) to about 73 kDa; a mature protein (excluding plastidial transit peptide) molecular weight of from about 60 kDa to about 67 kDa; isoelectric point (pI) of from about 4.5 to about 5.0 as determined by isoelectric focussing; a mature protein pH optimum of from about 7.5 to about 8.0; utilization of geranyl diphosphate as a substrate with $K_m$ less than 15 μM; a requirement for a divalent metal ion as a cofactor, with manganese ($Mn^{2+}$) being preferred over magnesium ($Mg^{2+}$), the Km for binding of $Mn^{2+}$ being less than 50 μM; biological activity is enhanced by the presence of $K^+$ ions at a concentration of 100 μM; the presence of the sequence motif DDXXD (SEQ ID NO:45) within the carboxy terminal half of the protein, and the presence of two tandem arginines immediately following the C-terminal end of the plastidial transit peptide. The foregoing characterisitics apply to the mature protein, unless otherwise stated.

EXAMPLE 14

Alteration of Monoterpene Levels and Composition in Plant Seeds

In accordance with the present invention, methods for increasing production of monoterpene compounds in a plant, particularly in plant seeds, are provided. The methods involve transforming a plant cell with a nucleic acid sequence encoding at least one monoterpene synthase, such as those encoded by the nucleic acid sequences set forth in SEQ ID NO:1, SEQ ID NO:3, SEQ ID NO:5, SEQ ID NO64:, SEQ ID NO:66, SEQ ID NO:68 and SEQ ID NO:77. This has the effect of altering monoterpene biosynthesis, thereby increasing the production of monoterpenes, as well as providing novel seed oils having desirable monoterpene compositions. In this manner, the transformed seed provides a factory for the production of modified oils. The modified oil itself may be used and/or the compounds in the oils can be isolated. Thus, the present invention allows for the production of particular monoterpenes of interest as well as speciality oils.

The nucleic acid encoding the monoterpene synthases of the present invention can be used in expression cassettes for expression in the transformed plant tissues. To alter the monoterpene levels in a plant of interest, the plant is transformed with at least one expression cassette comprising a transcriptional initiation region linked to a nucleic acid sequence encoding a monoterpene synthase. Such an expression cassette is provided with a plurality of restriction sites for insertion of the nucleic acid sequence encoding a monoterpene synthase so that it is under the transcriptional regulation of the regulatory regions.

The transcriptional initiation sequence may be native or analogous to the host or foreign or heterologous to the host. In this regard, the term "foreign" means that the transcriptional initiation sequence is not found in the wild-type host into which the transcriptional initiation region is introduced.

Of particular interest are those transcriptional initiation regions associated with storage proteins, such as napin, cruciferin, β-conglycinin, phaseolin, globulin or the like, and proteins involved in fatty acid biosynthesis, such as acyl carrier protein (ACP). See, U.S. Pat. No. 5,420,034, herein incorporated by reference.

The transcriptional cassette will preferably include, in the 5' to 3' direction of transcription, a transcriptional and translational initiation region, a monoterpene synthase DNA sequence of interest, and a transcriptional and translational termination region functional in plants. The termination region may be from the same organism as the transcriptional initiation region, may be from the same organism as the monoterpene synthase DNA, or may be derived from another source. Convenient termination regions are available from the Ti-plasmid of *A. tumefaciens,* such as the octopine synthase and nopaline synthase termination regions. Other termination sequences are set forth in Guerineau et al., (1991), *Mol. Gen. Genet.,* 262:141–144; Proudfoot, (1991), *Cell,* 64:671–674; Sanfacon et al., (1991), *Genes Dev.,* 5:141–149; Mogen et al., (1990), *Plant Cell,* 2:1261–1272; Munroe et al., (1990), *Gene,* 91:151–158; Ballas et al., (1989), *Nucleic Acids Res.,* 17:7891–7903; Joshi et al., (1987), *Nucleic Acid Res.,* 15:9627–9639).

In the presently preferred form of the invention, a nucleic acid sequence encoding a monoterpene synthase protein will be targeted to plastids, such as chloroplasts, for expression. Thus, the nucleic acid sequence, or sequences, encoding a monoterpene synthase protein, or proteins, may be inserted into the plastid for expression with appropriate plastid constructs and regulatory elements. Alternatively, nuclear transformation may be used in which case the expression cassette will contain a nucleic acid sequence encoding a transit peptide to direct the monoterpene biosynthesis enzyme of interest to the plastid. Such transit peptides are known in the art. See, for example, Von Heijne et al. (1991) Plant Mol. Biol. Rep. 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res. Commun.* 196:1414–1421; and, Shah et al. (1986) *Science* 233:478–481. Nucleic acid sequences encoding monoterpene synthases of the present invention may utilize native or heterologous transit peptides.

The construct may also include any other necessary regulators such as plant translational consensus sequences (Joshi, C. P., (1987), *Nucleic Acids Research*, 15:6643–6653), introns (Luehrsen and Walbot, (1991), *Mol. Gen. Genet.*, 225:81–93) and the like, operably linked to a nucleotide sequence encoding a monoterpene synthase of the present invention.

It may be beneficial to include 5' leader sequences in the expression cassette which can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology*, 154:9–20), and human immunoglobulin heavy-chain binding protein (BiP), (Macejak, D. G., and Sarnow, P. (1991), *Nature*, 353:90–94; untranslated leader from the coat protein mRNA of alfalfa mosaic virus (AMV RNA 4), (Jobling, S. A., and Gehrke, L. (1987), *Nature*, 325:622–625; tobacco mosaic virus leader (TMV), (Gallie, D. R. et al. (1989), *Molecular Biology of RNA*, pages 237–256; and maize chlorotic mottle virus leader (MCMV) (Lommel, S. A. et al. (1991), *Virology*, 81:382–385. See also, Della-Cioppa et al., (1987), *Plant Physiology*, 84:965–968.

Depending upon where the monoterpene synthase sequence of interest is to be expressed, it may be desirable to synthesize the sequence with plant preferred codons, or alternatively with chloroplast preferred codons. The plant preferred codons may be determined from the codons of highest frequency in the proteins expressed in the largest amount in the particular plant species of interest. See, EPA 0359472; EPA 0385962; WO 91/16432; Perlak et al. (1991) *Proc. Natl. Acad. Sci. USA* 88:3324–3328; and Murray et al. (1989) *Nucleic Acids Research* 17:477–498. In this manner, the nucleotide sequences can be optimized for expression in any plant. It is recognized that all or any part of the nucleic acid sequence encoding a monoterpene synthase protein may be optimized or synthetic. That is, synthetic or partially optimized sequences may also be used. For the construction of chloroplast preferred genes, see U.S. Pat. No. 5,545,817.

In preparing the transcription cassette, the various DNA fragments may be manipulated, so as to provide for the DNA sequences in the proper orientation and in the proper reading frame. Towards this end, adapters or linkers may be employed to join the DNA fragments or other manipulations may be involved to provide for aconvenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, such as transitions and transversions, may be involved.

The recombinant DNA molecules of the invention can be introduced into the plant cell in a number of art-recognized ways. Those skilled in the art will appreciate that the choice of method might depend on the type of plant, i.e., monocot or dicot, targeted for transformation. Suitable methods of transforming plant cells include microinjection (Crossway et al. (1986) *BioTechniques* 4:320–334), electroporation (Riggs et al. (1986) *Proc. Natl. Acad. Sci. USA* 83:5602–5606), Agrobacterium mediated transformation (Hinchee et al. (1988) *Biotechnology* 6:915–921) and ballistic particle acceleration (see, for example, Sanford et al., U.S. Pat. No. 4,945,050; and McCabe et al. (1988) *Biotechnology* 6:923–926). Also see, Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Datta et al. (1990) *Biotechnology* 8:736–740 (rice); Klein et al. (1988) *Proc. Natl. Acad Sci. USA*, 85:4305–4309 (maize); Klein et al. (1988) *Biotechnology* 6:559–563 (maize); Klein et al. (1988) *Plant Physiol.* 91:440–444 (maize); Fronun et al. (1990) *Biotechnology* 8:833–839; and Gordon-Kamm et al. (1990) *Plant Cell* 2:603–618 (maize).

Alternatively, a plant plastid can be transformed directly. Stable transformation of chloroplasts has been reported in higher plants, see, for example, SVAB etal. (1990) *Proc. Nat'l. Acad. Sci. USA* 87:85268530; SVAB & Maliga (1993) *Proc. Natl. Acad Sci. USA* 90:913–917; Staub & Maliga (1993) *Embo J.* 12:601–606. The method relies on particle gun delivery of DNA containing a selectable marker and targeting of the DNA to the plastid genome through homologous recombination. In such methods, plastid gene expression can be accomplished by use of a plastid gene promoter or by trans-activation of a silent plastid-borne transgene positioned for expression from a selective promoter sequence such as that recognized by T7 RNA polymerase. The silent plastid gene is activated by expression of the specific RNA polymerase from a nuclear expression construct and targeting of the polymerase to the plastid by use of a transit peptide. Tissue-specific expression may be obtained in such a method by use of a nuclear-encoded and plastid-directed specific RNA polymerase expressed from a suitable plant tissue specific promoter. Such a system has been reported in McBride et al. (1994) *Proc. Natl. Acad Sci. USA* 91:7301–7305.

The cells which have been transformed may be grown into plants by a variety of art-recognized means. See, for example, McConnick et al., *Plant Cell Reports* (1986), 5:81–84. These plants may then be grown, and either selfed or crossed with a different plant strain, and the resulting homozygotes or hybrids having the desired phenotypic characteristic identified. Two or more generations may be grown to ensure that the subject phenotypic characteristic is stably maintained and inherited and then seeds harvested to ensure the desired phenotype or other property has been achieved.

As a host cell, any plant variety may be employed. Of particular interest, are plant species which provide seeds of commercial value. For the most part, plants will be chosen where the seed is produced in high amounts, a seed-specific product of interest is involved, or the seed or a seed part is edible. Seeds of interest in the practice of the present invention include, but are not limited to, the oil seeds, such as oilseed Brassica seeds, cotton seeds, soybean, safflower, sunflower, coconut, palm, and the like; grain seeds such as wheat, barley, oats, amaranth, flax, rye, triticale, rice and corn; other edible seeds or seeds with edible parts including pumpkin, squash, sesame, poppy, grape, mung beans, peanut, peas, beans, radish, alfalfa, cocoa, and coffee; and tree nuts such as walnuts, almonds, pecans, and chick-peas.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated nucleic acid molecule that encodes a (−)-pinene synthase and that hybridizes under stringent conditions to the complement of SEQ ID NO:3, wherein said stringent conditions comprise hybridization in 3×SSC at 65° C. for 16 hours, followed by two washes in 2×SSC at 20° C. to 26° C. for twenty minutes per wash, followed by one wash in 0.5×SSC at 55° C. for thirty minutes.

2. An isolated nucleic acid molecule of claim 1 encoding a gymnosperm (−)-pinene synthase.

3. An isolated nucleic acid molecule of claim 1 encoding a Grand fir (−)-pinene synthase.

4. An isolated nucleic acid molecule of claim 1 which encodes the amino acid sequence of SEQ ID NO:4.

5. An isolated nucleic acid molecule of claim 1 consisting of the sequence SEQ ID NO:3.

6. A replicable expression vector comprising a nucleic acid sequence encoding a (−)-pinene synthase, wherein said nucleic acid sequence hybridizes under stringent conditions to the complement of SEQ ID NO:3, wherein said stringent conditions comprise hybridization in 3×SSC at 65° C. for 16 hours, followed by two washes in 2×SSC at 20° C. to 26° C. for twenty minutes per wash, followed by one wash in 0.5×SSC at 55° C. for thirty minutes.

7. A host cell comprising a vector of claim 6.

8. A method of enhancing the production of a (−)-pinene synthase in a suitable host cell comprising introducing into the host cell an expression vector of claim 6 under conditions enabling expression of the (−)-pinene synthase in the host cell.

9. The method of claim 8 wherein said host cell is a plant cell.

10. The method of claim 9 wherein said cell is from a plant selected from the group consisting of Brassica, cotton, soybean, safflower, sunflower, coconut, palm, wheat, barley, rice, corn, oats, amaranth, pumpkin, squash, sesame, poppy, grape, mung beans, peanut, peas, beans, broad beans, chick peas, lentils, radish, alfalfa, cocoa, coffee, tree nuts, spinach, culinary herbs, berries, stone fruit and citrus.

11. The method of claim 9 wherein said plant cell is a seed cell.

12. The method of claim 9 wherein said plant cell is a leaf cell.

* * * * *

UNITED STATES PATENT AND TRADEMARK OFFICE
CERTIFICATE OF CORRECTION

PATENT NO.   : 6,429,014 B1
DATED        : August 6, 2002
INVENTOR(S)  : C.L. Steele et al.

It is certified that error appears in the above-identified patent and that said Letters Patent is hereby corrected as shown below:

Column 1,
Line 10, "grant GM-3135A" should read -- grant GM-31354 --

Signed and Sealed this

Twentieth Day of July, 2004

JON W. DUDAS
*Acting Director of the United States Patent and Trademark Office*